(12) United States Patent
Bieniarz et al.

(10) Patent No.: US 12,215,118 B2
(45) Date of Patent: *Feb. 4, 2025

(54) QUINONE METHIDE ANALOG SIGNAL AMPLIFICATION

(71) Applicant: Ventana Medical Systems, Inc., Tucson, AZ (US)

(72) Inventors: Christopher Bieniarz, Tucson, AZ (US); Julia Ashworth-Sharpe, Tucson, AZ (US); Brian D. Kelly, Tucson, AZ (US); Nathan Polaske, Oracle, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 353 days.

This patent is subject to a terminal disclaimer.

(21) Appl. No.: 17/507,853

(22) Filed: Oct. 22, 2021

(65) Prior Publication Data

US 2022/0041633 A1  Feb. 10, 2022

Related U.S. Application Data

(60) Division of application No. 16/183,570, filed on Nov. 7, 2018, now Pat. No. 11,365,210, which is a (Continued)

(51) Int. Cl.
*G01N 33/58* (2006.01)
*C07D 209/14* (2006.01)
(Continued)

(52) U.S. Cl.
CPC .......... *C07F 9/6561* (2013.01); *C07D 209/14* (2013.01); *C07D 403/06* (2013.01);
(Continued)

(58) Field of Classification Search
CPC .. C07F 9/6561; C07F 9/06; C07F 9/12; C07F 9/65335; C07D 209/14; C07D 403/06; C07H 15/26; G01N 33/581; C12Q 1/42
See application file for complete search history.

(56) References Cited

U.S. PATENT DOCUMENTS

| | | | |
|---|---|---|---|
| 4,797,476 A | 1/1989 | Inagaki et al. | |
| 5,326,882 A | 7/1994 | Bronstein et al. | |

(Continued)

FOREIGN PATENT DOCUMENTS

| | | |
|---|---|---|
| CN | 107540597 A | 1/2018 |
| JP | 2017-512210 A | 5/2017 |

(Continued)

OTHER PUBLICATIONS

Mokry, Jaroslav. Versatility of Immunohistochemical Reactions: Comprehensive Survey of Detection Systems. Acta Medica (Hradec Kralove) 1996:39:129-140. (Year: 1996).*

(Continued)

*Primary Examiner* — Shafiqul Haq
(74) *Attorney, Agent, or Firm* — Charney IP Law LLC; Thomas M. Finetti

(57) ABSTRACT

Disclosed herein are novel quinone methide analog precursors and embodiments of a method and a kit of using the same for detecting one or more targets in a biological sample. The method of detection comprises contacting the sample with a detection probe, then contacting the sample with a labeling conjugate that comprises an enzyme. The enzyme interacts with a quinone methide analog precursor comprising a detectable label, forming a reactive quinone methide analog, which binds to the biological sample proximally to or directly on the target. The detectable label is then detected. In some embodiments, multiple targets can be detected by multiple quinone methide analog precursors (Continued)

interacting with different enzymes without the need for an enzyme deactivation step.

18 Claims, 43 Drawing Sheets
(36 of 43 Drawing Sheet(s) Filed in Color)

Related U.S. Application Data continuation of application No. 15/246,430, filed on Aug. 24, 2016, now Pat. No. 10,168,336, which is a continuation of application No. PCT/EP2015/053556, filed on Feb. 20, 2015.

(60) Provisional application No. 61/943,940, filed on Feb. 24, 2014.

(51) Int. Cl.

| | | |
|---|---|---|
| C07D 403/06 | (2006.01) | |
| C07F 9/06 | (2006.01) | |
| C07F 9/12 | (2006.01) | |
| C07F 9/58 | (2006.01) | |
| C07F 9/6503 | (2006.01) | |
| C07F 9/6518 | (2006.01) | |
| C07F 9/6533 | (2006.01) | |
| C07F 9/6558 | (2006.01) | |
| C07F 9/6561 | (2006.01) | |
| C07H 15/203 | (2006.01) | |
| C07H 15/207 | (2006.01) | |
| C07H 15/26 | (2006.01) | |
| C07H 17/02 | (2006.01) | |
| C12Q 1/42 | (2006.01) | |

(52) U.S. Cl.
CPC ............... *C07F 9/06* (2013.01); *C07F 9/12* (2013.01); *C07F 9/58* (2013.01); *C07F 9/65031* (2013.01); *C07F 9/6518* (2013.01); *C07F 9/65335* (2013.01); *C07F 9/65583* (2013.01); *C07H 15/203* (2013.01); *C07H 15/207* (2013.01); *C07H 15/26* (2013.01); *C07H 17/02* (2013.01); *C12Q 1/42* (2013.01); *G01N 33/581* (2013.01)

(56) References Cited

U.S. PATENT DOCUMENTS

| | | | |
|---|---|---|---|
| 10,168,336 B2 | | 1/2019 | Bieniarz et al. |
| 11,780,863 B2* | | 10/2023 | Bieniarz ............... C07D 209/14 536/17.4 |
| 2006/0003383 A1 | | 1/2006 | Graham |
| 2009/0099133 A1 | | 4/2009 | Gunzinger et al. |
| 2009/0318396 A1 | | 12/2009 | Baker |
| 2010/0061936 A1 | | 3/2010 | Shen |
| 2010/0144787 A1 | | 6/2010 | Montana et al. |
| 2010/0317831 A1 | | 12/2010 | Lo |
| 2011/0275643 A1 | | 11/2011 | Liou et al. |
| 2012/0171668 A1 | | 7/2012 | May et al. |
| 2012/0184579 A1 | | 7/2012 | Montana |
| 2013/0131018 A1 | | 5/2013 | Leblond et al. |
| 2017/0089911 A1 | | 3/2017 | Bieniarz et al. |
| 2019/0127405 A1 | | 5/2019 | Bieniarz et al. |
| 2024/0018174 A1* | | 1/2024 | Bieniarz ............... C07D 403/06 |

FOREIGN PATENT DOCUMENTS

| | | |
|---|---|---|
| JP | 2019148726 A | 9/2019 |
| WO | 2004111259 A2 | 12/2004 |
| WO | WO2010126953 A1 | 11/2010 |
| WO | WO2011081937 A1 | 7/2011 |
| WO | 2014139980 A1 | 9/2014 |
| WO | 2015124703 A1 | 8/2015 |

OTHER PUBLICATIONS

Pavlik et al., Phototransposition Chemistry of 1-Phenylpyrazole. Experimental and Computational Studies, J. Am. Chem. Soc., vol. 115, pp. 7645-7652, 1993.
Vasquez-Garzon, et al., Toxicology Mechanisms and Mthods 22:4, 296-304 (2012), Evlauation of three simple direct or Indirect carbonyl detection methods for characterization of oxidative modifications of proteins.
Pharmatutor, Oct. 19, 2016, Define and exemplify chromophores.
Smith, B. C., Spectroscopy, 32:9, 31-36 (2017), The Carbonyl Group, Part I: Introduction.
Hachey et al., Understanding Chemical Reactivity (1999), 179-230, The Rydberg Spectrum of Aldehydes and Ketones: A comparison using formaldehyde as a benchmark.
Ingram et al., Bioorganic & Medicinal Chemistry Letters 19 (2009) 1569-1571.
Zhu et al., Tetrahedron Letters 44 (2003) 2669-2672.
Kuo et al., Selective activation of SHP2 activity by cisplatin revealed by a novel chemical probe-based assay, Biochemical and Biophysical Research Communications 391 (2010) 230-234.
Kalidasan et al., Fluorescence-activated cell sorting and directed evolution of a-N-acetylgalactosaminidases using a quenched activity-based probe (qABP), Chem. Commun., 2013, 49, 7237.
Huang et al., Multiple Reactive Immunization Towards the Hydrolysis of Organophosphorus Nerve Agents: Hapten Design and Synthesis, Bioorganic & Medicinal Chemistry 9 (2001) 3185-3195.
Cavalli et al., Development of an Activity-Based Probe for Autotaxin, ChemBioChem 2010, 11, 2311-2317.
Encyclopedia of Reagents for Organic Synthesis—2006—Fauq—Diethylaminosulfurtrifluoride.
Lo et al., Study of the preferred modification sites of the quinone methide intermediate resulting from the latent trapping device of the activity probes for hydrolases, Biochemical and Biophysical Research Communications 326 (2005) 30-35.
Bakke et al., Journal of Environmental Science and Health, Part B: Pesticides, Food Contaminants, and Agricultural Wastes (1979), B14(4), 417-26, Abstract.
Betley, J R et al., Direct Screening for Phosphatase Activity by Tumover-Based Capture of Protein Catalysts, Angew Chem Int Edit, (2002), pp. 775-777, vol. 41 Issue 5.
Chen G et al., Developing a Strategy for Activity-Based Detection of Enzymes in a Protein Microarray, Chembiochem, (2003), pp. 336-339, vol. 4 Issue 4.
Chu, C-Y et al., Development and Evaluation of Novel Phosphotyrosine Mimetic Inhibitors Targeting the Src Homology 2 Domain of Signaling Lymphocytic Activation Molecule (SLAM) Associated Protein, J Med Chem, (2013), pp. 2841-2849, vol. 56 Issue 7.
Goerner, Photoprocesses of p-naphthoquinones and vitamin K1: effects of alcohols and amines on the reactivity in solution, Photochemical & Photobiological Sciences, 2004, pp. 71-78, 3(1).
Huang, Y-Y et al., Development of activity-based probes with tunable specificity for protein tyrosine phosphatase subfamilies, Tetrahedron, (2010), pp. 4521-4529, vol. 66 Issue 25.
Kalesh, Karunakaran A et al., Peptide-based activity-based probes (ABPs) for target-specific profiling of protein tyrosine phosphatases (PTPs), Chemical Communications, (2010), pp. 589-591, vol. 46.
Karpaviciene, I. et al., A Unique Cascade Reaction between 3-Arylprop-2-inylcarboxylates and Benzahldehydes Leading to the Formation of Morita-Baylis-Hillman Adducts, Organic Letters, 2013, 224-227, 15.
Lo, L-C et al., Rapid and selective isolation of B-xylosidase through an activity-based chemical approach, Biotech J, (2006), pp. 197-202, vol. 1 Issue 2.
Lo, LC et al., Study of the preferred modification sites of the quinone methide intermediate resulting from the latent rapping device of the activity probes for hydrolases, Biochem Biophys Res Comm, (2004), pp. 30-35, vol. 326 Issue 1.

(56) References Cited

OTHER PUBLICATIONS

Shen, K et al., Facile Incorporation of a Phosphatase Activity-Dependent Quinone Methide Generating Motif into Phosphotyrosine, Synthesis, (2009), pp. 3765-3768, vol. 2009 Issue 22.
Shen, K et al., Synthesis and peptide incorporation of an unnatural amino acid containing activity-based probe for protein tyrosine phosphatases, Bioorg Med Chem Lett, (2009), pp. 3264-3267, vol. 19 Issue 12.
Zhu, Q et al, Activity-based fluorescent probes that target phosphatases, Tetrahedron Letters, 2003, 2669-2672, 44.
Lo, L-C et al., Rapid and selective isolation of β-xylosidase through an activity-based chemical approach, Biotech J, (2006), pp. 197-202, vol. 1 Issue 2.
Garcia-Romeu et al. Current Drug Abuse Reviews 2014; 7(3) pp. 157-164 (abstract—2 pages).

\* cited by examiner

QUINONE METHIDE ANALOG SIGNAL AMPLIFICATION

CROSS REFERENCE TO RELATED APPLICATIONS

This patent application is a continuation of U.S. patent application Ser. No. 16/183,570 filed on Nov. 7, 2018, which application is a continuation of U.S. patent application Ser. No. 15/246,430 filed on Aug. 24, 2016, which is a continuation of International Application No. PCT/EP2015/053556 filed Feb. 20, 2015, which claims priority to and the benefit of U.S. Provisional Patent Application No. 61/943,940 filed Feb. 24, 2014. Each patent application is incorporated herein by reference as if set forth in its entirety.

FIELD

This disclosure concerns novel quinone methide analog precursors and embodiments of a method and a kit comprising the same.

BACKGROUND

Immunohistochemistry (IHC) refers to the processes of detecting, localizing, and/or quantifying antigens, such as a protein, in a biological sample using specific binding moieties, such as antibodies specific to the particular antigens. IHC provides the substantial advantage of identifying exactly where a particular protein is located within the tissue sample. It is also an effective way to examine the tissues themselves. In situ hybridization (ISH) refers to the process of detecting, localizing, and quantifying nucleic acids. Both IHC and ISH can be performed on various biological samples, such as tissue (e.g. fresh frozen, formalin fixed, paraffin embedded) and cytological samples. Recognition of the targets can be detected using various labels (e.g., chromogenic, fluorescent, luminescent, radiometric), irrespective of whether the target is a nucleic acid or an antigen. To robustly detect, locate, and quantify targets in a clinical setting, amplification of the recognition event is desirable as the ability to confidently detect cellular markers of low abundance becomes increasingly important for diagnostic purposes. For example, depositing at the marker's sites hundreds or thousands of label molecules in response to a single antigen detection event enhances, through amplification, the ability to detect that recognition event.

Adverse events often accompany amplification, such as non-specific signals that are apparent as an increased background signal. An increased background signal interferes with the clinical analysis by obscuring faint signals that may be associated with low, but clinically significant, expressions. Accordingly, while amplification of recognition events is desirable, amplification methods that do not increase background signal are highly desirable. One such method is Tyramide Signal Amplification (TSA), which has also been referred to as catalyzed reporter deposition (CARD). U.S. Pat. No. 5,583,001 discloses a method for detecting and/or quantitating an analyte using an analyte-dependent enzyme activation system that relies on catalyzed reporter deposition to amplify the detectable label signal. Catalysis of an enzyme in a CARD or TSA method is enhanced by reacting a labeled phenol molecule with an enzyme. Modern methods utilizing TSA effectively increase the signals obtained from IHC and ISH assays while not producing significant background signal amplification (see, for example, U.S. application publication No. 2012/0171668 which is hereby incorporated by reference in its entirety for disclosure related to tyramide amplification reagents). Reagents for these amplification approaches are being applied to clinically important targets to provide robust diagnostic capabilities previously unattainable (OPTIV-IEW® Amplification Kit, Ventana Medical Systems, Tucson AZ, Catalog No. 760-099).

TSA takes advantage of the reaction between horseradish peroxidase (HRP) and tyramide. In the presence of $H_2O_2$, tyramide is converted to a highly-reactive and short-lived radical intermediate that reacts preferentially with electron-rich amino acid residues on proteins. Covalently-bound detectable labels can then be detected by variety of chromogenic visualization techniques and/or by fluorescence microscopy. In solid-phase immunoassays such as IHC and ISH, where spatial and morphological context is highly valued, the short lifetime of the radical intermediate results in covalent binding of the tyramide to proteins on tissue in close proximity to the site of generation, giving discrete and specific signal. While CARD broadly defines the use of an analyte-dependent reporter enzyme (ADRE) to catalyze covalent binding of numerous detectable labels to proteins, HRP-based TSA is a commercially validated approach. No alternative ADRE systems exist despite a strong need in the field for alternative amplification systems.

U.S. Pat. No. 7,291,474 to Bobrow postulates using hydrolase-based CARD. In particular, Bobrow hypothesizes that the activity probes 2-difluoromethylphenyl and p-hydroxymandelic acid could be used as amplification reagents. The use of 2-difluoromethylphenyl and p-hydroxymandelic acid was described by Zhu et al., (2003) Tetrahedron Letters, 44, 2669-2672; Lo et al., (2002) J. Proteome Res., 1, 35-40; Cesaro-Tadic et al., (2003) Nature Biotechnology, 21, 679-685; Janda et al., (1997) Science 275, 945-948; Halazy et al., (1990) Bioorganic Chemistry 18, 330-344; and Betley et al., (2002) Angew. Chem. Int. Ed. 41, 775-777. Bobrow's suggested structures included the following:

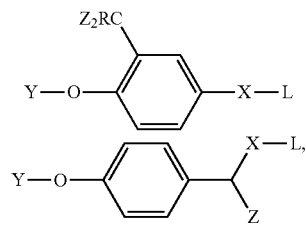

wherein Y is a moiety capable of being cleaved by a hydrolytic enzyme; L is a detectable label; X is a linking group; Z is a halogen; and R is hydrogen, alkyl, or halogen. In specific embodiments, R is hydrogen and the Z groups are fluorine. These structures are generalizations of the particular structures disclosed by Zhu et al., (2003) Tetrahedron Letters, 44, 2669-2672. In particular, Zhu et al. describes the following structures as known phosphatase inhibitors:

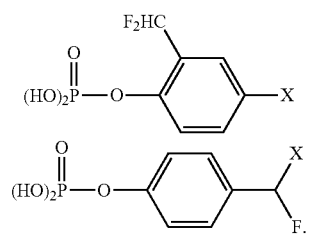

Based on these phosphatase inhibitors, Zhu et al. developed the following activity probes:

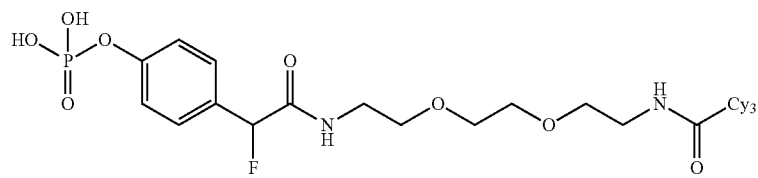

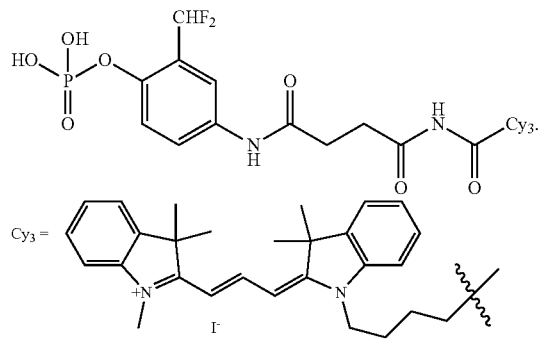

Zhu discloses that the activity-based profiling of proteins is a proven and powerful tool in proteomic studies, whereby subclasses of enzymatic proteins can be selectively identified. As such, Zhu developed the activity probes to signal the presence of active phosphatase enzymes. Zhu's strategy takes advantage of specific probes that react with different classes of enzymes, leading to the formation of covalent probe—protein complexes that are readily distinguished from other non-reactive proteins in a crude proteome mixture.

Zhu et al. state that it was known that 2-difluoromethylphenyl phosphate was a general phosphatase inhibitor against a broad spectrum of different phosphatases, including acid and alkaline phosphatases. Inhibition occurs as the phosphatases catalyze phosphate group cleavage to generate a reactive intermediary after a fluoride ion leaves. The reactive intermediary reacts with the enzyme's active site to covalently bind a fluorophore to the enzyme active site. But in doing so, it also inhibits the enzyme's ability to further hydrolytically cleave phosphates.

Using enzyme inhibitors in an amplification scheme to covalently bind signal generating moieties to a substrate is understood to be self-limiting as the generation of bound signal can destroy the activity of the enzyme. There has been a recognition in the art that pursuing enhancements made to these reagents would likely be self-defeating as the improved performance (e.g. turnover, specificity) would result in more efficient destruction of the enzyme's active site. Thus, in order to get signal amplification by binding multiple signal generating moieties, multiple enzymes first have to be bound proximally to the target. Accordingly, the compounds disclosed by Zhu et al. and Bobrow have never been developed into a commercially viable detection reagent for an amplification system for IHC or ISH.

Furthermore, the amplification approaches described thus far enable the deposition of fluorescent compounds. Fluorescence imaging is often implemented because it is extraordinarily sensitive; the detection of very few fluorophore molecules is now routine. However, this sensitivity is achieved using dark-field imaging, which has certain pragmatic limitations. For example, bright-field primary staining (e.g., hematoxylin and eosin staining) cannot be concurrently observed, making it more difficult to correlate fluorescent signal with morphological features. It is well known that fluorescence-based detection is routinely 1000 times more sensitive than absorbance-reflectance-based approaches (e.g. chromogenic-based detection). As such, a methodology appropriate for fluorescence detection would require a 1000-fold improvement for use as a chromogenic detection methodology. Increasing the performance of an enzyme-based detection system by 1000-fold is non-trivial. To date, only tyramide-based systems have achieved this increased performance.

While robust reagents are available, a need persists for alternative signal amplification approaches that produce robust amplification without increasing background signals. Moreover, methods for amplifying the detection of two or more distinct targets in a tissue sample are desirable.

SUMMARY

The quinone methide analog precursors (QMPs) and embodiments for using these QMPs disclosed herein provide substantially superior results to those disclosed in the prior art. The QMPs separate the detectable label function from the quinone methide generation and nucleophile stabilization functions within the molecule. Also disclosed herein are embodiments of a method for utilizing QMPs for IHC and/or ISH staining in tissue, such as formalin-fixed, paraffin-embedded (FFPE) tissue. To the inventors' knowledge, this has not been successfully demonstrated before. Embodiments of the method of using QMPs for amplifying the detection of one or more distinct targets in a tissue sample provide improved signal quality and reduced off-target staining, compared to previously known, non-QMP methods. When the disclosed method is used to detect multiple targets, either simultaneously or sequentially, the targets can be detected by chromogenic- or fluorescence-based detection methods, or a combination thereof.

In some embodiments, a QMP has a formula

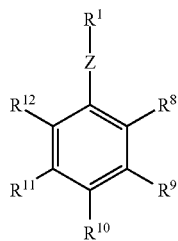

or a salt or solvate thereof, where Z is O, S or $NR^a$ and $R^1$ is an enzyme recognition group, or $ZR^1$ is an enzyme recognition group; $R^8$ is $—C(LG)(R^5)(R^3R^4)$, $—R^3R^4$ or $—C(LG)(R^5)(R^6)$; $R^9$, $R^{11}$ and $R^{12}$ are each independently hydrogen, halo, cyano, aliphatic, alkoxy, $NO_2$, $N(R^c)_2$, aryl, haloalkyl, —C(O)alkyl, —C(S)alkyl, —C(O)OH, —C(O)Oalkyl, $—C(O)NHR^c$, $—C(O)N(R^c)_2$, $—R^3R^4$ or two adjacent groups together form an aliphatic ring or aryl ring; and $R^{10}$ is hydrogen, halo, cyano, aliphatic, alkoxy, $NO_2$, $N(R^c)_2$, aryl, haloalkyl, —C(O)alkyl, —C(S)alkyl, —C(O)OH, —C(O)Oalkyl, $—C(O)NHR^c$, $—C(O)N(R^c)_2$, $—R^3R^4$, $—C(LG)(R^5)(R^6)$ or with one of $R^9$ or $R^{11}$ form an aliphatic ring or aryl ring.

Also with reference to the formula, LG is a leaving group, or $ZR^1$ and LG together form a phosphodiester; $R^3$ is a linker or a bond; $R^4$ is a detectable label; each $R^5$ is independently hydrogen, halo, cyano, lower alkyl, lower haloalkyl, —C(O)alkyl, —C(S)alkyl, —C(O)OH, —C(O)Oalkyl, —C(O)NHR$^c$ or $—C(O)N(R^c)_2$; each $R^6$ is independently hydrogen, halo, cyano, lower alkyl, lower haloalkyl, —C(O)alkyl, —C(S)alkyl, —C(O)OH, —C(O)Oalkyl, $—C(O)NHR^c$ or $—C(O)N(R^c)_2$; $R^a$ is hydrogen or aliphatic; and each $R^c$ independently is hydrogen, aryl, aliphatic or heteroaliphatic, or two $R^c$ moieties together form a heteroaliphatic ring. Additionally, at least one of $R^8$ and $R^{10}$ comprises LG, and at least one of $R^8$ and $R^{10}$ comprises or consists of $R^3R^4$, and if LG is halo, then $R^5$ and $R^6$ are not halo.

In certain embodiments, the QMP has a formula selected from

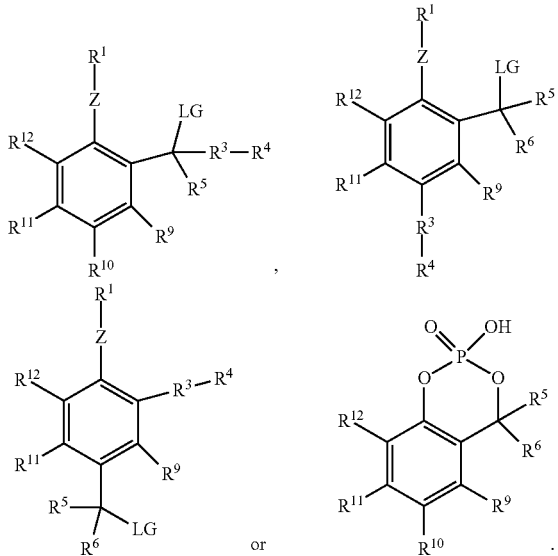

In some embodiments, $R^1$ or $ZR^1$ is a phosphate, amide, nitro, urea, sulfate, methyl, ester, beta-lactam or sugar. Z may be O and/or $ZR^1$ may be $—OP(O)(OH)_2$, $NO_2$, —NHC(O)R, $—OC(O)CH_3$, $—OC(O)CH_2CH_3$, $—NHC(O)NH_2$, $—OS(O)_2OH$, $OCH_3$ or a salt thereof. In some embodiments, the sugar is α-glucose, β-glucose, α-galactose, β-galactose, α-glucuronose or β-glucuronose.

LG may be any suitable leaving group, such as a halide, sulfate ester, carboxylate, inorganic ester, thiolate, amine, aryloxy, alkoxy, or heteroaryl. In some embodiments, LG is fluoride, chloride, azide, acetate, methoxy, ethoxy, isopropoxy, phenoxide, $—OS(O)_2CH_3$, $—OS(O)_2C_6H_4CH_3$, $—OS(O)_2C_6H_5$, $—OS(O)_2C_6H_4CX_3$, $—OC_6H_5$, $—N_2^+$, $—NH_3^+$, $—NC_5H_5^+$, —O-alkyl, —OC(O)alkyl, —OC(O)H, $—N(R^b)_3^+$ or 1,4-diazabicyclo[2.2.2]octane (DABCO), where each X independently is fluoro, chloro, bromo or iodo, and each $R^b$ independently is hydrogen, or lower alkyl, or two $R^b$ moieties together form a heteroaliphatic ring. In certain embodiments, LG is F.

Certain disclosed method embodiments comprise contacting a biological sample with a first detection probe specific to a first target. The biological sample is contacted with a first labeling conjugate comprising a first enzyme. The biological sample is also contacted with a first QMP comprising a first enzyme recognition group and a first detectable label. The first enzyme cleaves the first enzyme recognition group, thereby converting the first QMP into a first reactive quinone methide analog (QM), which covalently binds to the biological sample proximally to or directly on the first target. Contacting the biological sample comprises (i) contacting the biological sample with the first QMP at a precursor concentration, effective to give a desired level of amplification, such as a concentration from greater than zero to 1 mM; (ii) contacting the biological sample with the first QMP at a pH effective to reduce diffusion and/or off-target staining to a desired amount, such as a pH from greater than 7 to 14, or from 8 to 12; (iii) contacting the biological sample with the first QMP in the presence of a salt, such as magnesium chloride, at a salt concentration effective to reduce diffusion and/or off-target staining to a desired amount, typically from 0.1 M to 2 M, or from 0.5 M to 1.25 M; (iv) contacting the biological sample with a compound disclosed herein; or (v) any combination thereof. The first target is then detected by detecting the first detectable label. The method may be an automated process.

The precursor concentration may be from 50 μM to 500 μM for chromogenic staining, or from 50 nM to 10 μM for fluorescent staining and hapten amplification.

In some examples, the first labeling conjugate comprises an antibody coupled to the first enzyme. The antibody may be an anti-species or an anti-hapten antibody. The first labeling conjugate may be associated, either directly or indirectly, with the first detection probe. The first detection probe may comprise a hapten or an anti-species antibody and the first labeling probe comprise a corresponding anti-hapten or a second anti-species antibody. The first enzyme and first enzyme recognition group may be any suitable enzyme and enzyme recognition group that will interact to form a QM.

The first reactive QM reacts with a nucleophile within the biological sample, the first labeling conjugate, the first detection probe, or combinations thereof. Typical nucleophiles comprise an amino, sulfhydryl, or hydroxyl group on an amino acid, nucleic acid residue or carbohydrate.

The first QMP may have a formula as disclosed above, or alternatively, a formula selected from

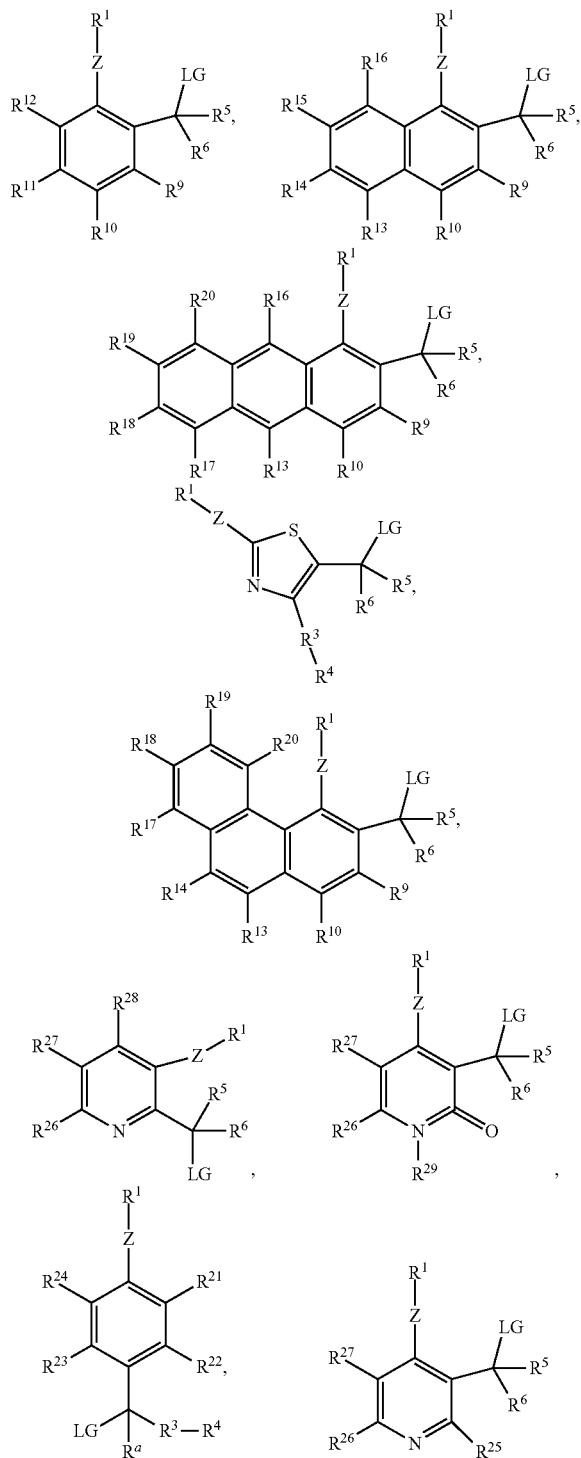

or a salt or solvate thereof. With respect to these formulas, Z, LG, $R^a$, $R^c$, $R^1$, $R^3$, $R^4$, $R^5$, $R^6$ and $R^9$-$R^{12}$ are as previously defined, $R^{13}$-$R^{29}$ are each independently defined as for $R^9$, $R^{11}$ and $R^{12}$, and at least one of $R^9$-$R^{29}$ comprises or consists of $R^3R^4$.

The method may be a multiplexed method. In some embodiments, in addition to detecting a first target the method further comprises contacting the biological sample with a second binding moiety specific to a second target. The second target is labeled with a second enzyme through the second binding moiety. The biological sample is contacted with a second detection precursor compound that interacts with the second enzyme to deposit a second detection compound directly on or proximally to the second target. The second detection compound is then detected. The first enzyme and second enzyme typically are different enzymes. Contacting the first and second targets with the respective binding moieties and/or detecting the first and second detection compounds may occur sequentially or substantially contemporaneously.

In certain embodiments, the first enzyme reacts selectively with the first QMP, and the second enzyme reacts selectively with the second detection precursor compound. In particular embodiments, the first enzyme is an alkaline phosphatase and the first enzyme recognition group is a phosphate. The second enzyme may be a peroxidase.

In some embodiments, the second detection precursor compound is a second QMP comprising a second enzyme recognition group and a second detectable label. The second QMP interacts with the second enzyme to form a second QM that covalently binds to the biological sample proximally to or directly on the second target. The second enzyme typically is a different enzyme than the first, such as a β-galactosidase where the second enzyme recognition group is a β-galactoside.

A person of ordinary skill in the art will understand that the method can be expanded to include detecting additional distinct targets. This can be achieved by contacting the biological sample with additional binding moieties specific to the targets, labeling the binding moieties with different enzymes, contacting the sample with detection precursor compounds selected for the enzymes and detecting the detection compounds.

A kit comprising a staining amplification compound disclosed herein is also disclosed. In some embodiments, the kit comprises an enzyme-antibody conjugate, a QMP, a solvent mixture, and a pH adjust solution. The solvent mixture may comprise an organic solvent and an aqueous buffer. In some embodiments, the organic solvent is DMSO. The aqueous buffer may have a pH range of from pH 0 to pH 5 or from pH 1 to pH 3. In some embodiments, the pH adjust solution has a pH range of from pH 8 to pH 12. In particular embodiments, the kit includes a salt, such as magnesium chloride, which may have a concentration of from 0.25 M to 1.5 M. In some embodiments, the QMP is a compound disclosed herein, the solvent mixture comprises DMSO and a glycine buffer at pH 2, the pH adjust solution is a Tris buffer with a pH range of from pH 8 to pH 10, and/or the kit comprises further comprising magnesium chloride at a concentration of from 0.5 M to 1.25 M.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. Definitions

Figure 1:
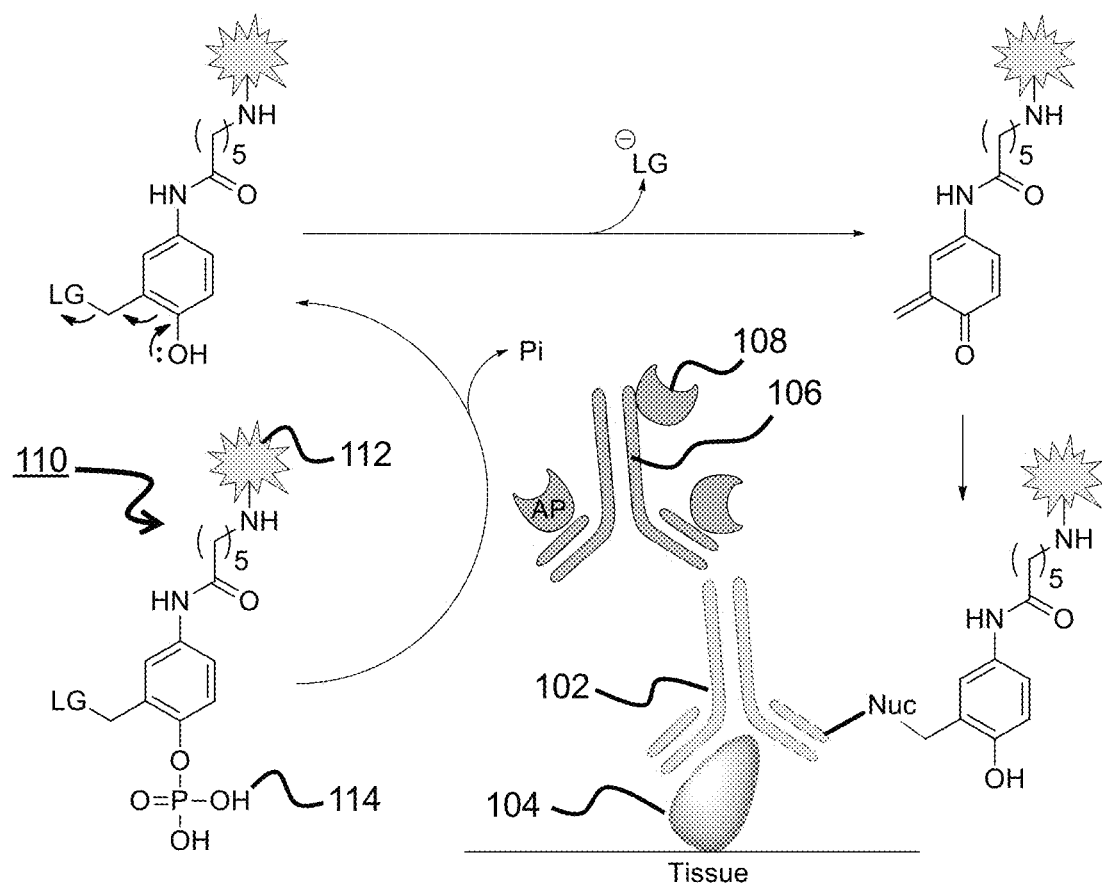
FIG. 1 is a schematic diagram illustrating detecting a target using a QMP comprising a detectable label.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Unless otherwise indicated, all numbers expressing quantities of components, molecular weights, percentages, temperatures, times, concentrations, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

For the general formulas provided below, if no substituent is indicated, a person of ordinary skill in the art will appreciate that the substituent is hydrogen. A bond that is not connected to an atom, but is shown, for example, extending to the interior of a ring system, indicates that the position of such substituent is variable. A curved line drawn through a bond indicates that some additional structure is bonded to that position. Moreover, if no stereochemistry is indicated for compounds having one or more chiral centers, all enantiomers and diastereomers are included. Similarly, for a recitation of aliphatic or alkyl groups, all structural isomers thereof also are included.

In order to facilitate review of the various embodiments of the disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing 1-10 carbon atoms. Unless expressly referred to as an "unsubstituted aliphatic," an aliphatic group can either be unsubstituted or substituted.

Alkyl: A hydrocarbon group having a saturated carbon chain. The chain may be cyclic, branched or unbranched. The term lower alkyl means the chain includes 1-10 carbon atoms. Unless otherwise stated, an alkyl group may be substituted or unsubstituted.

Alkoxy: A group having a formula —O-alkyl, where alkyl is as defined herein.

Analog: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28).

Aromatic or aryl: An aromatic carbocyclic or heterocyclic group of, unless specified otherwise, from 6 to 15 ring atoms having a single ring (e.g., phenyl, pyridyl) or multiple condensed rings in which at least one ring is aromatic (e.g., quinoline, indole, benzodioxole, and the like), provided that the point of attachment is through an atom of an aromatic portion of the aryl group. If any aromatic ring portion contains a heteroatom, the group is a heteroaryl, otherwise the group is a carbocyclic aryl group. Aryl groups may be monocyclic, bicyclic, tricyclic or tetracyclic. Unless otherwise stated, an aryl group may be substituted or unsubstituted.

Aryloxy: A group having a formula —O-aryl, where aryl is as defined herein.

Conjugate: Two or more moieties directly or indirectly coupled together. For example, a first moiety may be covalently or noncovalently (e.g., electrostatically) coupled to a second moiety. Indirect attachment is possible, such as by using a "linker" (a molecule or group of atoms positioned between two moieties).

Conjugated system: As used herein, the term "conjugated system" refers to a compound including overlapping orbitals (typically p-orbitals) with delocalized pi electrons. Typically the compound includes alternating single and multiple bonds. The overlapping p-orbitals bridge the single bonds between adjacent overlapping p-orbitals. Lone pairs, radicals, and carbenium ions may be part of the system. The system may be cyclic, acyclic, or a combination thereof. Exemplary conjugated systems include, but are not limited to aromatic compounds such as benzene, pyrazole, imidazole, pyridine, pyrimidine, pyrrole, furan, thiophene, naphthalene, anthracene, indole, benzoxazole, benzimidazole, and purine.

Contacting: Placement that allows association between two or more moieties, particularly direct physical association, for example both in solid form and/or in liquid form (for example, the placement of a biological sample, such as a biological sample affixed to a slide, in contact with a composition, such as a solution containing the compositions disclosed herein).

Detect: To determine if an agent (such as a signal or particular antigen, protein or nucleic acid) is present or absent, for example, in a sample. In some examples, this can further include quantification, and/or localization, for example localization within a cell or particular cellular compartment. "Detecting" refers to any method of determining if something exists, or does not exist, such as determining if a target molecule is present in a biological sample. For example, "detecting" can include using a visual or a mechanical device to determine if a sample displays a specific characteristic. In certain examples, light microscopy and other microscopic means are used to detect a detectable label bound to or proximally to a target.

Detectable Label: A molecule or material that can produce a detectable (such as visually, electronically or otherwise) signal that indicates the presence and/or concentration of a target, such as a target molecule, in a sample, such as a tissue sample. When conjugated to a molecule capable of binding directly or proximally to a target, the detectable label can be used to locate and/or quantify the target. Thereby, the presence and/or concentration of the target in a sample can be detected by detecting the signal produced by the detectable label. A detectable label can be detected directly or indirectly, and several different detectable labels conjugated to different molecules can be used in combination to detect one or more targets. Multiple detectable labels that can be separately detected can be conjugated to different molecules that bind directly or proximally to different targets to provide a multiplexed assay that can provide detection of the multiple targets in a sample. As used herein, detectable labels include colored, fluorescent, phosphorescent, and luminescent molecules, and haptens.

Electron donating group: An atom or functional group capable of donating some of its electron density into a conjugated system. Electron density can be donated through σ bonds (inductive) or through n bonds (resonance). Some functional groups are donating groups by one mechanism and withdrawing groups through the other mechanism. Exemplary electron donating groups include, but are not limited to, —$NH_2$, —NHR, —$NR_2$, —OH, —CH=$CH_2$, —NHC(O)R, —OR, —R, where R is alkyl, such as lower alkyl (e.g., methyl, ethyl).

Electron withdrawing group: An atom or functional group capable of withdrawing electron density from a conjugated system. Electron density can be withdrawn through σ bonds (inductive) or through n bonds (resonance). Some functional groups are donating groups by one mechanism and withdrawing groups through the other mechanism. Exemplary electron withdrawing groups include, but are not limited to, halo, haloalkyl, —$NH_3^+$, —$NO_2$, —CH=$CH_2$, —CN, —$SO_3H$, —C(O)OH, —C(O)H, —C(O)R, —CN, —C(O)OR, —$NR_3^+$, where R is alkyl, such as lower alkyl (e.g., methyl, ethyl).

Heteroaliphatic: An aliphatic compound where one or more carbon has been replaced with a heteroatom. Exemplary heteroatoms include, but are not limited to, O, S, N, P, Si or B. Heteroaliphatic moieties may be substituted or unsubstituted. Substitution may be at a carbon atom or at a heteroatom.

Heteroaryl: An aromatic compound or group having at least one heteroatom, i.e., one or more carbon atoms in the ring has been replaced with an atom having at least one lone pair of electrons, typically nitrogen, oxygen, phosphorus, silicon, or sulfur. Unless otherwise stated, a heteroaryl group may be substituted or unsubstituted.

Inorganic ester: An ester derived from an inorganic acid and an alcohol. Exemplary inorganic acids include, but are not limited to, phosphoric acid, sulfuric acid, nitric acid or boric acid. Inorganic esters include, but are not limited to, sulfates, phosphates, nitrates or borates, for example, triphenyl phosphate.

Leaving group: A molecular fragment that is eliminated with a pair of electrons during heterolytic bond cleavage. Another term for leaving group is nucleofuge. Leaving groups may be anions or neutral molecules (if a leaving group is positively charged while bound to the molecule, it will become neutral when it leaves with a pair of electrons). The ability of a molecular fragment to be a leaving group (i.e., its nucleofugality or nucleofugacity) is correlated with its stability. In some circumstances, e.g., when the leaving group is a weak base, the ability of a leaving group to depart may be related to the $pK_a$ of the leaving group's conjugate acid, with lower $pK_a$ often but not always being correlated with better leaving group ability. A person of ordinary skill in the art is aware of readily available tables, e.g., in organic chemistry textbooks, that indicate the relative nucleofugality of leaving groups.

Substantially non-inhibiting: A QMP is substantially non-inhibiting if it forms a quinone methide that so diffuses from the enzyme as to not react with the reactive site of the enzyme. Substantially non-inhibiting can be established by functionally testing a particular enzyme and QMP. Generally, if staining, as described herein, increases over extended periods of time (e.g. >5 minutes), the QMP is substantially non-inhibiting. If a QMP inhibits the enzyme, the amount of staining will not increase over time or with the addition of more QMP.

Nucleophile: A chemical species capable of donating an electron pair to a positively-charged (or partially positive) atom to form a chemical bond during a chemical reaction. Anions and molecules with a lone pair of electrons or at least one pi bond can act as nucleophiles.

Oligonucleotide: A plurality of joined nucleotides joined by phosphodiester bonds, between about 6 and about 300 nucleotides in length. As used herein, the term oligonucleotide refers to DNA oligonucleotides, RNA oligonucleotides, synthetic oligonucleotides (e.g., non-naturally occurring DNA or RNA sequences), and oligonucleotide analogs. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid molecules.

Probe: A substance used to detect or identify another substance in a sample. As used herein, a probe may be an antibody, an antibody fragment, an isolated nucleic acid, or an isolated synthetic oligonucleotide capable of specifically binding to a desired target, e.g., a target protein or nucleic acid sequence present in a tissue sample. The probe may comprise a detectable label or reporter molecule (e.g., a hapten).

Substituted: A fundamental compound, such as an aryl or aliphatic compound, or a radical thereof, having coupled thereto, typically in place of a hydrogen atom, another atom or group, i.e., a substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as one or more halogens, oxygen such as a hydroxyl or =O, an aryl group, a cyclic group, a heteroaryl group or a heterocyclic group.

Target: A molecule for which the presence, location and/or concentration is to be determined. Exemplary targets include proteins and nucleic acid sequences present in tissue samples.

Thiolate: A moiety having a formula —S—R, where R is an aryl, aliphatic or heteroaliphatic moiety.

II. Quinone Methide Analog Precursors

A. Overview

The present disclosure concerns compositions, kits and methods relating to QMs and their precursors. QMPs of the present disclosure have been developed for amplification of detection events using an enzyme-catalyzed conversion of quinone method precursors into reactive quinone methides, which can bind directly or proximally to the enzyme.

Quinone methides are quinone analogs where one of the carbonyl oxygens on the corresponding quinone is replaced by a methylene group ($CH_2$) to form an alkene, as shown below:

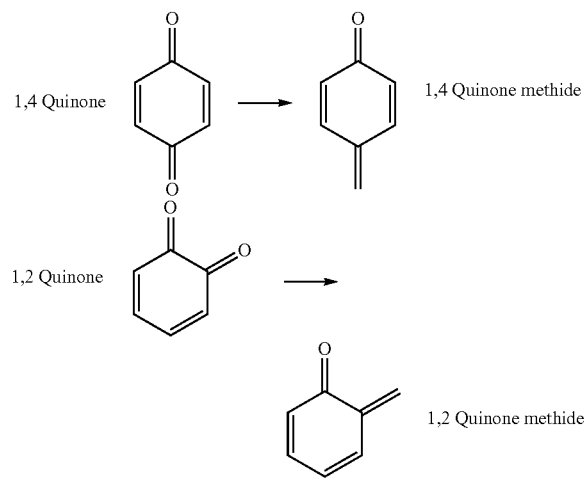

See, e.g., Rokita, *Quinone Methides*, April 2009, John Wiley & Sons, Inc. which is hereby incorporated by reference herein for general disclosure related to quinone methides).

The methylene moiety of a quinone methide is an extremely reactive electrophile that will react with suitable reactive nucleophiles. The reactive nucleophiles can be provided by a staining reagent enzyme, the antibody that the enzyme is conjugated to, and the biological sample itself in immunohistochemistry applications. Generating quinone methides in situ enables labels to be covalently bound to nucleophilic residues present within a matrix (e.g., tissue). Exemplary nucleophilic residues include biological molecules comprising reactive nitrogen-, oxygen-, and sulfur-containing groups, such as amino, hydroxyl, and thiol groups of amino acids (e.g., lysine, tyrosine, threonine, serine, and cysteine) and amino, carbonyl, and hydroxyl groups of nucleic acids.

Enzyme substrates capable of forming quinone methides (QMs) were initially investigated as potential mechanism-based inhibitors of hydrolase enzymes. For example, QMPs were investigated for inhibiting steroid sulfatase (STS), which catalyzes the desulfation of biologically inactive, sulfated steroids to biologically active steroids. According to this approach, the QM generated by STS would react with the STS to inhibit its activity, for example, as a therapeutic approach (Ahmed et al. *ChemBioChem.* 2009; 10:1457; which is incorporated herein by reference for disclosure related to the use of QM for inhibiting enzymes).

According to another approach, Lenger et al. disclose profiling active sulfatases using quinone methide (QM) traps (i.e. activity-based proteomic probes). To profile active sulfatases in health and disease, an activity-based proteomic tool directed against sulfatases, the quinone methide (QM) trap, was evaluated as an activity-based proteomic probes (ABPPs). The QM trap concept applied by Lenger et al. involved in situ generation of a reactive QM intermediate that is dependent on enzymatic turnover of an enzyme inhibitor. Fluoromethylphenolate sulfate substrates were used as the QM precursor to generate a QM which would then spontaneously fragment by fluoride elimination. The QM was used to capture an active site residue conserved in the sulfatase, resulting in turnover-dependent inactivation and specific protein labelling. The traps were designed to have broad-ranged reactivity against sulfatases (Lenger et al. *Bioorg Med Chem.* Jan. 15, 2012; 20(2): 622-627, which is hereby incorporated by reference herein for disclosure related to the use of QM traps for ABPP).

The approaches of Lenger et al. and Ahmed et al. are contrary to the presently disclosed technology because enzyme inactivation is not a goal of the present embodiments. Instead, enzyme inactivation is to be avoided when the enzyme is being used to amplify detection using QM-based labels. When used for detection, maintaining enzymatic activity is desirable so that each enzyme can produce greater signaling. In general, quenching the enzyme is contrary to the amplification objective described herein. In other terms, the QM precursor is selected and/or designed to avoid enzyme quenching. Instead, the QM precursor is selected and/or designed such that the QM can diffuse from the catalytic site of the enzyme. While not inactivating the enzyme, the QM should be sufficiently reactive with nucleophiles in the vicinity of the enzyme to provide appropriate target labeling.

In yet another example, a disclosure by Qing Shao et al. described using a QM precursor as a covalent reporter of beta-lactamase activity for fluorescent imaging and rapid screening of antibiotic-resistant bacteria (Shao, Q.; Zheng, Y.; Dong, X. M.; Tang, K.; Yan, X. M.; Xing, B. G. *Chem-Eur J* 2013, 19, 10903; which is hereby incorporated by reference herein for disclosure related to the use of QM labels for fluorescently labeling whole bacterial cells). According to this approach, the QM is used as a fluorescent probe that can be activated by the resistance-associated beta-lactamase, which is a naturally occurring bacterial enzyme that destroys penicillin and cephalosporin antibiotics. The disclosed QM probe requires cleavage of a fluorescence-quenching Fluorescence Resonance Energy Transfer (FRET) group, along with the formation of a reactive quinone methide, which can then bind to the antibiotic-resistant bacteria. This approach relies on active endogenous enzymes and seeks to non-specifically label the entire antibiotic-resistant bacteria. Furthermore, the bacteria cells were stained in solution. This solution staining is advantageous because the concentration of cells in solution dictates intercellular distance and dilution can be used to increase intercellular distances.

The present disclosure uses non-endogenous enzymes to avoid creating false negatives in a staining protocol. QMPs disclosed herein were designed to bind proximally to the enzyme without inhibiting the enzyme (i.e. the QMPs are substantially non-inhibiting to the enzyme). While long range diffusion of the reactive QM compound was irrelevant according to the approach of Qing Shao et al., the QM precursor of the present disclosure is selected and/or designed to be sufficiently reactive to limit diffusion distances from the target. For example, when used in a formalin-fixed paraffin embedded (FFPE) tissue sample, long range diffusion of the reactive species would result in diffuse and blurred staining. Accordingly, overly stable reactive QM compounds would be unsuitable for use in tissue staining. Examples included herein demonstrate this unfavorable staining result when using overly stable QM compound reactive compounds.

A recent publication from Kwan et al. (Angew *Chem Int Edit* 2011, 50, 300, which is incorporated by reference herein for disclosure related to the use of QM labels for fluorescently labeling) reported fluorescent plant histological staining utilizing coumarin glycosides modified to generate QMs upon reaction with its cognate glycosidase. This report demonstrated the potential of QMs for covalent labeling of solid-phase proteins with minimal diffusion from the site of generation, which is imperative for solid-phase immunoassays, and is an important feature of the current TSA technology. A key limitation of the probe described by Kwan et al. is the requirement that each reporter molecule be modified synthetically to contain QM precursor functionality. That is, in labeling enzymes of interest in plant cells, the coumarin was modified to be both the quinone methide generating species and the label. This approach adds significant cost and complexity to the generation of various labels and would be unsuitable for many detectable labels (e.g. those detectable labels that have a structure which cannot be modified to include a quinone methide generating moiety). As such, Kwan et al. does not describe a QM detectable molecule with a separate quinone methide generating moiety and a detectable moiety. Kwan et al. also establish that the previously developed QM precursors have been ineffectively implemented. Accordingly, a need still persists in the art for QM precursor compounds that comprise a separate QM generating moiety and a detectable moiety, and result in a QM that does not inhibit the enzyme. In particular, Kwan et al. concludes that the time required for the (di)halomethyl phenol to decompose, and for the quinone methide thereby generated to react, is often sufficiently long that the reagent can diffuse from the active site and react with other available nucleophiles, including water. Further, Kwan et al. discloses QM precursor compounds comprising a difluoromethyl moiety and describes their superiority over the monofluoromethyl derivative based on greater stability of the difluoromethyl QM precursor compound towards solvolysis and on greater stability of the fluoro-QM compound generated from the precursor compound.

The currently described quinone precursors and methods of using the same use a generalized approach in which the detectable label and the quinone methide generation and nucleophile stabilization functions are separated within a molecule. One approach is to use a single QM precursor scaffold containing an amine-functionalized linker group that allows simple conjugation to nearly any detectable molecule. One important embodiment concerns applying CARD to solid-phase immunoassays, such as IHC on FFPE tissue. Accordingly, using a phosphate group to exemplify the enzyme-cleavable recognition group was a logical choice due to the ubiquity of its cognate enzyme alkaline phosphatase (AP) in current immunoassays.

Referring now to FIG. 1, the application of AP-based CARD for IHC begins with the incubation of a primary antibody (Ab) 102 with a sample. Ab 102 recognizes an antigen 104 of interest. The sample is then incubated with a secondary Ab 106 that binds the primary Ab by typical anti-species Ab binding. Secondary antibody 106 is labeled with an enzyme 108, for example alkaline phosphatase (AP). The detectable-labeled QM precursor 110 is then applied. The detectable-labeled QM precursor 110 includes a reporter group 112 and an enzyme recognition group 114 (a phosphate in this example).

AP recognizes and cleaves the phosphate group, resulting in ejection of the leaving group, and the formation of a QM. These QMs either react with immobilized tissue nucleophiles in close proximity to the site of generation, or are quenched by nucleophiles in the reaction media. The detectable molecules that are covalently bound to the tissue are then detected by one of a variety of visualization techniques in the case of haptens, or by fluorescence microscopy in the case of fluorophores.

B. Compounds

As disclosed herein, a QMP comprises a conjugated system that includes an enzyme recognition group, a leaving group, a detectable label attached to the system through a linker, which may be a bond or may be a linker moiety. The conjugated system may be an aromatic system. The system is conjugated such that when the enzyme recognition group interacts with the corresponding enzyme, and the leaving group leaves, a QM results.

The enzyme recognition group is selected on the basis of its suitability for interaction with a particular enzyme. For example, for suitable interaction with a phosphatase the enzyme recognition group is a phosphate (—P(O)(OH)$_2$), typically attached through an oxygen, nitrogen or sulfur to the conjugated system; for a phosphodiesterase, the enzyme recognition group is a phosphodiester; for an esterase, it is an ester; for an amidase or a protease, it is an amide; for a nitroreductase, it is a nitro group; for a urease, it is a urea group; for a sulfatase, it is a sulfate; for a cytochrome P450 enzyme, it is typically an alkoxy; for a lactamase, the enzyme recognition group is a β-lactam-containing moiety; and for glucosidases, galactosidases and glucoronidases, it is an enzyme-appropriate sugar (e.g. alpha- or beta-glucose, alpha- or beta-galactose, etc.) attached by an oxygen to the conjugated system.

The leaving group and the detectable label and linker may be part of the same substituent of the conjugated system, and in some embodiments, they are located adjacent, or ortho, to the enzyme recognition group.

In some embodiments, the staining amplification composition comprises a QMP according to formulas I and II

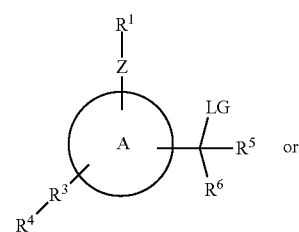

I

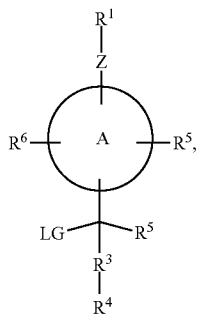

wherein A is a conjugated system such as a cyclic conjugated system with one or more rings, an acylic conjugated system or a conjugated system with a combination of cyclic and acyclic features. In particular embodiments, conjugated system A is a substituted or unsubstituted aryl ring system, such as a carbocyclic aryl or heteroaryl ring system. $ZR^1$ is an enzyme recognition group, or $R^1$ is an enzyme recognition group and Z is O, S or $NR^a$, where $R^a$ is hydrogen or aliphatic, typically alkyl and in some embodiments, lower alkyl. LG is a leaving group, and the —$C(LG)(R^5)(R^6)$ and —$C(R^5)LG$- moieties are capable of forming an alkene (C=C) functional group in a QM. Z- and LG-containing moieties are bound at relative positions on the conjugated system such that when $R^1$ is cleaved from Z a transitional structure is formed that rearranges to eliminate LG to form a QM. Alternatively, —$C(LG)(R^5)(R^6)$ and $R^1$ are positioned ortho- to each other and together form a phosphodiester, with LG-$ZR^1$ being —O—P(O)(OH)O—. In such embodiments, a quinone methide is formed when the phosphodiester is cleaved from both Z and the —$C(R^5)(R^6)$— moiety.

Also with reference to formula I or II, $R^5$ and $R^6$ independently are hydrogen, halo, cyano, lower alkyl, lower haloalkyl, —C(O)alkyl, —C(S)alkyl, —C(O)OH, —C(O)Oalkyl, —C(O)NHR$^c$ or —C(O)N(R$^c$)$_2$ where each R$^c$ independently is hydrogen, aryl, aliphatic or heteroaliphatic, or two R$^c$ moieties together form a heteroaliphatic ring. $R^3$ is a linker or a bond, and $R^4$ is a detectable label.

In some embodiments, LG is a halide, alkoxy, carboxylate, inorganic ester, thiolate, amine, carboxylate or phenoxide. In other embodiments, LG is fluoro, chloro, azide, methoxy, ethoxy, isopropoxy, acetate, pyridium, DABCO (1,4-diazabicyclo[2.2.2]octane) or triethylamine. In some embodiments, —C(R$^5$)LG or —C(LG)R$^3$— forms an epoxide ring where LG is the oxygen in the ring.

In some embodiments, the QMP has a formula III

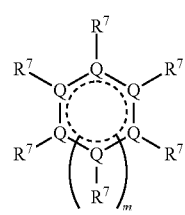

where each Q independently is carbon or a heteroatom selected from O, N or S and the ring has sufficient conjugation to allow the formation of the QM, such as an aryl ring or other conjugated system; each $R^7$ independently is $ZR^1$, a moiety comprising LG, a moiety comprising a detectable label, hydrogen, lone pair, halo, cyano, oxo (=O), aliphatic, alkoxy, NO$_2$, N(R$^c$)$_2$, aryl, haloalkyl, —C(O)alkyl, —C(S)alkyl, —C(O)OH, —C(O)Oalkyl, —C(O)NHR$^c$, —C(O)N(R$^c$)$_2$, or two adjacent $R^7$ groups together form an aliphatic ring or aryl ring; m is 0 or 1; and Z, $R^1$, LG, $R^a$ and $R^c$ are as previously defined for formulas I and II. Also with reference to formula III, at least one $R^7$ is $ZR^1$, at least one $R^7$ comprises LG, and the QMP comprises at least one detectable label. In some embodiments, at least one $R^7$ comprises a detectable label. In some embodiments, LG is the oxygen of an epoxide ring. A person of ordinary skill in the art will appreciate that each $R^7$ is also selected to satisfy valence requirements. For example, if Q is oxygen, then $R^7$ is a lone pair.

In some embodiments, the conjugated ring is a 6-membered ring and $ZR^1$ and the LG-containing moiety are ortho or para to each other.

In particular embodiments, the QMP has a formula IV

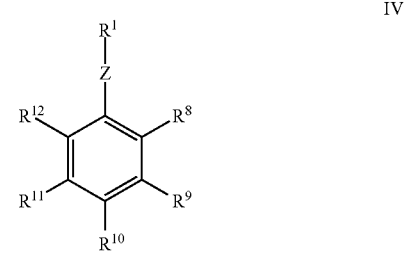

where Z is O, S or NR$^a$ and $R^1$ is an enzyme recognition group, or $ZR^1$ is an enzyme recognition group; $R^8$ is —C(LG)(R$^5$)(R$^3$R$^4$), —R$^3$R$^4$ or —C(LG)(R$^5$)(R$^6$); $R^9$, $R^{11}$ and $R^{12}$ are each independently hydrogen, halo, cyano, aliphatic, alkoxy, NO$_2$, N(R$^c$)$_2$, aryl, haloalkyl, —C(O)alkyl, —C(S)alkyl, —C(O)OH, —C(O)Oalkyl, —C(O)NHR$^c$, —C(O)N(R$^c$)$_2$, —R$^3$R$^4$ or two adjacent groups together form an aliphatic ring or aryl ring; $R^{10}$ is hydrogen, halo, cyano, aliphatic, alkoxy, NO$_2$, N(R$^c$)$_2$, aryl, haloalkyl, —C(O)alkyl, —C(S)alkyl, —C(O)OH, —C(O)Oalkyl, —C(O)NHR$^c$, —C(O)N(R$^c$)$_2$, —R$^3$R$^4$, —C(LG)(R$^5$)(R$^6$) or with one of $R^9$ or $R^{11}$ form an aliphatic ring or aryl ring; each $R^a$ independently is hydrogen or aliphatic, typically alkyl or lower alkyl; LG is a leaving group, or $ZR^1$ and LG together form a phosphodiester; $R^3$ is a bond or a linker; $R^4$ is a detectable label; each $R^c$ independently is hydrogen, aryl, aliphatic or heteroaliphatic, or two R$^c$ moieties together form a heteroaliphatic ring; each $R^5$ is independently hydrogen, halo, cyano, lower alkyl, lower haloalkyl, —C(O)alkyl, —C(S)alkyl, —C(O)OH, —C(O)Oalkyl, —C(O)NHR$^c$ or —C(O)N(R$^c$)$_2$; each $R^6$ is independently hydrogen, halo, cyano, lower alkyl, lower haloalkyl, —C(O)alkyl, —C(S)alkyl, —C(O)OH, —C(O)Oalkyl, —C(O)NHR$^c$ or —C(O)N(R$^c$)$_2$; and if LG is halo, then $R^5$ and $R^6$ are not halo. Also with reference to formula IV, at least one of $R^8$ and $R^{10}$ comprises LG, and the QMP comprises at least one —R$^3$R$^4$ moiety. In some embodiments, at least one of $R^8$-$R^{12}$ comprises or consists of R$^3$R$^4$, and in certain embodiments, at least one of $R^8$ and $R^{10}$ comprises or consists of R$^3$R$^4$.

Several exemplary analogs of formula IV include

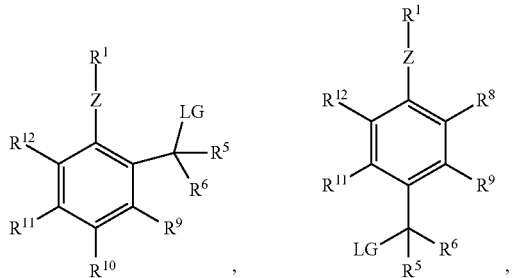

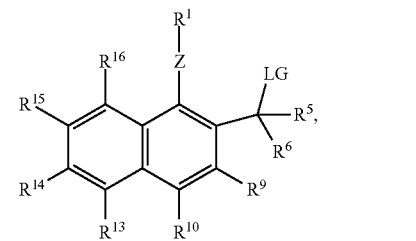

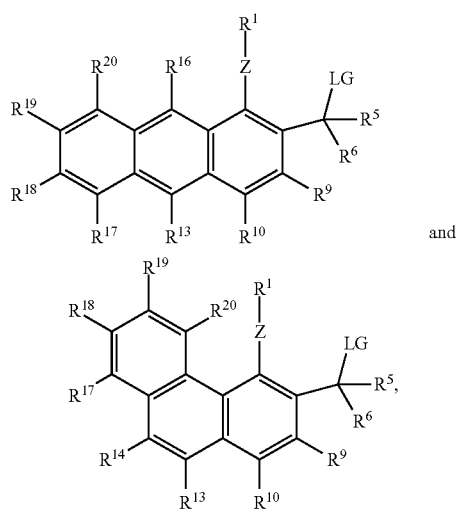

where $R^{13}$-$R^{20}$ are each independently hydrogen, halo, cyano, aliphatic, alkoxy, $NO_2$, $N(R^c)_2$, aryl, haloalkyl, —C(O)alkyl, —C(S)alkyl, —C(O)OH, —C(O)Oalkyl, —C(O)NHR$^c$, —C(O)N(R$^c$)$_2$, —R$^3$R$^4$ or two adjacent groups together form an aliphatic ring or aryl ring, and at least one of $R^8$-$R^{20}$ comprises or consists of $R^3R^4$.

Other particular exemplary analogs of formula IV include

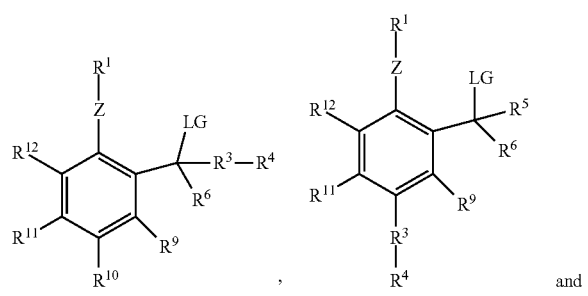

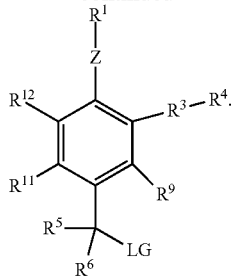

LG may be a halide, alkoxy, carboxylate, inorganic ester, thiolate, amine, carboxylate or phenoxide. In other examples, LG is fluoro, chloro, azide, methoxy, ethoxy, isopropoxy, acetate, pyridium, DABCO (1,4-diazabicyclo[2.2.2]octane) or triethylamine. In certain embodiments, LG is F, Cl, —OS(O)$_2$CH$_3$, —OS(O)$_2$C$_6$H$_4$CH$_3$, —OS(O)$_2$C$_6$H$_5$, —OS(O)$_2$C$_6$H$_4$CX$_3$, —OC$_6$H$_5$, —N$_2^+$, —NH$_3^+$, —N$_3$, —NC$_5$H$_5^+$, —O-alkyl —OC(O)alkyl, —OC(O)H, —N(R$^b$)$_3^+$ or DABCO, where X is F, Cl, Br or I, and each R$^b$ independently is hydrogen or lower alkyl or two R$^b$ moieties together form a heteroaliphatic ring.

In some embodiments, $R^3$ is —(CH$_2$)$_n$NH—, —O(CH$_2$)$_n$NH—, —N(H)C(O)(CH$_2$)$_n$NH—, —C(O)N(H)(CH$_2$)$_n$NH—, —(CH$_2$)$_n$O—, —O(CH$_2$)$_n$—, —O(CH$_2$CH$_2$O)$_n$—, —N(H)C(O)(CH$_2$)$_n$O—, —C(O)N(H)(CH$_2$)$_n$O—, —C(O)N(H)(CH$_2$CH$_2$O)$_n$—, —(CH$_2$)$_n$S—, —O(CH$_2$)$_n$S—, —N(H)C(O)(CH$_2$)$_n$S—, —C(O)N(H)(CH$_2$)$_n$S—, —(CH$_2$)$_n$NH—, —C(O)N(H)(CH$_2$CH$_2$O)$_n$CH$_2$CH$_2$NH—, —C(O)(CH$_2$CH$_2$O)$_n$CH$_2$CH$_2$NH—, —C(O)N(H)(CH$_2$)$_n$NHC(O)CH(CH$_3$)(CH$_2$)$_n$NH— or —N(H)(CH$_2$)$_n$NH—, where each n independently is 1, 2, 3, 4, 5, 6, 7, 8, 9, 10, 11 or 12. In certain embodiments, $R^3$ is —CH$_2$CH$_2$NH—, —OCH$_2$CH$_2$NH—, —NHCO(CH$_2$)$_5$NH—, —CONH(CH$_2$)$_5$NH—, —NHCO(CH$_2$)$_6$NH—, —CONH(CH$_2$)$_6$NH—, —CONH(CH$_2$)$_2$NH—, —(CH$_2$CH$_2$O)$_4$—, —(CH$_2$CH$_2$O)$_8$—, —C(O)N(H)(CH$_2$CH$_2$O)$_2$CH$_2$CH$_2$NH—, —CO(CH$_2$CH$_2$O)$_4$CH$_2$CH$_2$NH—, —CO(CH$_2$CH$_2$O)$_8$CH$_2$CH$_2$NH— or —C(O)N(H)(CH$_2$)$_6$NHC(O)CH(CH$_3$)(CH$_2$)$_4$NH—. $R^3$ may comprise a triazole, and in come embodiments, $R^3$ is

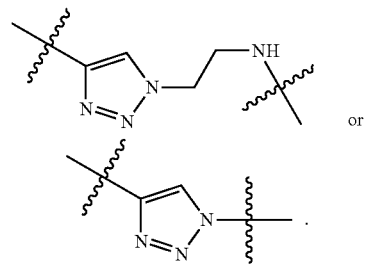

In some embodiments, —C(LG)R$^3$— or —C(LG)R$^5$— forms an epoxide ring.

$R^4$ may be a hapten, fluorophore, luminophore, or chromogen. In certain examples, —R$^4$ or linker-detectable label (—R$^3$R$^4$) is biotin conjugated to the molecule by an aliphatic linker, nitropyrazole (NP), NP with a PEG linker, such as a PEG-8 linker, TAMRA, DNP, Fast Red, HQ, HQ with a PEG linker, such as a PEG-8 linker, benzofurazan, Rhod 110, Dabsyl with a PEG linker, such as a PEG-8 linker, or Cy.

In some embodiments, $ZR^1$ is —OP(O)(OH)$_2$, —SP(O)(OH)$_2$, —NR$^a$P(O)(OH)$_2$, —OC(=O)R$^a$, —N(R$^a$)C(=O)R$^a$, —NO$_2$, —NR$^a$—C(=O)—N(R$^c$)$_2$, —OSO$_3$H, —OR$^a$, —O-β-lactam-containing moiety, —S-β-lactam-containing moiety or —O-sugar where the sugar is an enzyme-appropriate sugar, such as alpha- or beta-glucose, alpha- or beta-galactose, etc. or a salt thereof. In other embodiments, $ZR^1$ and LG together form a phosphodiester, —OP(O)(OH)O—.

In certain embodiments, LG is F, and in particular embodiments, LG is F and $R^5$ or $R^5$ and $R^6$ are H.

In certain embodiments of formula IV, $R^8$ and $ZR^1$ together form a phosphodiester, leading to QMPs having a formula V

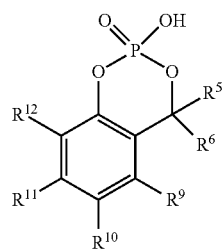

where $R^5$, $R^6$ and $R^9$-$R^{12}$ are as previously defined for formula IV, and at least one of $R^9$-$R^{12}$ comprises or consists of $R^3R^4$. In particular embodiments, $R^{10}$ comprises or consists of $R^3R^4$.

For certain exemplary embodiments of formula IV, the QMP is selected from

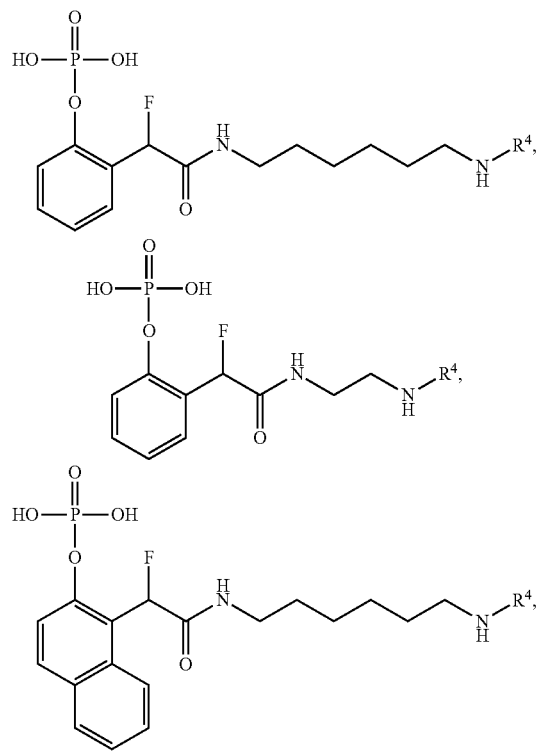

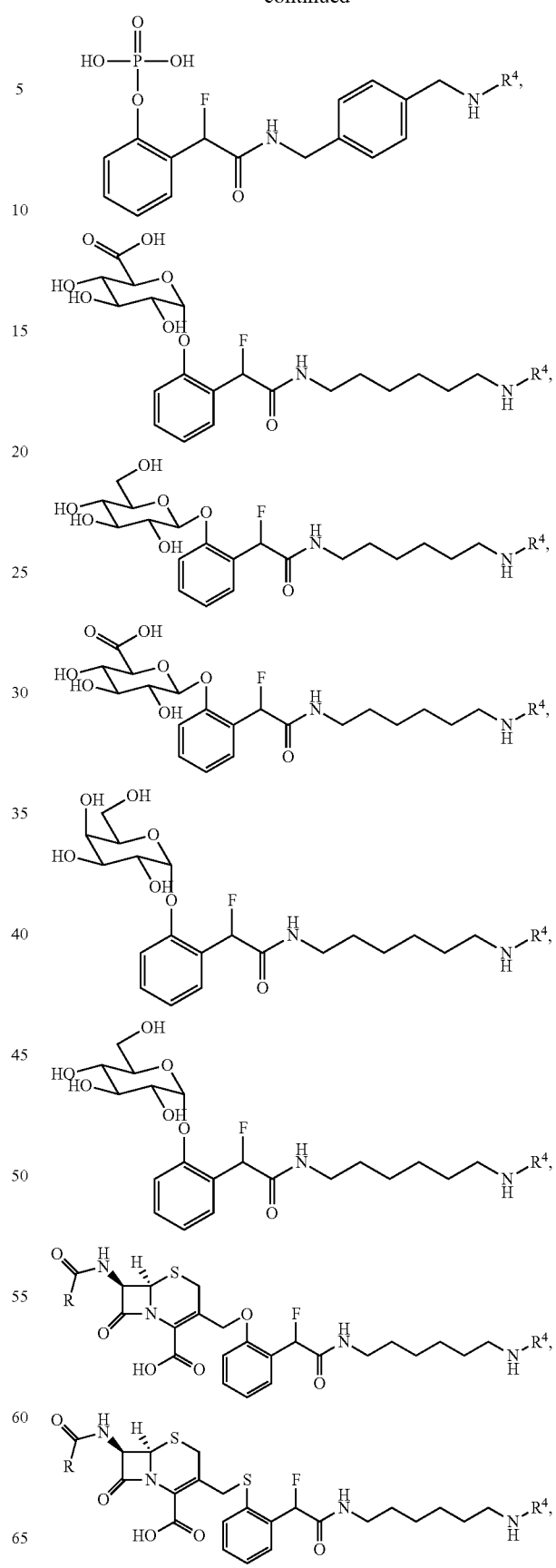

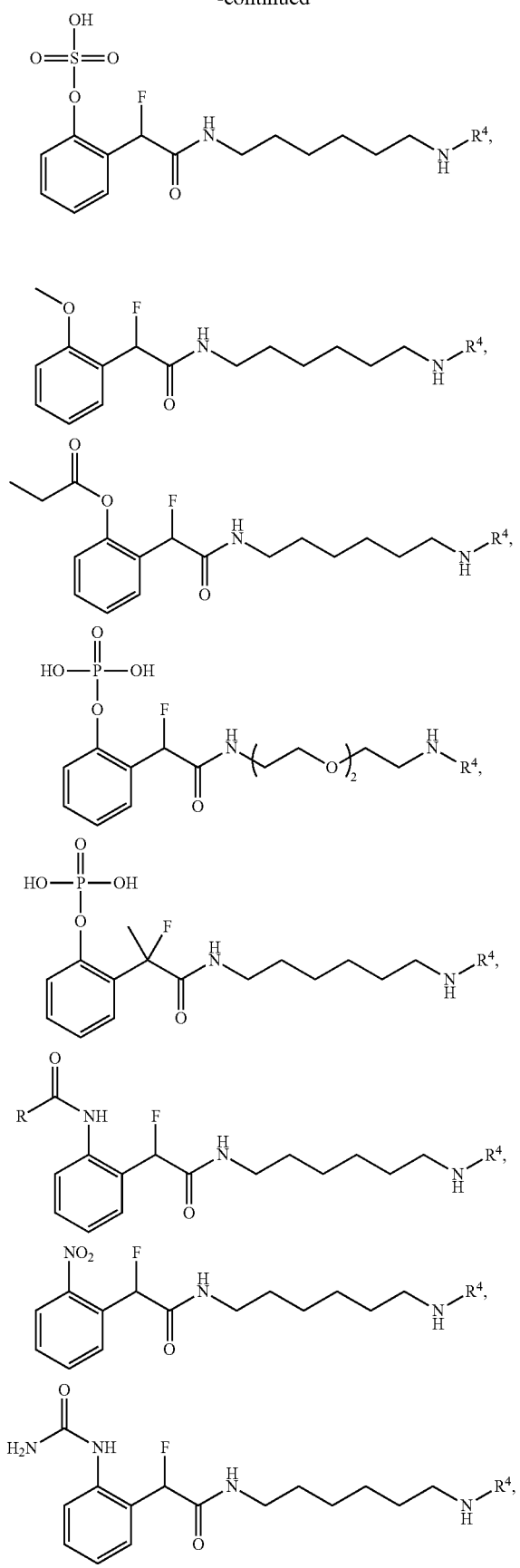
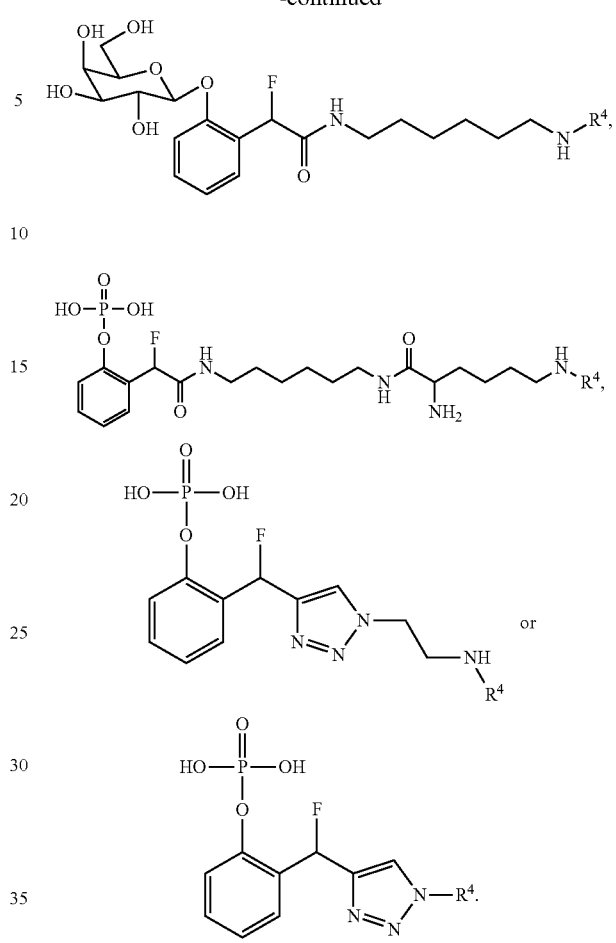
In other exemplary embodiments of formula IV, the QMP is selected from
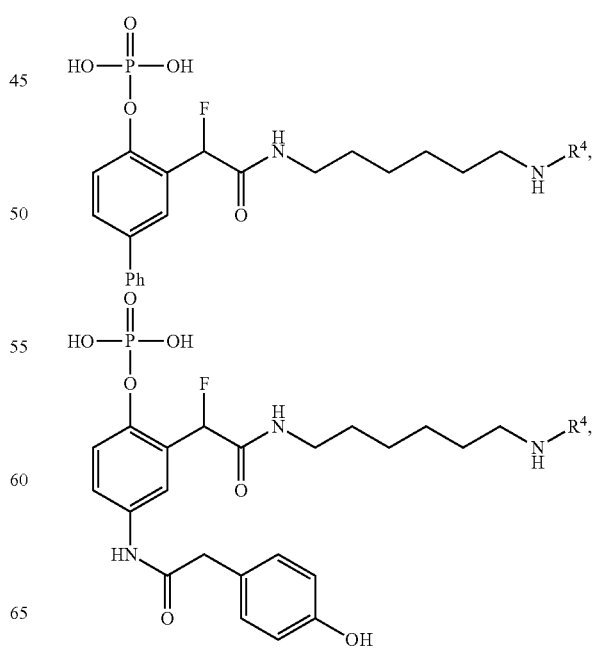

-continued
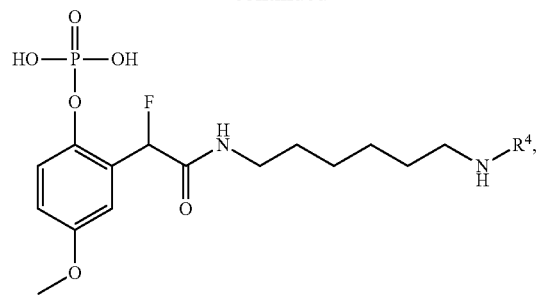
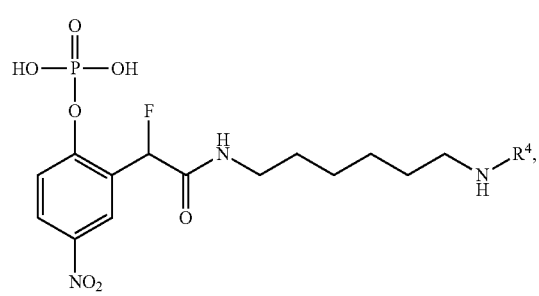
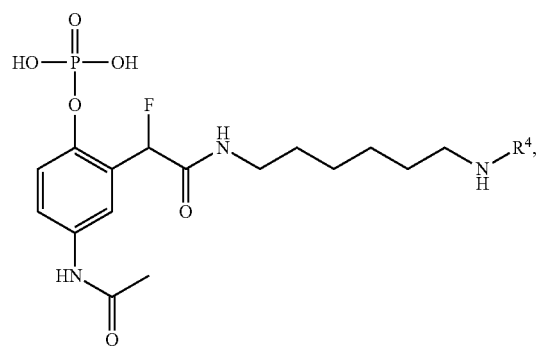
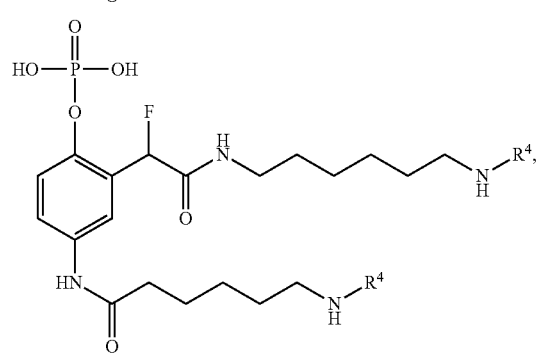
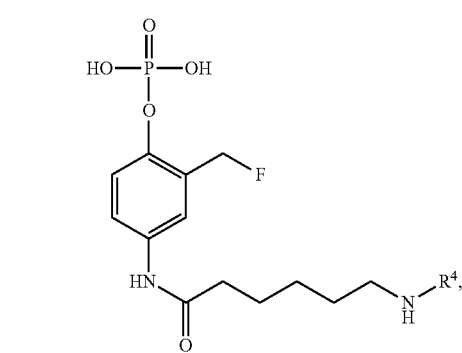
-continued
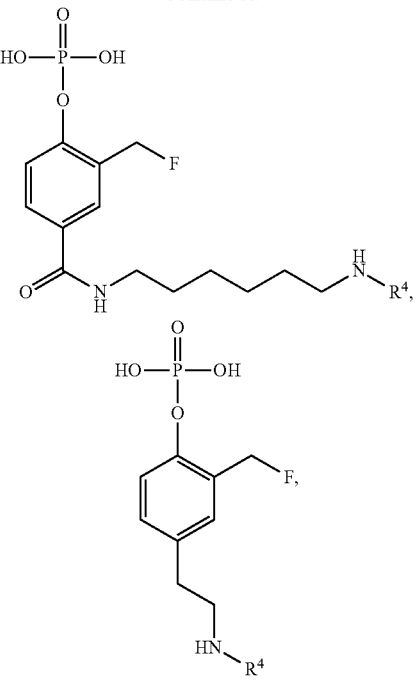
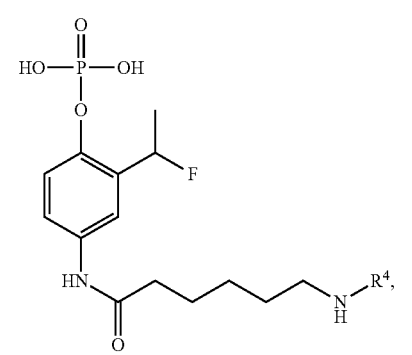
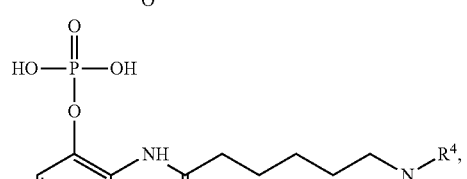
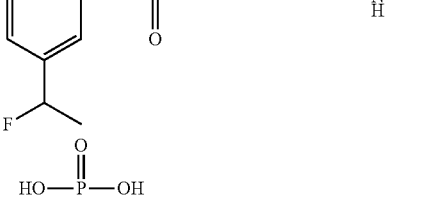
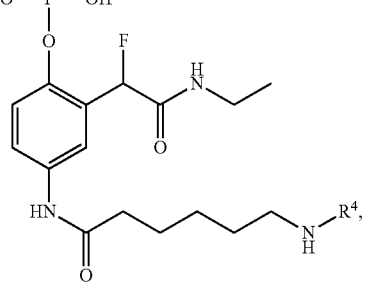

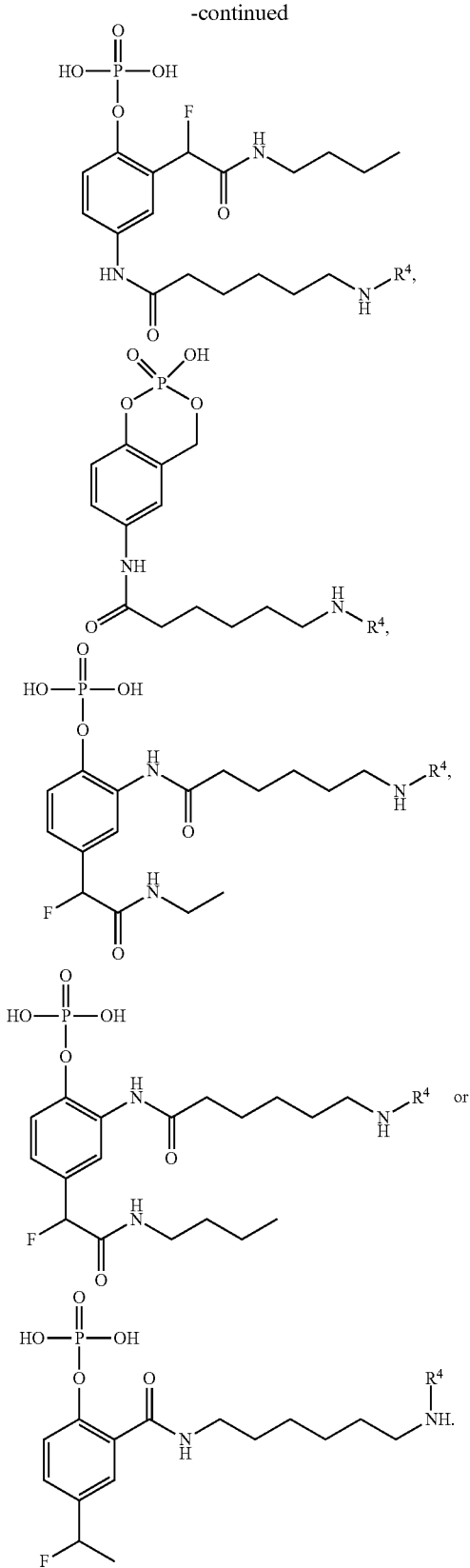

In the above examples, R⁴ is a detectable label, such as a hapten, fluorophore, luminophore, or chromogen. A person of ordinary skill in the art will appreciate that the $ZR^1$, LG and $R^3$ moieties shown in each case are exemplary moieties, and may be replace with any $ZR^1$, LG and $R^3$ moiety disclosed herein.

In some exemplary embodiments, the compound according to formula IV comprises at least one detectable label and a moiety selected from 2-(2-(((6-(amino)hexyl)amino)-1-fluoro-2-oxoethyl)phenyl dihydrogen phosphate;

2-(2-((2-aminoethyl)amino)-1-fluoro-2-oxoethyl)phenyl dihydrogen phosphate;

1-(2-(((6-aminohexyl)amino)-1-fluoro-2-oxoethyl)naphthalen-2-yl dihydrogen phosphate;

2-(2-((4-(aminomethyl)benzyl)amino)-1-fluoro-2-oxoethyl) phenyl dihydrogen phosphate;

(2S,3S,4S,5R,6R)-6-(2-(2-(((6-aminohexyl)amino)-1-fluoro-2-oxoethyl)phenoxy)-3,4,5-trihydroxytetrahydro-2H-pyran-2-carboxylic acid;

N-(6-aminohexyl)-2-fluoro-2-(2-(((2S,3R,4S,5S,6R)-3,4,5-trihydroxy-6-(hydroxymethyl)tetrahydro-2H-pyran-2-yl) oxy)phenyl)acetamide;

(2S,3S,4S,5R,6S)-6-(2-(2-(((6-aminohexyl)amino)-1-fluoro-2-oxoethyl)phenoxy)-3,4,5-trihydroxytetrahydro-2H-pyran-2-carboxylic acid;

N-(6-aminohexyl)-2-fluoro-2-(2-(((2R,3R,4S,5R,6R)-3,4,5-trihydroxy-6-(hydroxymethyl)tetrahydro-2H-pyran-2-yl) oxy)phenyl)acetamide;

N-(6-aminohexyl)-2-fluoro-2-(2-(((2R,3R,4S,5S,6R)-3,4,5-trihydroxy-6-(hydroxymethyl)tetrahydro-2H-pyran-2-yl) oxy)phenyl)acetamide;

(6R,7R)-7-acetamido-3-((2-(2-(((6-aminohexyl)amino)-1-fluoro-2-oxoethyl)phenoxy)methyl)-8-oxo-5-thia-1-azabicyclo[4.2.0]oct-2-ene-2-carboxylic acid;

(6R,7R)-7-acetamido-3-(((2-(2-(((6-aminohexyl)amino)-1-fluoro-2-oxoethyl)phenyl)thio)methyl)-8-oxo-5-thia-1-azabicyclo[4.2.0]oct-2-ene-2-carboxylic acid;

2-(2-(((6-aminohexyl)amino)-1-fluoro-2-oxoethyl)phenyl hydrogen sulfate;

N-(6-aminohexyl)-2-fluoro-2-(2-methoxyphenyl)acetamide;

2-(2-(((6-aminohexyl)amino)-1-fluoro-2-oxoethyl)phenyl propionate;

2-(2-((2-(2-(2-aminoethoxy)ethoxy)ethyl)amino)-1-fluoro-2-oxoethyl)phenyl dihydrogen phosphate;

2-(1-(((6-aminohexyl)amino)-2-fluoro-1-oxopropan-2-yl) phenyl dihydrogen phosphate;

2-(2-acetamidophenyl)-N-(6-aminohexyl)-2-fluoroacetamide;

N-(6-aminohexyl)-2-fluoro-2-(2-nitrophenyl)acetamide;

N-(6-aminohexyl)-2-fluoro-2-(2-ureidophenyl)acetamide;

N-(6-aminohexyl)-2-fluoro-2-(2-(((2S,3R,4S,5R,6R)-3,4,5-trihydroxy-6-(hydroxymethyl)tetrahydro-2H-pyran-2-yl) oxy)phenyl)acetamide;

2-(2-(((6-(2,6-diaminohexanamido)hexyl)amino)-1-fluoro-2-oxoethyl)phenyl dihydrogen phosphate;

2-((1-(2-aminoethyl)-1H-1,2,3-triazol-4-yl)fluoromethyl) phenyl dihydrogen phosphate; or 2-(fluoro(1H-1,2,3-triazol-4-yl)methyl)phenyl dihydrogen phosphate.

In other embodiments, the moiety is selected from 3-(2-(((6-aminohexyl)amino)-1-fluoro-2-oxoethyl)-[1,1'-biphenyl]-4-yl dihydrogen phosphate;

2-(2-(((6-aminohexyl)amino)-1-fluoro-2-oxoethyl)-4-(2-(4-hydroxyphenyl)acetamido)phenyl dihydrogen phosphate;

2-(2-(((6-aminohexyl)amino)-1-fluoro-2-oxoethyl)-4-methoxyphenyl dihydrogen phosphate;

2-(2-(((6-aminohexyl)amino)-1-fluoro-2-oxoethyl)-4-nitrophenyl dihydrogen phosphate;

4-acetamido-2-(2-((6-aminohexyl)amino)-1-fluoro-2-oxo-ethyl)phenyl dihydrogen phosphate;
4-(6-aminohexanamido)-2-(2-((6-aminohexyl)amino)-1-fluoro-2-oxoethyl)phenyl dihydrogen phosphate;
4-(6-aminohexanamido)-2-(fluoromethyl)phenyl dihydrogen phosphate;
4-((6-aminohexyl)carbamoyl)-2-(fluoromethyl)phenyl dihydrogen phosphate;
4-(2-aminoethyl)-2-(fluoromethyl)phenyl dihydrogen phosphate;
4-(6-aminohexanamido)-2-(1-fluoroethyl)phenyl dihydrogen phosphate;
2-(6-aminohexanamido)-4-(1-fluoroethyl)phenyl dihydrogen phosphate;
4-(6-aminohexanamido)-2-(2-(ethylamino)-1-fluoro-2-oxo-ethyl)phenyl dihydrogen phosphate;
4-(6-aminohexanamido)-2-(2-(butylamino)-1-fluoro-2-oxo-ethyl)phenyl dihydrogen phosphate;
6-amino-N-(2-hydroxy-2-oxido-4H-benzo[d][1,3,2]dioxa-phosphinin-6-yl)hexanamide;
2-(6-aminohexanamido)-4-(2-(ethylamino)-1-fluoro-2-oxo-ethyl)phenyl dihydrogen phosphate;
2-(6-aminohexanamido)-4-(2-(butylamino)-1-fluoro-2-oxo-ethyl)phenyl dihydrogen phosphate; or
2-((6-aminohexyl)carbamoyl)-4-(1-fluoroethyl)phenyl dihydrogen phosphate;
where the detectable label is a hapten, fluorophore, luminophore, or chromogen, and that the enzyme recognition group, leaving group and linker moiety are exemplary, and may be replaced by any enzyme recognition group, leaving group and linker moiety disclosed herein.

In other examples of formula II where the conjugated ring is phenyl, the QMP has

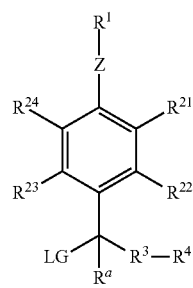

VI wherein Z, LG, $R^1$, $R^3$, $R^4$, $R^5$, $R^6$, $R^a$ and $R^c$ are as previously defined for formula IV; $R^{21}$, $R^{22}$, $R^{23}$ and $R^{24}$ are each independently hydrogen, halo, cyano, aliphatic, alkoxy, $NO_2$, $N(R^c)_2$, aryl, haloalkyl, —C(O)alkyl, —C(S)alkyl, —C(O)OH, —C(O)Oalkyl, —C(O)NHR$^c$, —C(O)N(R$^c$)$_2$, —R$^3$R$^4$, or two adjacent groups together form an aliphatic ring or aryl ring.

In certain embodiments, LG is F, and in particular embodiments, LG is F and $R^5$ and $R^6$, and/or $R^a$, are hydrogen.

In some embodiments of formula VI, the QMP has a structure

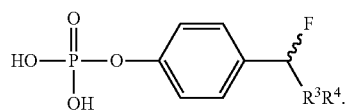

In other embodiments of formula VI, the QMP has a structure selected from

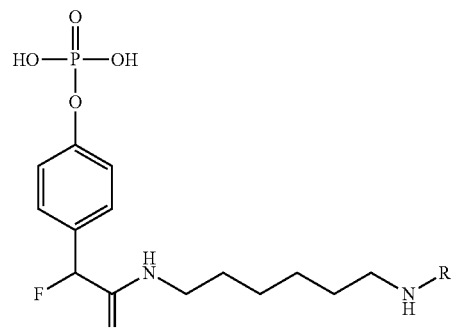

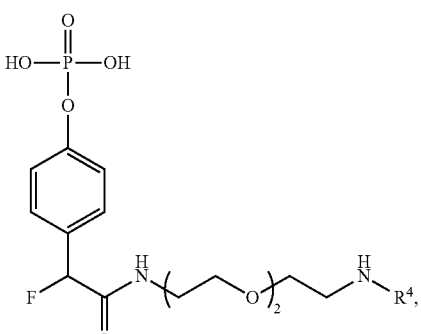

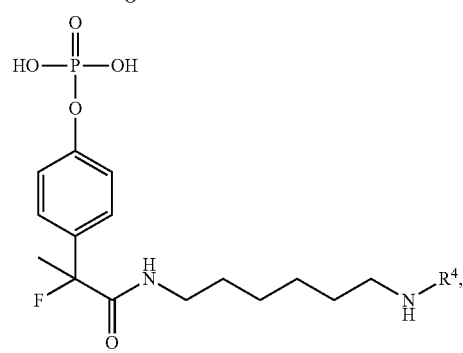

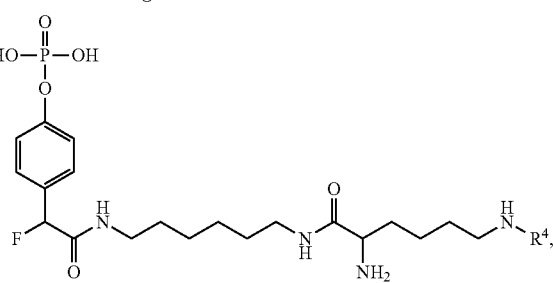

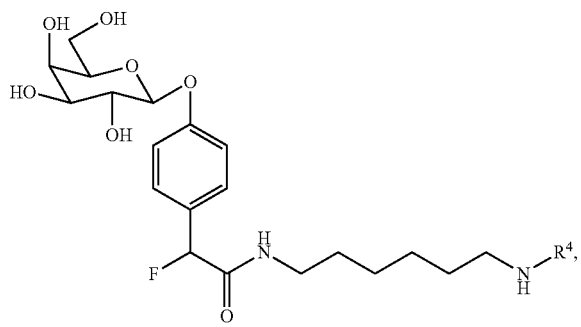

35
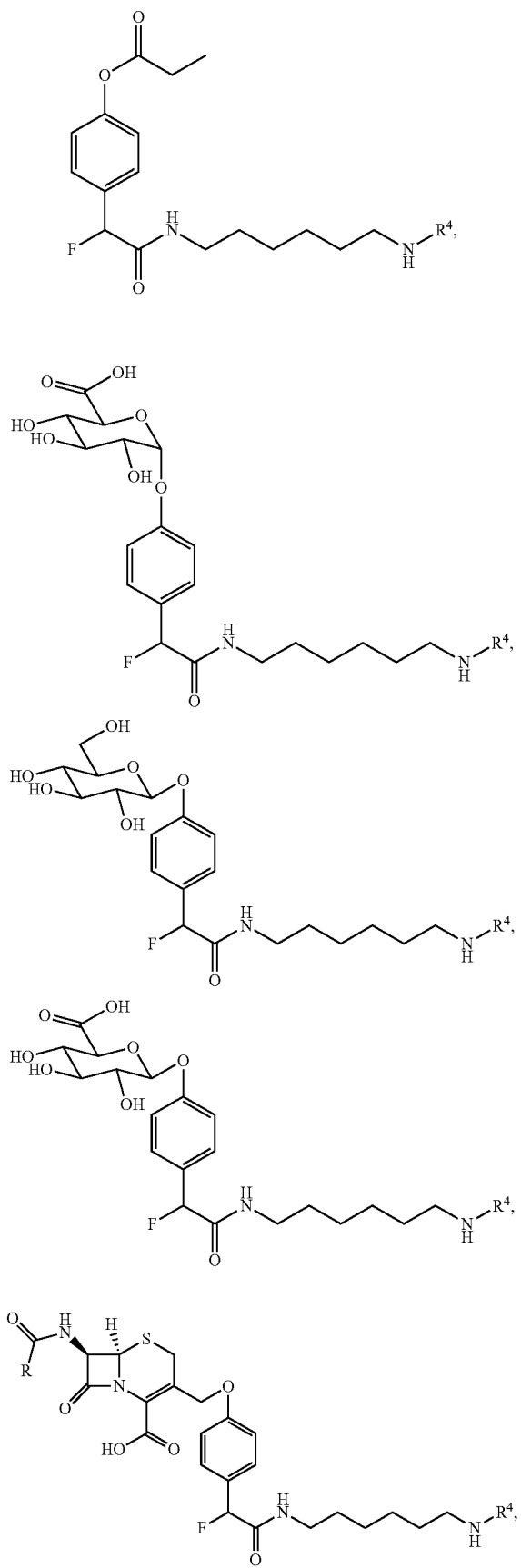
36
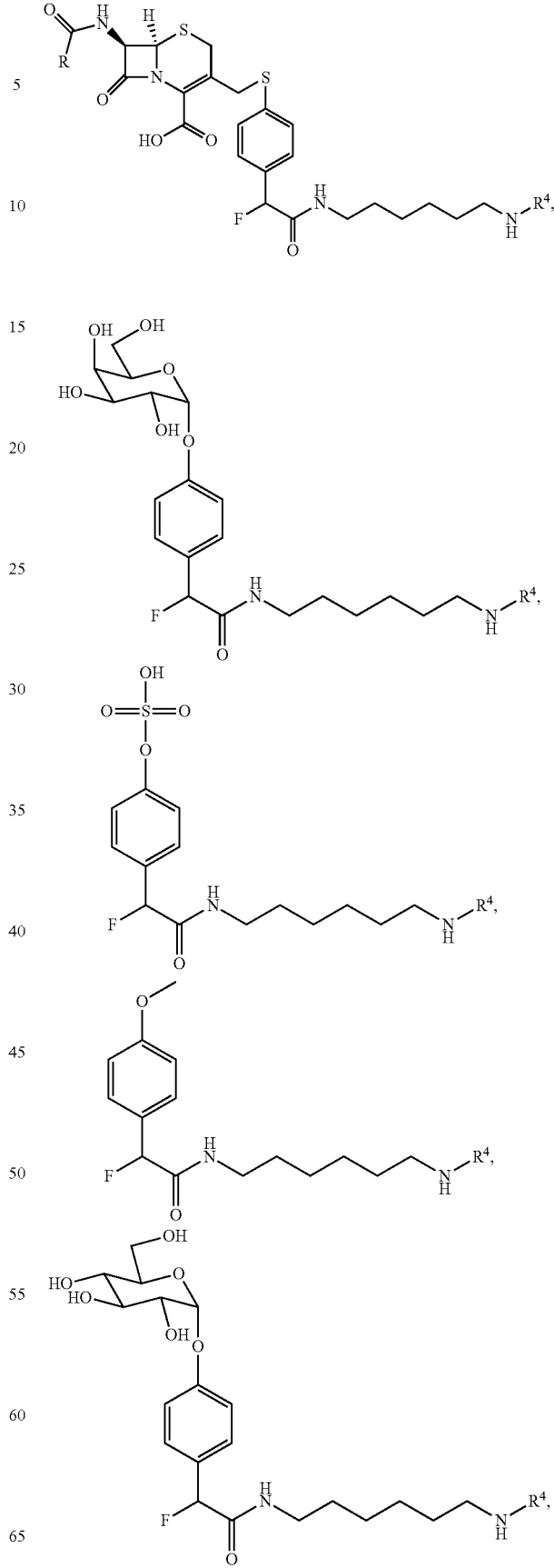

-continued

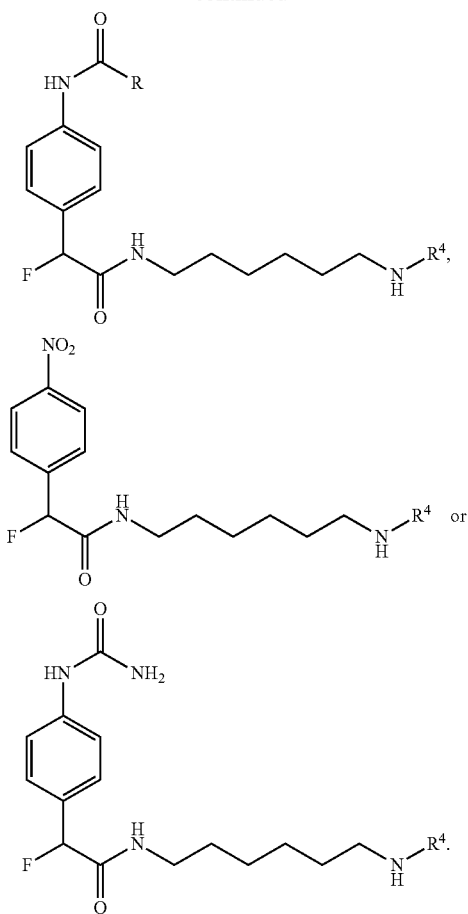

In other examples, the QMP has a structure selected from

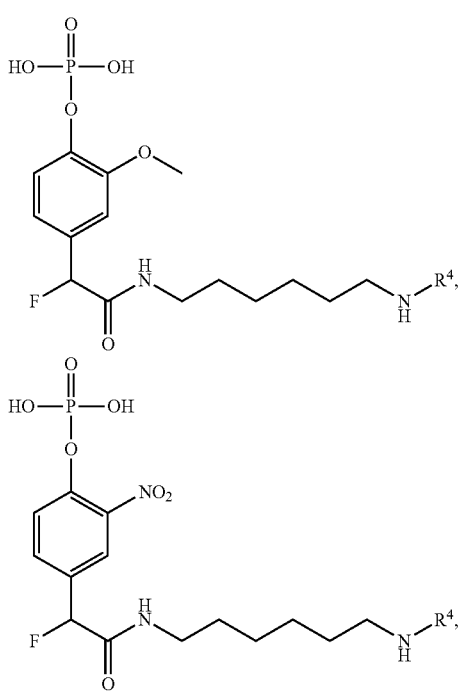

-continued

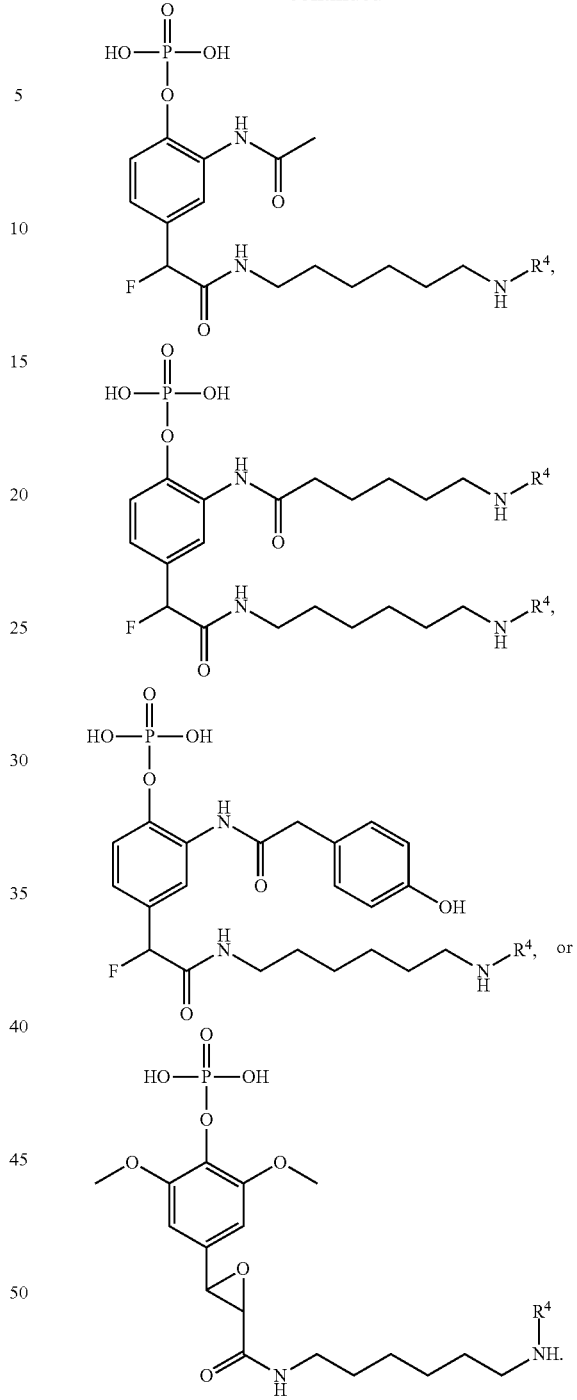

In any of the above examples, $R^4$ is a detectable label, such as a hapten, fluorophore, luminophore, or chromogen. A person of ordinary skill in the art will appreciate that the $ZR^1$, LG and $R^3$ moieties shown in each case are exemplary moieties, and may be replaced with any $ZR^1$, LG and $R^3$ moiety disclosed herein.

In some exemplary embodiments, the compound according to formula VI comprises at least one detectable label and a moiety selected from 4-(2-(((6-aminohexyl)amino)-1-fluoro-2-oxoethyl)phenyl dihydrogen phosphate;

4-(2-((2-(2-(2-aminoethoxy)ethoxy)ethyl)amino)-1-fluoro-2-oxoethyl)phenyl dihydrogen phosphate;
4-(1-((6-aminohexyl)amino)-2-fluoro-1-oxopropan-2-yl)phenyl dihydrogen phosphate;
4-(2-((6-(2,6-diaminohexanamido)hexyl)amino)-1-fluoro-2-oxoethyl)phenyl dihydrogen phosphate;
N-(6-aminohexyl)-2-fluoro-2-(4-(((2S,3R,4S,5R,6R)-3,4,5-trihydroxy-6-(hydroxymethyl)tetrahydro-2H-pyran-2-yl)oxy)phenyl)acetamide;
4-(2-((6-aminohexyl)amino)-1-fluoro-2-oxoethyl)phenyl propionate;
(2S,3S,4S,5R,6R)-6-(4-(2-((6-aminohexyl)amino)-1-fluoro-2-oxoethyl)phenoxy)-3,4,5-trihydroxytetrahydro-2H-pyran-2-carboxylic acid;
N-(6-aminohexyl)-2-fluoro-2-(4-(((2S,3R,4S,5S,6R)-3,4,5-trihydroxy-6-(hydroxymethyl)tetrahydro-2H-pyran-2-yl)oxy)phenyl)acetamide;
(2S,3S,4S,5R,6S)-6-(4-(2-((6-aminohexyl)amino)-1-fluoro-2-oxoethyl)phenoxy)-3,4,5-trihydroxytetrahydro-2H-pyran-2-carboxylic acid;
(6R,7R)-7-acetamido-3-((4-(2-((6-aminohexyl)amino)-1-fluoro-2-oxoethyl)phenoxy)methyl)-8-oxo-5-thia-1-azabicyclo[4.2.0]oct-2-ene-2-carboxylic acid;
(6R,7R)-7-acetamido-3-(((4-(2-((6-aminohexyl)amino)-1-fluoro-2-oxoethyl)phenyl)thio)methyl)-8-oxo-5-thia-1-azabicyclo[4.2.0]oct-2-ene-2-carboxylic acid;
N-(6-aminohexyl)-2-fluoro-2-(4-(((2R,3R,4S,5R,6R)-3,4,5-trihydroxy-6-(hydroxymethyl)tetrahydro-2H-pyran-2-yl)oxy)phenyl)acetamide;
4-(2-((6-aminohexyl)amino)-1-fluoro-2-oxoethyl)phenyl hydrogen sulfate;
N-(6-aminohexyl)-2-fluoro-2-(4-methoxyphenyl)acetamide;
N-(6-aminohexyl)-2-fluoro-2-(4-(((2R,3R,4S,5S,6R)-3,4,5-trihydroxy-6-(hydroxymethyl)tetrahydro-2H-pyran-2-yl)oxy)phenyl)acetamide;
2-(4-acetamidophenyl)-N-(6-aminohexyl)-2-fluoroacetamide;
N-(6-aminohexyl)-2-fluoro-2-(4-nitrophenyl)acetamide;
N-(6-aminohexyl)-2-fluoro-2-(4-ureidophenyl)acetamide;
4-(2-((6-aminohexyl)amino)-1-fluoro-2-oxoethyl)-2-methoxyphenyl dihydrogen phosphate;
4-(2-((6-aminohexyl)amino)-1-fluoro-2-oxoethyl)-2-nitrophenyl dihydrogen phosphate;
2-acetamido-4-(2-((6-aminohexyl)amino)-1-fluoro-2-oxoethyl)phenyl dihydrogen phosphate;
2-(6-aminohexanamido)-4-(2-((6-aminohexyl)amino)-1-fluoro-2-oxoethyl)phenyl dihydrogen phosphate;
4-(2-((6-aminohexyl)amino)-1-fluoro-2-oxoethyl)-2-(2-(4-hydroxyphenyl)acetamido)phenyl dihydrogen phosphate; or
4-(3-((6-aminohexyl)carbamoyl)oxiran-2-yl)-2,6-dimethoxyphenyl dihydrogen phosphate;

where the detectable labels is a hapten, fluorophore, luminophore, or chromogen, and that the enzyme recognition group, leaving group and linker moiety are exemplary, and may be replaced by any enzyme recognition group, leaving group and linker moiety disclosed herein.

Figure 2A:
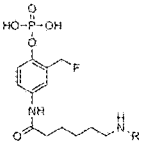
FIG. 2(A) is a table providing exemplary QMPs.

FIG. 2(A) provides a table illustrating some additional exemplary QM precursors.

In some embodiments, the compound is selected from 2-(fluoromethyl)-4-(6-(5-(2-oxohexahydro-1H-thieno[3,4-d]imidazol-4-yl)pentanamido)hexanamido)phenyl dihydrogen phosphate;
4-(6-(2-((2,4-dinitrophenyl)amino)acetamido)hexanamido)-2-(fluoromethyl)phenyl dihydrogen phosphate;
2-(fluoromethyl)-4-(1-(5-nitro-1H-pyrazol-3-yl)-1,29-dioxo-5,8,11,14,17,20,23,26-octaoxa-2,30-diazahexatriacontan-36-amido)phenyl dihydrogen phosphate;
(E)-4-(6-(4-((3-((4-chloro-2-methylphenyl)carbamoyl)-2-hydroxynaphthalen-1-yl)diazenyl)benzamido)hexanamido)-2-(fluoromethyl)phenyl dihydrogen phosphate;
4-(6-(3',6'-bis(dimethylamino)-3-oxo-3H-spiro[isobenzofuran-1,9'-xanthene]-5-carboxamido)hexanamido)-2-(fluoromethyl)phenyl dihydrogen phosphate;
4-(6-(3',6'-diamino-3-oxo-3H-spiro[isobenzofuran-1,9'-xanthene]-5-carboxamido)hexanamido)-2-(fluoromethyl)phenyl dihydrogen phosphate;
1-(6-((6-((3-(fluoromethyl)-4-(phosphonooxy)phenyl)amino)-6-oxohexyl)amino)-6-oxohexyl)-3,3-dimethyl-2-((1E,3E)-5-((Z)-1,3,3-trimethylindolin-2-ylidene)penta-1,3-dien-1-yl)-3H-indol-1-ium chloride;
2-(methoxymethyl)-4-(6-(5-(2-oxohexahydro-1H-thieno[3,4-d]imidazol-4-yl)pentanamido)hexanamido)phenyl dihydrogen phosphate;
5-(6-(5-(2-oxohexahydro-1H-thieno[3,4-d]imidazol-4-yl)pentanamido)hexanamido)-2-(phosphonooxy)benzyl acetate;
1-(5-(6-(5-(2-oxohexahydro-1H-thieno[3,4-d]imidazol-4-yl)pentanamido)hexanamido)-2-(phosphonooxy)benzyl)pyridin-1-ium;
1-(5-(6-(5-(2-oxohexahydro-1H-thieno[3,4-d]imidazol-4-yl)pentanamido)hexanamido)-2-(phosphonooxy)benzyl)-1,4-diazabicyclo[2.2.2]octan-1-ium;
N,N-diethyl-N-(5-(6-(5-(2-oxohexahydro-1H-thieno[3,4-d]imidazol-4-yl)pentanamido)hexanamido)-2-(phosphonooxy)benzyl)ethanaminium;
5-(6-(5-(2-oxohexahydro-1H-thieno[3,4-d]imidazol-4-yl)pentanamido)hexanamido)-2-(phosphonooxy)benzyl diethylcarbamate;
2-(fluoromethyl)-4-((5-(5-(2-oxohexahydro-1H-thieno[3,4-d]imidazol-4-yl)pentanamido)pentyl)carbamoyl)phenyl dihydrogen phosphate; or
2-(fluoromethyl)-4-(2-(5-(2-oxohexahydro-1H-thieno[3,4-d]imidazol-4-yl)pentanamido)ethyl)phenyl dihydrogen phosphate.

In other embodiments of formula II, the conjugated ring is a heteroaryl or heterocyclic ring. Exemplary heteroaryl or heterocyclic ring include, but are not limited to, pyrazole, imidazole, pyridine, pyrimidine, pyridazine, pyrazine, pyrrole, furan, thiophene, indole, benzoxazole, benzimidazole, thiazole, oxazole, imidazole, or purine.

Some exemplary analogs of formula II where the conjugated ring is a heteroaryl or heterocyclic ring include:

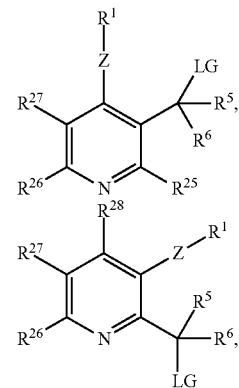

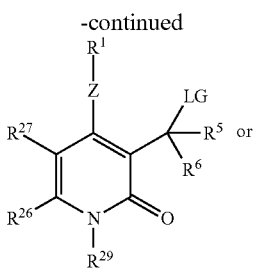

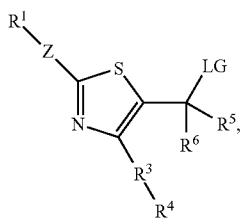

where Z, $R^1$ and LG are as previously defined with respect to formula IV; $R^5$ and $R^6$ are each independently hydrogen, halo, cyano, lower alkyl, lower haloalkyl, —C(O)alkyl, —C(S)alkyl, —C(O)OH, —C(O)Oalkyl, —C(O)NHR$^c$ or —C(O)N(R$^c$)$_2$; $R^{25}$-$R^{29}$ are each independently hydrogen, halo, cyano, aliphatic, alkoxy, NO$_2$, N(R$^c$)$_2$, aryl, haloalkyl, —C(O)alkyl, —C(S)alkyl, —C(O)OH, —C(O)Oalkyl, —C(O)NHR$^c$, —C(O)N(R$^c$)$_2$, —R$^3$R$^4$, or two adjacent groups together form an aliphatic ring or aryl ring; each R$^c$ independently is hydrogen, aryl, aliphatic or heteroaliphatic, or two R$^c$ moieties together form a heteroaliphatic ring; and at least one of $R^5$, $R^6$ and $R^{25}$-$R^{29}$ comprises or consists of $R^3R^4$. In some embodiments, when LG is halo, $R^5$ and $R^6$ are not halo.

In some embodiments of formulas I-VI, when $R^1$ is —P(O)(OH)$_2$, —C(LG)(R$^5$)(R$^6$) is —CH$_2$F, —CH$_2$OH, —CH$_2$OCH$_3$, —CH$_2$OC(O)CH$_3$, —CH$_2$N(C$_2$H$_5$)$_3$$^+$, —CH$_2$(—NC$_5$H$_5$)$^+$, or —CH$_2$(DABCO)$^+$ where DABCO is 1,4-diazabicyclo[2.2.2]octane. In certain embodiments, —C(LG)(R$^5$)(R$^6$) is —CH$_2$F, —CH$_2$OCH$_3$, or —CH$_2$OCOCH$_3$.

i) Enzyme Recognition Group

The enzyme recognition group can be selected from any group that is suitable for enzyme recognition. In illustrative embodiments, the enzyme recognition group is selected from phosphate, phosphodiester, amide, nitro, urea, sulfate, methyl, ester, alpha- or beta-glucose, beta-lactam, alpha- or beta-galactose, alpha- or beta-lactose, and alpha- or beta-glucuronic acid. A person of ordinary skill in the art can select an appropriate enzyme recognition group based on the enzyme being used, such as, groups suitable for recognition by a phosphatase, phosphodiesterase, esterase, lipase, amidase, protease, nitroreductase, urease, sulfatase, cytochrome P450, alpha- or beta-glucosidase, alpha- or beta-lactamase, alpha- or beta-glucoronidase, alpha- or beta-galactosidase, alpha- or beta lactase.

Embodiments provided below illustrate exemplary enzyme recognition groups for a particular QMP

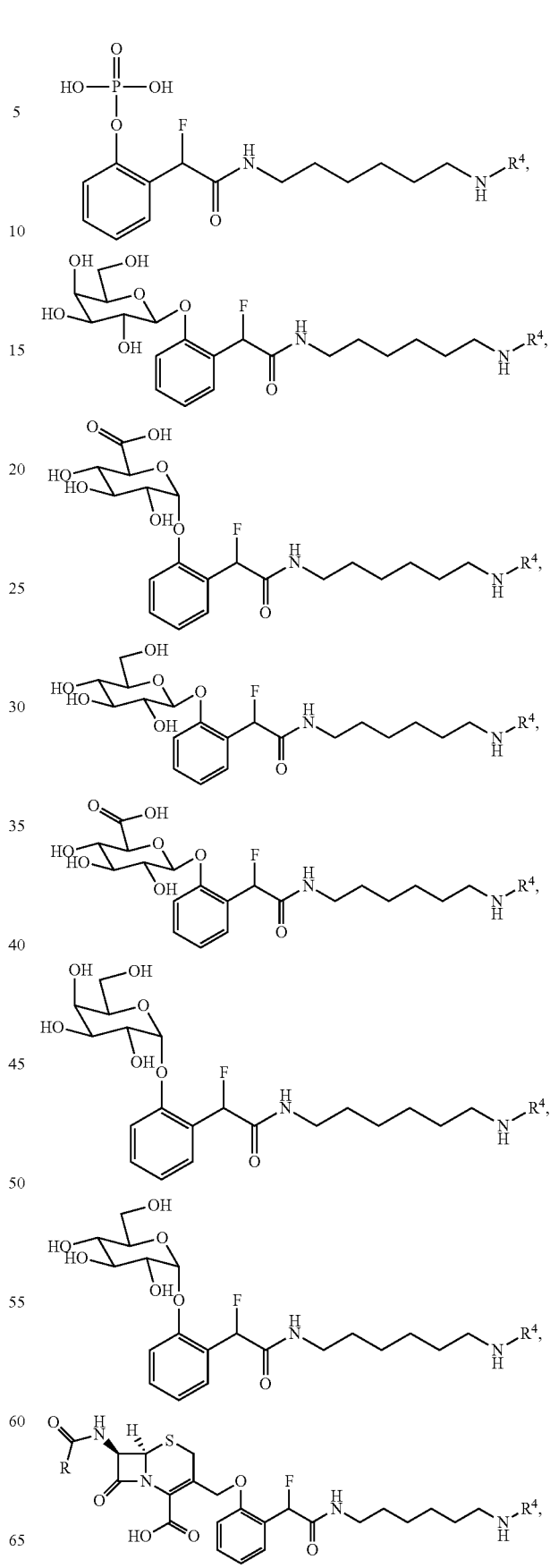

-continued

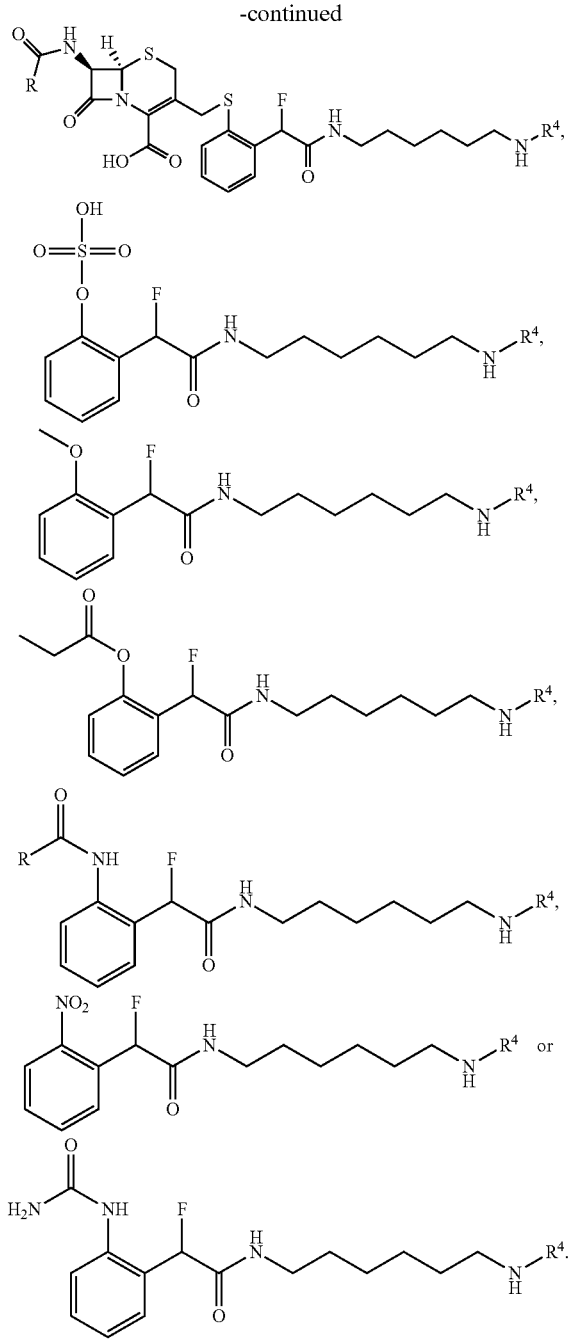

Figure 3A:
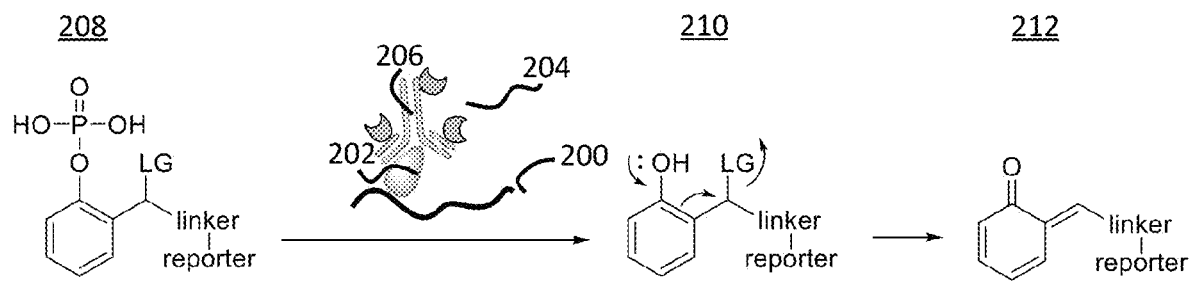
FIG. 3(A) illustrates phosphatase-mediated conversion of a QMP with detectable label to a quinone methide that amplifies a target signal.
Figure 3B:
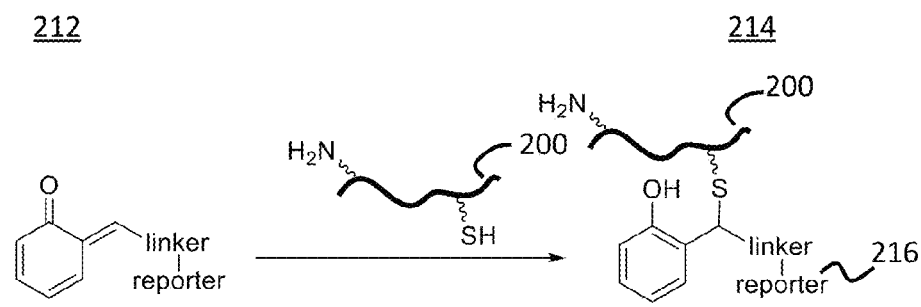
FIG. 3(B) is an additional illustration of phosphatase-mediated conversion of a QMP with detectable label to a quinone methide that amplifies a target signal.
Figure 3C:
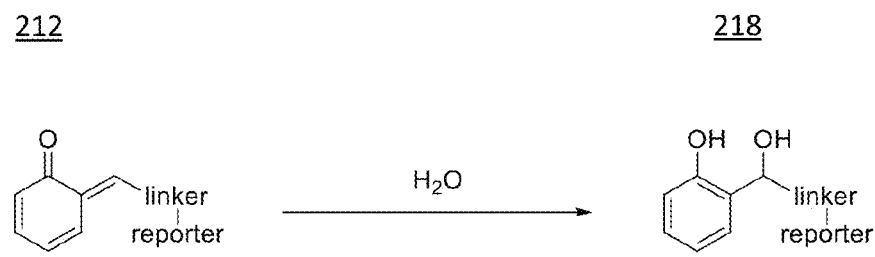
FIG. 3(C) is an additional illustration of phosphatase-mediated conversion of a QMP with detectable label to a quinone methide that amplifies a target signal.

Referring now to FIGS. 3(A)-(C), a sample 200 having a target 202 is contacted by an antibody 204. Target 202 is shown being specifically bound by the antibody 204. Antibody 204 is conjugated to one or more enzymes 206. When contacted with a QMP 208, enzyme 206 catalyzes cleavage of an enzyme recognition group, exemplified by a phosphate group, from QMP 208 to produce a phenol intermediate 210. The phenol eliminates the leaving group (LG) to produce a QM conjugate 212. QM conjugate 212 is a reactive electrophile capable of reacting with nucleophiles.

Referring now to FIG. 3(B), QM conjugate 212 can react with nucleophiles present in sample 200, such as amine or sulfhydryl groups, as illustrated. A covalently bound complex 214 between the QM conjugate 212 and the sample 200 forms when the electrophilic QM conjugate and the nucleophilic groups on the sample react. Since enzyme 206 was located proximally to target 202 through antibody 204, detectable label 216 is covalently bound to sample 200 proximally to target 202. Thus, the detectable label 216 can be detected to identify the presence of target 202. This reaction occurs iteratively so that many complexes 214 are formed at each target, thereby amplifying the signal associated with the detection event. The detectable label 216 can be any compound useful therefore, such as a hapten, fluorophore, luminophore, or chromogen that can be detected by suitable means. The enzyme 206 may be bound directly or indirectly to a target 202.

Referring now to FIG. 3(C), a person of ordinary skill in the art will understand that a competing reaction between QM conjugate 212 and a solvent (e.g. water) may result in the formation of non-bound compounds 218. Non-bound compounds 218 may be washed away, thereby reducing indiscriminate staining of the sample at other locations.

Covalently bound compound 214 has a general structure according to formulas VII or VIII:

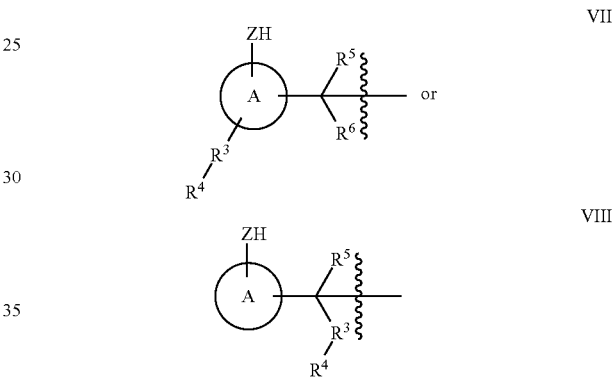

wherein A, Z and $R^3$-$R^6$ are as previously defined.

Alkaline phosphatase (ALP, ALKP) (EC 3.1.3.1) is a hydrolase enzyme responsible for removing phosphate groups from many types of molecules, including nucleotides, proteins, and alkaloids. The process of removing the phosphate group is called dephosphorylation. As the name suggests, alkaline phosphatases (also referred to as basic phosphatases) are most effective in an alkaline environment. Alkaline phosphatases have several attributes that are advantageous relative to available enzymes including, for example: (1) alkaline phosphatase has a kcat/Km approximating the diffusion-controlled limit of $1\times10^9$ liter/mole-sec; (2) alkaline phosphatase's optimal pH is 9-10, a pH suitable for subsequent reaction of the QM; (3) alkaline phosphatases are very stable enzymes that resist thermal and chemical degradation better than most enzymes; and (4) alkaline phosphatases are reasonably small and methods of conjugation to other biological molecules have been developed.

Sulfatases (EC 3.1.6) are esterase enzymes that catalyze the hydrolysis of sulfate esters in many types of molecule including steroids, carbohydrates and proteins. They hydrolytically cleave sulfate esters through a unique catalytic aldehyde, which is introduced by a post-translational oxidation. Sulfatases are distributed in a wide range of tissues throughout the body.

Glycosidases, also known as glycoside hydrolases (EC 3.2.1), catalyze the hydrolysis of glycosidic bonds in complex sugars. They are extremely common enzymes in nature and catalyze hydrolysis both O- and S-glycosides.

Lipases are enzymes that catalyze the hydrolysis of fats. They are a subclass of esterase enzymes, and are found in a wide range of organisms and tissue types.

β-lactamases (EC 3.5.2.6) are enzymes that open β-lactam rings by a hydrolysis mechanism. They are produced by some bacteria and can result in resistance to β-lactam antibiotics, such as penicillins.

ii) Leaving Group

The leaving group can be any suitable group that can act as a leaving group to form a quinone methide when the QMP is contacted by a suitable enzyme. In some embodiments, the leaving group is a group that can leave as an anion, with a formal negative charge. In other embodiments, the leaving group has a positive charge before leaving the QMP, and leaves as a neutral species. Suitable leaving groups include, but are not limited to, halide, azide, sulfate ester, carboxylate, inorganic ester, thiolate, amine, aryloxy, alkoxy, or heteroaryl. In particular embodiments, LG is fluoride, chloride, acetate, methoxy, ethoxy, isopropoxy, phenoxide, —OS(O)$_2$CH$_3$, —OS(O)$_2$C$_6$H$_4$CH$_3$, —OS(O)$_2$C$_6$H$_5$, —OS(O)$_2$C$_6$H$_4$CX$_3$ where X is halo, —OC$_6$H$_5$, —N$_2^+$, —NH$_3^+$, —NC$_5$H$_5^+$, —O— alkyl, —OC(O)alkyl, —OC(O)H, —N(R$^b$)$_3^+$ where each R$^b$ independently is hydrogen or lower alkyl or two R$^b$ moieties together form a heteroaliphatic ring, or DABCO.

iii) Detectable Labels

Figure 4:
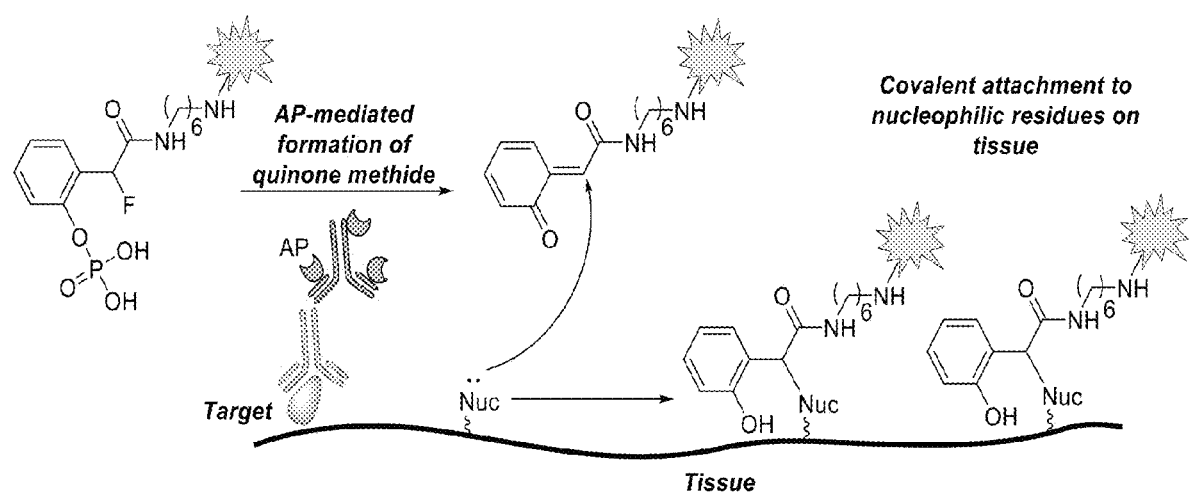
FIG. 4 illustrates one exemplary embodiment of a method for amplifying target detection in biological tissue.
Figure 5:
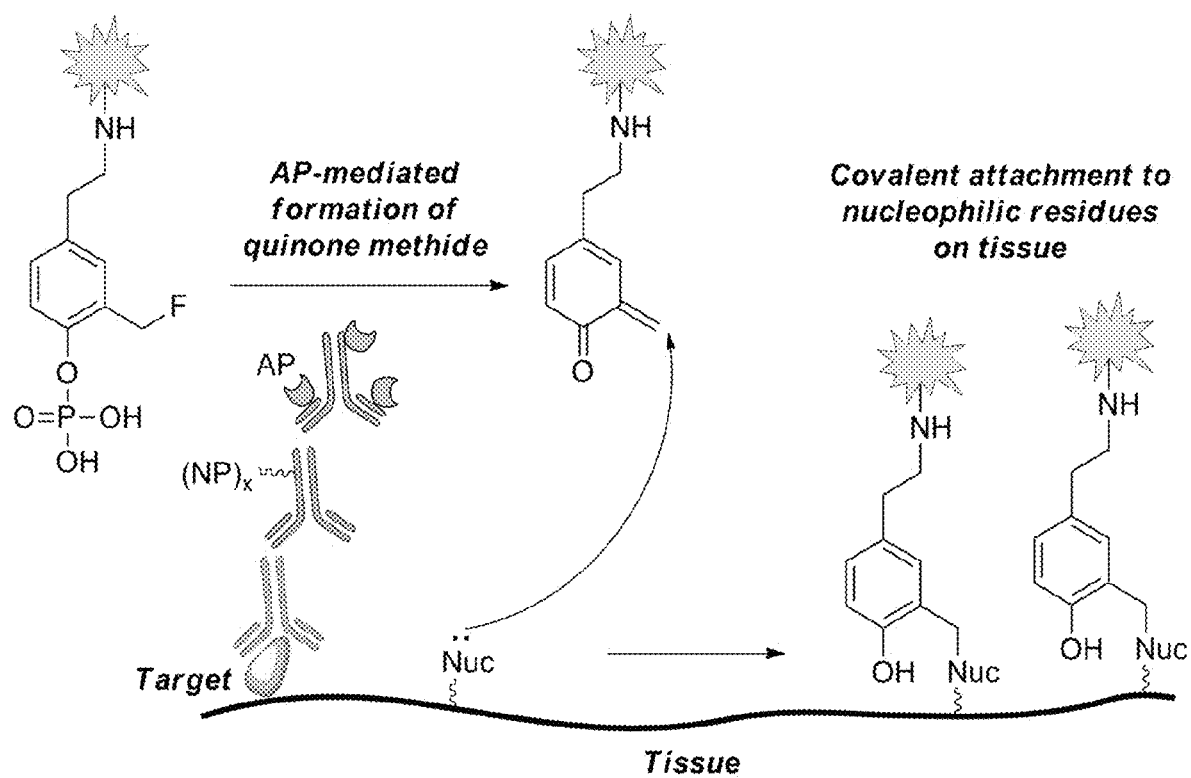
FIG. 5 illustrates a second exemplary embodiment of a method for amplifying target detection in biological tissue.

As shown in FIGS. 4 and 5, QMPs are synthesized to allow the use of many different detectable labels or reporter moieties, such as haptens, dyes, and other detection tags (R$^4$ in formulas I-VI), to determine the presence of a target in a sample. Suitable detectable labels include luminophores (phosphors, fluorophores), chromophores, and/or haptens. A luminophore is a compound capable of luminescence, including phosphorescence or fluorescence. Luminescence is the emission of light by a compound caused by absorption of excitation energy in the form of photons, charged particles, or chemical changes. A fluorophore is a fluorescent compound that absorbs light of a specific wavelength and re-emits light at a longer wavelength. A chromophore is a species capable of absorbing visible light. A preferred chromophore is capable of absorbing a sufficient quantity of visible light with sufficient wavelength specificity so that the chromophore can be visualized using bright-field illumination. A hapten is a molecule, typically a small molecule that can combine specifically with an antibody, but typically is substantially incapable of being immunogenic except in combination with a carrier molecule. Certain luminophores, fluorophores, and chromophores also are haptens. Several exemplary detectable labels are shown in FIG. 2(A).

While not exhaustive, WO2012024185, which is incorporated in its entirety herein by reference, provides disclosure concerning presently available chromogens and haptens. Embodiments of detectable labels include haptens, such as pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by Podophyllotoxin and Podophyllotoxin derivatives; and combinations thereof. Embodiments of haptens and methods for their preparation and use are disclosed in U.S. Pat. No. 7,695,929, which is incorporated in its entirety herein by reference.

Exemplary haptens include, but are not limited to, BD (benzodiazepine), BF (benzofurazan), DABSYL (4-(dimethylamino)azobenzene-4'-sulfonamide, which has a $\lambda_{max}$ of about 436 nm), DCC (7-(diethylamino)coumarin-3-carboxylic acid), DIG (digoxigenin), DNP (dinitrophenyl), HQ (3-hydroxy-2-quinoxalinecarbamide) NCA (nitrocinnamic acid), NP (nitropyrazole), PPT (Podophyllotoxin), Rhod (rhodamine), ROT (rotenone), and TS (thiazolesulfonamide). Other suitable haptens include biotin and fluorescein derivatives (FITC (fluorescein isothiocyanate), TAMRA (tetramethylrhodamine), Texas Red).

Suitable chromophores include coumarin and coumarin derivatives. Exemplary coumarin-based chromophores include DCC and 2,3,6,7-tetrahydro-11-oxo-1H,5H,11H-[1]benzopyrano[6,7,8-ij]quinolizine-10-carboxylic acid. Another class of chromogenic moieties suitable for use includes diazo-containing chromogens, such as tartrazine, which has a $\lambda_{max}$ of about 427 nm In yet other embodiments, the chromophore may be a triarylmethane compound. Exemplary triarylmethane chromophores are provided below:

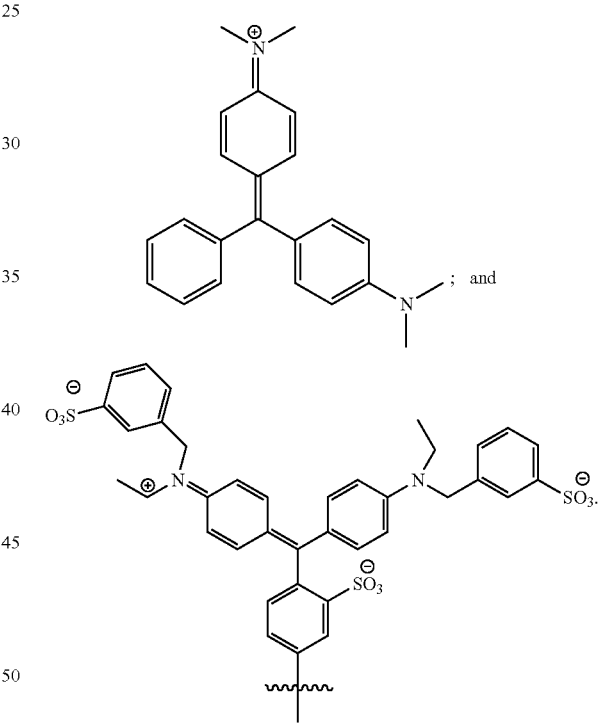

Exemplary annulated chromophores include, but are not limited to:

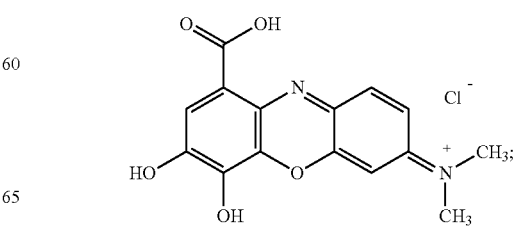

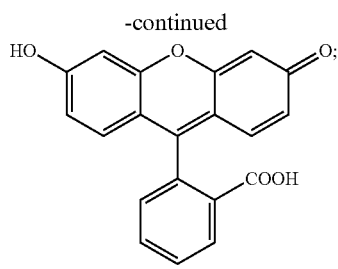

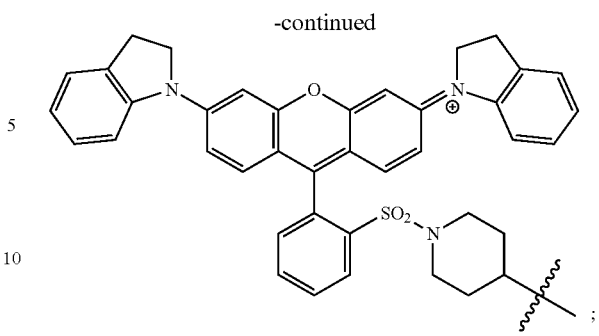

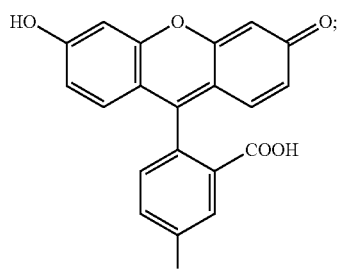

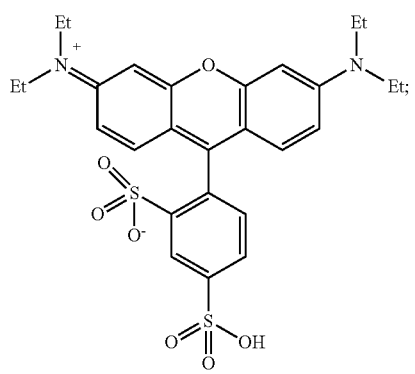

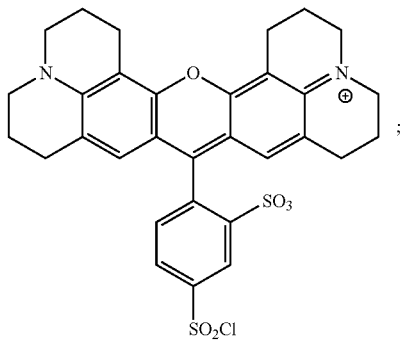

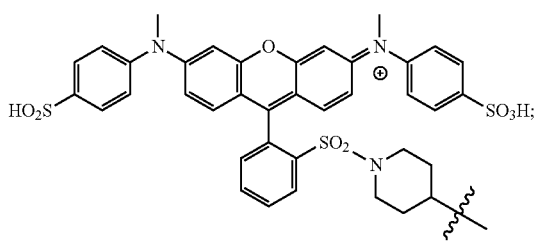

and other rhodamine derivatives, such as tetramethylrhodamines (including TMR, TAMRA, and reactive isothiocyanate derivatives), and diarylrhodamine derivatives, such as the QSY 7, QSY 9, and QSY 21 dyes.

Other exemplary detectable labels include resorufin; DAB; AEC; CN; BCIP/NBT; fast red; fast blue; fuchsin; NBT; ALK GOLD; Cascade Blue acetyl azide; Dapoxylsulfonic acid/carboxylic acid; DY-405; Alexa Fluor® 405; Cascade Yellow; pyridyloxazole (PyMPO); Pacific Blue; DY-415; 7-hydroxycoumarin-3-carboxylic acid; DYQ-425; 6-FAM phosphoramidite; Lucifer Yellow; iodoacetamide; Alexa Fluor® 430; Dabcyl; NBD chloride/fluoride; QSY 35; DY-485XL; Cy2; DY-490; Oregon Green 488 carboxylic acid; Alexa Fluor® 488; BODIPY 493/503 C3; DY-480XL; BODIPY FL C3; BODIPY FL C5; BODIPY FL-X; DYQ-505; Oregon Green 514 carboxylic acid; DY-510XL; DY-481XL; 6-carboxy-4',5'-dichloro-2',7'-dimethoxyfluorescein (JOE); DY-520XL; DY-521XL; BODIPY R6G C3; erythrosin isothiocyanate; 5-carboxy-2',4',5',7'-tetrabromosulfonefluorescein; Alexa Fluor® 532; 6-carboxy-2',4,4',5'7, 7'-hexachlorofluorescein (HEX); BODIPY 530/550 C3; DY-530; BODIPY TMR-X; DY-555; DYQ-1; DY-556; Cy3; DY-547; DY-549; DY-550; Alexa Fluor® 555; Alexa Fluor® 546; DY-548; BODIPY 558/568 C3; Rhodamine red-X; QSY 7; BODIPY 564/570 C3; BODIPY 576/589 C3; carboxy-X-rhodamine (ROX); Alexa Fluor® 568; DY-590; BODIPY 581/591 C3; DY-591; BODIPY TR-X; Alexa Fluor® 594; DY-594; carboxynaphthofluorescein DY-605; DY-610; Alexa Fluor® 610; DY-615; BODIPY 630/650-X; erioglaucine; Alexa Fluor® 633; Alexa Fluor® 635; DY-634; DY-630; DY-631; DY-632; DY-633; DYQ-2; DY-636; BODIPY 650/665-X; DY-635; Cy5; Alexa Fluor® 647; DY-647; DY-648; DY-650; DY-654; DY-652; DY-649; DY-651; DYQ-660; DYQ-661; Alexa Fluor® 660; Cy5.5; DY-677; DY-675; DY-676; DY-678; Alexa Fluor® 680; DY-679; DY-680; DY-682; DY-681; DYQ-3; DYQ-700; Alexa Fluor® 700; DY-703; DY-701; DY-704; DY-700; DY-730; DY-731; DY-732; DY-734; DY-750; Cy7; DY-749; DYQ-4; and Cy7.5.

Figure 6A:
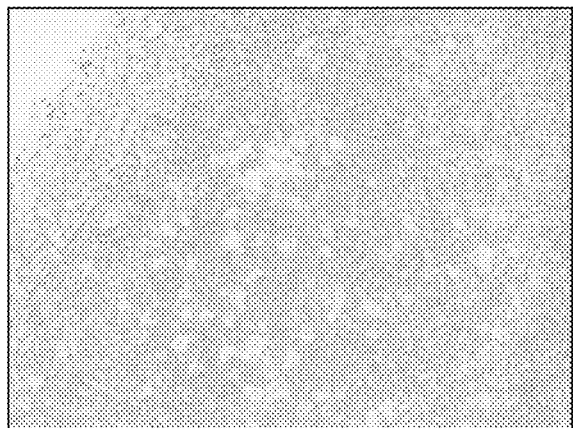
FIG. 6(A) is a microphotograph illustrating the increase in staining intensity of QMP-Dabsyl derivatives with PEG linkers, for Bcl-6 on tonsil tissue at 20× magnification using phosphate-QMP-Dabsyl (250 uM).
Figure 6B:
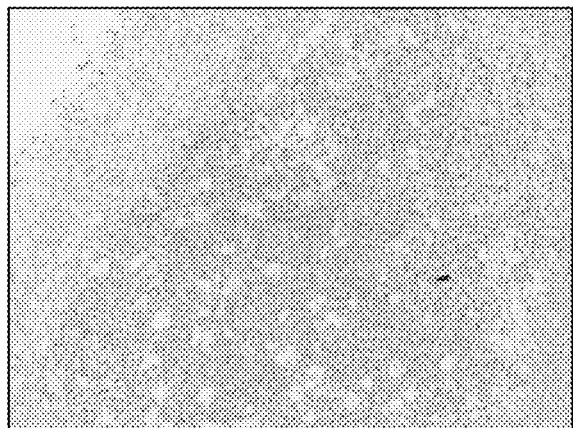
FIG. 6(B) is a microphotograph illustrating the increase in staining intensity of QMP-Dabsyl derivatives with PEG linkers, for Bcl-6 on tonsil tissue at 20× magnification using phosphate-QMP-PEG$_4$-Dabsyl (250 uM).
Figure 6C:
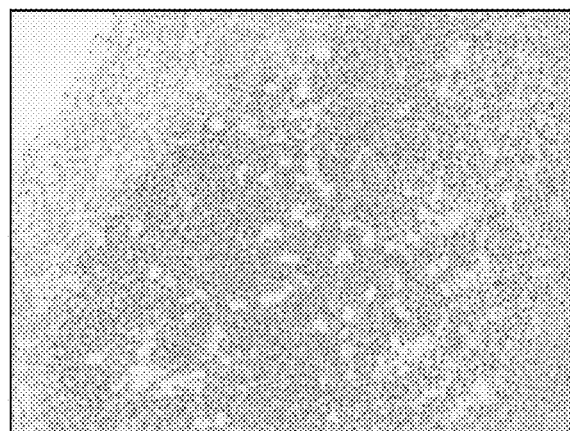
FIG. 6(C) is a microphotograph illustrating the increase in staining intensity of QMP-Dabsyl derivatives with PEG linkers, for Bcl-6 on tonsil tissue at 20× magnification using phosphate-QMP-PEG$_8$-Dabsyl (250 uM).

In some embodiments, the detectable label includes a linker moiety, such as a PEG moiety. In certain embodiments, the addition of a PEG moiety can improve the staining intensity. FIGS. 6 and 7 illustrate the increase in staining intensity of QMP-Dabsyl and QMP-Tamra derivatives with PEG linkers, respectively. FIGS. 6(A)-6(C) provide microphotographs of Bcl-6 staining on tonsil tissue at 20× magnification, using phosphate-QMP-Dabsyl (250 uM) (FIG. 6(A)), phosphate-QMP-PEG$_4$-Dabsyl (250 uM) (FIG. 6(B)) and phosphate-QMP-PEG$_8$-Dabsyl (250 uM) (FIG. 6(C)). As FIGS. 6(A)-6(C) show, the inclusion of a PEG linker in a phosphate-QMP-Dabsyl derivative increases the staining intensity substantially, compared to a phosphate-QMP-Dabsyl derivative without a PEG linker (FIGS. 6(A)-

6(C)). Additionally, FIGS. 6(B) and 6(C) illustrate the difference in staining intensity between incorporating PEG$_4$ (FIG. 6(B)) and PEG$_8$ (FIG. 6(C)) moieties into phosphate-QMP-Dabsyl derivatives. Also, the PEG$_8$ moiety increases staining intensity relative to the PEG$_4$ moiety.

Figure 7A:
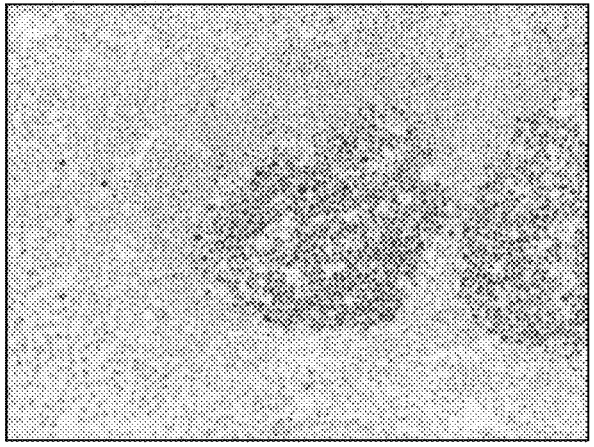
FIG. 7(A) is a microphotograph illustrating the increase in staining intensity of QMP-Tamra derivatives with PEG linkers, for Bcl-6 on tonsil tissue at 20× magnification using phosphate-QMP-Tamra (250 uM).
Figure 7B:
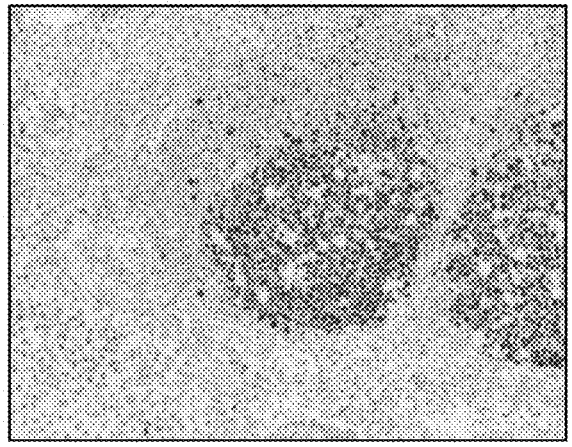
FIG. 7(B) is a microphotograph illustrating the increase in staining intensity of QMP-Tamra derivatives with PEG linkers, for Bcl-6 on tonsil tissue at 20× magnification using phosphate-QMP-PEG$_4$-Tamra (250 uM).
Figure 7C:
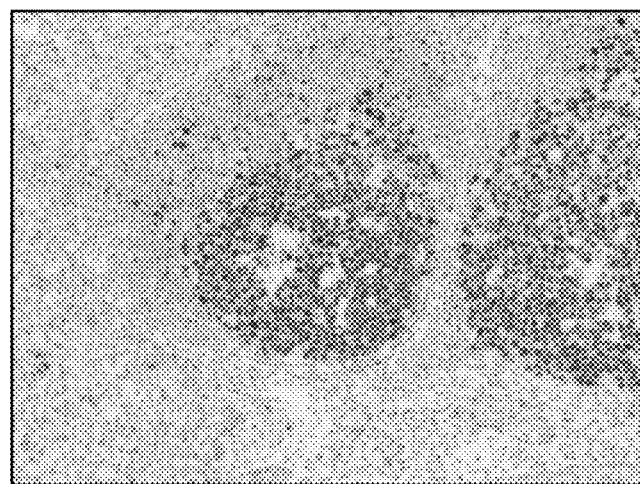
FIG. 7(C) is a microphotograph illustrating the increase in staining intensity of QMP-Tamra derivatives with PEG linkers, for Bcl-6 on tonsil tissue at 20× magnification using phosphate-QMP-PEG$_8$-Tamra (250 uM).

A similar result is shown in FIGS. 7A-7(C), which illustrate the increase in staining intensity achieved by the incorporation of PEG linkers into phosphate-QMP-Tamra derivatives. FIGS. 7A-7(C) provide microphotographs of Bcl-6 staining on tonsil tissue at 20× magnification, using phosphate-QMP-Tamra (250 uM) (FIG. 7(A)), phosphate-QMP-PEG$_4$-Tamra (250 uM) (FIG. 7(B)) and phosphate-QMP-PEG$_8$-Tamra (250 uM) (FIG. 7(C)).

FIGS. 6 and 7 illustrates that incorporating PEG in the linker leads to an increase in functional staining intensity. However, it can also lead to an increase in diffusion of signal for the Tamra derivatives, especially with the PEG$_8$ linker (FIG. 7(C)).

With reference to formulas I-VIII, in particular embodiments the detectable label —R$^4$ or linker-detectable label (—R$^3$R$^4$) is

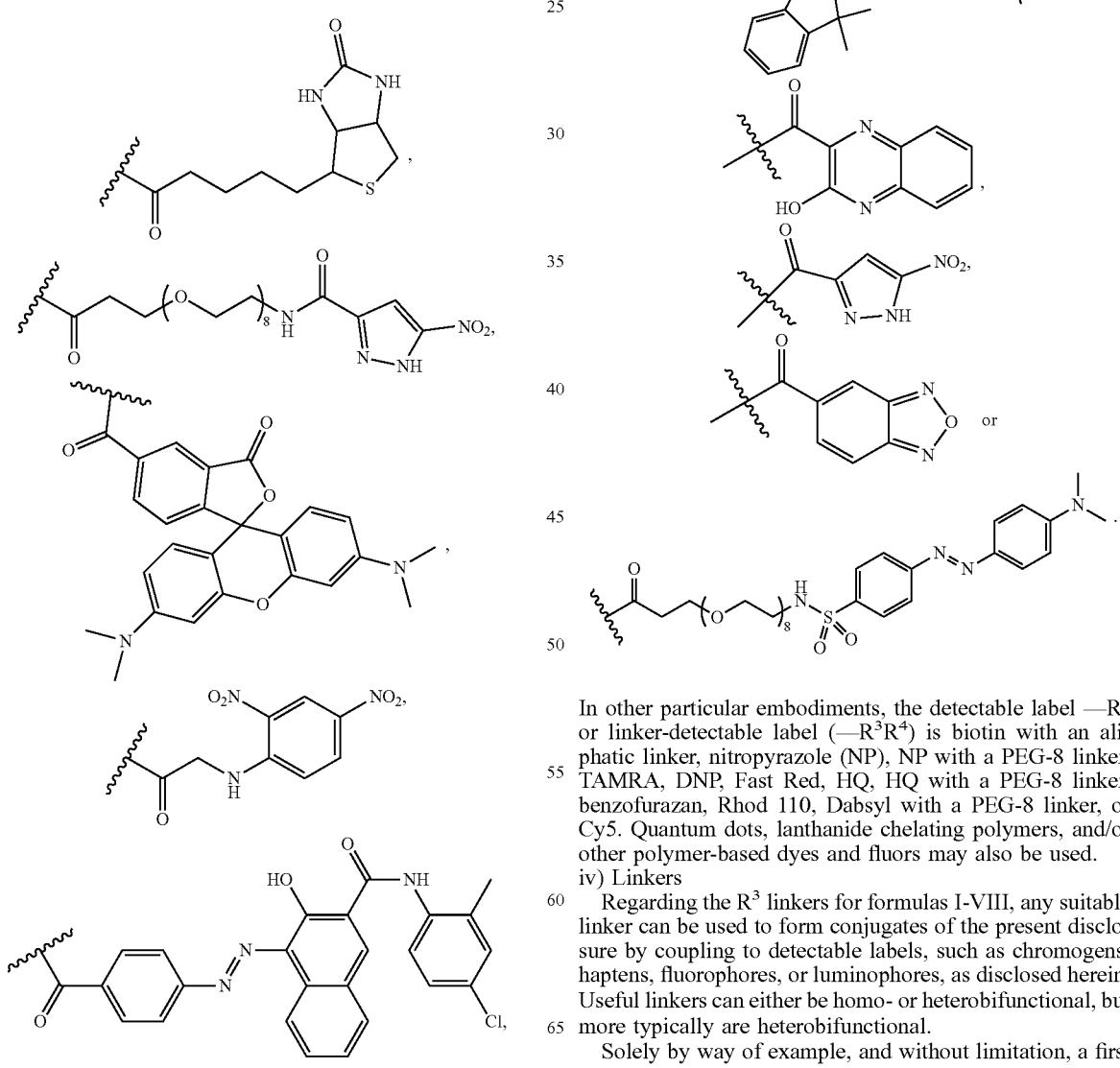

In other particular embodiments, the detectable label —R$^4$ or linker-detectable label (—R$^3$R$^4$) is biotin with an aliphatic linker, nitropyrazole (NP), NP with a PEG-8 linker, TAMRA, DNP, Fast Red, HQ, HQ with a PEG-8 linker, benzofurazan, Rhod 110, Dabsyl with a PEG-8 linker, or Cy5. Quantum dots, lanthanide chelating polymers, and/or other polymer-based dyes and fluors may also be used.

iv) Linkers

Regarding the R$^3$ linkers for formulas I-VIII, any suitable linker can be used to form conjugates of the present disclosure by coupling to detectable labels, such as chromogens, haptens, fluorophores, or luminophores, as disclosed herein. Useful linkers can either be homo- or heterobifunctional, but more typically are heterobifunctional.

Solely by way of example, and without limitation, a first class of linkers includes aliphatic compounds, such as aliphatic hydrocarbon chains having one or more sites of unsaturation, or alkyl chains. The aliphatic chain also typically includes terminal functional groups, including by way of example and without limitation, a carbonyl-reactive group, an amine-reactive group, a thiol-reactive group, carbon-reactive group or a photo-reactive group, that facilitate coupling to a detectable label as disclosed herein. The length of the chain can vary, but typically has an upper practical limit of about 30 atoms. Chain links greater than about 30 carbon atoms have proved to be less effective than compounds having smaller chain links. Thus, aliphatic chain linkers typically have a chain length of from about 1 carbon atom to about 30 carbon atoms. However, a person of ordinary skill in the art will appreciate that, if a particular linker has greater than 30 atoms, and still operates efficiently for linking the detectable label to the QMP, and the conjugate still functions as desired, then such linkers are within the scope of the present disclosure.

A second class of linkers useful for practicing embodiments of the present disclosure is the alkylene oxides. The alkylene oxides are represented herein by reference to glycols, such as ethylene glycols. A person of ordinary skill in the art will appreciate that, as the number of oxygen atoms increases, the hydrophilicity of the compound also may increase. Thus, suitable linkers may have a formula of (—OCH$_2$CH$_2$O—)$_n$ where n is from about 2 to about 15, but more typically is from about 2 to about 8.

Heterobifunctional polyalkyleneglycol linkers useful for practicing certain disclosed embodiments are described in assignee's applications, including "Nanoparticle Conjugates," U.S. patent application Ser. No. 11/413,778, filed Apr. 28, 2006; "Antibody Conjugates," U.S. application Ser. No. 11/413,418, filed Apr. 27, 2006; and "Molecular Conjugate," U.S. application Ser. No. 11/603,425, filed Nov. 21, 2006; all of which applications are incorporated herein by reference. Heterobifunctional polyalkyleneglycol linkers are disclosed below, and their use exemplified by reference to coupling tyramine to detectable labels.

One particular embodiment of a linker for use with disclosed conjugates is a heterobifunctional polyalkyleneglycol linker having the general structure shown below:

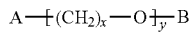

wherein A and B include different reactive groups, x is an integer from 2 to 10 (such as 2, 3 or 4), and y is an integer from 1 to 50, for example, from 2 to 30 such as from 3 to 20 or from 4 to 12. One or more hydrogen atoms can be substituted for additional functional groups such as hydroxyl groups, alkoxy groups (such as methoxy and ethoxy), halogen atoms (F, Cl, Br, I), sulfato groups and amino groups (including mono- and di-substituted amino groups such as dialkyl amino groups.

A and B of the linker independently are reactive functional groups, such as a carbonyl-reactive group, an amine-reactive group, a thiol-reactive group, carbon-reactive group or a photo-reactive group. A and B typically are not the same reactive functional group. Examples of carbonyl-reactive groups include aldehyde- and ketone-reactive groups like hydrazine derivatives and amines. Examples of amine-reactive groups include active esters such as NHS or sulfo-NHS, isothiocyanates, isocyanates, acyl azides, sulfonyl chlorides, aldehydes, glyoxals, epoxides, oxiranes, carbonates, aryl halides, imidoesters, anhydrides and the like. Examples of thiol-reactive groups include non-polymerizable Michael acceptors, haloacetyl groups (such as iodoacetyl), alkyl halides, maleimides, aziridines, acryloyl groups, vinyl sulfones, benzoquinones, aromatic groups that can undergo nucleophilic substitution such as fluorobenzene groups (such as tetra and pentafluorobenzene groups), and disulfide groups such as pyridyl disulfide groups and thiols activated with Ellman's reagent. Examples of carbon-reactive groups include halo-alkyl groups such as chloromethyl. Examples of photo-reactive groups include aryl azide and halogenated aryl azides. Alternatively, A and/or B can be a functional group that reacts with a specific type of reactive group. For example, A and/or B can be an amine group, a thiol group, or a carbonyl-containing group that will react with a corresponding reactive group (such as an amine-reactive group, thiol-reactive group or carbonyl-reactive group, respectively) that has been introduced or is otherwise present on a hapten and/or a tyramine or tyramine derivative. Additional examples of each of these types of groups will be apparent to those of ordinary skill in the art. Further examples and information regarding reaction conditions and methods for exchanging one type of reactive group for another are provided in Hermanson, "Bioconjugate Techniques," Academic Press, San Diego, 1996, which is incorporated by reference herein.

In some embodiments the heterobifunctional linker has the formula:

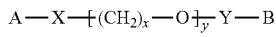

wherein A and B are different reactive groups and are as stated above; x and y are as stated above, and X and Y are additional spacer groups, for example, spacer groups having between 1 and 10 carbons such as between 1 and 6 carbons or between 1 and 4 carbons, and optionally containing one or more amide linkages, ether linkages, ester linkages and the like. Spacers X and Y can be the same or different, and can be straight-chained, branched or cyclic (for example, aliphatic or aromatic cyclic structures), and can be unsubstituted or substituted. Functional groups that can be substituents on a spacer include carbonyl groups, hydroxyl groups, halogen (F, Cl, Br and I) atoms, alkoxy groups (such as methoxy and ethoxy), nitro groups, and sulfate groups.

In particular embodiments, the heterobifunctional linker comprises a heterobifunctional polyethylene glycol linker having the formula:

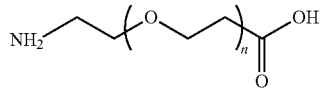

wherein n=1 to 50, for example, n=2 to 30 such as n=3 to 20 or n=4 to 12. In particular embodiments, n=4 or 8.

Another class of linkers are aryl linkers. The aryl linkers can be carbocyclic or heterocyclic moieties, such as phenyl, pyridyl, pyrolyl, imidazolyl, pyrazolyl, triazolyl, oxazolyl or thiazolyl. In certain embodiments, the linker is a triazole, such as a 1,2,3 triazole. The aryl group can be attached to the detectable label and/or QMP-moieties through either a carbon or heteroatom. In an exemplary embodiment, the triazole is formed by a reaction between an azide and an alkyne, such as a QMP moiety comprising an alkyne and an azide-functionalized detectable label, or a detectable label comprising an alkyne and an azide-functionalized QMP moiety (see, for example, Example 2, Scheme 11). The azide and/or alkyne may be attached to the respective moieties via a linker group, such as a linker moiety disclosed herein, or may be directly attached through a covalent bond. In some embodiments, the azide and/or alkyne may be attached via an aliphatic chain, such as an alkyl chain or lower alkyl chain. In other embodiments, the azide and/or alkyne is attached via a polyalkyleneglycol linker.

Figure 2B:
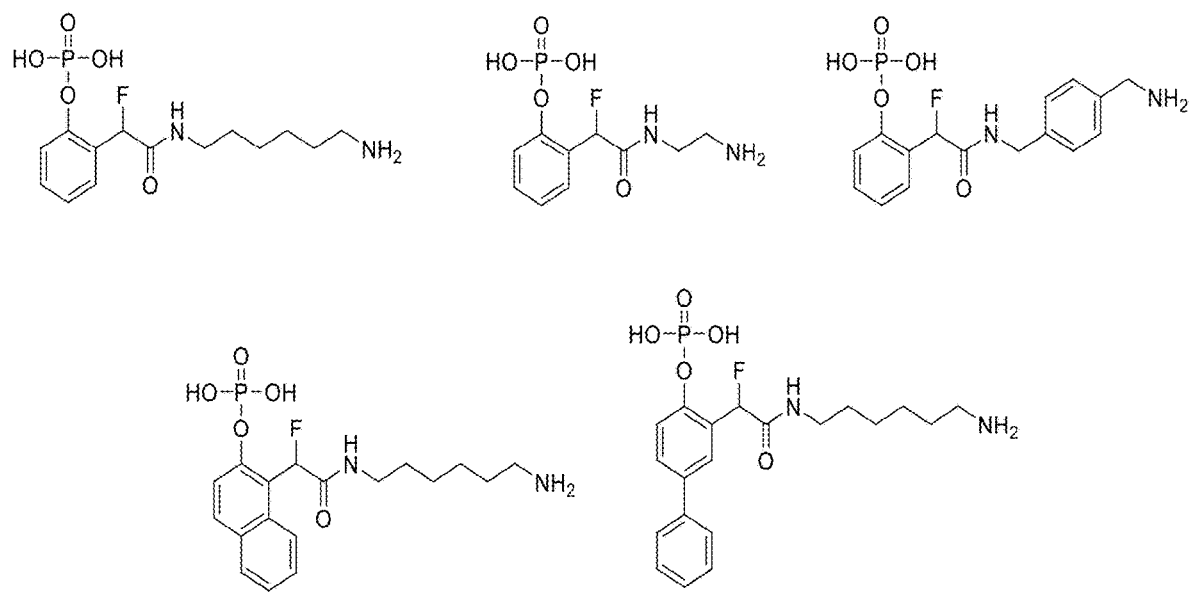
FIG. 2(B) illustrates the structures of exemplary QMPs.

Several exemplary linkers are shown in FIGS. 2(A) and 2(B), third panel, and in the Examples.

III. Methods of Use

Embodiments of the disclosed QMs and their precursors are useful for detecting targets, e.g., detecting a target in a biological sample. Detection can be performed, for example, using immunohistochemistry techniques and/or in situ hybridization techniques. In some embodiments, a target, such as a biomarker, within a tissue is detected.

In certain embodiments, the tissue is formalin-fixed, paraffin-embedded (FFPE) tissue. As understood by those skilled in the art, "tissue" as used herein may further comprise cervical cell smears, frozen tissues, circulating tumor cells on glass slides and blood smears. Thus, for example, the cervical cell smears may be used in cytology preparations etc.

As now described with reference to FIG. 3(A)-(C) and detailed further in the examples below, some method embodiments include contacting sample 200 (e.g. tissue), which includes target 202 with antibody 204. In some embodiments, targets may be detected with a primary antibody that is not conjugated to enzymes, and a secondary antibody is used to detect the primary antibody associated with the target. In either approach, the result is localization of enzyme 206 in close proximity to target 202. The embodiment of FIG. 3 further includes contacting the tissue with a QMP conjugate 208 comprising (i) a phosphate or phosphodiester group and (ii) a detectable label or reporter 216. While shown as an antibody, any suitable binding moieties may be used, for example nucleic acid oligomers, such as hapten labeled nucleic acid oligomers, and antibodies capable of recognizing and binding to the target. Labeling the target 202 with enzyme 206 may include contacting the tissue with enzyme-antibody conjugate comprising an antibody 204 to which the enzyme 206 is linked. Antibody 204 is capable of recognizing and binding specifically to the target. The QMP 208 interacts with the enzyme 206 to form a phenol intermediate 210 that rearranges to form a QM 212, which reacts with the binding moiety, the enzyme 206, the antibody 204, or the tissue to covalently link the detectable label 216 directly on or proximally to the target 202. The detectable label 216 then is detected using a method appropriate for the particular detectable label.

In particular embodiments, the QMP includes a phosphate or phosphodiester group, the enzyme is a phosphatase or phosphodiesterase, respectively, and the detectable label is a chromogen, a fluorophore, a luminophore, or a hapten. In some examples, alkaline phosphatase can be used as a phosphatase or a phosphodiesterase. In other embodiments, the QMP includes a β-galactoside, the enzyme is a β-galactosidase, and the detectable label is a chromogen, a fluorophore, a luminophore, or a hapten.

In some embodiments, antibody 204 recognizes and binds directly to target 202 as shown in FIG. 3(A). In other embodiments, an antibody may be bound indirectly to any specific binding moiety. For example, a hapten-labeled, anti-binding moiety antibody may first be bound to the binding moiety, followed by an anti-hapten antibody-enzyme conjugate.

Still further embodiments involve a method for forming an immunohistochemistry (IHC) or in situ hybridization (ISH) amplification composition comprising a QMP. One exemplary embodiment comprises the step of cleaving a phosphate or phosphodiester group covalently bound to a carbon or adjacent carbons, respectively, in a conjugated system (e.g., an aromatic ring system). When the QMP includes a phosphate group, an electronic rearrangement results in elimination of a leaving group (LG) from a carbon ortho- or para- to the phosphate group. The reaction is performed under conditions suitable for the formation of the QM. The precursor further comprises a detectable label bound to the conjugated system by a linker.

In some embodiments, the identity of the leaving group and/or the QMP conjugate concentration may influence target detection (e.g., staining) specificity. The reactivity of the QM depends at least in part on the rate of QM formation, and therefore the leaving group ability of LG. Poor LGs may have a lower rate of QM formation, resulting in poor specificity due to high QM stability and high diffusion from the site of generation. In some embodiments, the identity of $R^5$ and/or $R^6$ also affects target detection (e.g., staining) specificity. For example, certain groups (e.g., large groups) at $R^5$ and/or $R^6$ may sterically hinder the QM's ability to react with and bind to a nucleophile.

In certain embodiments, when the leaving group was fluoride (e.g., LG=F), superior results were obtained, resulting in specific, amplified IHC staining in which the stained areas when magnified have sharp, well-defined perimeters. Without being bound by a particular theory of operation, a fluoride leaving group may produce a more reactive QMP, resulting in rapid conversion to a QM and subsequent binding proximal to the target. Less reactive QMPs may diffuse away from the target during the time between cleavage of the enzyme recognition group and elimination of the leaving group, followed by deposition and binding of the QM to a nucleophilic site. Additionally, nanomolar QMP conjugate concentrations (e.g., 10 nM to 100 nM) may facilitate specific staining.

Further method embodiments relate to an immunohistochemistry or in situ hybridization amplification method that includes contacting a sample with an immunohistochemistry or in situ hybridization amplification composition comprising a compound according to the structures disclosed herein; and contacting the amplification composition with a reagent under conditions suitable to effect detection.

Yet other embodiments involve a method of detecting two or more distinct targets in a tissue sample. One exemplary embodiment comprises: contacting the tissue with a first binding moiety specific to a first target, and a second binding moiety specific to a second target. The first target is labeled with a first enzyme through the first binding moiety, and the second target is labeled with a second enzyme through the second binding moiety. The tissue is then contacted with a QMP comprising (i) an enzyme recognition group, and (ii) a detectable label, and a second detection precursor compound (e.g., a second QMP or a labeled tyramide compound), wherein the QMP interacts with the first enzyme to form a QM that reacts with the tissue to covalently link the detectable label directly on or proximally to the first target, and the second detection precursor compound interacts with the second enzyme to deposit a second detection compound directly on or proximally to the second target. The detectable compounds are then detected.

Advantageously, for the methods just described, the first enzyme and the second enzyme are different enzymes. For example, the first enzyme can be a phosphatase or phosphodiesterase, and the second enzyme can be a peroxidase. In certain embodiments, the first enzyme is alkaline phosphatase and the second enzyme is horseradish peroxidase. Also advantageously, the first enzyme does not interact with the second detection precursor compound to deposit the second detection compound proximally to the first target, and/or the second enzyme does not interact with the QMP to form the QM. In other words, the first enzyme reacts specifically with the QMP and the second enzyme reacts specifically with the second detection precursor compound. For example, the first enzyme can be a phosphatase and the second enzyme a β-galactosidase. In this example, the first enzyme, the phosphatase, does not react with the QMP comprising a β-galactoside, and the second enzyme, the β-galactosidase, does not react with the QMP comprising the phosphate, Advantageously, these methods do not include an enzyme deactivation step.

In the interests of efficiency, the two or more target amplification methods may be practiced by contacting the tissue with the first binding moiety specific to the first target and contacting the tissue with the second binding moiety specific to the second target such that they occur substantially contemporaneously. The first and second binding moieties also may be contacted with the first and second enzymes substantially contemporaneously. Additionally, the tissue may be contacted with the QMP and the second detection precursor compound substantially contemporaneously. However, a person of ordinary skill in the art will appreciate that the tissue may be serially contacted with the first binding moiety followed by the second binding moiety, and vice versa.

Similarly, the first target may be labeled by the first enzyme followed by labeling the second target with the second enzyme, and vice versa. Also, the tissue may be serially contacted with the QMP followed by the second detection precursor compound, and vice versa.

Figure 8A:
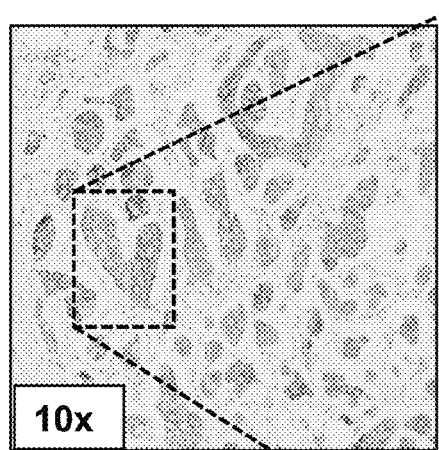
FIG. 8(A) is a microphotograph from a duplex brightfield IHC assay of breast tissue at 10× magnification, illustrating simultaneous antibody incubation and sequential chromogenic detection of Pan-Keratin (QM-PEG8-Dabsyl, yellow) and Her2 (Tyr-TAMRA, purple).
Figure 8B:
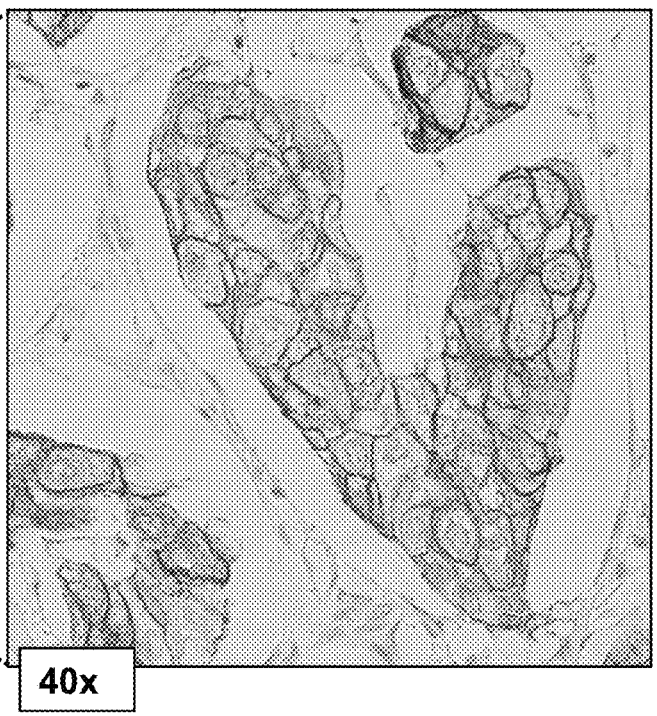
FIG. 8(B) is a portion of FIG. 8(A) magnified to 40× magnification.
Figure 9:
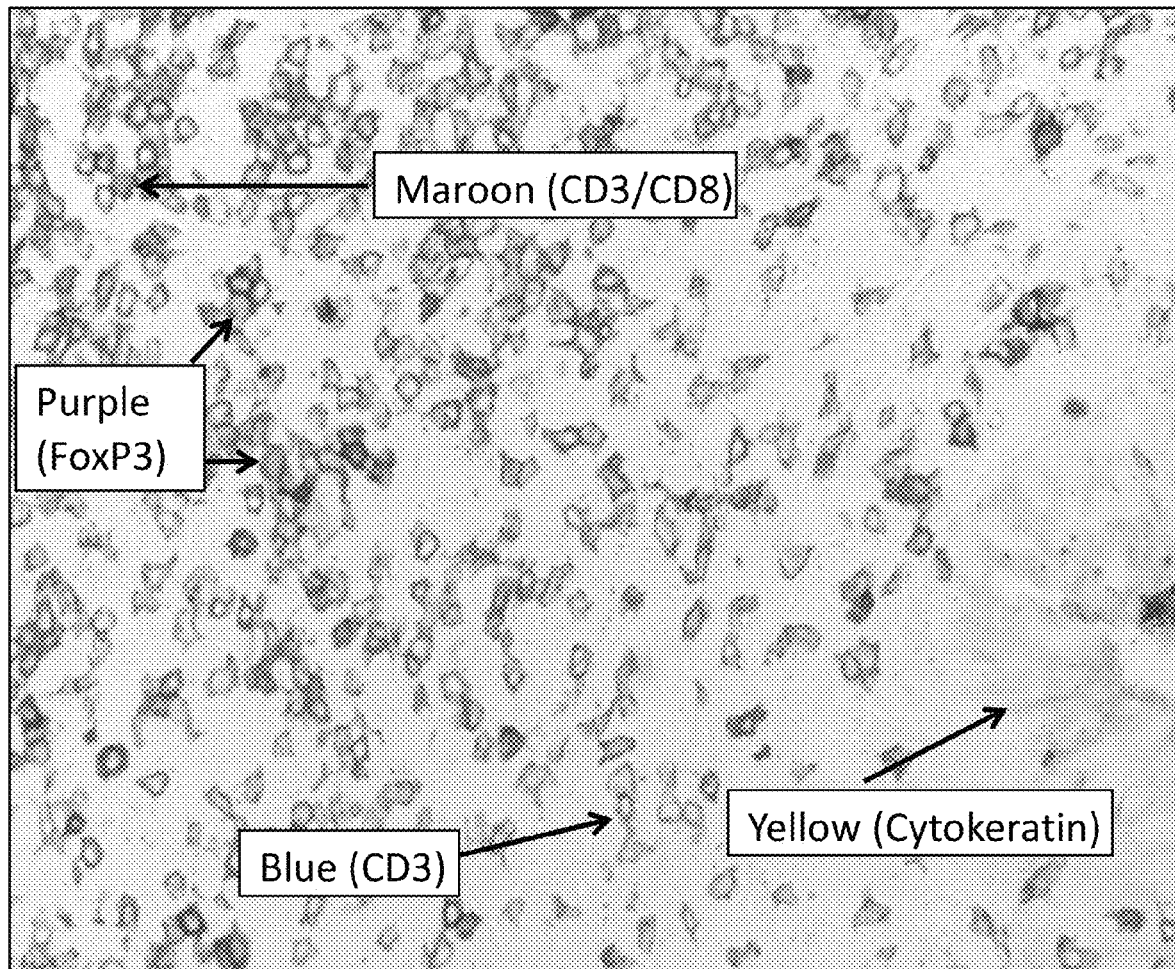
FIG. 9 is a microphotograph from a quadruplex brightfield IHC assay of tonsil tissue at 40× magnification, illustrating sequential detection of CD8 (Tyr-Rhodamine-110, maroon), CD3 (QM-Cy5, blue), FoxP3 (Tyr-Tamra, purple) and Pan-keratin (QM-PEG8-Dabsyl, yellow).

FIGS. 8(A) and 8)B) and illustrate the results of simultaneous antibody incubation followed by sequential chromogenic detection. In FIGS. 8(A) and 8(B), Her2 is detected by a GAR antibody conjugated to HRP, and Pan-keratin is contacted with a GAM antibody conjugated to AP. Sequential detection by Tyramide-Tamra and QMP-PEG$_8$-Dabsyl resulted in the image shown in FIG. 8(A). And FIG. 9 shows the results of a quadruplex sequential detection assay, detecting CD8 (Tyr-Rhodamine-110, maroon), CD3 (QMP-Cy5, blue), FoxP3 (Tyr-Tamra, purple) and Pan-keratin (QMP-Dabsyl, yellow) on tonsil tissue.

Figure 10:
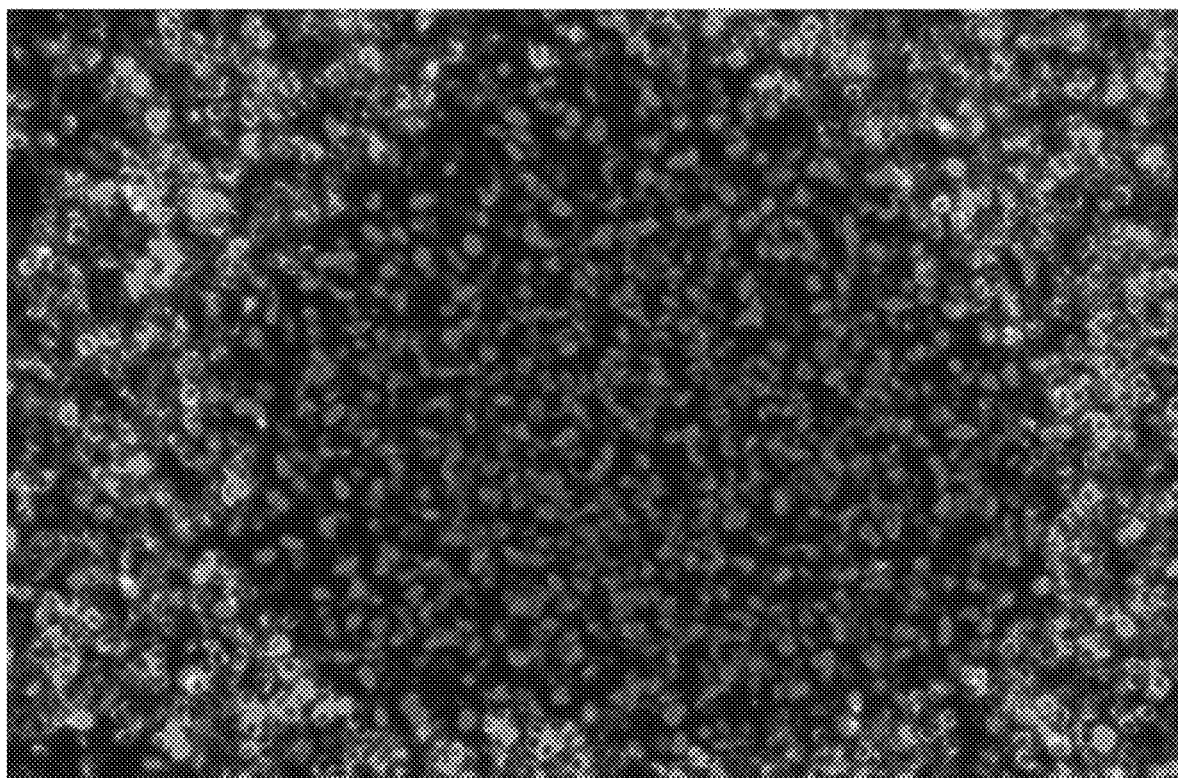
FIG. 10 is a microphotograph of a fluorescent duplex assay utilizing both AP-based QMP (Ki67, dark red, nuclear) and HRP-based TSA (Bcl2, light green, membrane) detections on FFPE tonsil tissue.

In certain embodiments, two targets are detected, either sequentially or substantially simultaneously, in a duplex assay. The detection precursors may be, for example, two QMPs comprising different enzyme recognition groups, or a QMP and a non-QMP-based detection method, such as HRP-based TSA. In certain embodiments, a duplex assay comprises a QMP comprising a phosphate, and a tyramine, for reaction with an alkaline phosphatase and HRP respectively. The detection method may be chromogenic or fluorescent IHC. FIG. 10 provides a microphotograph from a fluorescent duplex assay utilizing both AP-based QMP and HRP-based TSA detections, but without an enzyme kill step. In other embodiments, a duplex assay comprises a QMP comprising a phosphate and a QMP comprising a β-galactoside.

A triplex assay may be used to detect three targets. A triplex assay may use three QMPs with different enzyme recognition groups, or a combination of QMPs and other detection methods, such as HRP-based TSA. In certain embodiments, a triplex assay includes a QMP comprising a phosphate, a QMP comprising a β-galactoside and a tyramine, for reaction with an alkaline phosphatase, a β-galactosidase and HRP respectively. The assay may be a sequential assay or a substantially simultaneous assay. In some embodiments, the detection method is chromogenic IHC.

A quadruplex assay may be used to detect four targets. A quadruplex assay may use four QMPs with different enzyme recognition groups, or a combination of QMPs and other detection methods, such as HRP-based TSA. In some embodiments, the quadruplex assay comprises the sequential addition of a QMP comprising a phosphate which reacts with an alkaline phosphatase, a QMP comprising a β-galactoside which reacts with a β-galactosidase and two sequential additions of tyramine, each of which reacts with HRP. In other embodiments, the quadruplex assay comprises a QMP comprising a phosphate which reacts with an alkaline phosphatase, a QMP comprising a β-galactoside which reacts with a β-galactosidase, and tyramine and DAB, each of which react with HRP. The detection method for a quadruplex may be chromogenic IHC.

In multiplexing assays that use different enzymes for each detection step, the presently described assays do not require enzyme kill steps, thereby reducing time and reagent waste. In addition, because the QM and TSA bind to different reactive sites on tissue, co-expressing markers can be confidently detected without the possibility of the first detection step exhausting the reactive sites for the second.

Some embodiments concern a method for labeling an oligonucleotide. An oligonucleotide is combined with a QMP comprising (i) a enzyme recognition group, and (ii) a detectable label as described herein. An enzyme (e.g., a phosphatase, phosphodiesterase, etc.) then is added to the combined oligonucleotide and QMP. The enzyme catalyzes conversion of the QMP into a reactive QM which covalently binds to the oligonucleotide to form a labeled oligonucleotide. In some embodiments, the detectable label is a hapten, such as a fluorophore. In one embodiment, the QMP comprises a phosphate or phosphodiester group and the enzyme is alkaline phosphatase. In some embodiments, the QMP is used in an ISH amplification assay, such as to detect gene amplification.

In certain embodiments, the oligonucleotide is a detection probe capable of recognizing and binding specifically to a target within a sample, such as a biological sample. The method may further include contacting the sample with the labeled oligonucleotide, whereby the labeled oligonucleotide binds to the target, and then detecting the target by detecting the label. In contrast to some oligonucleotide labeling agents (e.g., aziridinium-based reagents (e.g., Mirus, Madison, WI)), certain embodiments of hapten- or fluorophore-labeled QMPs are not toxic.

Functional staining performance of QMPs is sensitive to several factors including reaction time, temperature, substrate concentration, salt concentration and the pH of the reaction media. An effective pH may be from greater than 7 to 14, such as from 8 to 12, or from 9 to 11. The QMP concentration may be from greater than zero to 1 mM or greater, such as from 50 nM to 500 μM, from 50 nM to 100 μM, or from 100 nM to 1 μM. In certain embodiment concerning chromogenic staining, the concentration is from 10 μM to 750 μM, or from 50 μM to 500 μM. In certain embodiments concerning fluorescent staining and/or hapten amplification, the concentration is from 10 nM to 50 μM, or from 50 nM to 10 μM. These factors allow both the intensity and diffusivity of the stain to be altered in a predictable manner. However, a person of ordinary skill in the art will appreciate that the staining conditions should also be compatible with the enzyme. For example, changing the buffer, pH, cofactors, etc. to such a degree that the enzyme's activity is substantially reduced may have a negative effect on the staining performance of the QMP.

Figure 11:
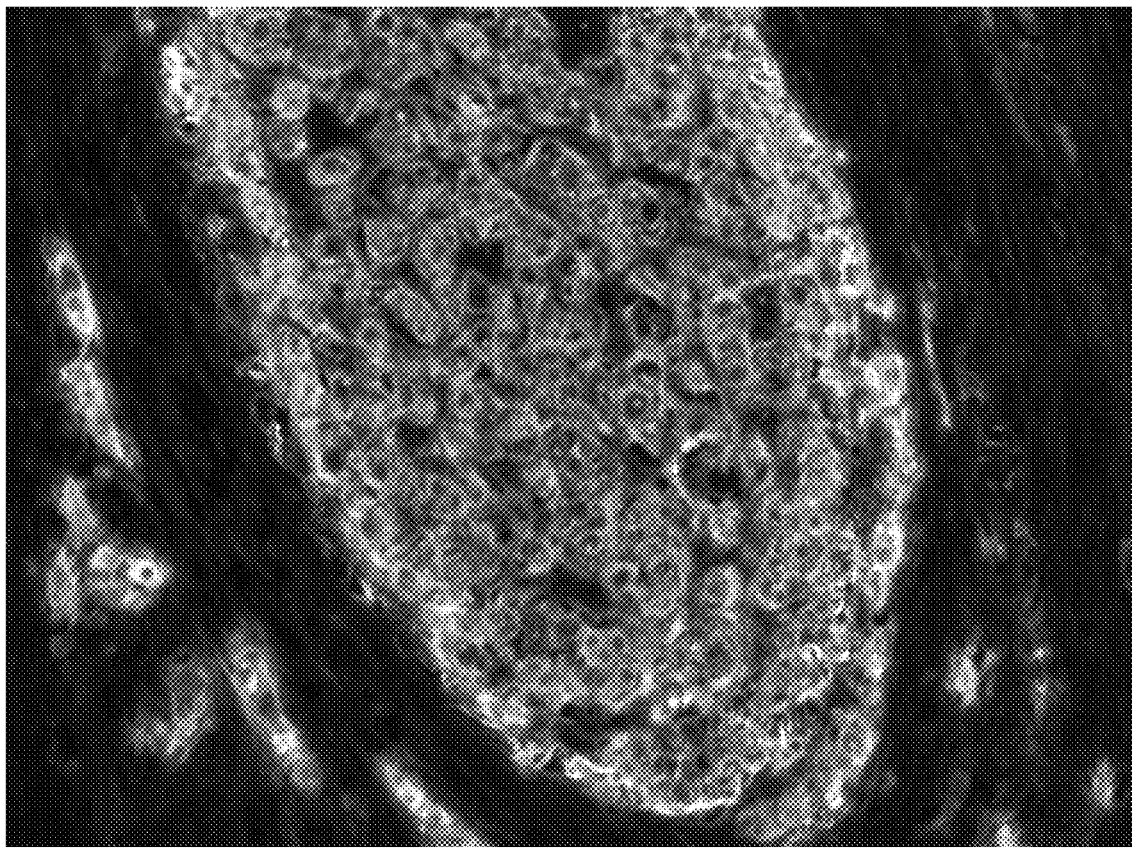
FIG. 11 is a microphotograph of quinone methide staining of E-cadherin on breast tissue at pH 7.5.
Figure 12:
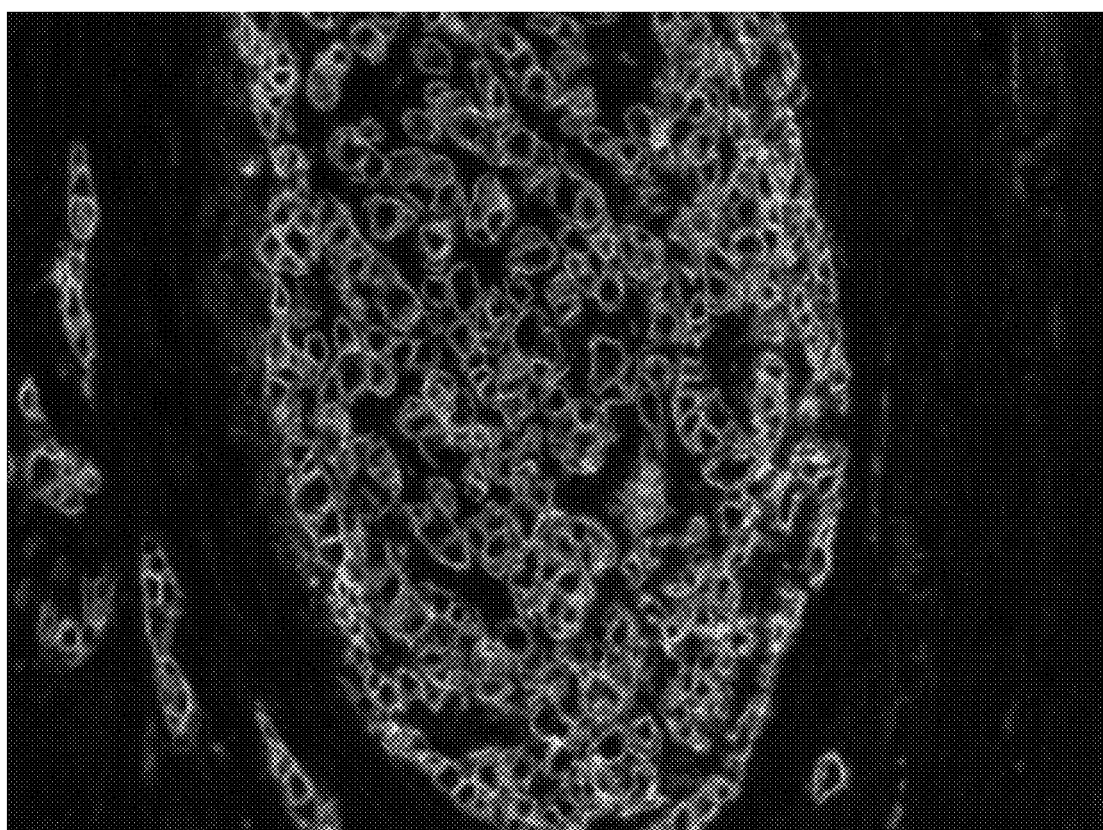
FIG. 12 is a microphotograph of quinone methide staining of E-cadherin on breast tissue at pH 10.

An example of the pH effect is illustrated by FIGS. 11 and 12. Without being bound to a particular theory, at a relatively low pH of 7.5, fewer hydroxide nucleophiles were present in the reaction media. The result was longer QM lifetime, leading to more intense signal along with greater diffusion (FIG. 11). Increasing the pH to 10 increased the concentration of hydroxide nucleophiles, effectively decreasing QM lifetime. The result was decreased signal with much less diffusion (FIG. 12).

An effective salt concentration may be from greater than zero to at least 2 M, such from 0.1 M to 2 M, from 0.25 M to 1.5 M, or from 0.5 M to 1.25 M. In certain embodiments, the salt concentration is about 1 M. The salt may be any salt effective to act as a cofactor of the enzyme, to improve signal intensity and/or to improve staining quality. Signal quality may be improved due to an improvement in signal localization, discreteness, and/or reduced diffusion. In some embodiments, the salt is magnesium chloride or sodium chloride.

IV. Quinone Methide Analog Conjugates

Also within the scope of the present disclosure are conjugates including embodiments of the disclosed QMs. In some embodiments, a conjugate comprises a QM covalently bound to another substance, e.g., a biological sample, an oligonucleotide, an antibody, or an enzyme. The bound QM has a general structure according to formulas VII or VIII:

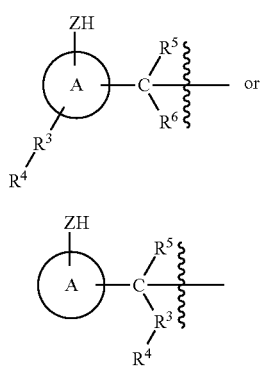

wherein A is a conjugated system; Z is O, S or $NR^a$ where $R^a$ is hydrogen or aliphatic, typically alkyl; $R^3$ is a bond or a linker; $R^4$ is a detectable label; and $R^5$ and $R^6$ independently are hydrogen, halo, cyano, lower alkyl, lower haloalkyl, —C(O)alkyl, —C(S)alkyl, —C(O)OH, —C(O)Oalkyl, —C(O)$NHR^c$ or —C(O)$N(R^c)_2$ where each $R^c$ independently is hydrogen, aryl, aliphatic or heteroaliphatic, or two $R^c$ moieties together form a heteroaliphatic ring. In certain examples, $R^4$ is a hapten, a chromogen, a fluorophore, or a luminophore.

V. Automated Embodiments

A person of ordinary skill in the art will appreciate that embodiments of the method disclosed herein for using QMPs can be automated. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. published application Nos. 20030211630 and 20040052685, each of which is incorporated herein by reference.

VI. Targets

Embodiments of the QMP and method disclosed herein may be used to identify and/or quantify many different biological targets. Throughout this disclosure when reference is made to a target, it is understood that the target may be a target protein and that any polynucleotides associated with that protein can also be used as a target. The target may be a protein or nucleic acid molecule from a pathogen, such as a virus, bacteria, or intracellular parasite, such as from a viral genome. For example, a target protein may be produced from a target polynucleotide associated with (e.g., correlated with, causally implicated in, etc.) a disease. In certain disclosed embodiments, the target (or targets) of interest may be a particular nucleic acid sequence that may comprise a genetic aberration, such as a single nucleotide polymorphism, promoter methylation, mRNA expression, siRNA, a particular copy number change, a mutation, a certain expression level, a rearrangement, or combination thereof. In some embodiments, the targets are soluble proteins obtained from biological samples, such as serum, plasma, and/or urine. Some embodiments of the disclosed method may be used to detect and quantify DNA, RNA, and proteins of the same target (e.g., HER2) simultaneously from the same sample (e.g., from the same tissue section).

The disclosed method may be used to detect microRNA (miRNA or miR). MicroRNAs are small, non-coding RNAs that negatively regulate gene expression, such as by translation repression. For example, miR-205 regulates epithelial to mesenchymal transition (EMT), a process that facilitates tissue remodeling during embryonic development. However, EMT also is an early step in tumor metastasis. Down-regulation of microRNAs, such as miR-205, may be an important step in tumor progression. For instance, expression of miR-205 is down-regulated or lost in some breast cancers. MiR-205 also can be used to stratify squamous cell and non-small cell lung carcinomas (*J. Clin. Oncol.*, 2009, 27(12):2030-7). Other microRNAs have been found to modulate angiogenic signaling cascades. Down-regulation of miR-126, for instance, may exacerbate cancer progression through angiogenesis and increased inflammation. Thus, microRNA expression levels may be indicative of a disease state.

A target nucleic acid sequence can vary substantially in size. Without limitation, the nucleic acid sequence can have a variable number of nucleic acid residues. For example a target nucleic acid sequence can have at least about 10 nucleic acid residues, or at least about 20, 30, 50, 100, 150, 500, 1000 residues. Similarly, a target polypeptide can vary substantially in size. The target polypeptides typically include at least one epitope that binds to a peptide specific antibody, or fragment thereof. In some embodiments that polypeptide can include at least two epitopes that bind to a peptide specific antibody, or fragment thereof.

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. In some examples, therefore, at least a portion of the target molecule is produced by a nucleic acid sequence (e.g., genomic target nucleic acid sequence) amplified or deleted in at least a subset of cells in a sample. In one example, the genomic target nucleic acid sequence is selected to include a gene (e.g., an oncogene) that is reduplicated in one or more malignancies (e.g., a human malignancy). Oncogenes are known to be responsible for several human malignancies.

For example, chromosomal rearrangements involving the SYT gene located in the breakpoint region of chromosome 18q11.2 are common among synovial sarcoma soft tissue tumors.

For example, HER2, also known as c-erbB2 or HER2/neu, is a gene that plays a role in the regulation of cell growth (a representative human HER2 genomic sequence is provided at GENBANK™ Accession No. NC_000017, nucleotides 35097919-35138441). The gene codes for a 185 kDa transmembrane cell surface receptor that is a member of the tyrosine kinase family. HER2 is amplified in human breast, ovarian, and other cancers; therefore, a HER2 gene (or a region of chromosome 17 that includes the HER2 gene) can be used as a genomic target nucleic acid sequence. Other breast cancer relevant proteins include the estrogen receptor (ER) and progesterone receptor (PR).

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods.

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as Plasmodium falciparum and other Plasmodium species, Leishmania (sp.), *Cryptosporidium parvum*, Entamoeba *histolytica*, and *Giardia* lamblia, as well as Toxoplasma, Eimeria, Theileria, and Babesia species). In some examples, the target protein is produced from a nucleic acid sequence (e.g., genomic target nucleic acid sequence) from a viral genome.

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

VII. Kits

In illustrative embodiments, a kit includes a composition comprising a QMP disclosed herein. In certain embodiments, a kit also comprises one or more enzyme-antibody conjugates, such as a phosphatase-antibody conjugate or a phosphodiesterase-antibody conjugate. In some examples, the kit includes an alkaline phosphatase/anti-species antibody conjugate or an alkaline-phosphatase/anti-hapten antibody conjugate. The kit may also include a pH adjust, and/or enzyme cofactors.

In some embodiments, the QMP is stored in an organic solvent, such as DMSO, or in an organic solvent/aqueous buffer mixture, with up to 100% aqueous buffer. The aqueous buffer and/or the storage solution may have a pH of less than 7, such as from pH 0 to pH 5, or from pH 1 to pH 3, and in certain embodiments, the solution has a pH of about 2. The storage solution may also comprise one or more salts, such as magnesium chloride or sodium chloride. In some embodiments, the concentration of the salt is from greater than zero to 2 M, such as from 0.25 M to about 1.5 M, from 0.5 M to 1.25 M, or about 1 M. In exemplary embodiments, the QMP storage solution comprises the QMP in a mixture of DMSO and 10 mM glycine at pH 2, and with a concentration of magnesium chloride of up to 1 M.

In some embodiments, the pH adjust is a solution suitable for adjusting the pH of a solution from a pH suitable for storage of a QMP to a pH suitable to enable effective use of a QMP in a staining and/or amplification assay. The storage pH may be from pH 0 to pH 5, and the pH suitable for effective use of the QMP may be from pH 8 to pH 12. In certain embodiments, the pH adjust comprises a Tris solution at about pH 10, such as a 0.5 M Tris solution, or a Tris solution at about pH 8, such as a 0.25 mM Tris solution.

Exemplary options for the chromogen portion of the kit include, but are not limited to:

3 dispensers—(i) QMP in 100% organic solvent; (ii) pH adjust; (iii) enzyme cofactors; 3 dispensers—(i) QMP in organic/aqueous buffer mix (up to 100% buffer); (ii) pH adjust; (iii) enzyme cofactors; and 2 dispensers—(i) QMP in organic/aqueous buffer mix (up to 100% buffer)+enzyme cofactors; (ii) pH adjust.

A person of ordinary skill in the art will appreciate that in the kit, the enzyme and the antibody conjugates are typically stored separately to prevent unwanted reactions in storage.

VIII. EXAMPLES

The following examples are provided to illustrate certain specific features of working embodiments and general protocols. The scope of the present invention is not limited to those features exemplified by the following examples.

Example 1

Synthesis and Characterization of QMPs

Synthetic Materials and Methods. NMR data was collected on a Bruker 400 MHz Spectrometer running Topspin (Bruker). Chemical shifts were referenced to the deuterated solvent resonance for $^3$H (7.26 ppm for CDCl$_3$, 2.50 ppm for DMSO-d$_6$, and 3.31 ppm for CD$_3$OD) and $^{13}$C (77.0 ppm for CDCl$_3$, 39.51 ppm for DMSO-d$_6$, and 49.15 ppm for CD$_3$OD). Chemical shifts were referenced to external standards for $^{31}$P (0 ppm for H$_3$PO$_4$) and $^{19}$F (76.55 ppm for trifluoroacetic acid). MS data was collected on a JEOL ESI-TOF (AccuTOF JMS-T100LC) running Mass Center (JEOL). Prep HPLC was performed on a Waters 2535 with Waters Sunfire columns (Prep C$_{18}$ OBD 10 μm 50×250 mm) running Empower 3 (Waters). All chemicals were purchased from commercial suppliers and used as received unless otherwise noted.

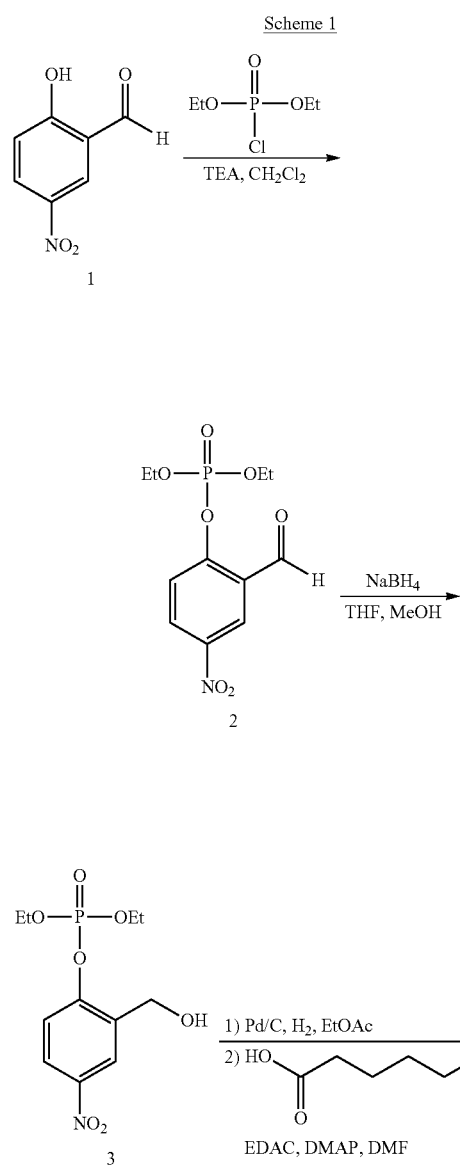

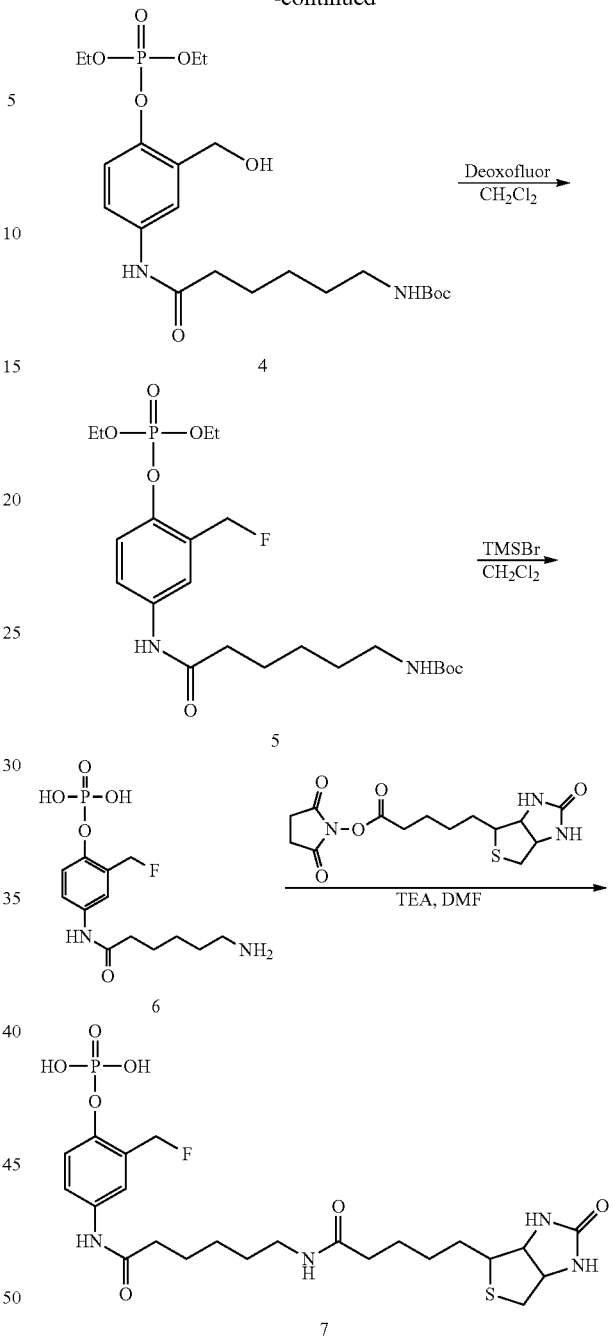

Compound 2. 5-Nitrosalicylaldehyde (1) (10.0 g, 59.8 mmol) was suspended in CH$_2$Cl2 (100 mL) followed by addition of triethylamine (12.1 g, 120 mmol) and diethyl chlorophosphate (15.5 g, 89.7 mmol) in a round bottom flask. The reaction mixture was stirred at room temperature for 1 hour. The reaction mixture was then extracted with 0.5M HCl (100 mL), the organic layer collected and dried over MgSO$_4$. The suspension was filtered, the filtrate collected and the solvents removed under reduced pressure. The resulting residue was purified by flash chromatography in two batches (hexanes:EtOAc) to give compound 2 as a colorless viscous oil (15.4 g, 85% yield): $^1$H NMR (400 MHz, CDCl$_3$) δ 10.37 (s, 1H), 8.70 (dd, J=8.4 Hz and 1.0 Hz, 1H), 8.42 (dd, J=9.0 Hz and 2.8 Hz, 1H), 7.69 (dd, J=9.0

Hz and 1.0 Hz, 1H), 4.28 (m, 4H), 1.37 (m, 6H); $^{13}$C NMR (125 MHz, CDCl$_3$) δ 186.2, 156.64, 156.58, 129.9, 127.5, 127.4, 124.5, 122.1, 122.0, 65.7, 65.6, 16.1, 16.0; MS (ESI) m/z (M+H)$^+$ calcd for $C_{11}H_{15}NO_7P^+$ 304.1, found 303.7.

Compound 3. Compound 2 (3.50 g, 11.5 mmol) was dissolved in a mixture of THF and MeOH (1:1, 40 mL) followed by addition of NaBH$_4$ (655 mg, 17.3 mmol) in a round bottom flask. The reaction mixture was stirred at room temperature for 2 hours. The reaction was then quenched with 0.5M HCl (40 mL) and the resulting solution extracted with EtOAc (3×100 mL). The organic layers were combined and dried over MgSO$_4$. The suspension was filtered, the filtrate collected and the solvents removed under reduced pressure. The resulting residue was purified by flash chromatography (hexanes:EtOAc) to give compound 3 as a colorless viscous oil (2.55 g, 73% yield): $^1$H NMR (400 MHz, CDCl$_3$) δ 8.39 (d, J=2.4 Hz, 1H), 8.13 (dd, J=9.0 Hz and 2.8 Hz, 1H), 7.38 (dd, J=9.0 Hz and 1.0 Hz, 1H), 4.73 (s, 2H), 4.24 (m, 4H), 1.37 (m, 6H); $^{13}$C NMR (125 MHz, CDCl$_3$) δ 152.6, 152.5, 145.1, 134.6, 134.5, 125.3, 124.3, 121.1, 121.0, 65.65, 65.59, 59.3, 16.12, 16.06; MS (ESI) m/z (M+H)$^+$ calcd for $C_{11}H_{17}NO_7P^+$ 306.1, found 305.7.

Compound 4. Compound 3 (2.00 g, 6.55 mmol) was dissolved in EtOAc (50 mL) in a round bottom flask followed by addition of Pd/C (200 mg). The flask was sealed and stirred under a H$_2$ atmosphere for 16 hours, at which point the reaction mixture was diluted with CH$_2$Cl$_2$ (10 mL). A spatula-tip of celite was then added and the reaction mixture filtered. The filtrate was collected and the solvents removed under reduced pressure to give a colorless oil. The oil was dissolved in DMF (20 mL) followed by addition of DMAP (80 mg, 0.655 mmol), EDAC (1.38 g, 7.21 mmol), and N-boc-aminocaproic acid (1.67 g, 7.21 mmol) in a round bottom flask. The reaction mixture was stirred at room temperature for 16 hours, followed by quenching with H$_2$O (20 mL). The resulting emulsion was extracted with EtOAc (3×100 mL), the organic layers combined and dried over MgSO$_4$. The suspension was filtered, the filtrate collected and the solvents removed under reduced pressure. The resulting residue was purified by flash chromatography (hexanes:EtOAc) to give compound 4 as a colorless viscous oil (2.08 g, 65% yield): $^1$H NMR (400 MHz, CDCl$_3$) δ 8.90 (s, 1H), 7.64 (dd, J=8.4 Hz and 2.4 Hz, 1H), 7.40 (d, J=2.4 Hz, 1H), 7.04 (dd, J=9.0 Hz and 1.0 Hz, 1H), 4.84 (br s, 1H), 4.55 (s, 2H), 4.41 (br s, 1H), 4.16 (m, 4H), 3.02 (t, J=6.8 Hz, 2H), 2.27 (t, J=7.2 Hz, 2H), 1.63 (m, 2H), 1.44-1.40 (m, 11H), 1.38-1.32 (m, 8H); $^{13}$C NMR (125 MHz, CDCl$_3$) δ 172.0, 156.1, 143.6, 143.5, 136.25, 133.01, 132.96, 121.3, 120.69, 120.67, 120.3, 79.0, 65.07, 65.01, 59.5, 40.3, 36.9, 29.6, 28.3, 26.2, 25.1, 16.0, 15.9; MS (ESI) m/z (M+H)$^+$ calcd for $C_{22}H_{37}N_2NaO_8P^+$ 511.2, found 510.5.

Compound 5. Compound 4 (600 mg, 1.23 mmol) was dissolved in CH$_2$Cl$_2$ (10 mL) in a sealed scintillation vial and cooled to 0° C. in an ice bath. Deoxo-fluor® (bis(2-methoxyethyl)aminosulfur trifluoride, available from Sigma-Aldrich, 299 mg, 1.35 mmol) was then added drop wise and the reaction vessel sealed. The reaction mixture was stirred at 0° C. for 1 hour, followed by quenching with H$_2$O (10 mL). The organic layer was separated and dried over MgSO$_4$. The suspension was filtered, the filtrate collected and the solvents removed under reduced pressure. The resulting residue was purified by prep RP-HPLC (0.05% TFA in H$_2$O:ACN) to give compound 5 as a colorless viscous oil (420 mg, 70% yield): $^1$H NMR (400 MHz, CDCl$_3$) δ 8.69 (s, 1H), 7.64 (s, 1H), 7.44 (dd, J=9.0 and 0.8 Hz, 1H), 7.19 (dd, J=9.0 Hz and 1.0 Hz, 1H), 5.38 (d, J=76 Hz, 2H), 4.71 (br s, 1H), 4.18 (m, 4H), 3.06 (t, J=7.2 Hz, 2H), 2.29 (t, J=7.6 Hz, 2H), 1.66 (m, 2H), 1.47-1.41 (m, 11H), 1.35-1.31 (m, 8H); $^{13}$C NMR (125 MHz, CDCl$_3$) δ 171.8, 156.1, 144.06, 144.01, 143.99, 143.94, 135.8, 127.74, 127.67, 127.57, 127.50, 121.3, 120.92, 120.85, 120.06, 80.5, 78.9, 64.9, 64.8, 40.4, 36.9, 29.7, 28.3, 26.3, 25.0, 16.02, 15.95; MS (ESI) m/z (M+H)$^+$ calcd for $C_{22}H_{37}FN_2O_7P^+$ 491.2, found 491.5.

Compound 6. Compound 5 (140 mg, 0.286 mmol) was dissolved in CH$_2$Cl$_2$ (3 mL) followed by addition of trimethylsilyl bromide (131 mg, 0.857 mmol) in a scintillation vial. The reaction vessel was sealed and the reaction mixture stirred at room temperature for 16 hours, at which point the reaction was quenched with MeOH (3 mL). The solvents were removed under reduced pressure and the resulting residue directly purified by prep RP-HPLC (0.05% TFA in H$_2$O:ACN) to give compound 6 as a white solid (61 mg, 64% yield): $^1$H NMR (400 MHz, CD$_3$OD) δ 7.68 (s, 1H), 7.52 (d, J=8.0 Hz, 1H), 7.31 (d, J=8.0 Hz, 1H), 5.49 (d, J=48 Hz, 2H), 2.94 (t, J=8.0 Hz, 2H), 2.42 (t, J=8.0 Hz, 2H), 1.78-1.66 (m, 4H), 1.51-1.43 (m, 2H); $^{31}$P NMR (162 MHz, CD$_3$OD) δ-4.83; $^{19}$F NMR (376 MHz, CD$_3$OD) δ-77.5. MS (ESI) m/z (M+H)$^+$ calcd for $C_{13}H_{21}FN_2O_5P^+$ 335.1, found 334.7. $^{13}$C NMR was not determined due to low solubility and lack of signal.

Example of Conjugation to Compound 6:

Compound 7. Compound 6 (50 mg, 0.15 mmol) was dissolved in DMF (2 mL) in a scintillation vial, followed by addition of NHS-biotin (60 mg, 0.16 mmol) and triethylamine (76 mg, 0.75 mmol). The reaction vessel was sealed and stirred at room temperature for 16 hours. The reaction mixture was directly purified by prep RP-HPLC (0.05% TFA in H$_2$O:ACN) to give compound 7 as a white solid (46 mg, 58% yield): $^1$H NMR (400 MHz, DMSO-d$_6$) δ 9.93 (s, 1H), 7.75 (t, J=5.7 Hz, 1H), 7.70 (s, 1H), 7.53 (d, J=8.8 Hz, 1H), 7.21 (d, J=8.8 Hz, 1H), 5.44 (d, J=47.6 Hz, 2H), 4.36-4.24 (m, 1H), 4.17-4.06 (m, 1H), 3.09 (q, J=6.0 Hz, 1H), 3.02 (q, J=6.5 Hz, 2H), 2.81 (dd, J=12.4, 5.0 Hz, 1H), 2.57 (d, J=12.4 Hz, 1H), 2.28 (t, J=7.4 Hz, 2H), 2.03 (t, J=7.3 Hz, 2H), 1.67-1.18 (m, 12H). $^{13}$C NMR (101 MHz, DMSO-d$_6$) δ 171.8, 171.1, 162.7, 135.6, 120.7, 120.4, 119.7, 119.6, 80.5, 78.9, 61.0, 59.2, 55.4, 38.3, 36.2, 35.2, 29.0, 28.2, 28.0, 26.1, 25.3, 24.8. $^{31}$P NMR (162 MHz, DMSO-d$_6$) δ-5.21; $^{19}$F NMR (376 MHz, DMSO-d$_6$) δ-76.57. MS (ESI) m/z (M-H)$^-$ calcd for $C_{23}H_{33}FN_4O_7PS^-$ 559.2, found 559.0.

Scheme 2

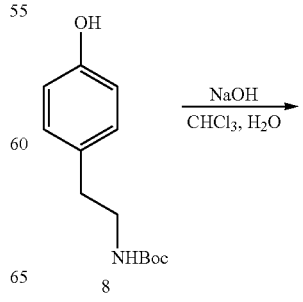

8

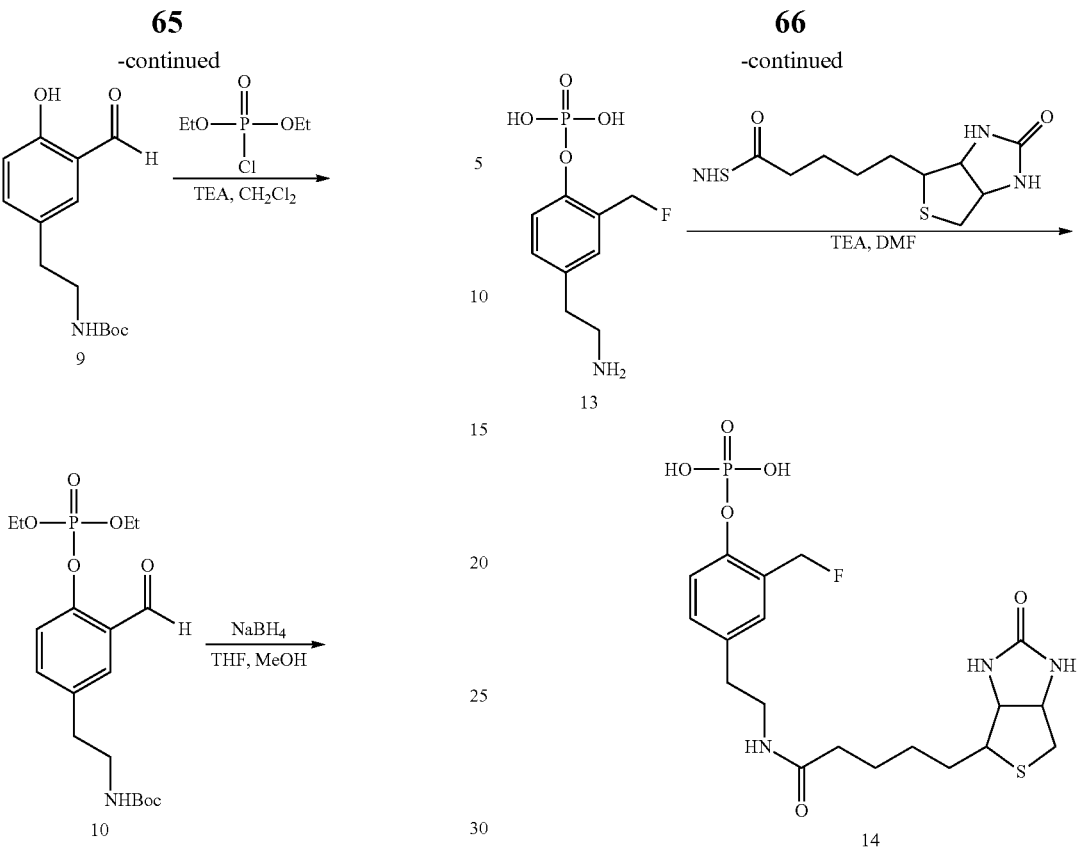

Compound 9. N-Boc-tyramine (10.0 g, 42.1 mmol) 8 was dissolved in CHCl$_3$ (80 mL) followed by addition of H$_2$O (40 mL) in a round bottom flask equipped with a reflux condenser. Powdered NaOH (16.8 g, 421 mmol) was then added and the reaction mixture heated to 60° C. in an oil bath with vigorous stirring. After 1 hour, a second portion of NaOH (8.4 g, 210 mmol) was added and the stirring continued for an additional 1 hour. After 1 hour, a third portion of NaOH (8.4 g, 210 mmol) was added and the stirring continued for an additional 5 hours. The reaction mixture was then extracted with 0.5M HCl, the organic layer collected and dried over MgSO$_4$. The suspension was filtered, the filtrate collected and the solvents removed under reduced pressure. The resulting residue was purified by flash chromatography (hexanes:EtOAc) to give compound 9 as an off-white low-melting solid (5.43 g, 49% yield): $^1$H NMR (400 MHz, CDCl$_3$) δ 10.9 (s, 1H), 9.86 (s, 1H), 7.36 (d, J=20 Hz, 2H), 6.94 (d, J=20 Hz, 1H), 4.58 (br s, 1H), 3.34 (br s, 2H), 2.79 (t, J=6.8 Hz, 2H), 1.43 (s, 9H); $^{13}$C NMR (125 MHz, CDCl$_3$) δ 196.5, 160.3, 155.9, 137.6, 133.4, 130.4, 120.5, 117.8, 79.4, 41.7, 35.1, 28.4; MS (ESI) m/z (M–H)$^-$ calcd for C$_{14}$H$_{18}$NO$_4^-$ 264.1, found 264.1.

Compound 10. Compound 9 (2.00 g, 7.54 mmol) was dissolved in CH$_2$Cl$_2$ (50 mL) followed by addition of triethylamine (1.53 g, 15.1 mmol) and diethyl chlorophosphate (1.95 g, 11.3 mmol) in a round bottom flask. The reaction mixture was stirred at room temperature for 4 hours. The reaction mixture was then extracted with 0.5M HCl (50 mL), the organic layer collected and dried over MgSO$_4$. The suspension was filtered, the filtrate collected and the solvents removed under reduced pressure. The resulting residue was purified by flash chromatography (hexanes:EtOAc) to give compound 10 as a colorless viscous oil (2.20 g, 73% yield): $^1$H NMR (400 MHz, CDCl$_3$) δ 10.3 (s, 1H), 7.66 (s, 1H), 7.38-7.34 (m, 2H), 4.66 (br s, 1H), 4.21 (m, 4H), 3.32

(br s, 2H), 2.78 (t, J=7.2 Hz, 2H), 1.38-1.30 (m, 15H); $^{13}$C NMR (125 MHz, CDCl$_3$) δ 188.4, 155.7, 151.4, 151.3, 136.5, 136.0, 128.6, 127.10, 127.04, 121.17, 121.14, 79.2, 65.03, 64.97, 41.4, 35.3, 28.3, 16.02, 15.95; MS (ESI) m/z (2M+Na)$^+$ calcd for $C_{36}H_{56}N_2NaO_{14}P_2^+$ 825.3, found 825.3.

Compound 11. Compound 10 (1.00 g, 2.49 mmol) was dissolved in a mixture of THF and MeOH (1:1, 10 mL) followed by addition of NaBH$_4$ (141 mg, 3.74 mmol) in a round bottom flask. The reaction mixture was stirred at room temperature for 3 hours. The reaction was then quenched with 0.5M HCl (10 mL) and the resulting solution extracted with CH$_2$Cl$_2$ (3×25 mL). The organic layers were combined and dried over MgSO$_4$. The suspension was filtered, the filtrate collected and the solvents removed under reduced pressure. The resulting residue was purified by flash chromatography (hexanes:EtOAc) to give compound 11 as a colorless viscous oil (540 mg, 53% yield): $^1$H NMR (400 MHz, CDCl$_3$) δ 7.29 (s, 1H), 7.14 (s, 2H), 4.65 (s, 2H), 4.60 (br s, 1H), 4.27 (m, 4H), 3.37 (br s, 2H), 2.80 (t, J=6.8 Hz, 2H), 1.45 (s, 9H), 1.39 (t, J=6.8 Hz, 6H); $^{13}$C NMR (125 MHz, CDCl$_3$) δ 155.8, 146.9, 146.8, 136.8, 133.04, 133.00, 131.4, 129.5, 121.12, 121.10, 79.3, 65.13, 65.07, 60.2, 41.6, 35.5, 28.4, 16.11, 16.04; MS (ESI) m/z (M+H)$^+$ calcd for $C_{18}H_{31}NO_7P^+$ 404.2, found 404.2.

Compound 12. Compound 11 (250 mg, 0.620 mmol) was dissolved in CH$_2$Cl$_2$ (5 mL) in a sealed scintillation vial and cooled to 0° C. in an ice bath. Deoxo-fluor® (bis(2-methoxyethyl)aminosulfur trifluoride, available from Sigma-Aldrich, 151 mg, 0.682 mmol) was then added drop wise and the reaction vessel sealed. The reaction mixture was stirred at 0° C. for 15 minutes, followed by quenching with H$_2$O (5 mL). The organic layer was separated and dried over MgSO$_4$. The suspension was filtered, the filtrate collected and the solvents removed under reduced pressure. The resulting residue was purified by prep RP-HPLC (0.05% TFA in H$_2$O:ACN) to give compound 12 as a colorless viscous oil (110 mg, 44% yield): $^1$H NMR (400 MHz, CDCl$_3$) δ 7.30-7.25 (m, 2H), 7.15 (d, J=8.4 Hz, 1H), 5.45 (d, J=48 Hz, 2H), 4.70 (br s, 1H), 4.25-4.17 (m, 4H), 3.34 (br s, 2H), 2.78 (t, J=7.2 Hz, 2H), 1.42 (s, 9H), 1.34 (t, J=6.8 Hz, 6H); $^{13}$C NMR (125 MHz, CDCl$_3$) δ 155.8, 146.91, 146.86, 146.84, 146.79, 136.0, 130.3, 129.7, 129.6, 127.6, 127.5, 127.4, 127.3, 119.9, 80.5, 79.2, 78.8, 64.82, 64.76, 41.6, 35.3, 28.2, 16.0, 15.9; MS (ESI) m/z (M+H)$^+$ calcd for $C_{18}H_{30}FNO_6P^+$ 406.2, found 405.7.

Compound 13. Compound 12 (110 mg, 0.247 mmol) was dissolved in CH$_2$Cl$_2$ (1 mL) followed by addition of trimethylsilyl bromide (TMSB) (113 mg, 0.740 mmol) in a scintillation vial. The reaction vessel was sealed and the reaction mixture stirred at room temperature for 16 hours, at which point the reaction was quenched with MeOH (1 mL). The solvents were removed under reduced pressure and the resulting residue directly purified by prep RP-HPLC (0.05% TFA in H$_2$O:ACN) to give compound 13 as a white solid (45 mg, 72% yield): $^1$H NMR (400 MHz, DMSO-d$_6$) δ 7.25 (d, J=9.6 Hz, 2H), 7.17 (d, J=8.4 Hz, 1H), 5.38 (d, J=48 Hz, 2H), 3.00 (t, J=7.6 Hz, 2H), 2.83 (t, J=7.6 Hz, 2H); $^{31}$P NMR (162 MHz, DMSO-d$_6$) δ 0.22; $^{19}$F NMR (376 MHz, DMSO-d$_6$) δ-75.6. MS (ESI) m/z (M-H)$^-$ calcd for $C_9H_{12}FNO_4P^-$ 248.0, found 248.0. $^{13}$C NMR was not determined due to low solubility and lack of signal.

Example of Detectable Label Conjugation to Compound 13:

Compound 14. Compound 13 (15 mg, 0.060 mmol) was dissolved in DMF (2 mL) in a scintillation vial, followed by addition of NHS-biotin (23 mg, 0.066 mmol) and triethylamine (18 mg, 0.18 mmol). The reaction vessel was sealed and stirred at room temperature for 16 hours. The reaction mixture was directly purified by prep RP-HPLC (0.05% TFA in H$_2$O:ACN) to give compound 14 as a white solid (25 mg, 86% yield): $^1$H NMR (400 MHz, CD$_3$OD) δ 7.33-7.21 (m, 3H), 5.42 (d, J=48 Hz, 2H), 4.52-4.49 (m, 1H), 4.31-4.28 (m, 1H), 3.43-3.40 (m, 2H), 3.19-3.17 (m, 1H), 2.96-2.92 (m, 1H), 2.83-2.79 (m, 2H), 2.72 (d, J=13 Hz, 1H), 2.15 (t, J=7.2 Hz, 2H), 1.71-1.57 (m, 4H), 1.48-1.38 (m, 2H); $^{13}$C NMR (125 MHz, CD$_3$OD) δ 176.3, 166.3, 149.15, 149.09, 149.04, 137.4, 131.4, 130.9, 130.8, 129.7, 129.6, 129.5, 129.4, 121.5, 81.8, 80.1, 63.6, 61.8, 57.1, 41.8, 41.2, 36.9, 35.8, 29.8, 29.6, 27.1; $^{31}$P NMR (162 MHz, CD$_3$OD) δ-5.12; $^{19}$F NMR (376 MHz, CD$_3$OD) δ-77.3. MS (ESI) m/z (M-H)$^-$ calcd for $C_{19}H_{26}FN_3O_6PS^-$ 474.1, found 474.0.

Additional examples of detectable label conjugation to compound 13 are shown in Scheme 3.

Scheme 3

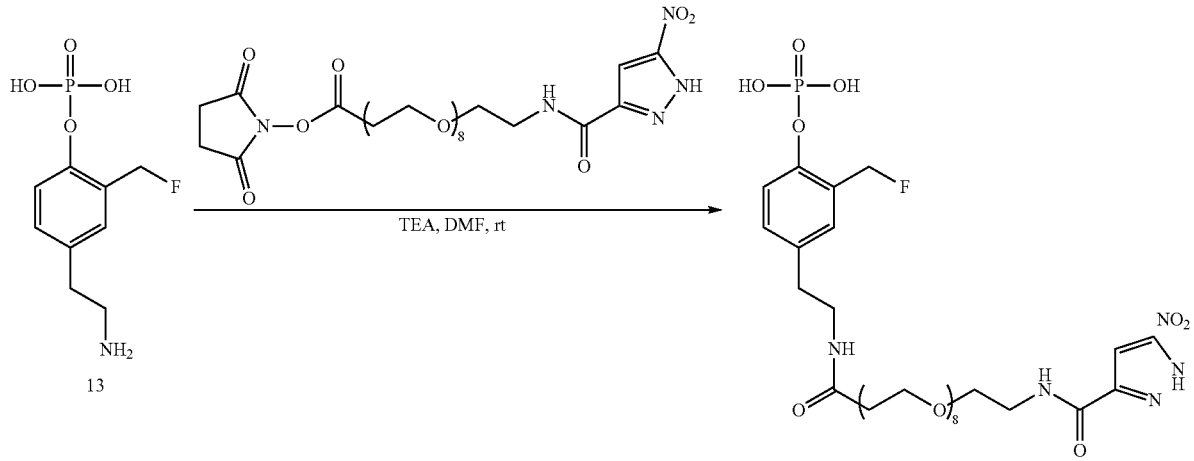

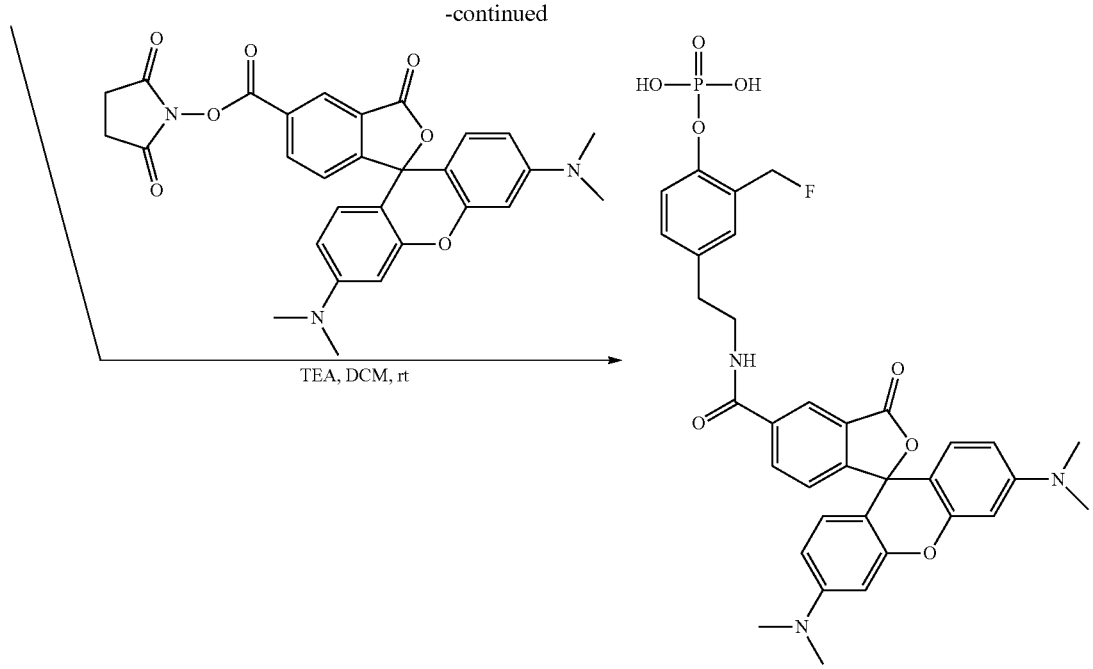
Additional QMPs can be synthesized according to Schemes 4-10.
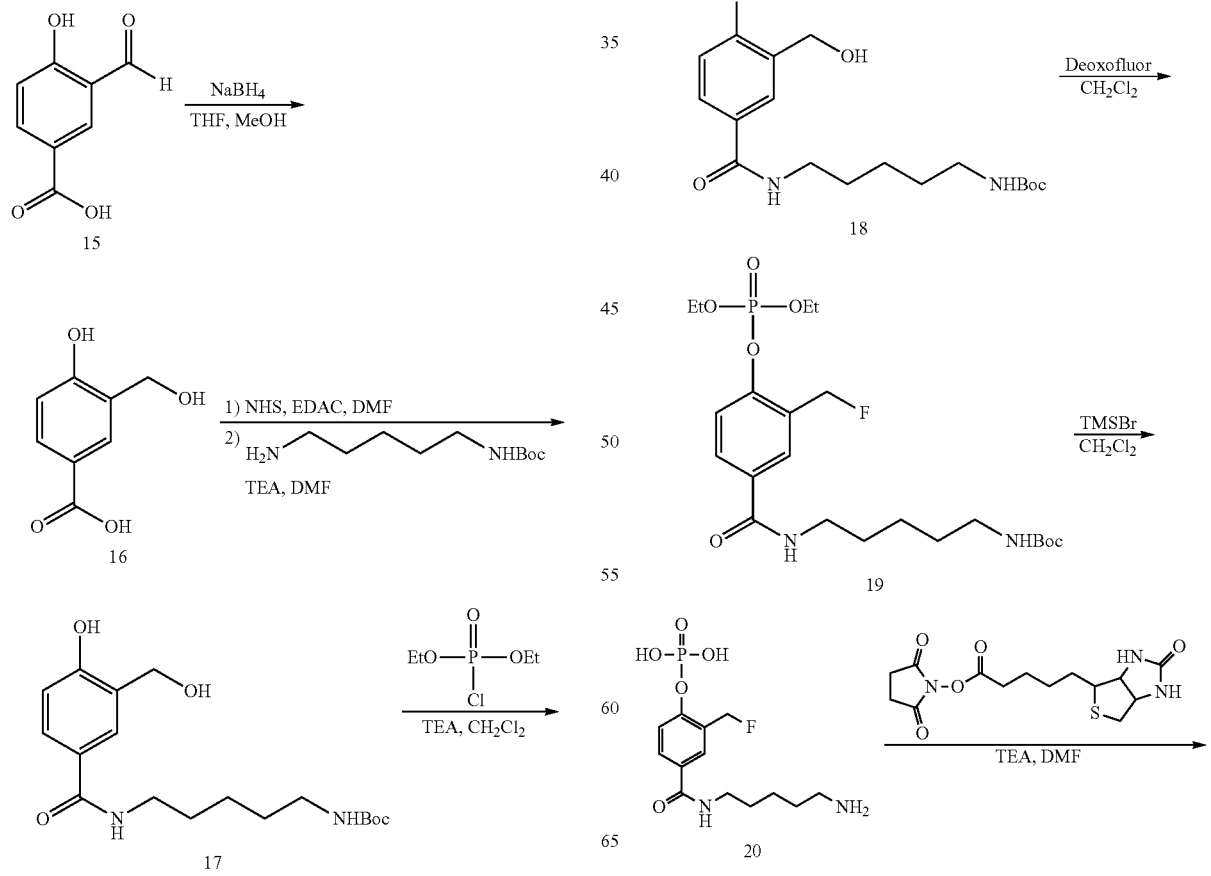

-continued

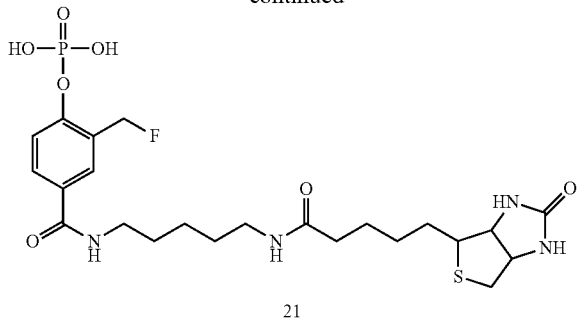

21

Compound 15 is treated with sodium borohydride in THF and methanol to form compound 16. Compound 16 is then treated first with N-hydroxysuccinimide in the presence of a carbodiimide crosslinking agent such as 1-ethyl-3-(3-dimethylaminopropyl)carbodiimide (EDAC), in DMF to form an activated acid (not shown). The activated acid compound is then reacted with 1-BOC pentanediamine in DMF and in the presence of a base such as triethylamine, to form compound 17. Compound 17 is then reacted with diethyl chlorophosphate and triethylamine in dichloromethane to form compound 18, by the method used to make compound 10 in Scheme 2, above. Compound 18 is then reacted with Deoxo-fluor® in dichloromethane to form compound 19, which in turn, is reacted with trimethylsilyl bromide (TMSB) to form the deprotected amine compound 20. Compound 20 is then conjugated to biotin to form compound 21. The methods to make compounds 19, 20 and 21 are the same as those used for compounds 12, 13 and 14 in Scheme 2, above.

Scheme 5

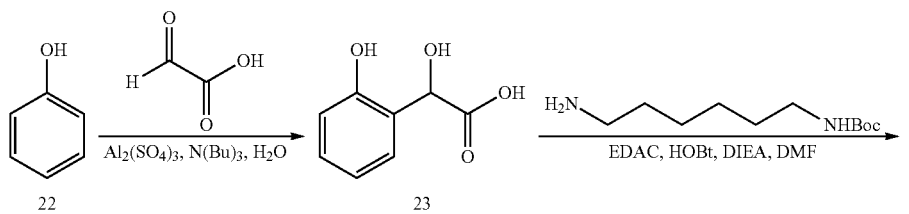

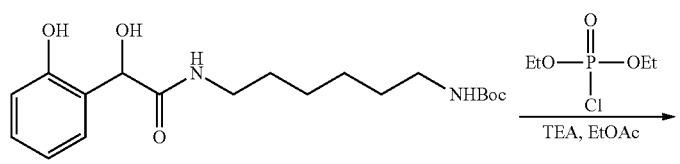

24

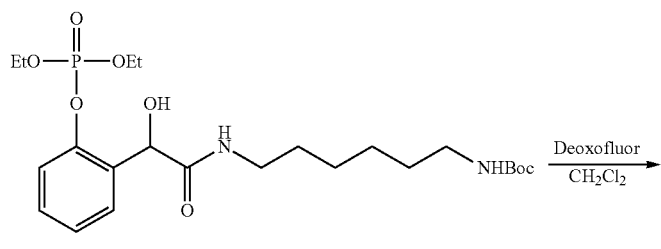

25

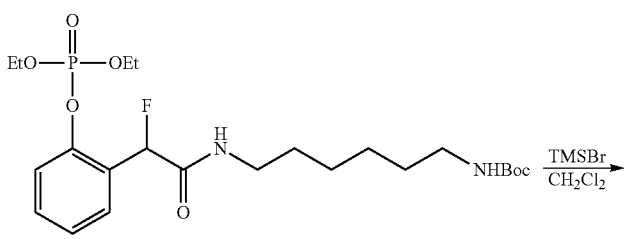

26

-continued
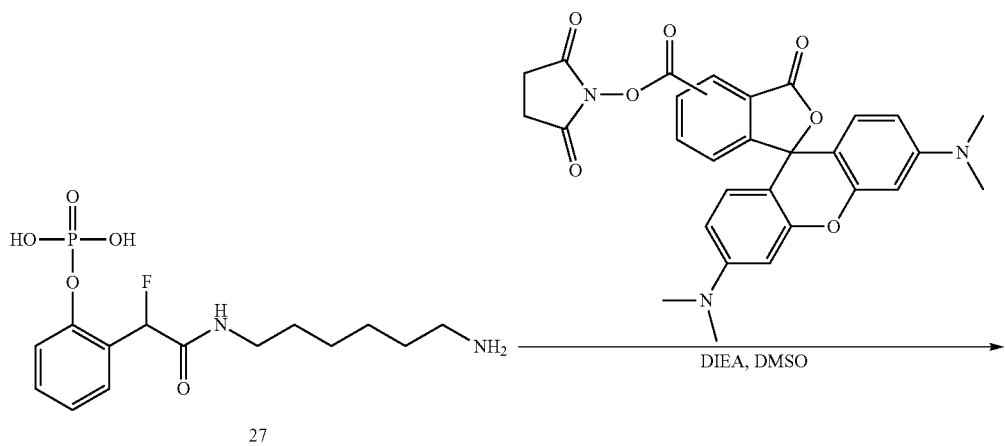
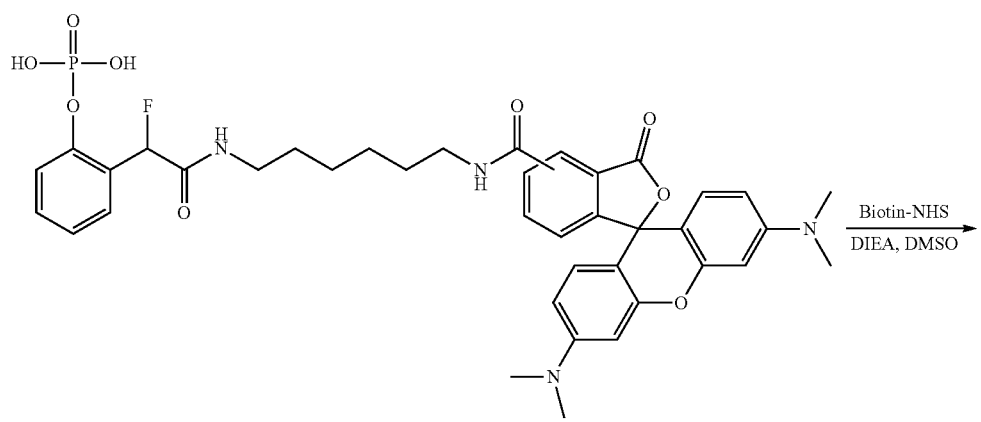
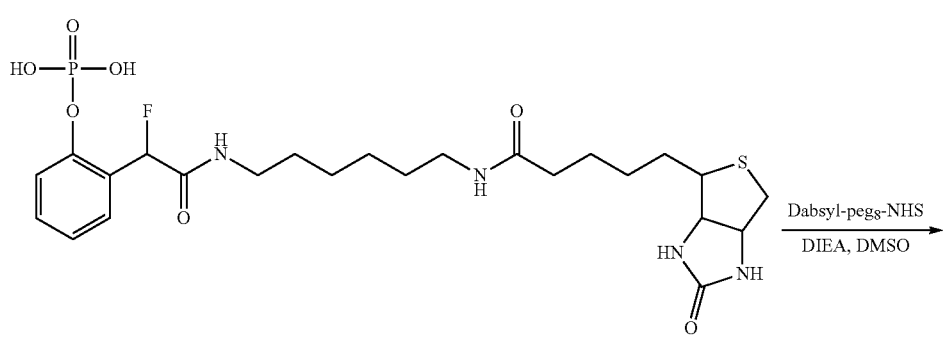
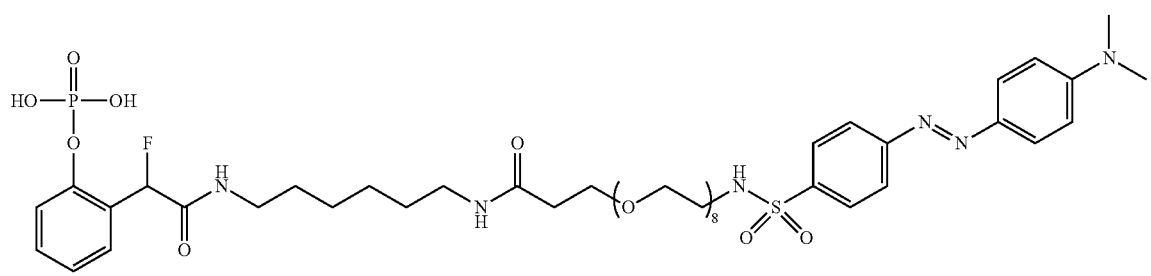

Compound 23. Phenol (22) (75.3 g, 800 mmol), glyoxylic acid monohydrate (9.21 g, 100 mmol), tributylamine (17.6 g, 22.6 mL, 95 mmol), $Al_2(SO_4)_3$ (3.33 g, 5 mmol), and $H_2O$ (4 mL) were combined in a round bottom flask and the reaction mixture was heated to 50° C. for 8 hours. The reaction mixture was cooled to room temperature followed by addition of 1M NaOH (100 mL) and extraction with 1,2-dichloroethane (3×100 mL). The NaOH layer was then acidified to pH=2 by careful addition of conc. HCl. The resulting solution was extracted with EtOAc (5×200 mL). The organics were collected, combined and dried over $MgSO_4$. The solvents were then removed under reduced pressure, giving compound 23 as a viscous light brown oil (13.4 g, 80% yield).

Compound 24. Compound 23 (12.0 g, 71.4 mmol) and N-boc-diaminohexane (23.2 g, 107 mmol) were dissolved in DMF (125 mL) followed by sequential addition of HOBt (965 mg, 7.14 mmol), EDAC (20.5 g, 107 mmol), and finally DIEA (13.8 g, 18.6 mL, 107 mmol). The reaction mixture was stirred under $N_2$ for 16 hours, followed by reduction of the DMF to about 25 mL under reduced pressure. The resulting mixture was then quenched with 1M HCl (100 mL) and extracted with EtOAc (3×100 mL). The organics were collected, combined, and dried over $MgSO_4$. The solvent was removed under reduced pressure and the resulting residue was purified by flash chromatography in three separate and equal portions (Biotage Snap 50; hex:EA 1:0 to 5:95) to give compound 24 as a colorless viscous oil (16.0 g, 61% yield). MS (ESI) m/z $(M+2H-boc)^+$ calcd for $C_{14}H_{23}N_2O_3^+$ 267.2, found 266.6.

Compound 25. Compound 24 (13.0 g, 35.5 mmol) was dissolved in EtOAc (25 mL) and cooled to 0° C. in an ice bath under $N_2$. Triethylamine (10.8 g, 14.8 mL, 107 mmol) was then added and allowed to stir for 10 minutes. Diethyl chlorophosphate (6.73 g, 7.69 mL, 39.0 mmol) was then added dropwise over a period of 5 minutes. The reaction mixture was removed from the ice bath and stirred under $N_2$ for 4 hours. The reaction mixture was then quenched with 1M HCl (200 mL) and extracted with EtOAc (3×200 mL). The organics were collected, combined, and dried over $MgSO_4$. The solvent was removed under reduced pressure and the resulting residue was purified by flash chromatography (Biotage Snap 340; hex:EA 1:0 to 5:95) to give compound 25 as a colorless viscous oil (16.2 g, 91% yield). MS (ESI) m/z $(M+H)^+$ calcd for $C_{23}H_{40}N_2O_8P^+$ 503.5, found 503.2.

Compound 26. Compound 25 (13.0 g, 25.9 mmol) was dissolved in dry $CH_2Cl_2$ (100 mL) followed by cooling to −40° C. in an ice bath under $N_2$. Deoxo-fluor® (6.02 g, 5.01 mL, 27.2 mmol) was then added drop wise over a period of 15 minutes. The reaction mixture was removed from the ice bath and stirred under $N_2$ for 1 hour. The reaction mixture was then quenched with a saturated $NaHCO_3$ solution followed by extraction with $CH_2Cl_2$ (3×100 mL). The organics were collected, combined, and dried over $MgSO_4$. The solvent was removed under reduced pressure and the resulting residue was purified by flash chromatography (Biotage Snap 340; $CH_2Cl_2$:MeOH 1:0 to 92:8) to give compound 26 as a light yellow viscous oil (11.5 g, 85% yield). MS (ESI) m/z $(M+2H-boc)^+$ calcd for $C_{18}H_{31}FN_2O_5P^+$ 405.2, found 405.0.

Compound 27. Compound 26 (11.0 g, 21.8 mmol) was dissolved in dry $CHCl_3$ (20 mL) followed by cooling to 0° C. in an ice bath under $N_2$. TMSBr (16.7 g, 14.3 mL, 109 mmol) was then added drop wise over a period of 10 minutes. The reaction mixture was then removed from the ice bath and stirred under $N_2$ for 16 hours. The reaction mixture was quenched with MeOH (50 mL) and solvents were removed under reduced pressure. The residue was purified in five equal portions using prep RP-HPLC (Cis, 50×250 mm, 40 mL/minute, 0.05% TFA in $H_2O$:$CH_3CN$ 99:1 to 5:95 over 40 minutes) to give compound 27 as a white solid (4.20 g, 55% yield). MS (ESI) m/z $(M+H)^+$ calcd for $C_{14}H_{22}FN_2O_5P^+$ 349.3, found 348.9.

Example of Conjugation to Compound 27: Compound 28. 5(6)-Carboxytetramethylrhodamine (500 mg, 1.16 mmol) was dissolved in dry DMSO (5 mL) followed by addition of DMAP (213 mg, 1.74 mmol) and N,N'-disuccinimidyl carbonate (327 mg, 1.28 mmol). The reaction vessel was sealed and the reaction mixture stirred at room temperature for 30 minutes. Compound 27 (446 mg, 1.28 mmol) was then added, followed by addition of DIEA (750 mg, 1.01 mL, 5.80 mmol). The resulting mixture was stirred at room temperature for 2 hours. The reaction mixture was diluted with MeOH (5 mL) and purified by prep RP-HPLC (0.05% TFA in $H_2O$:ACN 99:1 to 5:95 over 40 minutes) to give compound 28 as a dark purple solid (625 mg, 71% yield). MS (ESI) m/z $(M+H)^+$ calcd for $C_{39}H_{43}FN_4O_9P^+$ 761.3, found 761.3.

Compound 29 is made by the same method as compound 21, and compound 30 is made by the same method as compound 37, below.

Scheme 6

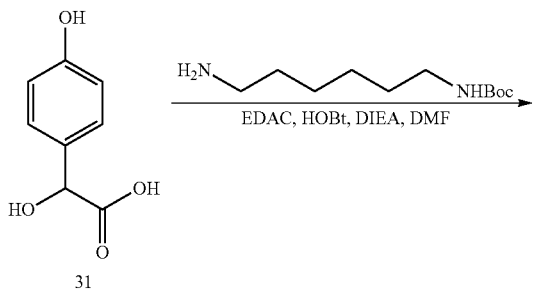

31

-continued
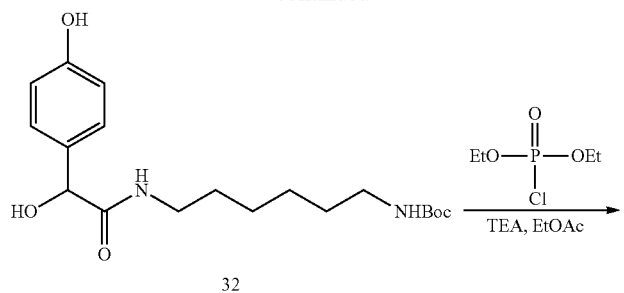
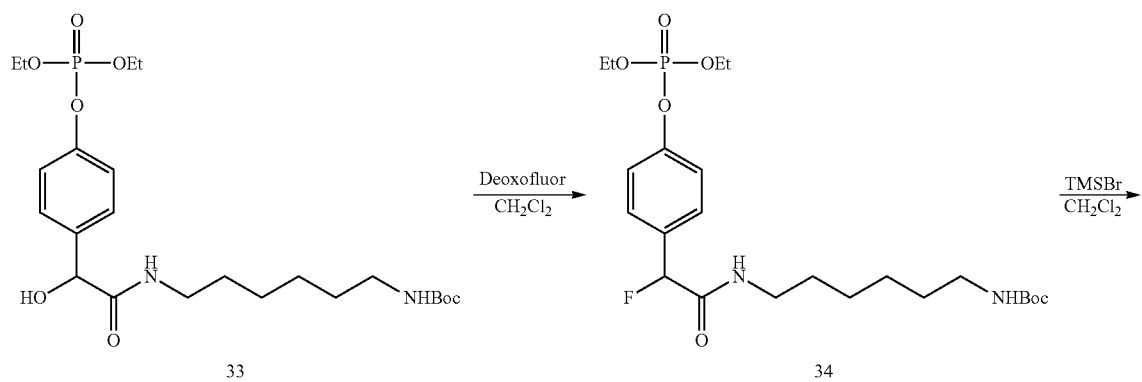
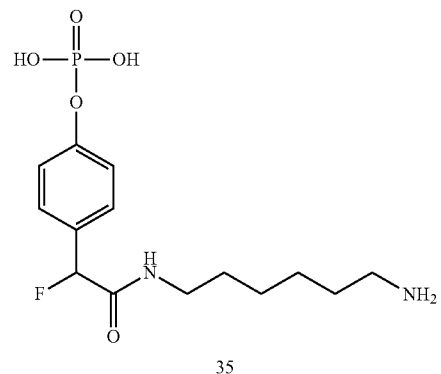
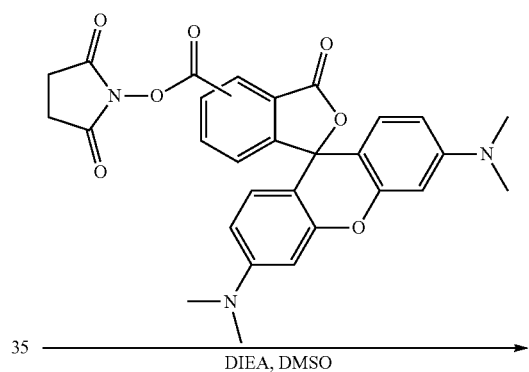

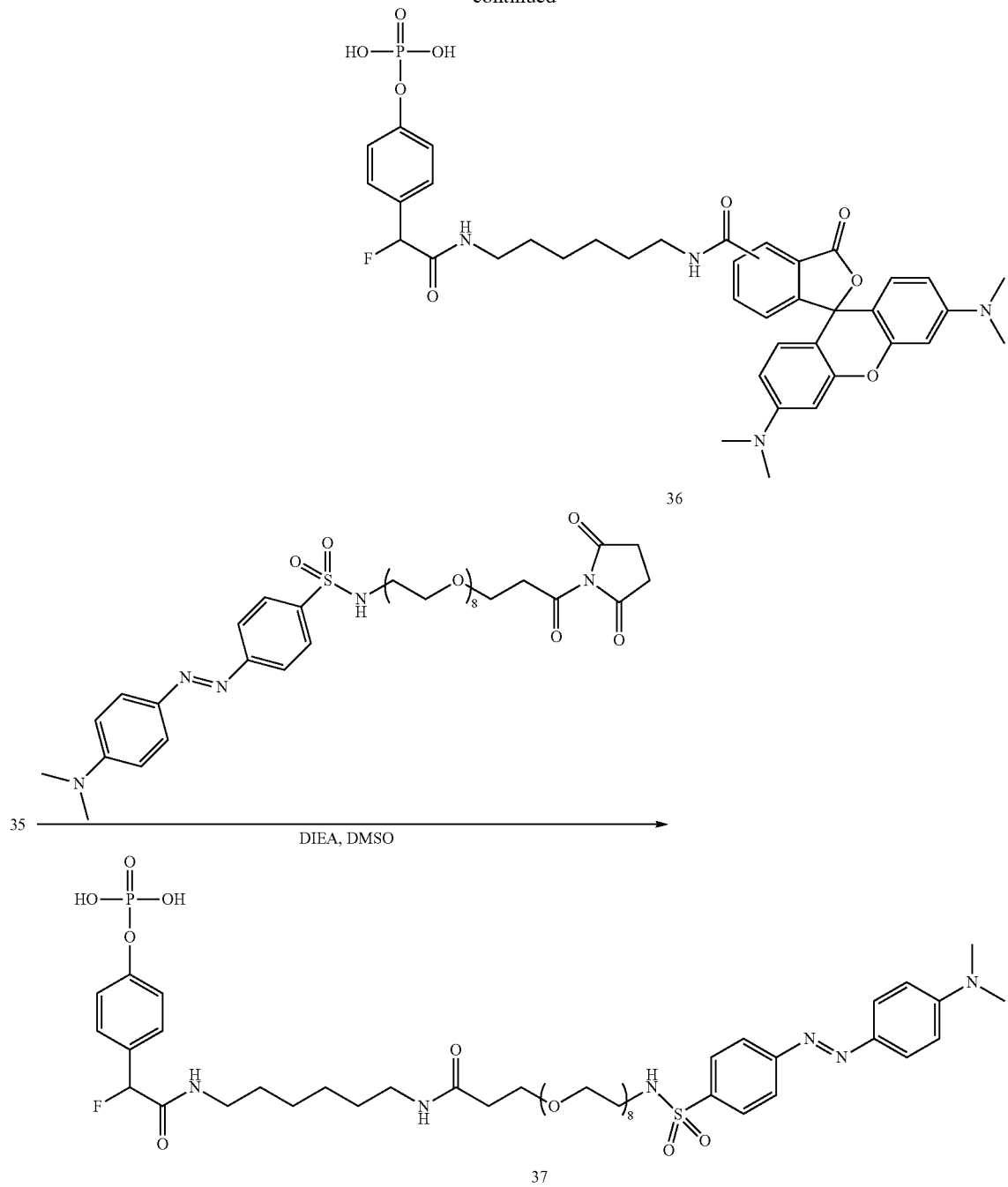

Compound 32. 4-Hydroxymandelic acid (31) (11.0 g, 59.1 mmol) and N-boc-diaminohexane (14.1 g, 65.0 mmol) were dissolved in DMF (125 mL) followed by sequential addition of HOBt (800 mg, 5.91 mmol), EDAC (17.0 g, 88.7 mmol), and finally DIEA (11.5 g, 15.4 mL, 88.7 mmol). The reaction mixture was stirred under $N_2$ for 16 hours, followed by reduction of the DMF to about 25 mL under reduced pressure. The resulting mixture was then quenched with 1M HCl (100 mL) and extracted with EtOAc (3×100 mL). The organics were collected, combined, and dried over $MgSO_4$. The solvent was removed under reduced pressure and the resulting residue was purified by flash chromatography in three separate and equal portions (Biotage Snap 50; hex:EA 1:0 to 5:95) to give compound 32 as a colorless viscous oil (18.7 g, 86% yield). $^1$H NMR (400 MHz, $CDCl_3$) δ 8.28 (s, 1H), 7.07 (d, 2H, J=8.4 Hz), 6.81 (br s, 1H), 6.64 (d, 2H, J=8.4 Hz), 4.87 (s, 1H), 4.78 (br s, 1H), 4.57 (br s, 1H), 3.23-3.11 (m, 2H), 2.99-2.97 (m, 2H), 1.42-1.35 (m, 13H), 1.18 (br s, 4H); $^{13}$C NMR (101 MHz, $CDCl_3$) δ 173.4, 162.7, 157.0, 128.2, 115.8, 79.4, 73.8, 40.34, 39.2, 36.5, 31.5, 29.7, 29.2, 28.4, 26.2, 26.1. MS (ESI) m/z (M+2H-boc)$^+$ calcd for $C_{14}H_{23}N_2O_3^+$ 267.2, found 266.6.

Compound 33. Compound 32 (18.5 g, 50.5 mmol) was dissolved in EtOAc (25 mL) and cooled to 0° C. in an ice bath under $N_2$. Triethylamine (25.6 g, 35.2 mL, 253 mmol) was then added and allowed to stir for 10 minutes. Diethyl chlorophosphate (9.15 g, 7.69 mL, 53.0 mmol) was then added dropwise over a period of 5 minutes. The reaction mixture was removed from the ice bath and stirred under $N_2$ for 4 hours. The reaction mixture was then quenched with 1M HCl (200 mL) and extracted with EtOAc (3×200 mL). The organics were collected, combined, and dried over $MgSO_4$. The solvent was removed under reduced pressure and the resulting residue was purified by flash chromatography (Biotage Snap 340; hex:EA 1:0 to 5:95) to give compound 33 as a colorless viscous oil (22.6 g, 89% yield). $^1$H NMR (400 MHz, $CDCl_3$) δ 7.36 (d, 2H, J=8.4 Hz), 7.14 (d, 2H, J=8.4 Hz), 6.66 (br s, 1H), 4.85 (s, 1H), 4.64 (br s, 2H), 4.20-4.13 (m, 4H), 3.24-3.20 (m, 2H), 3.08-3.03 (m, 2H), 1.40-1.25 (m, 23H); $^{13}$C NMR (101 MHz, $CDCl_3$) δ 172.1, 156.1, 150.5, 150.4, 136.9, 128.1, 120.04, 119.99, 79.1, 73.2, 64.8, 64.71, 64.65, 40.1, 39.1, 29.8, 29.2, 28.4, 26.04, 25.98, 16.07, 16.00; $^{31}$P NMR (162 MHz, $CDCl_3$) δ-5.9. MS (ESI) m/z (M+H)$^+$ calcd for $C_{23}H_{40}N_2O_8P^+$ 503.5, found 503.2.

Compound 34. Compound 33 (21.5 g, 42.3 mmol) was dissolved in dry $CH_2Cl_2$ (100 mL) followed by cooling to 0° C. in an ice bath under $N_2$. Deoxo-fluor® (10.4 g, 8.68 mL, 47.1 mmol) was then added dropwise over a period of 15 minutes. The reaction mixture was removed from the ice bath and stirred under $N_2$ for 1 hour. The reaction mixture was then quenched with a saturated $NaHCO_3$ solution followed by extraction with $CH_2Cl_2$ (3×100 mL). The organics were collected, combined, and dried over $MgSO_4$. The solvent was removed under reduced pressure and the resulting residue was purified by flash chromatography (Biotage Snap 340; $CH_2Cl_2$:MeOH 1:0 to 92:8) to give compound 34 as a light yellow viscous oil (14.9 g, 69% yield). $^1$H NMR (400 MHz, $CDCl_3$) δ 7.36 (d, 2H, J=8.4 Hz), 7.17 (d, 2H, J=8.4 Hz), 6.81 (br s, 1H), 5.67 (d, 2H, J=48 Hz), 4.73 (br s, 1H), 4.20-4.10 (m, 4H), 3.26-3.20 (m, 2H), 3.05-2.98 (m, 2H), 1.50-1.20 (m, 23H); $^{13}$C NMR (101 MHz, $CDCl_3$) δ 168.2, 168.0, 155.9, 151.28, 151.25, 151.21, 151.18, 131.7, 131.5, 128.03, 127.97, 119.95, 119.90, 91.9, 90.0, 78.7, 64.55, 64.48, 40.1, 38.7, 29.7, 29.1, 28.2, 26.07, 25.98, 15.90, 15.83; $^{19}$F NMR (376 MHz, $CDCl_3$) δ-175.5; $^{31}$P NMR (162 MHz, $CDCl_3$) δ-6.0. MS (ESI) m/z (M+2H-boc)$^+$ calcd for $C_{18}H_{31}FN_2O_5P^+$ 405.2, found 405.0.

Compound 35. Compound 34 (3.20 g, 6.34 mmol) was dissolved in dry $CHCl_3$ (20 mL) followed by cooling to 0° C. in an ice bath under $N_2$. TMSBr (4.85 g, 4.19 mL, 31.7 mmol) was then added dropwise over a period of 10 minutes. The reaction mixture was then removed from the ice bath and stirred under $N_2$ for 16 hours. The reaction mixture was quenched with MeOH (20 mL) and solvents were removed under reduced pressure. The residue was taken up in MeOH (10 mL) and the resulting mixture was added drop wise to a stirring flask of ice water (100 mL), resulting in a thick white precipitate. The solid was collected by vacuum filtration and washed with cold water. The resulting white solid was dried under high vacuum to give compound 35 as a white solid (1.50 g, 68% yield). $^1$H NMR (400 MHz, DMSO-$d_6$) δ 8.32 (t, 1H, J=5.4 Hz), 8.17 (br s, 3H), 7.36 (d, 2H, J=8.4 Hz), 7.16 (d, 2H, J=8.4 Hz), 5.72 (d, 2H, J=48 Hz), 3.13-3.07 (m, 2H), 2.29 (br s, 2H), 1.35-1.20 (m, 4H), 1.05-1.00 (m, 2H), 0.90-0.84 (m, 2H); $^{13}$C NMR (101 MHz, DMSO-$d_6$) δ 168.3, 168.1, 154.7, 129.6, 129.4, 127.23, 127.18, 91.4, 89.6, 38.3, 37.1, 28.6, 26.9, 25.5, 24.9; $^{19}$F NMR (376 MHz, DMSO-$d_6$) δ-174.2; $^{31}$P NMR (162 MHz, DMSO-$d_6$) δ-4.8. MS (ESI) m/z (M+H)$^+$ calcd for $C_{14}H_{22}FN_2O_5P^+$ 349.3, found 348.9.

Examples of Conjugation to Compound 35: Compound 36. 5(6)-Carboxytetramethylrhodamine (500 mg, 1.16 mmol) was dissolved in dry DMSO (5 mL) followed by addition of DMAP (213 mg, 1.74 mmol) and N,N'-disuccinimidyl carbonate (327 mg, 1.28 mmol). The reaction vessel was sealed and the reaction mixture stirred at room temperature for 30 minutes. Compound 35 (446 mg, 1.28 mmol) was then added, followed by addition of DIEA (750 mg, 1.01 mL, 5.80 mmol). The resulting mixture was stirred at room temperature for 2 hours. The reaction mixture was diluted with MeOH (5 mL) and purified by prep RP-HPLC (0.05% TFA in $H_2O$:ACN 99:1 to 5:95 over 40 minutes) to give compound 36 as a dark purple solid (625 mg, 71% yield). MS (ESI) m/z (M+H)$^+$ calcd for $C_{39}H_{43}FN_4O_9P^+$ 761.3, found 761.3.

Compound 37. Amino-pegs-acid (511 mg, 1.16 mmol) was added to a solution of dry DMSO (10 mL) and DIEA (449 mg, 605 μL, 3.47 mmol) followed by sonication until a clear solution was observed. Dabsyl chloride (750 mg, 2.32 mmol) was then added in ten equal portions over 15 minutes. The reaction vessel was sealed and the reaction mixture was stirred at room temperature for 1 hour. DMAP (212 mg, 1.74 mmol) was then added, followed by the addition of N,N'-disuccinimidyl carbonate (327 mg, 1.28 mmol) in ten equal portions over 15 minutes. The reaction vessel was sealed and the reaction mixture was stirred at room temperature for 15 minutes. Compound 35 (446 mg, 1.28 mmol) was then added, followed by addition of DIEA (750 mg, 1.01 mL, 5.80 mmol). The resulting mixture was stirred at room temperature for 2 hours. The reaction mixture was diluted with MeOH (5 mL) and purified by prep RP-HPLC (0.05% TFA in $H_2O$:ACN 99:1 to 5:95 over 40 minutes) to give compound 37 as a dark orange viscous oil (735 mg, 60% yield based on amino-pegs-acid). MS (ESI) m/z (M+2H)$^{2+}$ calcd for $C_{47}H_{74}FN_6O_{16}PS^{2+}$ 530.2, found 530.3.

Scheme 7

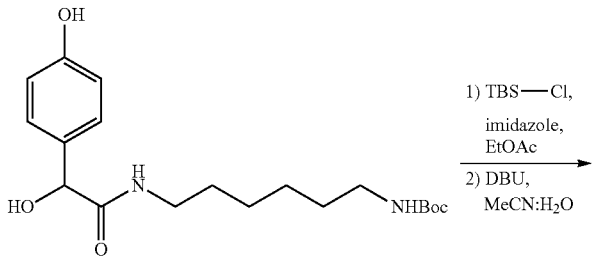

32

-continued
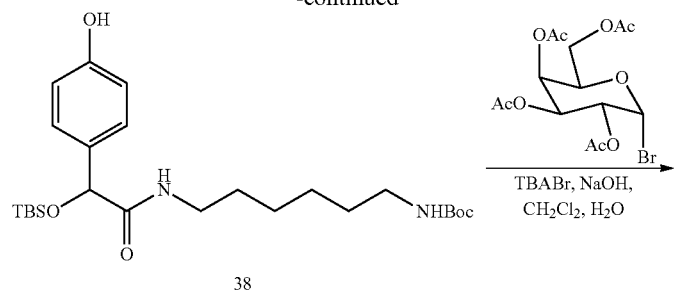
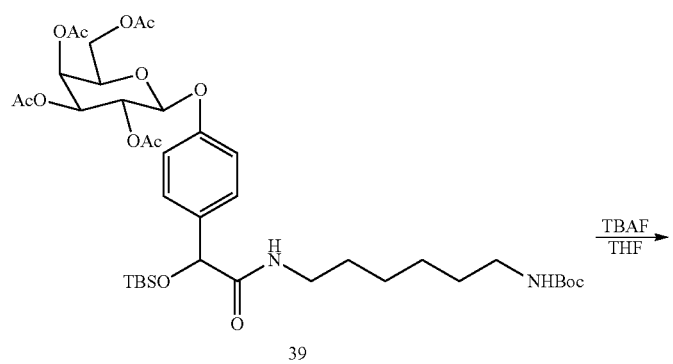
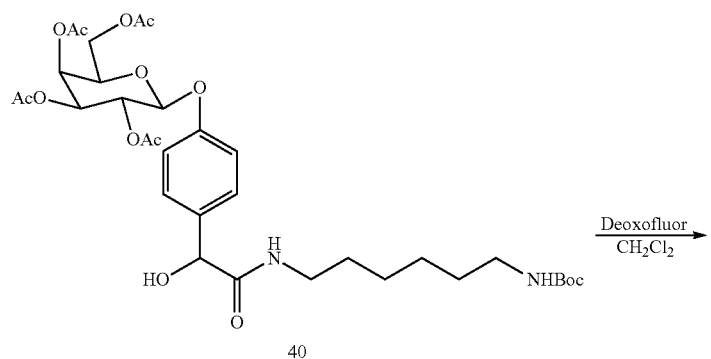
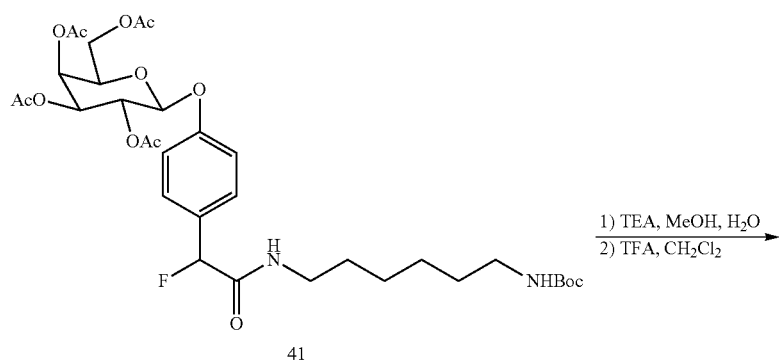

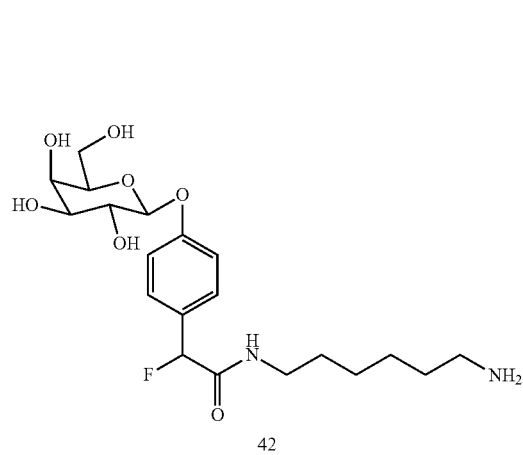

42

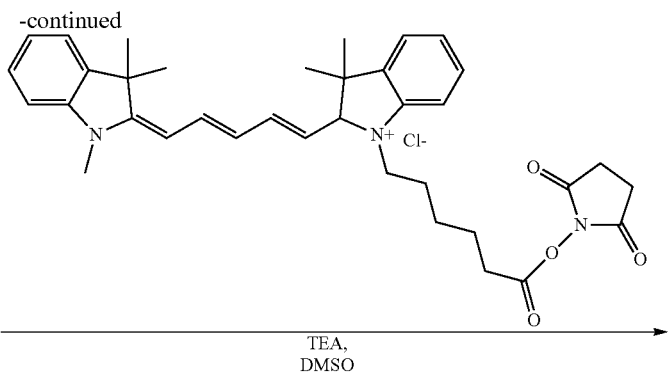

TEA, DMSO

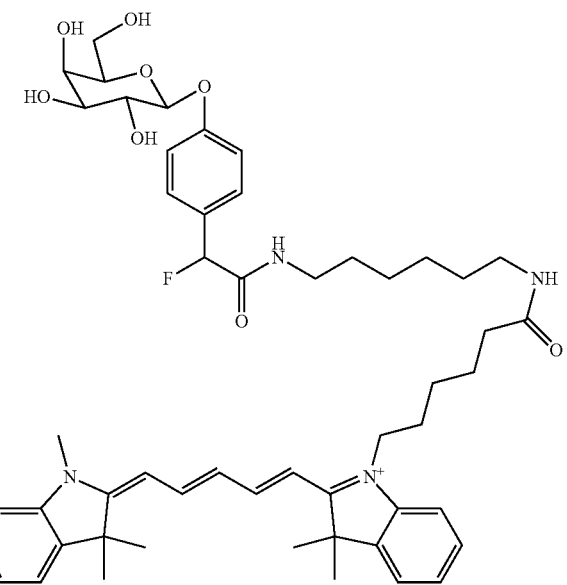

43

Compound 38. Compound 32 (4.49 g, 12.3 mmol) was dissolved in EtOAc (25 mL) followed by addition of imidazole (2.08 g, 30.6 mmol) and TBS-Cl (4.61 g, 30.6 mmol). The reaction vessel was sealed and stirred at room temperature for 4 hours. The solvent was then removed under reduced pressure and the resulting residue taken up in a mixture of MeCN:H$_2$O (10:1, 20 mL). DBU (1.87 g, 12.3 mmol) was then added and the reaction mixture stirred at room temperature for 16 hours. The reaction mixture was then extracted with EtOAc (50 mL) and 1M HCl (3×50 mL). The organic layer was collected, dried over MgSO$_4$, and the solvent removed under reduced pressure. The resulting residue was purified by flash chromatography (Biotage Snap 50; hex:EA 1:0 to 1:4) to give compound 38 as a colorless oil (5.10 g, 86% yield). $^1$H NMR (400 MHz, CDCl$_3$) δ 7.89 (br s, 1H), 7.06 (d, 2H, J=8.4 Hz), 7.01 (t, 1H, J=5.6 Hz), 6.54 (d, 2H, J=8.4 Hz), 4.95 (s, 1H), 4.62 (br s, 1H), 3.30-3.20 (m, 2H), 3.09-3.01 (m, 2H), 1.55-1.46 (m, 13H), 1.28 (s, 4H), 0.88 (s, 9H), 0.05 (s, 3H), −0.12 (s, 3H); $^{13}$C NMR (101 MHz, CDCl$_3$) δ 173.3, 156.7, 130.5, 127.6, 115.6, 79.2, 75.6, 40.4, 38.8, 29.9, 29.5, 28.4, 26.3, 25.7, 18.1, −4.7, −5.3. MS (ESI) m/z (M+H)$^+$ calcd for C$_{25}$H$_{45}$N$_2$O$_5$Si$^+$ 481.3, found 481.3.

Compound 39. Compound 38 (1.75 g, 3.64 mmol), TBABr (2.35 g, 7.28 mmol), and acetobromo-α-D-galactoside (2.99 g, 7.28 mmol) were combined in a round bottom flask and dissolved in CH$_2$Cl$_2$ (25 mL). An aqueous solution of NaOH (5% wt, 12 mL) was then added and the reaction mixture stirred vigorously at room temperature for 4 hours. The reaction mixture was then diluted with brine (50 mL) and extracted with CH$_2$Cl$_2$ (3×50 mL). The organic layer was collected, dried over MgSO$_4$, and the solvent removed under reduced pressure. The resulting residue was purified by flash chromatography (Biotage Snap 50; hex:EA 1:0 to 1:4) to give compound 39 as a colorless oil (2.45 g, 83% yield). $^1$H NMR (400 MHz, CDCl$_3$) δ 7.34 (dd, 2H, J=8.8 Hz and 2.0 Hz), 6.93 (d, 2H, J=8.8 Hz), 6.82-6.78 (m, 1H), 5.49-5.41 (m, 2H), 5.06 (dd, 1H, J=14 Hz and 3.6 Hz), 5.03-5.00 (m, 2H), 4.55 (br s, 1H), 4.25-4.00 (m, 3H), 3.33-3.25 (m, 1H), 3.17-3.02 (m, 3H), 2.16 (s, 3H), 2.04 (s, 6H), 1.99 (s, 3H), 1.50-1.40 (m, 13H), 1.29 (br s, 4H), 0.91 (s, 9H), 0.06 (s, 3H), −0.06 (s, 3H); $^{13}$C NMR (101 MHz, CDCl$_3$) δ 171.9, 170.3, 170.2, 170.0, 169.3, 156.66, 156.64, 155.9, 134.86, 136.84, 127.34, 127.28, 116.7, 99.60, 99.57, 79.0, 75.1, 75.0, 70.92, 70.89, 70.8, 68.6, 66.8, 61.3, 40.3, 38.7, 29.9, 29.5, 28.4, 26.4, 26.3, 25.7, 20.7, 20.6, 20.5, 18.1, −4.8, −5.4. MS (ESI) m/z (M+H)$^+$ calcd for C$_{39}$H$_{63}$N$_2$O$_{14}$Si$^+$ 811.4, found 811.7.

Compound 40. Compound 39 (2.15 g, 2.65 mmol) was dissolved in THF (20 mL) followed by purging with N$_2$ and cooling to 0° C. in an ice bath. TBAF (1M in THF, 2.65 mL, 2.65 mmol) was then added dropwise over a period of 5 minutes. The reaction mixture was stirred at 0° C. under $N_2$ for 15 minutes, followed by quenching with a solution of saturated $NaHCO_3$ (25 mL). The resulting suspension was extracted with EtOAc (3×50 mL). The organics were combined, dried over $MgSO_4$, and the solvent removed under reduced pressure. The resulting residue was purified by flash chromatography (Biotage Snap 50; hex:EA 1:0 to 1:9) to give compound 40 as a colorless oil that became a white foam upon exposure to high-vac (1.55 g, 84% yield). $^1$H NMR (400 MHz, $CDCl_3$) 7.35 (d, 2H, J=8.4 Hz), 6.99 (d, 2H, J=8.4 Hz), 6.36 (d, 1H, J=5.6 Hz), 5.50-5.43 (m, 2H), 5.10 (dd, 1H, J=10 Hz and 3.2 Hz), 5.05-4.98 (m, 2H), 4.57 (br s, 1H), 4.25-4.02 (m, 3H), 4.04 (br s, 1H), 3.30-3.20 (m, 2H), 3.21-3.03 (m, 2H), 2.18 (s, 3H), 2.05-2.00 (m, 9H), 1.53-1.33 (m, 13H), 1.32-1.20 (m, 4H); $^{13}$C NMR (101 MHz, $CDCl_3$) δ 172.1, 170.4, 170.2, 170.1, 169.4, 157.0, 156.1, 134.65, 134.63, 128.2, 117.2, 117.1, 99.62, 99.60, 79.2, 73.53, 73.49, 71.0, 70.8, 68.6, 66.8, 61.3, 40.0, 39.2, 29.8, 29.2, 28.4, 25.9, 20.70, 20.65, 20.64, 20.56. MS (ESI) m/z $(M+H)^+$ calcd for $C_{33}H_{49}N_2O_{14}^+$ 697.3, found 697.5.

Compound 41. Compound 40 (1.22 g, 1.75 mmol mmol) was dissolved in dry $CH_2Cl_2$ (20 mL) followed by cooling to 0° C. in an ice bath under $N_2$. Deoxo-fluor® (426 mg, 355 µL, 1.93 mmol) was then added dropwise over a period of 5 minutes. The reaction mixture was removed from the ice bath and stirred under $N_2$ for 15 minutes. The reaction mixture was then quenched with a saturated $NaHCO_3$ solution (20 mL) followed by extraction with $CH_2Cl_2$ (3×50 mL). The organics were collected, combined, and dried over $MgSO_4$. The solvent was removed under reduced pressure and the resulting residue was purified by flash chromatography (Biotage Snap 50; hex:EA 1:0 to 1:9) to give compound 41 as a colorless oil that became a white foam upon exposure to high-vacuum (840 mg, 69% yield). $^1$H NMR (400 MHz, $CDCl_3$) δ 7.35 (d, 2H, J=8.4 Hz), 6.99 (d, 2H, J=8.4 Hz), 6.63 (br s, 1H), 5.69 (d, 1H, J=5.6 Hz), 5.50-5.41 (m, 2H), 5.08 (dd, 1H, J=10 Hz and 3.6 Hz), 5.03 (d, 1H, J=8.0 Hz), 4.58 (br s, 1H), 4.23-4.01 (m, 3H), 4.04 (br s, 1H), 3.30-3.23 (m, 2H), 3.12-3.01 (m, 2H), 2.16 (s, 3H), 2.02-1.96 (m, 9H), 1.58-1.25 (m, 17H); $^{13}$C NMR (101 MHz, $CDCl_3$) δ 170.3, 170.1, 170.0, 169.3, 168.4, 168.2, 162.4, 157.62, 157.60, 157.57, 156.0, 129.94, 129.91, 129.75, 129.72, 128.31, 128.24, 128.18, 116.90, 116.89, 99.3, 92.27, 92.23, 90.40, 90.37, 79.0, 70.99, 70.98, 70.7, 68.5, 66.8, 61.3, 40.2, 38.9, 36.4, 31.2, 29.9, 29.3, 28.3, 26.2, 26.1, 20.62, 20.57, 20.48; $^{19}$F NMR (376 MHz, $CDCl_3$) δ -175.2, -175.6. MS (ESI) m/z $(M+Na)^+$ calcd for $C_{33}H_{47}FN_2NaO_{13}^+$ 721.3, found 721.2.

Compound 42. Compound 41 (300 mg, 0.429 mmol) was dissolved in a mixture of $TEA:MeOH:H_2O$ (1:8:1, 2 mL) and stirred at room temperature for 4 hours. The solvents were removed under reduced pressure followed by addition of a solution of $TFA:CH_2Cl_2$ (1:1, 5 mL). The reaction vessel was sealed and stirred at room temperature for 1 hours. The solvents were removed under reduced pressure and the resulting residue purified by prep RP-HPLC (0.05% TFA in $H_2O:ACN$ 99:1 to 5:95 over 60 minutes) to give compound 42 as a white solid (75 mg, 41% yield). $^1$H NMR (400 MHz, DMSO-$d_6$) δ 8.43 (t, 1H, J=5.6 Hz), 7.67 (br s, 3H), 7.35 (d, 2H, J=8.0 Hz), 7.05 (d, 2H, J=8.0 Hz), 5.77 (d, 1H, J=48 Hz), 5.18 (s, 1H), 4.95-4.80 (m, 2H), 4.67 (s, 1H), 4.53 (s, 1H), 3.70 (s, 1H), 3.60-3.25 (m, 7H), 3.20-3.05 (m, 2H), 1.55-1.38 (m, 4H), 1.37-1.20 (m, 4H); $^{13}$C NMR (101 MHz, DMSO-$d_6$) δ 168.8, 167.7, 158.0, 129.2, 129.0, 128.6, 128.5, 116.1, 100.6, 91.50, 91.45, 89.69, 89.63, 75.5, 73.3, 70.2, 68.1, 60.3, 38.8, 38.1, 28.7, 26.9, 25.7, 25.4; $^{19}$F NMR (376 MHz, $CDCl_3$) δ-170.4, -170.5. MS (ESI) m/z $(M+H)^+$ calcd for $C_{20}H_{32}FN_2O_7^+$ 431.2, found 431.1.

Example of Conjugation to Compound 42: Compound 43. Compound 42 (5 mg, 12 µmol) was dissolved in dry DMSO (1 mL) followed by addition of triethylamine (6 mg, 8 µL, 58 µmol) and finally Cy5-NHS ester (7 mg, 12 µmol). The reaction vessel was sealed and the reaction mixture stirred at room temperature for 1 hour. The reaction mixture was diluted with MeOH (1 mL) and directly purified by prep RP-HPLC (0.05% TFA in $H_2O:ACN$ 99:1 to 5:95 over 40 minutes) to give compound 43 (TFA salt) as a blue solid (8 mg, 68% yield). MS (ESI) m/z $(M)^+$ calcd for $C_{52}H_{68}FN_4O_8^+$ 895.5, found 895.2.

Scheme 8

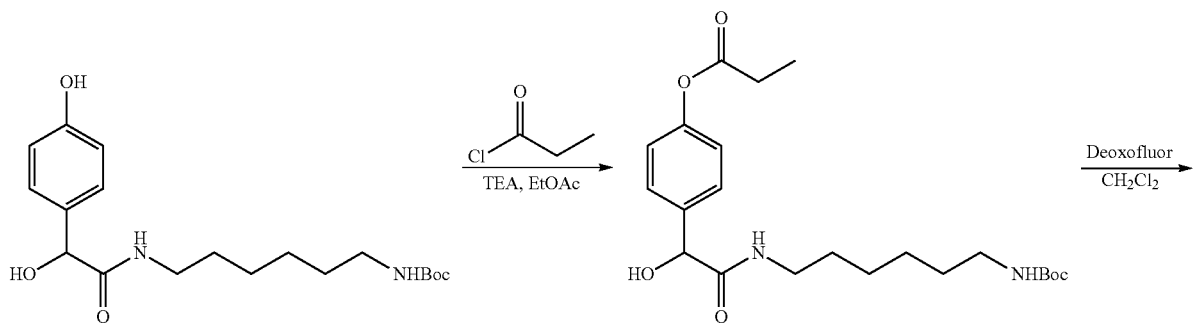

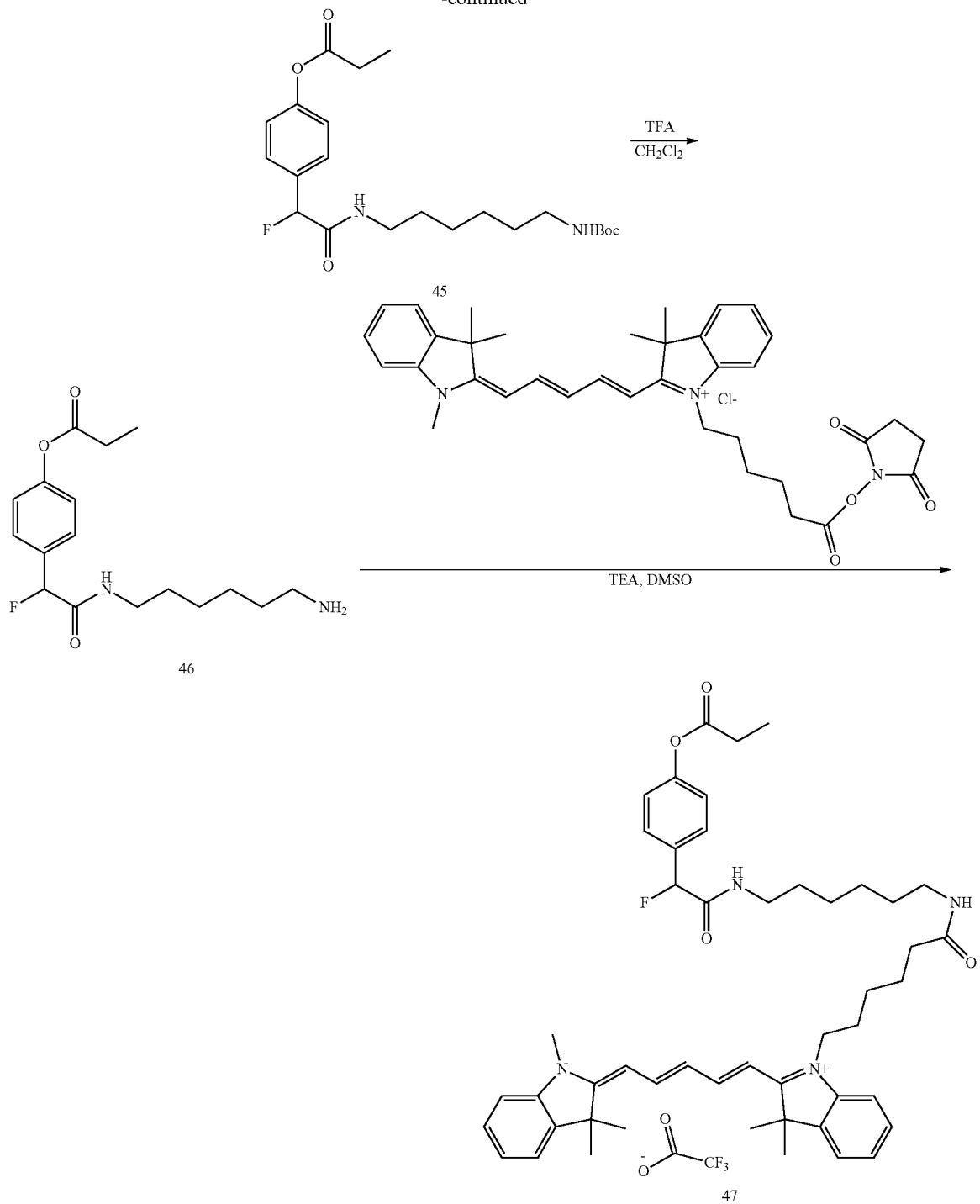

Compound 44. Compound 32 (200 mg, 0.546 mmol) was dissolved in EtOAc (1 mL) followed by addition of triethylamine (166 mg, 1.64 mmol) and propionyl chloride (56 mg, 0.600 mmol) in a round bottom flask. The reaction mixture was stirred at room temperature for 1 hour. The reaction mixture was then extracted with 0.5M HCl (5 mL) and EtOAc (3×10 mL), the organic layer collected and dried over MgSO$_4$. The suspension was filtered, the filtrate collected and the solvents removed under reduced pressure. The resulting residue was purified by flash chromatography (hex:EtOAc 1:0 to 1:9) to give compound 44 as a white solid (210 mg, 91% yield): $^1$H NMR (400 MHz, CD$_3$CN) δ 7.42 (d, 2H, J=8.4 Hz), 7.14 (br s, 1H), 7.06 (d, 2H, J=8.4 Hz), 5.34 (br s, 1H), 4.96 (d, 1H, J=4.0 Hz), 4.51 (d, 1H, J=4.0 Hz), 3.15 (q, 2H, J=6.8 Hz), 2.97 (q, 2H, J=6.8 Hz), 2.58 (q, 2H, J=7.6 Hz), 1.42-1.30 (m, 13H), 1.29-1.12 (m, 7H); $^{13}$C NMR (101 MHz, CD$_3$CN) δ 174.1, 173.0, 157.0, 151.6, 139.5, 128.8, 122.7, 78.98, 74.2, 41.0, 39.6, 30.7, 30.2, 28.7, 28.2, 27.07, 27.03, 9.36. MS (ESI) m/z (M+Na)$^+$ calcd for C$_{22}$H$_{34}$N$_2$NaO$_6^+$ 445.2, found 445.2.

Compound 45. Compound 44 (200 mg, 0.473 mmol) was dissolved in CHCl₃ (5 mL) in a sealed scintillation vial and cooled to 0° C. in an ice bath. Deoxo-fluor® (110 mg, 0.497 mmol) was then added drop wise and the reaction vessel sealed. The reaction mixture was stirred at 0° C. for 1 hour, followed by quenching with 0.5 M HCl (5 mL). The organic layer was separated and dried over MgSO₄. The suspension was filtered, the filtrate collected and the solvents removed under reduced pressure. The resulting residue was purified by flash chromatography (hex:EtOAc 1:0 to 1:9) to give compound 45 as a white solid (155 mg, 77% yield): $^1$H NMR (400 MHz, CDCl₃) δ 7.39 (d, 2H, J=8.4 Hz), 7.04 (d, 2H, J=8.4 Hz), 6.81 (br s, 1H), 5.68 (d, 1H, J=48 Hz), 4.77 (br s, 1H), 3.21 (q, 2H, J=6.0 Hz), 3.00-2.95 (m, 2H), 2.52 (q, 2H, J=7.6 Hz), 1.42-1.30 (m, 13H), 1.29-1.11 (m, 7H); $^{13}$C NMR (101 MHz, CDCl₃) δ 172.5, 168.1, 167.9, 155.9, 151.19, 151.17, 132.4, 132.2, 127.53, 127.47, 121.5, 91.9, 90.0, 78.6, 40.02, 38.65, 29.7, 29.1, 28.2, 27.4, 26.0, 25.9, 8.7; $^{19}$F NMR (376 MHz, CDCl₃) δ-178.0. MS (ESI) m/z (M+Na)⁺ calcd for $C_{22}H_{33}FN_2NaO_5^+$ 447.2, found 447.1.

Compound 46. Compound 45 (100 mg, 0.236 mmol) was dissolved in a 1:1 mixture of CH₂Cl₂:TFA (1 mL) in a scintillation vial. The vial was sealed and stirred at room temperature for 30 minutes. The solvents were then removed under reduced pressure and the resulting residue was found to be of suitable purity for subsequent synthetic steps. Compound 46 was obtained as a viscous oil determined to be the TFA salt (100 mg, 97% yield). A small sample was purified by prep RP-HPLC (0.05% TFA in H₂O:ACN 99:1 to 5:95 over 40 minutes) to obtain an analytical sample. $^1$H NMR (400 MHz, CDCl₃) δ 7.42 (d, 2H, J=7.6 Hz), 7.09 (d, 2H, J=7.6 Hz), 6.98 (br s, 1H), 5.72 (d, 1H, J=48 Hz), 3.23 (br s, 2H), 2.57 (q, 2H, J=7.6 Hz), 1.60-1.40 (m, 4H), 1.39-1.15 (m, 7H); $^{13}$C NMR (101 MHz, CDCl₃) δ 173.1, 169.0, 168.8, 151.52, 151.50, 132.5, 132.3, 128.0, 127.9, 121.9, 91.9, 90.1, 39.6, 38.7, 28.7, 27.6, 26.9, 25.5, 25.2, 8.9; $^{19}$F NMR (376 MHz, CDCl₃) δ-177.5. MS (ESI) m/z (M+H)⁺ calcd for $C_{17}H_{26}FN_2O_3^+$ 325.2, found 325.2.

Example of Conjugation to Compound 46: Compound 47. Compound 46 (TFA salt, 10 mg, 23 μmol) was dissolved in dry DMSO (1 mL) followed by addition of triethylamine (7 mg, 10 μL, 68 μmol) and finally Cy5-NHS ester (15 mg, 25 μmol). The reaction vessel was sealed and the reaction mixture stirred at room temperature for 1 hour. The reaction mixture was diluted with MeOH (1 mL) and directly purified by prep RP-HPLC (0.05% TFA in H₂O:ACN 99:1 to 5:95 over 40 minutes) to give compound 47 (TFA salt) as a blue solid (12 mg, 58% yield). MS (ESI) m/z (M)⁺ calcd for $C_{49}H_{62}FN_4O_4^+$ 789.5, found 789.1.

Scheme 10

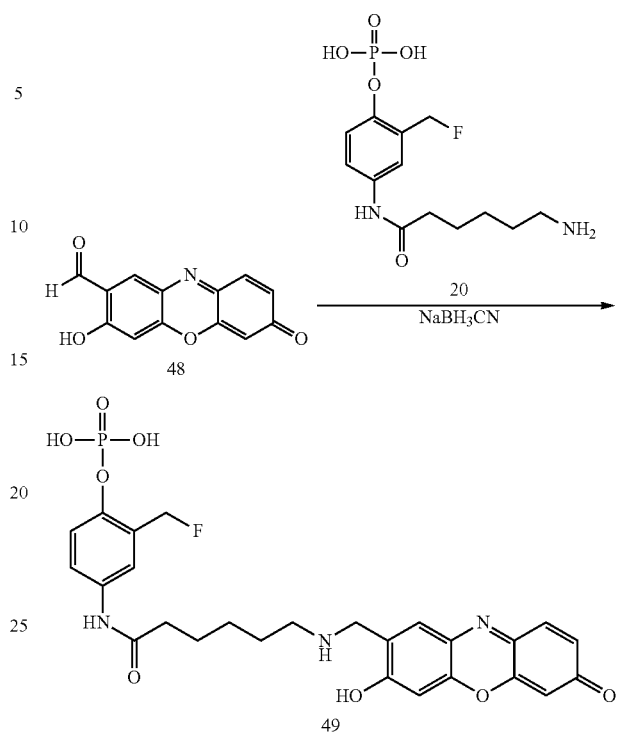

Resorufin is treated with sodium hydroxide in chloroform and water to form aldehyde 48. Aldehyde 48 is then reacted with compound 20 in the presence of a suitable reducing agent, such as sodium cyanoborohydride, to form compound 41.

Scheme 11

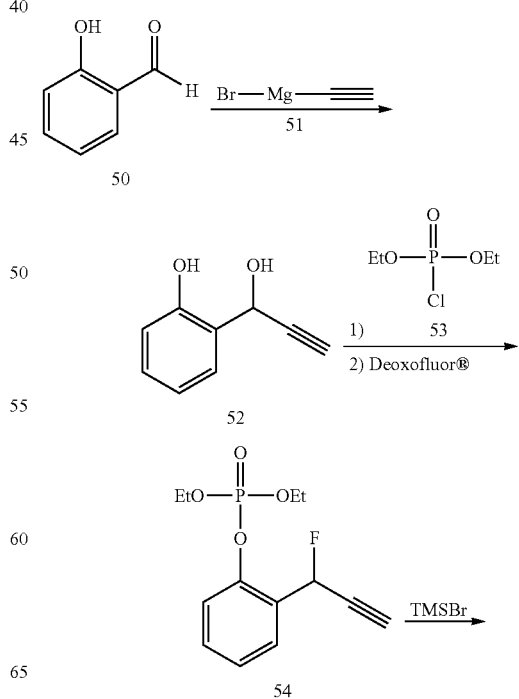

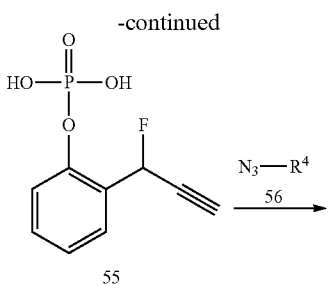

Synthesis of QMs Containing 1,2,3-Triazolyl Linker by Azide-Alkyne "Click" Chemistry Compound 57 is prepared by the reaction sequence shown in Scheme 11. First, salicylaldehyde (50) is reacted with ethynylmagnesium bromide (51) to give compound 52. Then, compound 52 is reacted in sequence with diethylchlorophosphate (53) and Deoxofluor® to give compound 54. Compound 54 is deprotected with TMSBr to give the aryl phosphate 55. Finally, compound 55 is reacted with terminal azide-functionalized reporter molecules ($N_3$—$R^4$, compound 56) to give the QM-reporter conjugates containing a 1,2,3-triazolyl linker (57).

Example 2

Target Detection Using QMPs

General Immunohistochemistry (IHC) Protocol(s) for QMPs. All IHC staining experiments were carried out on a VENTANA BenchMark® XT automated tissue staining platform and the reagents used in these protocols were from Ventana Medical Systems, Inc. (Tucson, AZ, USA; "Ventana") unless otherwise specified. Polyclonal goat anti-rabbit antibodies, goat anti-mouse antibodies, horseradish peroxidase (HRP) and alkaline phosphatase (AP) were obtained from Roche Diagnostics (Mannheim, Germany).

The following common steps were performed: (1) deparaffinization with EZ Prep detergent solution (Ventana Medical Systems, Inc. (VMSI), #950-101) (75° C.; 20 minutes); (2) washing with Reaction Buffer (VMSI, #950-300); (3) antigen retrieval in Cell Conditioning 1 (VMSI #950-124) (100° C.; time dependent on antigen of interest); (4) washing (same as step 2); (5) for protocols with subsequent HRP detection steps endogenous peroxidase was inactivated using iVIEW inhibitor (VMSI, E253-2187) (37° C.; 4 minutes); (6) washing (same as step 2); (7) primary antibody (Ab) incubation (37° C.; time dependent on primary antibody ranging from 8-32 minutes); and (8) washing (same as step 2). All subsequent reagent incubation steps were separated by washing as in step (2).

Two experimental staining protocols were used, as illustrated in FIGS. 4 and 5 Primary antibody (anti-target antibody) incubation and washing were followed by secondary antibody incubation with a goat polyclonal anti-species antibody conjugated to AP (37° C.; 8 minutes) (FIG. 4). Primary antibody incubation and washing were followed by secondary antibody incubation with a goat polyclonal anti-species antibody, hapten labeled with nitropyrazole (NP) (37° C.; 8 minutes). After washing, AP-conjugated mouse anti-NP monoclonal antibody was added (37° C.; 8 minutes) (FIG. 5).

Figure 13A:
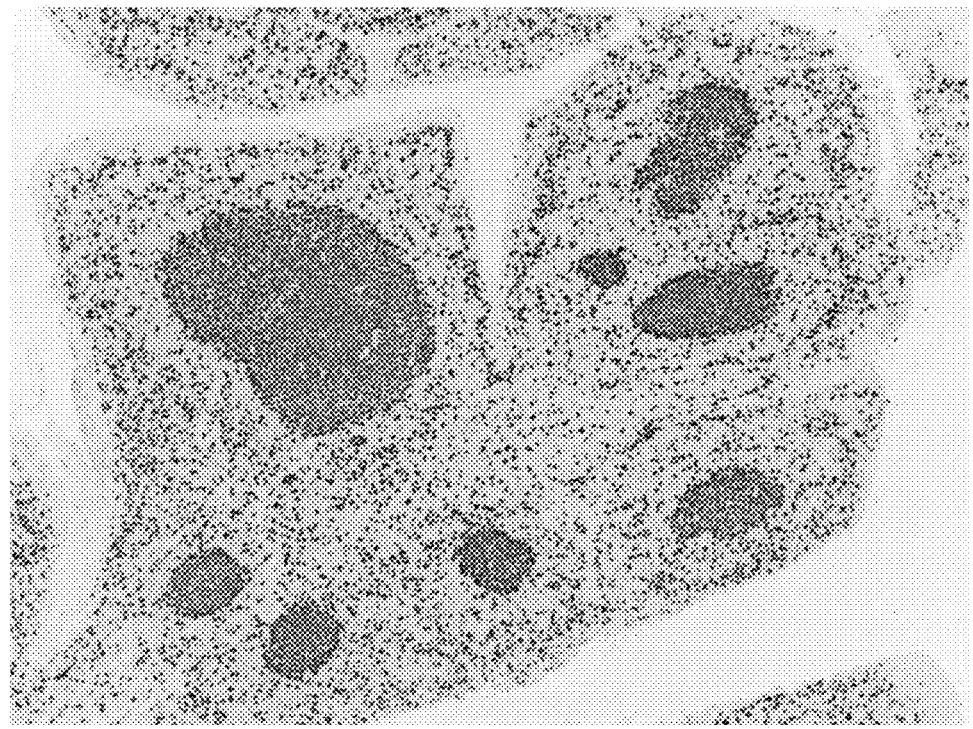
FIG. 13(A) is a microphotograph illustrating functional staining amplification of Ki67 on FFPE tonsil tissue by a QMP having a monofluoro leaving group and a 5-nitro-3-pyrazolecarbamide (nitropyrazole) detectable label.

Detection 1—HRP DAB. After incubating with the AP conjugate the slides were washed with Special Stains wash (VMSI #860-015). QMP reagents were dissolved in 100 mM CHES (3-cyclo-hexylamino-ethylsulfonic acid), pH 10.0, 0.05% Brij-35. QMP turnover was achieved by adding 100 μL of AP Enhancer (VMSI #253-2182) followed by 100 μL of hapten labeled QMP and incubating at 37° C. for 16 minutes. Compound 29 is an exemplary hapten-QMP that could be used according to this method. The deposited hapten was subsequently bound by a mouse-anti-hapten-HRP conjugate (or streptavidin-HRP) (37° C.; 8 minutes), and visualized via a brown precipitate produced by HRP upon the addition of hydrogen peroxide and DAB (37° C.; 8 minutes). The DAB was toned by the addition of copper sulfate (37° C.; 4 minutes). The stained tissue sections were counterstained with modified Mayer's hematoxylin (Hematoxylin II, VMSI #790-2208) (37° C.; 4 minutes) and then incubated with Bluing Reagent (VMSI #760-2037) (37° C.; 4 minutes). The slides were then dehydrated through a graded ethanol series, cleared with xylene, and manually cover-slipped. FIG. 13(A) shows an exemplary microphotograph of a slide stained according to this method.

Detection 2—AP Red. After incubating with the AP conjugate the slides were washed with Special Stains wash. QMP reagents were dissolved in 100 mM CHES, pH 10.0, 0.05% Brij-35. QMP turnover was achieved by adding 100 μL of AP Enhancer followed by 100 μL of hapten labeled QMP and incubating at 37° C. for 16 minutes. Compound 29 is an exemplary hapten-QMP that could be used according to this method. The deposited hapten was subsequently bound by a mouse-anti-hapten-AP conjugate (or streptavidin-AP conjugate) (37° C.; 8 minutes), and detection was achieved by adding 100 μL of AP Enhancer, followed by 100 μL of Naphthol AS-TR Phosphate and 200 μL of Fast Red KL (37° C.; 16 minutes). The stained tissue sections were counterstained with modified Mayer's hematoxylin (37° C.; 4 minutes) and then incubated with Bluing Reagent (37° C.; 4 minutes). The slides were rinsed with a detergent water mixture, air dried and manually cover-slipped. FIGS. 14(B)-14(D) show exemplary microphotographs of slides stained according to this method.

Figure 15A:
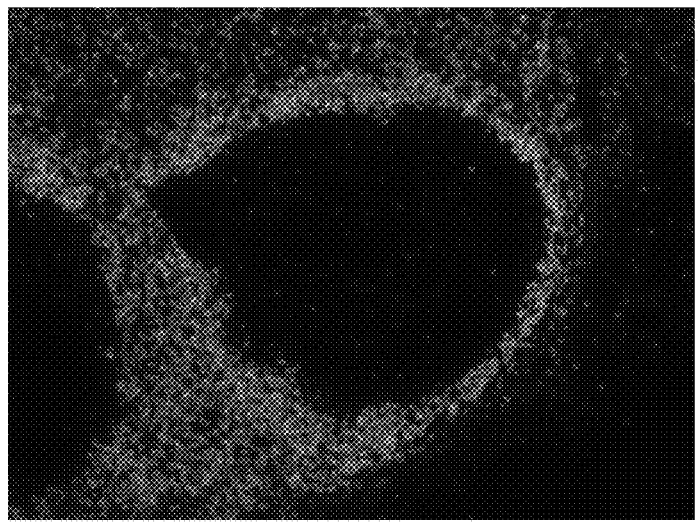
FIG. 15(A) is a microphotograph illustrating functional staining amplification of Bcl2 on FFPE tonsil tissue by a QMP having a monofluoro leaving group and a TAMRA detectable moiety.

Detection 3—Quantum Dot. After incubating with the AP conjugate the slides were washed with Special Stains wash. QMP reagents were dissolved in 100 mM CHES, pH 10.0, 0.05% Brij-35. QMP turnover was achieved by adding 100 μL of AP Enhancer followed by 100 μL of hapten labeled QMP and incubating at 37° C. for 16 minutes. Compound 29 is an exemplary hapten-QMP that could be used according to this method. The deposited hapten was subsequently visualized by incubation with a mouse-anti-hapten quantum dot conjugate (or streptavidin quantum dot conjugate) (37° C.; 32 minutes). The slides were washed with Reaction Buffer, dehydrated through a graded ethanol series, cleared with xylene, and manually cover-slipped. FIG. 15C shows an exemplary microphotograph of a slide stained according to this method.

Figure 16A:
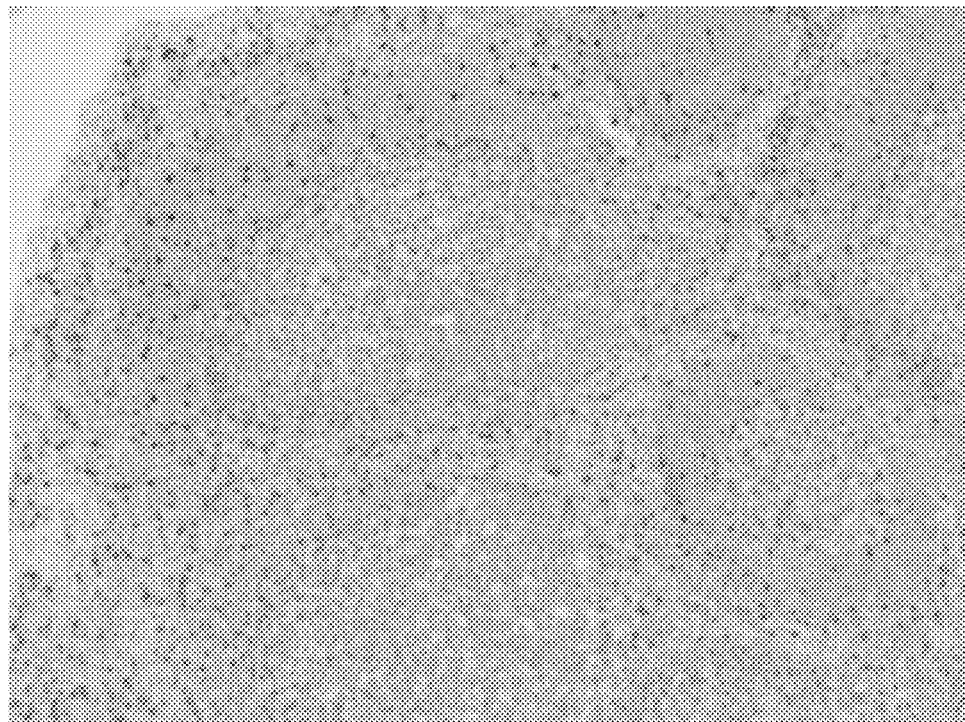
FIG. 16(A) is a microphotograph illustrating functional staining amplification of Ki67 on FFPE tonsil tissue by a QMP having a monofluoro leaving group and a Dabsyl detectable moiety.
Figure 16B:
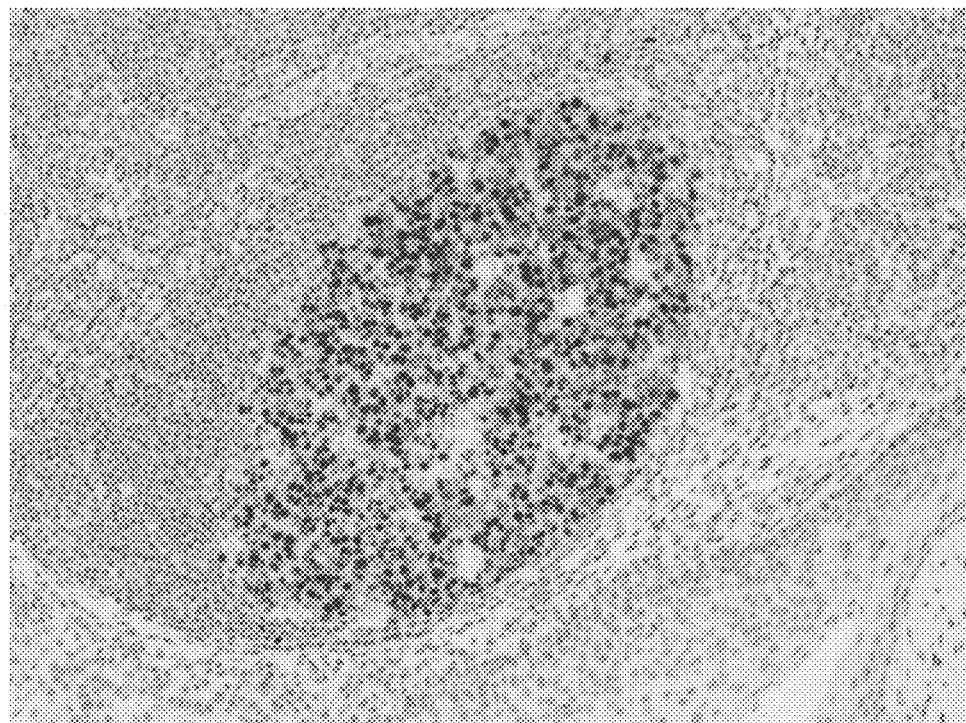
FIG. 16(B) is a microphotograph illustrating functional staining amplification of Ki67 on FFPE tonsil tissue by a QMP having a TAMRA detectable moiety.
Figure 16C:
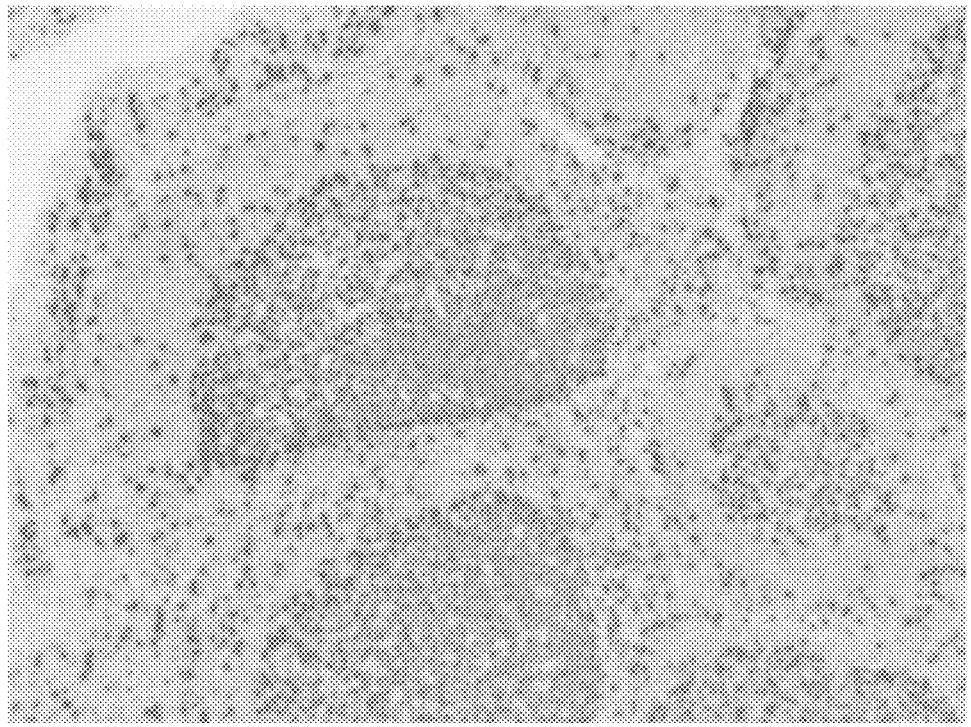
FIG. 16(C) is a microphotograph illustrating functional staining amplification of Ki67 on FFPE tonsil tissue by a QMP having a Cy5 detectable moiety.
Figure 16D:
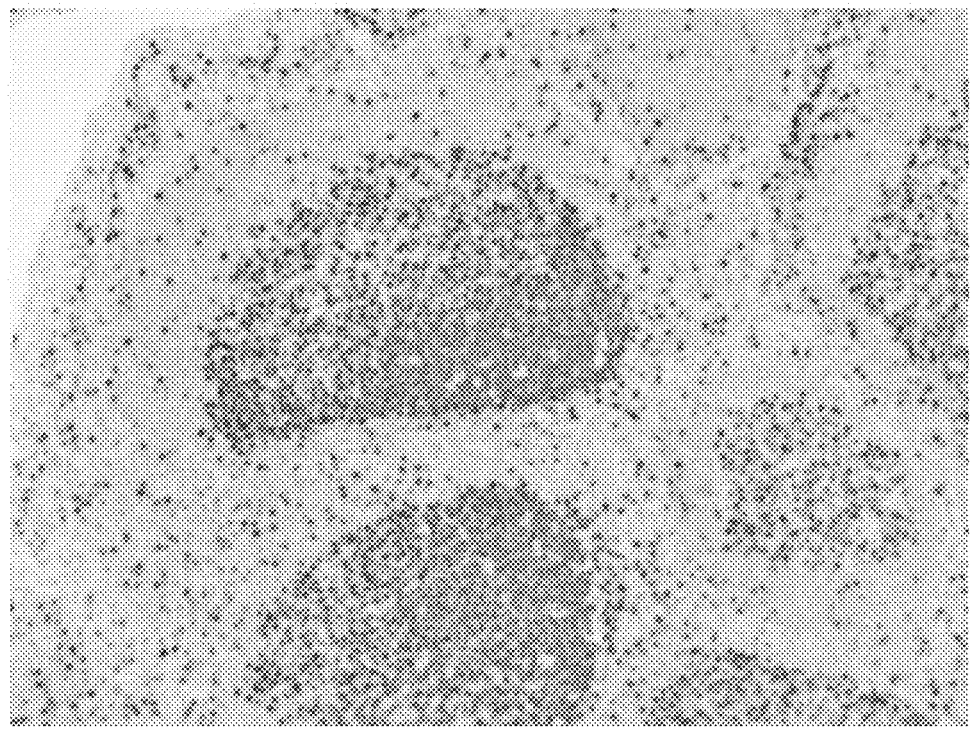
FIG. 16(D) is a microphotograph illustrating functional staining amplification of Ki67 on FFPE tonsil tissue by a QMP having a Rhodamine 110 detectable moiety.

Detection 4—Fluorophore. After incubating with the AP conjugate the slides were washed with saline sodium citrate buffer (SSC, VMSI #950-110). QMP reagents were dissolved in 250 mM Tris, pH 10.0, 0.05% Brij-35. QMP turnover was achieved by adding 100 μL of AP Enhancer followed by 100 μL of fluorophore labeled QMP (at a concentration <50 μM) and incubating at 37° C. for 16 minutes. Compound 28 is an exemplary fluorophore-QMP that could be used according to this method. The slides were washed with Reaction Buffer, dehydrated through a graded ethanol series, cleared with xylene, and manually cover-slipped. The slides were viewed by fluorescence microscopy using the appropriate filter sets. FIG. 15A shows an exemplary microphotograph of a slide stained according to this method Detection 5—Chromogenic QMP. After incubating with the AP conjugate the slides were washed with SSC. QMP reagents were dissolved in 250 mM Tris, pH 10.0, 0.05% Brij-35. QMP turnover was achieved by adding 100 μL of AP Enhancer followed by 100 μL of chromophore labeled QMP (at a concentration >50 μM) and incubating at 37° C. for 16 minutes. Compound 30 is an exemplary chromogen-QMP that could be used according to this method. In some cases the stained tissue sections were counterstained with modified Mayer's hematoxylin (37° C.; 4 minutes) and then incubated with Bluing Reagent (37° C.; 4 minutes). The slides were rinsed with a detergent water mixture, then dehydrated through a graded ethanol series, cleared with xylene, and manually cover-slipped. The slides were viewed by brightfield microscopy. FIG. 16(A) shows an exemplary microphotograph of a slide stained according to this method.

Example 3

Figure 17A:
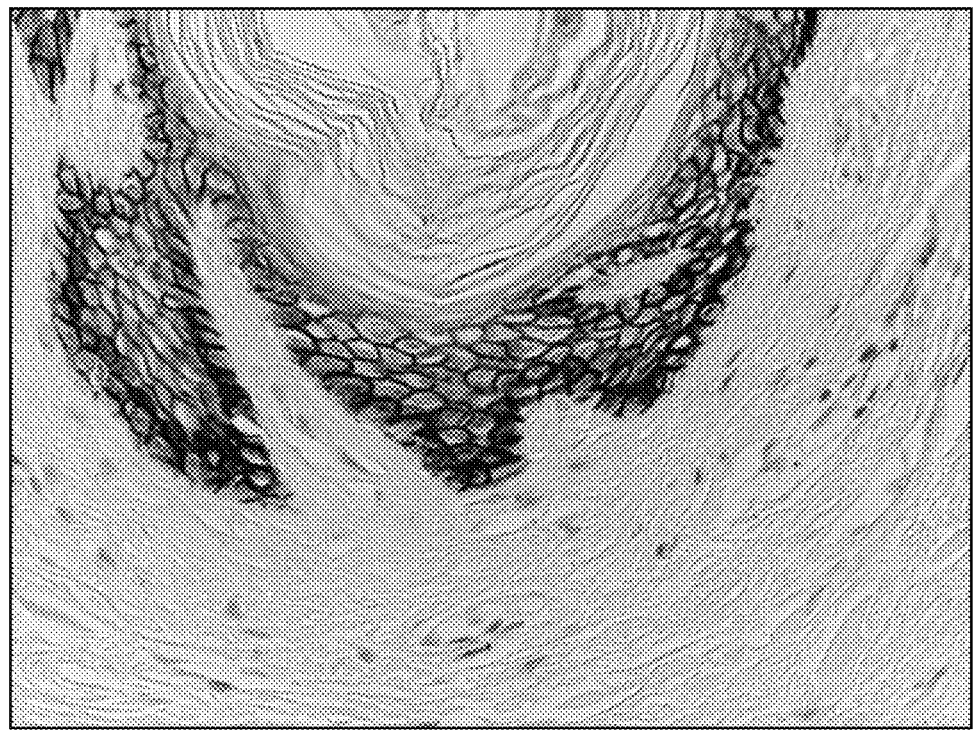
FIG. 17(A) is a microphotograph illustrating functional staining amplification of epidermal growth factor receptor (EGFR) in formalin-fixed, paraffin-embedded (FFPE) skin tissue by ultraView 3,3'-diaminobenzidine (DAB).
Figure 17B:
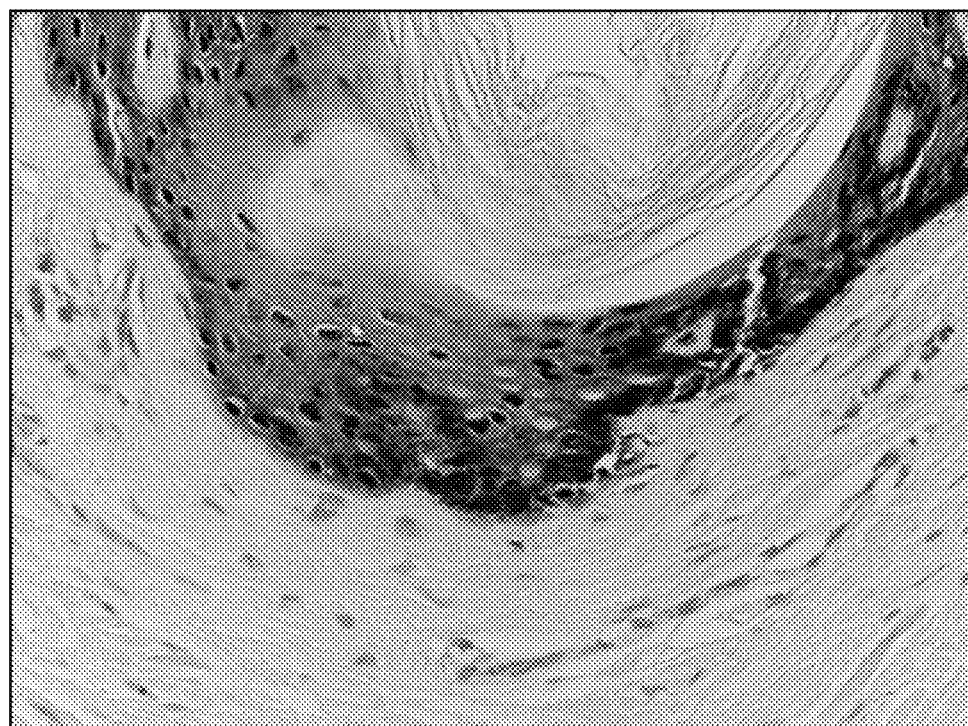
FIG. 17(B) is a microphotograph illustrating functional staining amplification of epidermal growth factor receptor (EGFR) in formalin-fixed, paraffin-embedded (FFPE) skin tissue utilizing a QMP having a difluoro leaving group and conjugated with a biotin detectable label.

HRP DAB Amplified by Difluoro QMP-Biotin (FIGS. 17(A)-(B))

(a) ultraView Control (FIG. 17(A)). The tissue was deparaffinized as described in the general procedures, followed by antigen retrieval with Protease 1 (VMSI #760-2018) (37° C., 8 minutes). Mouse-anti-EGFR antibody incubation (37° C., 32 minutes) and washing were followed by secondary antibody incubation with a goat polyclonal anti-mouse antibody conjugated to HRP (37° C.; 8 minutes). The antigen was visualized via a brown precipitate produced by HRP upon the addition of hydrogen peroxide and DAB (37° C.; 8 minutes). The DAB was toned by the addition of copper sulfate (37° C.; 4 minutes). The stained tissue sections were counterstained with modified Mayer's hematoxylin (37° C.; 4 minutes) and then incubated with Bluing Reagent (37° C.; 4 minutes) to change the hematoxylin hue to blue. They were then dehydrated through a graded ethanol series, cleared with xylene, and manually cover-slipped.

(b) QMP amplified DAB (FIG. 17(B)). The tissue was deparaffinized as described in the general procedures, followed by antigen retrieval with Protease 1 (37° C., 8 minutes). Mouse-anti-EGFR antibody incubation (37° C., 32 minutes) and washing were followed by secondary antibody incubation with a goat polyclonal anti-mouse antibody conjugated to AP (37° C.; 12 minutes). After incubating with the AP conjugate the slides were washed with Special Stains wash. Difluoro QMP-biotin was dissolved in 100 mM CHES, pH 10.0, 0.05% Brij-35 to a final concentration of 100 nM. QMP turnover was achieved by adding 100 μL of AP Enhancer followed by 100 μL of biotin labeled QMP and incubating at 37° C. for 16 minutes. The deposited hapten was subsequently bound by streptavidin-HRP conjugate (37° C.; 8 minutes), and visualized via a brown precipitate produced by HRP upon the addition of hydrogen peroxide and DAB (37° C.; 8 minutes). The DAB was toned by the addition of copper sulfate (37° C.; 4 minutes). The stained tissue sections were counterstained with modified Mayer's hematoxylin (37° C.; 4 minutes) and then incubated with Bluing Reagent (37° C.; 4 minutes). They were then dehydrated through a graded ethanol series, cleared with xylene, and manually cover-slipped.

In evaluating QM precursors for IHC staining, it was found that the identity of the leaving group influenced the activity of the QMP. Two phosphate-protected ortho-QM precursors were prepared, based on 4-nitrosalicylaldehyde starting material, containing benzyl monofluoro (Scheme 1, compound 7) and benzyl difluoro (compound 58) functionalities:

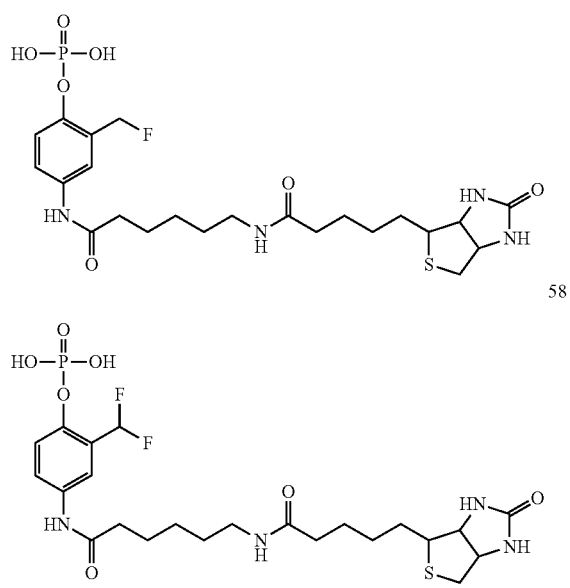

Figure 18:
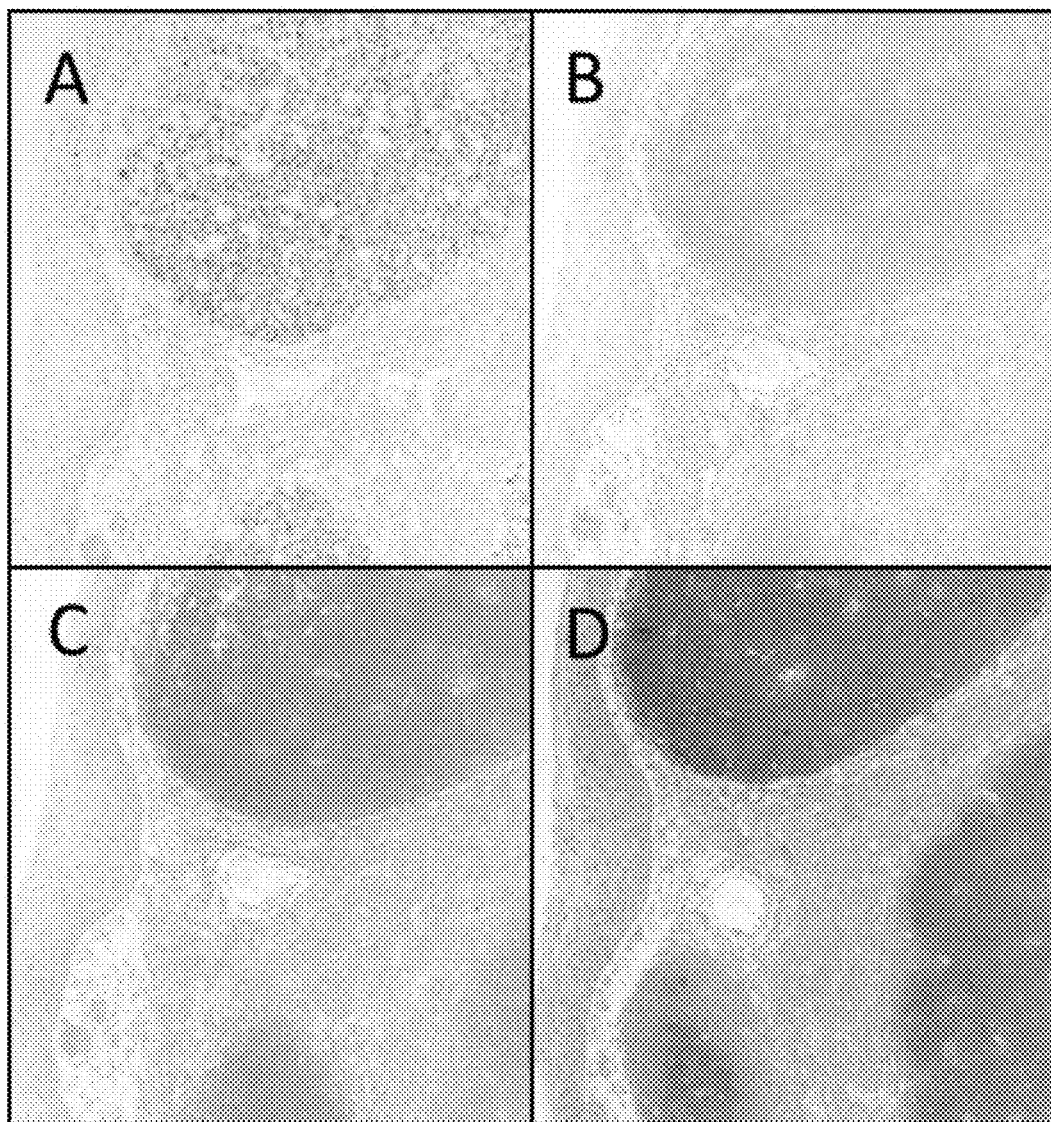
FIG. 18 is a microphotographs illustrating AP-based CARD IHC (BCL6 on FFPE tonsil tissue) using a biotinylated difluoro QM precursor followed by DAB detection at varying concentrations of the QM precursor where panel A—DAB control, panel B—1 µM, panel C—10 µM and panel D—20 µM.

Both compounds utilize fluoride as the leaving group, but the reactivity of the QM derived from difluoro compound 58 should be considerably lower than monofluoro 7 due to the electronic stabilization offered by the geminal fluorine atom. In fact, previous reports have suggested QMs derived from some monofluoro precursors may be excessively reactive as probes of enzyme activity, resulting in active site labeling and subsequent enzyme inhibition. Therefore, the difluoro QM precursor compound 58 was evaluated first for IHC staining performance on FFPE tissue using the nuclear marker BCL6 on FFPE tonsil tissue as a model system. The biotin-labeled difluoro QM precursor successfully bound to the sample as evidenced by subsequent biotin visualization using diaminobenzidine (DAB) detection. FIG. 18 provides microphotographs illustrating the detection level at varying concentrations of the difluoro QM precursor in a Tris buffer at pH=8.5 (panel A—DAB control, panel B—1 μM, panel C—10 μM and panel D—20 μM). In addition, significant amplification of signal was observed compared to the DAB control sample when on-slide concentrations of difluoro QM precursor compound 58 greater than 20 μM were utilized. However, increased diffusion of signal was also observed in all cases, resulting in considerable, non-desirable off-target staining.

It was suggested that the diffusion of signal by the difluoro QM precursor may have arisen from a combination of two kinetic factors: (1) the rate of leaving group ejection and subsequent QM formation after the cleavage of the phosphate group; and (2) the rate of QM quenching, either by a nucleophile on the tissue or in the reaction media. In the case of the difluoro QM precursor compound 58, the germinal fluorine atom provided stabilization that may have decelerated both factors, resulting in unacceptable diffusion from the target site. It was hypothesized that by increasing the pH of the reaction media, the rates of both QM formation and quenching may be accelerated, leading to better staining results. For (1), a more alkaline pH would increase the population of deprotonated phenol after phosphate cleavage, therefore encouraging fluoride ejection and QM formation. For (2), increased pH would increase the population of available quenchers from both the water and the buffer (Tris), effectively decreasing the distance the QMs would be able to diffuse from the target before reaction with a nucleophile.

Figure 19:
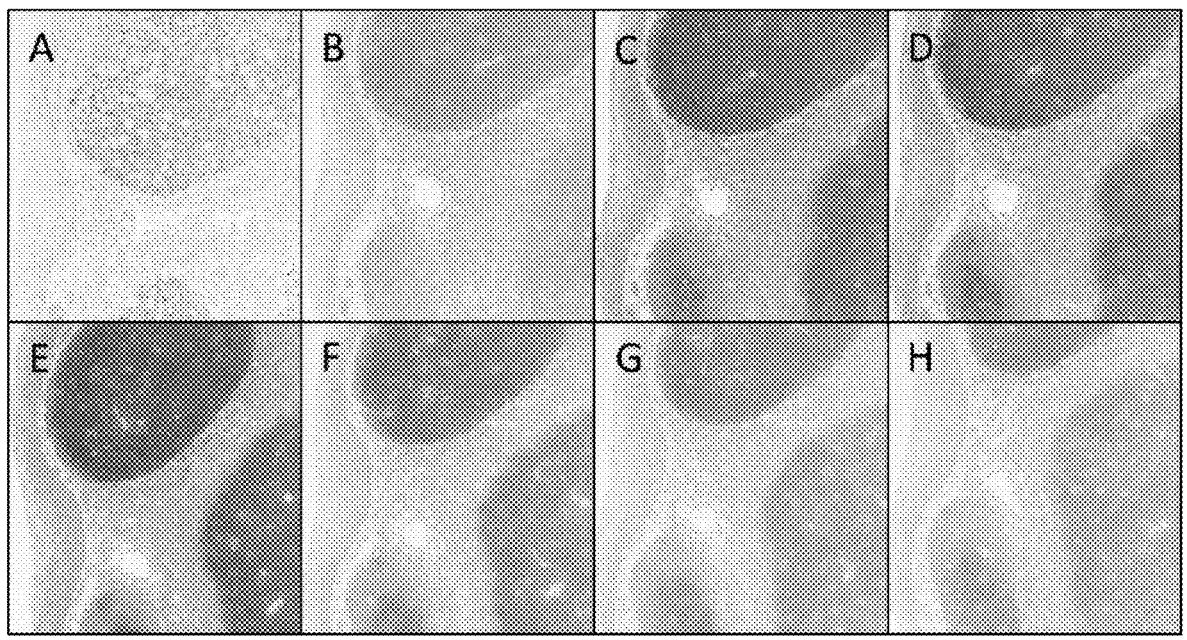
FIG. 19 is a microphotographs of AP-based CARD IHC (BCL6 on FFPE tonsil tissue) using 20 µM biotinylated difluoro QM precursor followed by DAB detection illustrating staining results with varying pH where panel A—DAB control; panel B pH=7.0; panel C pH=8.0; panel D pH=8.5; panel E pH=9.0; panel F pH=10.0; panel G pH=11.0; panel H pH=12.0.

To test the effect of pH on signal diffusion, difluoro QM precursor compound 58 was deposited as before at various pH levels within the working range for AP (7-12 with two shoulders of maximal activity at pH=8.5 and 11). The nuclear marker BCL6 on FFPE tonsil tissue was again chosen as the model. Positive staining was observed across the entire pH range, although a balance between overall signal and diffusion was seen. FIG. 19, panels A-H provide microphotographs of the detection levels of 20 M QM precursor in Tris buffer with varying pH: panel A—DAB control; panel B pH=7.0; panel C pH=8.0; panel D pH=8.5; panel E pH=9.0; panel F pH=10.0; panel G pH=11.0; panel H pH=12.0. The diffusion appears to decrease with increasing pH. At a pH of 7, almost no on-target staining was observed with a nearly homogeneous signal seen across the entire tissue section. As pH rose, the off-target staining gradually decreased, although overall signal diffusion and off-target staining remained significant even at a pH of 12. The level of amplification increased only as the pH rose to 8.5 and then decreased gradually over the rest of the range. This effect may be due to a combination of enzyme activity and the population of QM quenchers in the reaction media. At pH levels well below the optimal AP reaction conditions (7.0), the activity of AP was depressed, resulting in low signal. As the pH increased (8.0-8.5) but remained near the pKa of Tris (8.1), the activity of AP increased at a faster rate than the population of quenchers in the reaction media, leading to a significant increase in signal. Raising the pH further (9-10) increased the quencher population while decreasing AP activity, resulting in a decrease of signal. Although AP had maximal activity at pH 11 in Tris, a slight decrease in staining intensity was observed, most likely due to the excessively high population of quenchers that could not be overcome by the increased AP activity (raising the pH from 8.5 to 11 increases [Tris base] about 50%, with AP activity increasing by only about 20%). It was determined that even at the upper end of the pH range, the diffusion from the difluoro QM precursor compound 58 was still too great to be of clinical use for IHC. This is in contract to Bobrow's disclosure, which suggested that a difluoro based QMP was suitable for use as an IHC reagent.

Figure 20:
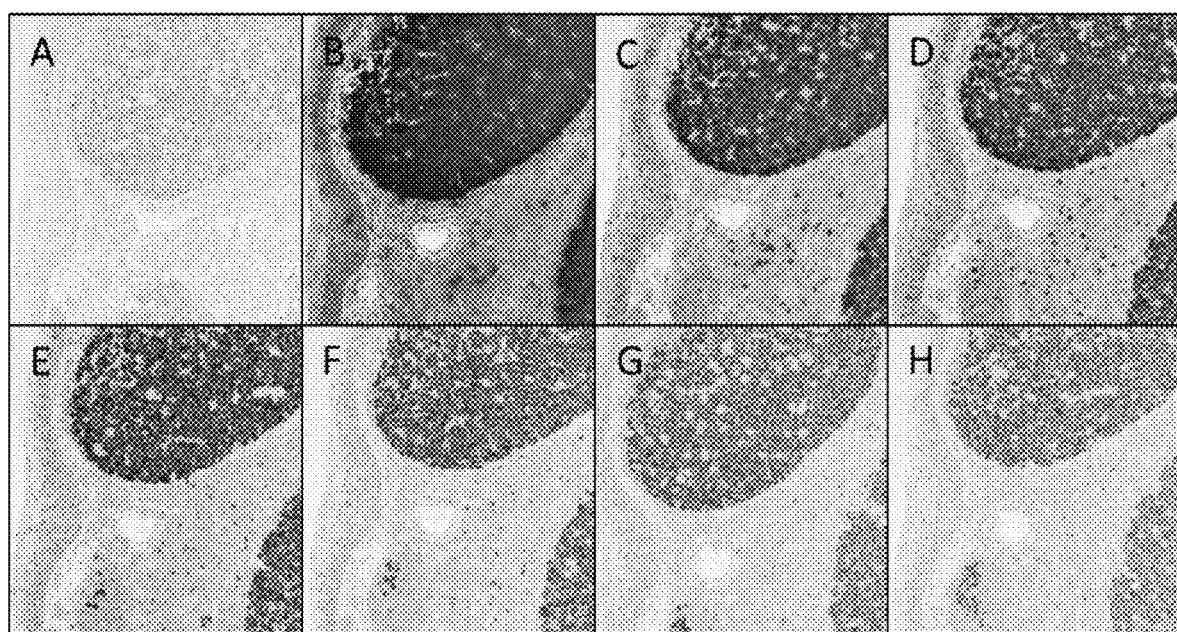
FIG. 20 is a microphotographs of AP-based CARD IHC (BCL6 on FFPE tonsil tissue) using 250 nM biotinylated monofluoro QM precursor followed by DAB detection illustrating staining results with varying pH with panel A—DAB control; panel B— pH=7.0; panel C— pH=8.0; panel D—pH=8.5; panel E pH=9.0; panel F pH=10.0; panel G—pH=11.0; panel H— pH=12.0.

It was suggested that by utilizing the less stable monofluoro QM precursor 7, diffusion may be reduced for reasons described above. IHC staining was first carried out under typical AP IHC condition (pH 8.5 in Tris buffer) across a wide concentration range using the nuclear marker BCL6 on FFPE tonsil tissue to determine the optimal concentration of monofluoro QM precursor 7 (data not shown). Surprisingly, a much lower concentration of monofluoro QM precursor 7 (250 nM) was required to give the desired level of amplification when compared to difluoro QM precursor 58 (20 µM). In addition, overall diffusion was greatly reduced compared to difluoro QM precursor 58, although some diffusion and off-target staining were still evident at pH=8.5. In an effort to reduce diffusion and off-target staining, a pH range (7-12) was tested in Tris buffer (FIG. 20: panel A—DAB control; panel B— pH=7.0; panel C— pH=8.0; panel D—pH=8.5; panel E pH=9.0; panel F pH=10.0; panel G—pH=11.0; panel H— pH=12.0). At low pH (7.0-8.0), significant diffusion was seen, creating a stain similar to those observed with the difluoro QM precursor 58. However, diffusion and off-target staining was gradually reduced as pH rose, without an unacceptable decrease in overall signal. At a pH of 10, diffusion and off-target staining were nearly eliminated, producing a stain with a high level of signal along with comparable specificity to the DAB control. Increasing the pH further to 11-12 resulted in slightly cleaner stains as evidenced by the more vibrant blue hematoxylin counterstain. However, a slight reduction in overall signal was observed at these higher pH levels.

Example 4

HRP DAB Amplified by QMP-Biotin with Quaternary Amine Leaving Groups (FIGS. 21(A)-(D)

Figure 21A:
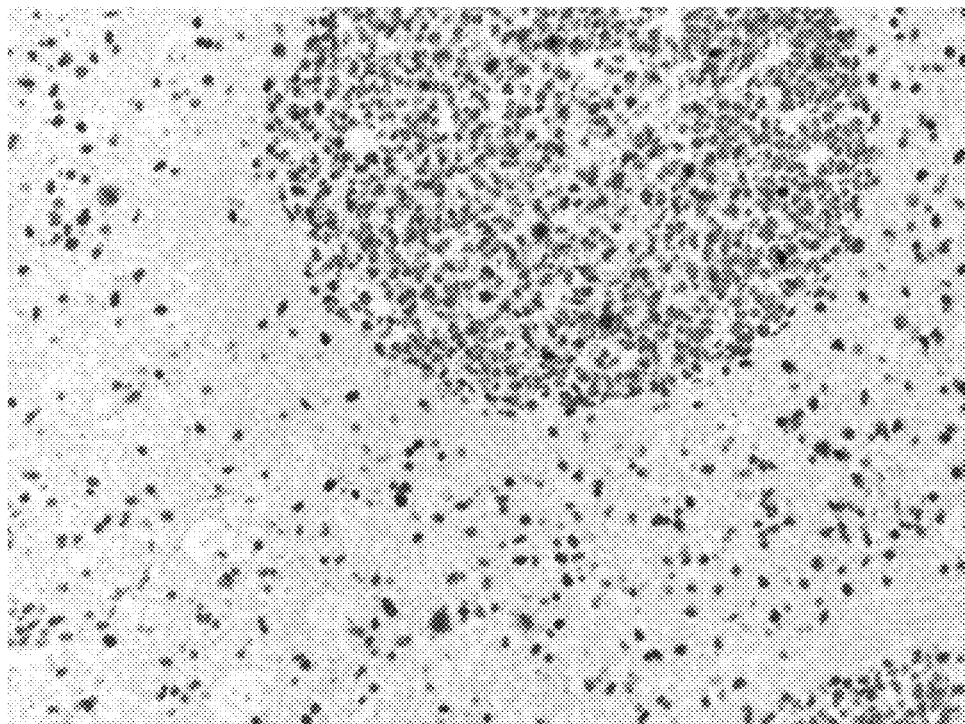
FIG. 21(A) is a microphotograph illustrating optimal staining amplification of Ki67 on FFPE tonsil tissue by ultraView control.

(a) ultraView Control (FIG. 21(A)). The tissue was deparaffinized and retrieved as described in the general procedures. Rabbit-anti-Ki-67 antibody incubation (37° C., 16 minutes) and washing were followed by secondary antibody incubation with a goat polyclonal anti-rabbit antibody conjugated to HRP (37° C.; 8 minutes). The antigen was visualized via a brown precipitate produced by HRP upon the addition of hydrogen peroxide and DAB (37° C.; 8 minutes). The DAB was toned by the addition of copper sulfate (37° C.; 4 minutes). The stained tissue sections were counterstained with modified Mayer's hematoxylin (37° C.; 4 minutes) and then incubated with Bluing Reagent (37° C.; 4 minutes) to change the hematoxylin hue to blue. They were then dehydrated through a graded ethanol series, cleared with xylene, and manually cover-slipped.

Figure 21B:
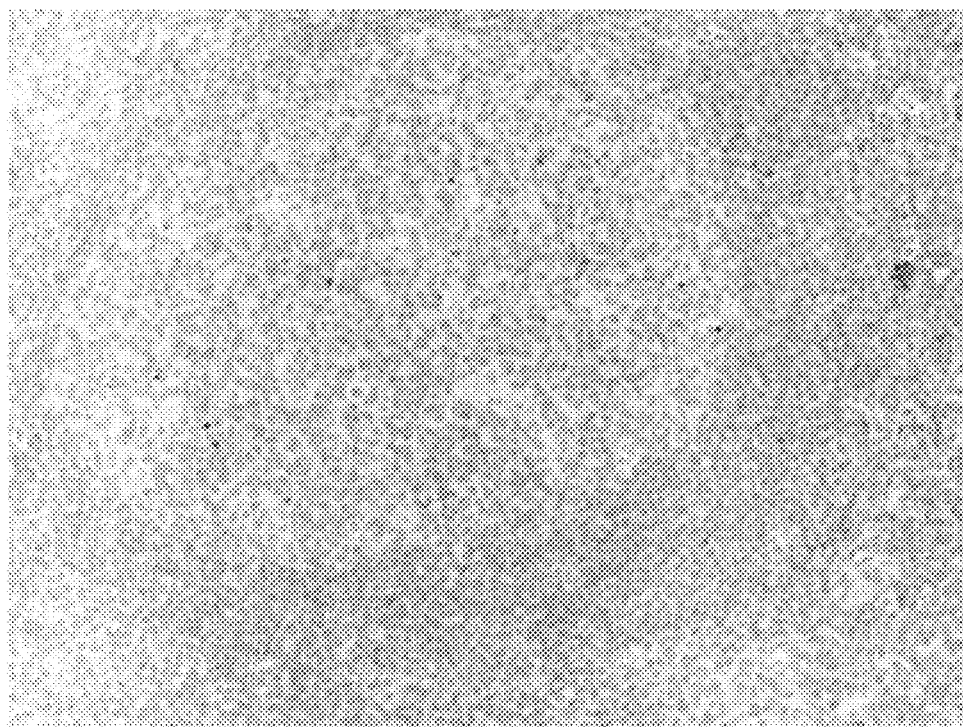
FIG. 21(B) is a microphotograph illustrating optimal staining amplification of Ki67 on FFPE tonsil tissue with a QMP having a pyridine leaving group and conjugated with a biotin detectable label.
Figure 21C:
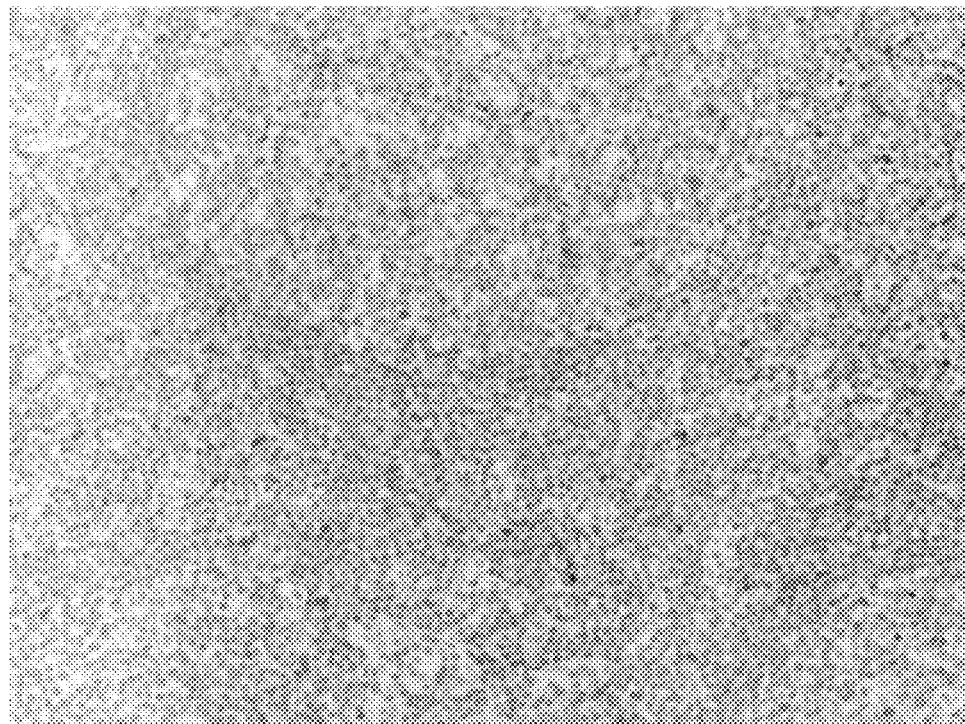
FIG. 21(C) is a microphotograph illustrating optimal staining amplification of Ki67 on FFPE tonsil tissue with a DABCO leaving group and conjugated with a biotin detectable label.
Figure 21D:
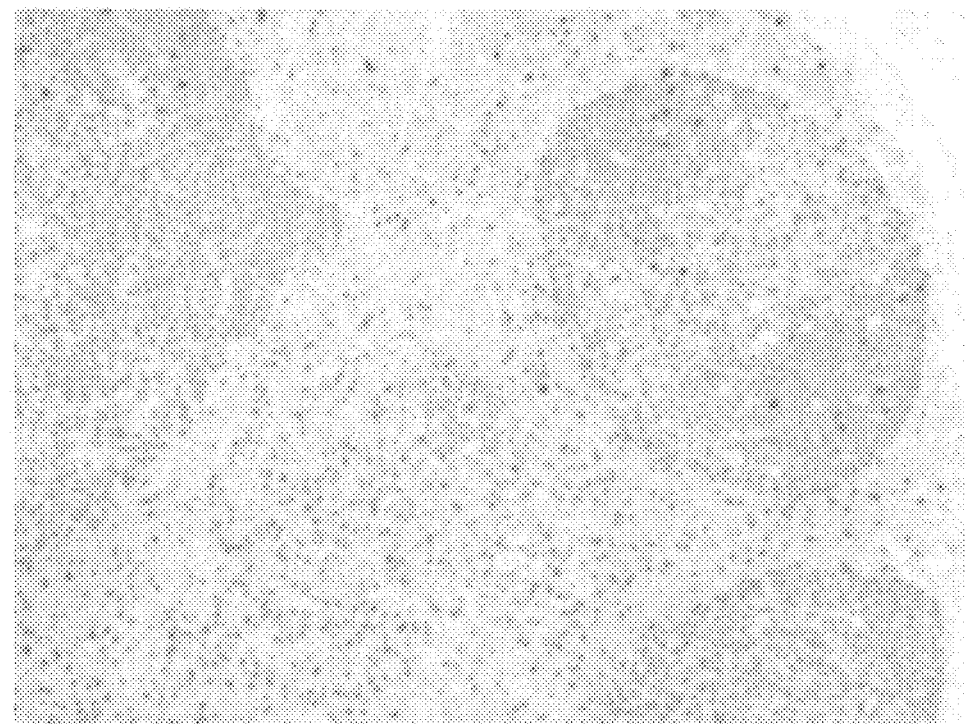
FIG. 21(D) is a microphotograph illustrating optimal staining amplification of Ki67 on FFPE tonsil tissue with a triethylamine leaving group and conjugated with a biotin detectable label.

(b) Quinone methide analog precursor amplified DAB (FIGS. 21(B)-(D)). The tissue was deparaffinized and retrieved as described in the general procedures. Rabbit-anti-Ki-67 antibody incubation (37° C., 16 minutes) and washing were followed by secondary antibody incubation with a goat polyclonal anti-rabbit antibody conjugated to AP (37° C.; 12 minutes). After incubating with the AP conjugate the slides were washed with Special Stains wash. Pyridine QMP-biotin (100 µM) (FIG. 21(B)) or DABCO QMP-biotin (100 µM) (FIG. 21(C)) or triethylamine QMP-biotin (100 µM) (FIG. 21(D)) was dissolved in 100 mM CHES, pH 10.0, 0.05% Brij-35 to a final concentration of 100 nM. QMP turnover was achieved by adding 100 µL of AP Enhancer followed by 100 µL of biotin labeled QMP and incubating at 37° C. for 16 minutes. The deposited hapten was subsequently bound by streptavidin-HRP conjugate (37° C.; 8 minutes), and visualized via a brown precipitate produced by HRP upon the addition of hydrogen peroxide and DAB (37° C.; 8 minutes). The DAB was toned by the addition of copper sulfate (37° C.; 4 minutes). The stained tissue sections were counterstained with modified Mayer's hematoxylin (37° C.; 4 minutes) and then incubated with Bluing Reagent (37° C.; 4 minutes). They were then dehydrated through a graded ethanol series, cleared with xylene, and manually cover-slipped.

These results demonstrate the sub-optimal performance of quaternary amines as LG for this application, when compared to the control. The pyridine, DABCO and triethylamine QMP-biotin derivatives all show much lower staining intensity and greatly diffuse signals (FIGS. 21(B)-(D)) compared to the control slide (FIG. 21(A)).

Example 5

HRP DAB Amplified by QMP-Biotin with Various Leaving Groups (FIGS. 22(A)-(D)

Figure 22A:
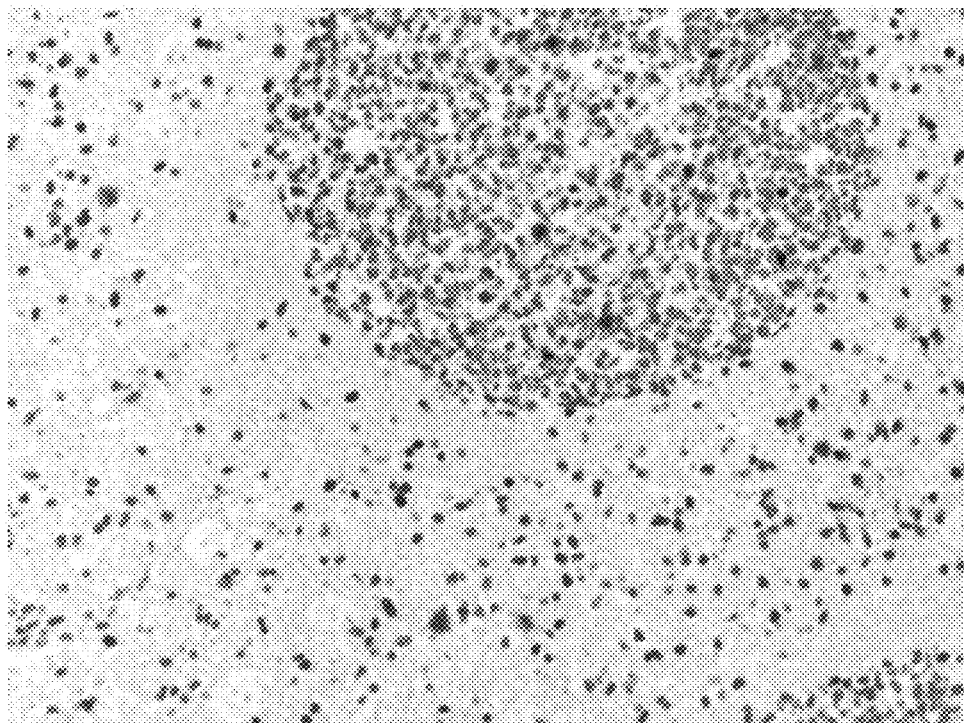
FIG. 22(A) is a microphotograph illustrating optimal functional staining amplification of Ki67 on FFPE tonsil tissue by ultraView DAB
Figure 22B:
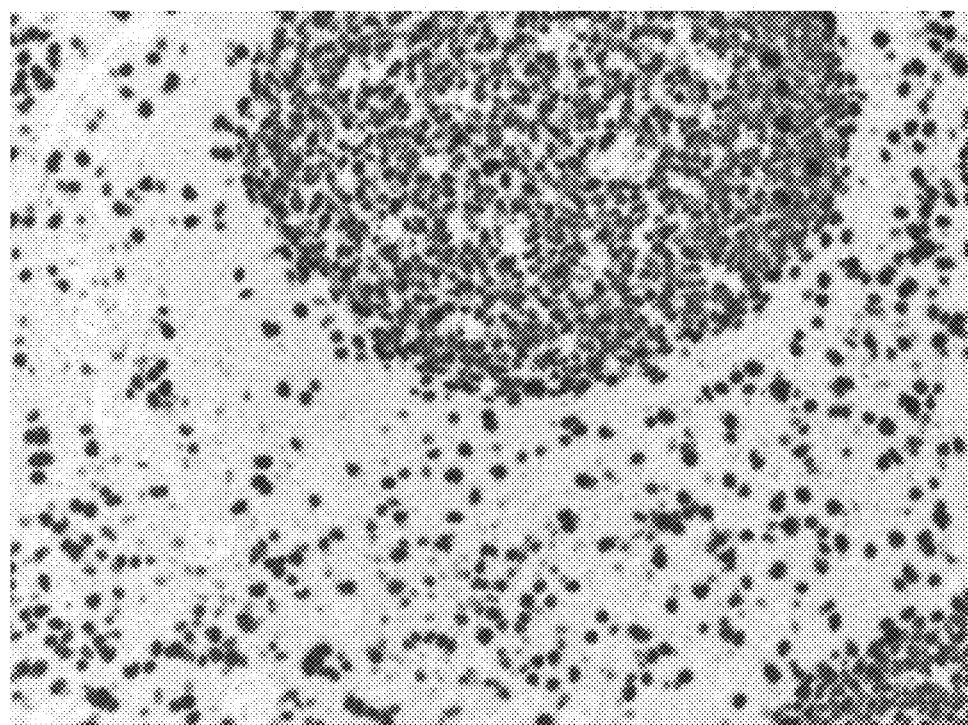
FIG. 22(B) is a microphotograph illustrating optimal functional staining amplification of Ki67 on FFPE tonsil tissue with a QMP having a monofluoro leaving group with a biotin detectable label.
Figure 22C:
FIG. 22(C) is a microphotograph illustrating optimal functional staining amplification of Ki67 on FFPE tonsil tissue with a QMP having an acetate leaving group.
Figure 22D:
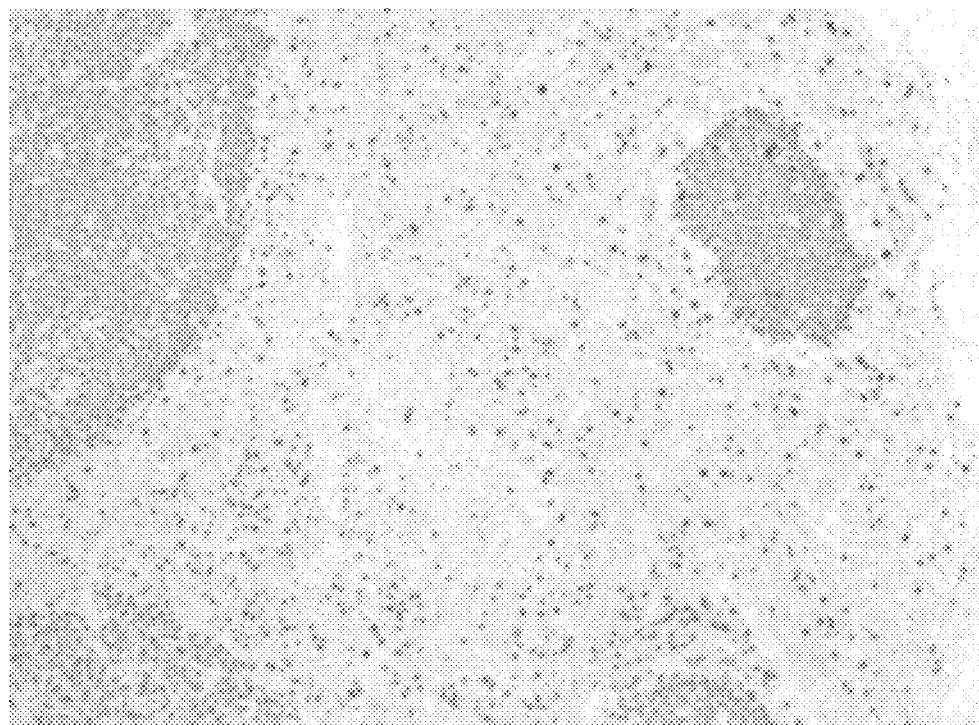
FIG. 22(D) is a microphotograph illustrating optimal functional staining amplification of Ki67 on FFPE tonsil tissue a methoxy leaving group and a biotin detectable label.

(a) ultraView Control (FIG. 22(A)). See Example 4(a).
(b) QMP amplified DAB (FIGS. 22(B)-22(D)). The tissue was deparaffinized and retrieved as described in the general procedures. Rabbit-anti-Ki-67 antibody incubation (37° C., 16 minutes) and washing were followed by secondary antibody incubation with a goat polyclonal anti-rabbit antibody conjugated to AP (37° C.; 12 minutes). After incubating with the AP conjugate the slides were washed with Special Stains wash. Monofluoro QMP-biotin (400 nM) (FIG. 22(B)) or acetate QMP-biotin (100 µM) (FIG. 22(C)) or methoxy QMP-biotin (100 µM) (FIG. 22(D)) was dissolved in 100 mM CHES, pH 10.0, 0.05% Brij-35 to a final concentration of 100 nM. QMP turnover was achieved by adding 100 µL of AP Enhancer followed by 100 µL of biotin labeled QMP and incubating at 37° C. for 16 minutes. The deposited biotin was subsequently bound by a streptavidin-HRP conjugate (37° C.; 8 minutes), and visualized via a brown precipitate produced by HRP upon the addition of hydrogen peroxide and DAB (37° C.; 8 minutes). The DAB was toned by the addition of copper sulfate (37° C.; 4 minutes). The stained tissue sections were counterstained with modified Mayer's hematoxylin (37° C.; 4 minutes) and then incubated with Bluing Reagent (37° C.; 4 minutes). They were then dehydrated through a graded ethanol series, cleared with xylene, and manually cover-slipped.

Two sub-optimal and one optimal LG's are shown in this example. The QMP-biotin with an acetate LG (FIG. 22(C)) generates weak, very diffuse signal and the QMP-biotin with a methoxy LG shows well resolved signal but with low intensity (FIG. 22(D)). The monofluoro LG derivative of QMP-biotin ((FIG. 22(B)) demonstrates well resolved signal with greater or equal intensity to the control slide (FIG. 22(A)). Of all the LG groups evaluated the monofluoro gives the best performance.

Example 6

Figure 23A:
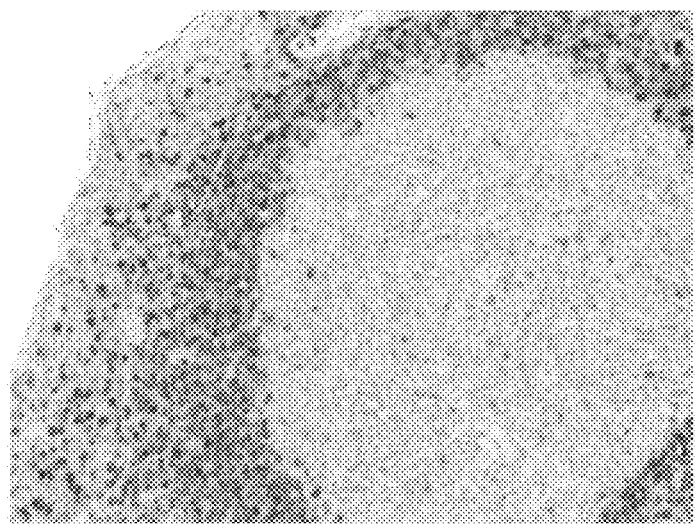
FIG. 23(A) is a microphotograph illustrating functional staining amplification of Bcl2 on FFPE tonsil tissue by a QMP having a monofluoro leaving group, a biotin detectable label, and an aniline amide linker (Compound 7).
Figure 23B:
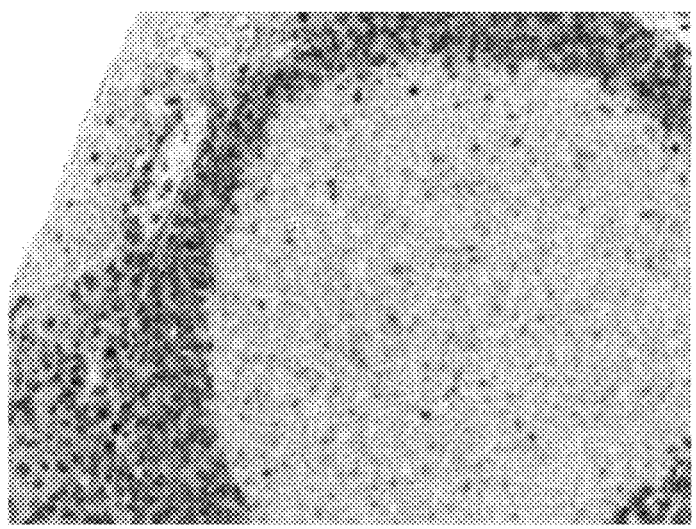
FIG. 23(B) is a microphotograph illustrating functional staining amplification of Bcl2 on FFPE tonsil tissue by a QMP having a monofluoro leaving group, a biotin detectable label, and a benzoic amide linker (Compound 21).
Figure 23C:
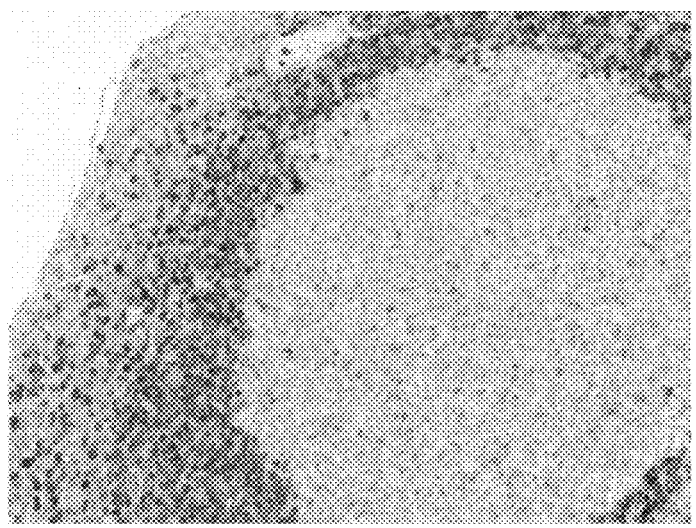
FIG. 23(C) is a microphotograph illustrating functional staining amplification of Bcl2 on FFPE tonsil tissue by a QMP having a monofluoro leaving group, a biotin detectable label, and a tyramide amide linker (Compound 14).

HRP DAB Amplified by QMP-Biotin with Different Linkers (FIGS. 23(A)-(C)

The tissue was deparaffinized and retrieved as described in the general procedures. Mouse-anti-Bcl-2 antibody incubation (37° C., 16 minutes) and washing were followed by secondary antibody incubation with a goat polyclonal anti-mouse antibody conjugated to AP (37° C.; 12 minutes). After incubating with the AP conjugate the slides were washed with Special Stains wash. Monofluoro QMP-biotin (with aniline amide (FIG. 23(A)), benzoic amide (FIG. 23(B)) or tyramide amide linker (FIG. 23(C)) (100 nM) was dissolved in 100 mM CHES, pH 10.0, 0.05% Brij-35 to a final concentration of 100 nM. QMP turnover was achieved by adding 100 µL of AP Enhancer followed by 100 µL of biotin labeled QMP and incubating at 37° C. for 16 minutes. The deposited biotin was subsequently bound by a streptavidin-HRP conjugate (37° C.; 8 minutes), and visualized via a brown precipitate produced by HRP upon the addition of hydrogen peroxide and DAB (37° C.; 8 minutes). The DAB was toned by the addition of copper sulfate (37° C.; 4 minutes). The stained tissue sections were counterstained with modified Mayer's hematoxylin (37° C.; 4 minutes) and then incubated with Bluing Reagent (37° C.; 4 minutes). They were then dehydrated through a graded ethanol series, cleared with xylene, and manually cover-slipped.

This experiment demonstrates the subtle effect of mildly electron withdrawing groups (EWG) and electron donating groups (EDG) on the functional staining performance of the QMP-biotin. The benzoic amide linker (Compound 21, FIG. 2(A)) is mildly EWG and results in more diffuse, less resolved signal. The other linkers which are neutral (aniline amide (Compound 7, FIG. 2(A))) or mildly EDG (tyramide amide (Compound 14, FIG. 2(A))) generate well resolved signals. Other experiments (not included here) with strong EDG (e.g. methoxy) or EWG (e.g. nitro) show much more deleterious effect on staining performance. This illustrates the influence of electronics on the reactivity of the QMP intermediates and the effect on staining performance.

Example 7

AP Fast Red Amplified by Monofluoro-QMP-NP (FIGS. 14A-(D)

Figure 14A:
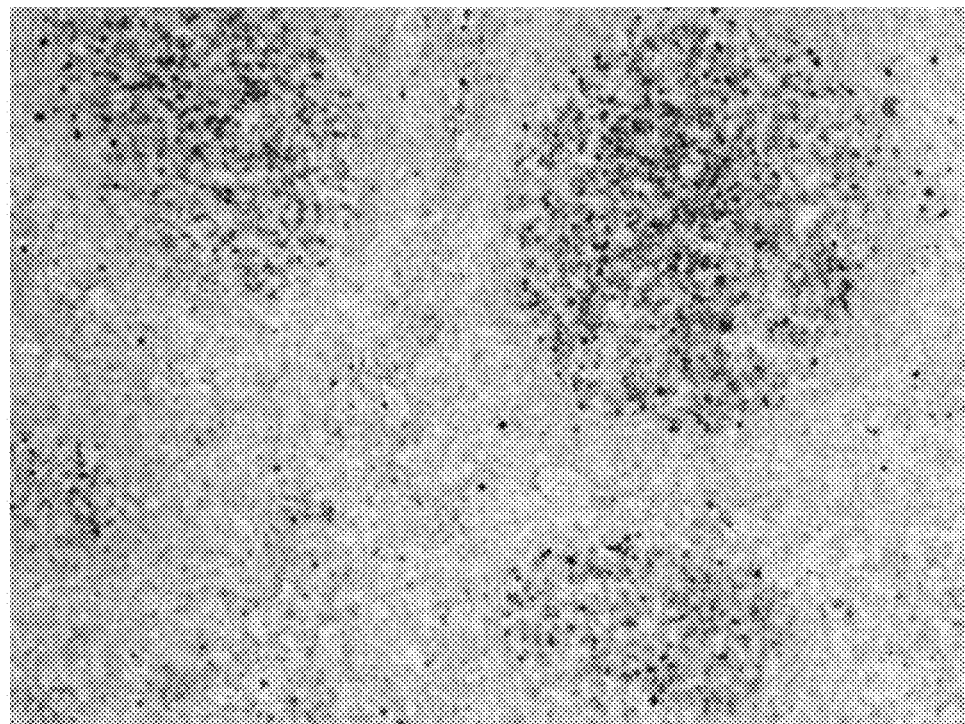
FIG. 14(A) is a microphotograph illustrating functional staining of CD-10 on FFPE tonsil tissue by a QMP having a monofluoro leaving group and a 5-nitro-3-pyrazolecarbamide (nitropyrazole, NP) detectable label.
Figure 14B:
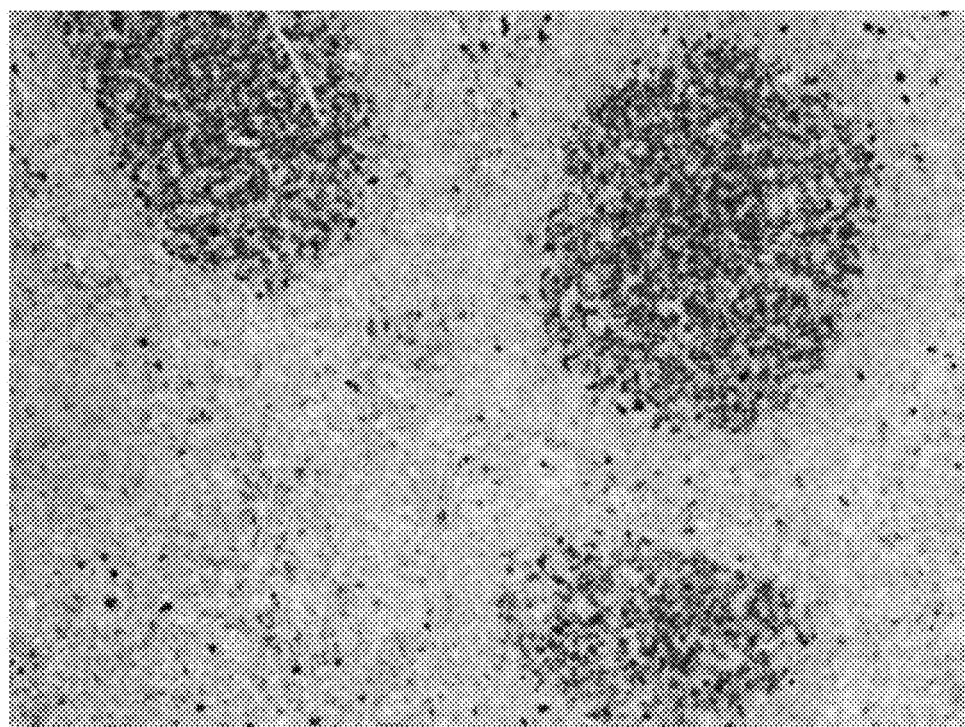
FIG. 14(B) is a microphotograph illustrating functional staining of amplification of CD-10 on FFPE tonsil tissue by a QMP having a monofluoro leaving group and a 5-nitro-3-pyrazolecarbamide (nitropyrazole, NP) detectable label, followed by an anti-NP antibody/alkaline phosphatase conjugate and fast red staining.
Figure 14C:
FIG. 14(C) is a microphotographs illustrating functional staining of Bcl2 on FFPE tonsil tissue by a QMP having a monofluoro leaving group and a 5-nitro-3-pyrazolecarbamide (nitropyrazole, NP) detectable label, followed by an anti-NP antibody/alkaline phosphatase conjugate and fast red staining.
Figure 14D:
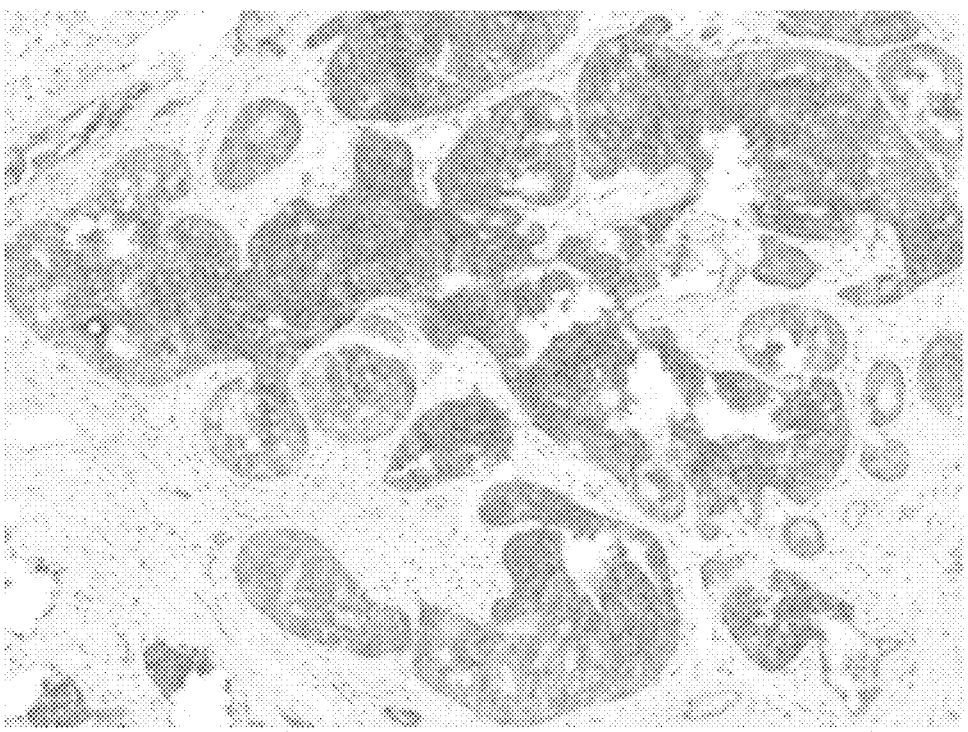
FIG. 14(D) is a microphotograph illustrating functional staining Her3 on FFPE breast tissue by a QMP having a monofluoro leaving group and a 5-nitro-3-pyrazolecarbamide (nitropyrazole, NP) detectable label, followed by an anti-NP antibody/alkaline phosphatase conjugate and fast red staining.

Fast Red control (FIG. 14(A)). The tissue was deparaffinized and retrieved as described in the general procedures. Rabbit-anti-CD-10 antibody incubation (37° C., 16 minutes) and washing were followed by incubation with a goat-anti-rabbit polyclonal antibody, hapten labeled with nitropyrazole (NP) (37° C.; 8 minutes). After washing AP-conjugated mouse anti-NP monoclonal antibody was added (37° C.; 12 minutes). Detection was achieved by adding 100 µL of AP Enhancer, followed by 100 µL of naphthol AS-TR phosphate and 200 µL of Fast Red KL (37° C.; 16 minutes). The stained tissue sections were counterstained with modified Mayer's hematoxylin (37° C.; 4 minutes) and then incubated with Bluing Reagent (37° C.; 4 minutes). The slides were rinsed with a detergent water mixture, air dried and manually cover-slipped.

QMP amplified Fast Red (FIG. 14(B)-14(D)). The tissue was deparaffinized and retrieved as described in the general procedures. Rabbit-anti-CD-10, mouse-anti-Bcl-2 or mouse-anti-Her3 antibody incubation (37° C., 32 minutes) and washing were followed by incubation with a goat polyclonal anti-rabbit or anti-mouse antibody, hapten labeled with nitropyrazole (NP) (37° C.; 8 minutes). After washing AP-conjugated mouse anti-NP monoclonal antibody was used as a tertiary antibody (37° C.; 12 minutes). After incubating with the AP conjugate the slides were washed with Special Stains wash. Monofluoro QMP-NP (100 nM) was dissolved in 100 mM CHES, pH 10.0, 0.05% Brij-35 to a final concentration of 100 nM. QMP turnover was achieved by adding 100 µL of AP Enhancer followed by 100 µL of NP labeled QMP and incubating at 37° C. for 16 minutes. The deposited hapten was subsequently bound by a mouse-anti-hapten-AP conjugate (37° C.; 12 minutes), and detection was achieved by adding 100 µL of AP Enhancer, followed by 100 µL of naphthol AS-TR phosphate and 200 µL of Fast Red KL (37° C.; 16 minutes). The stained tissue sections were counterstained with modified Mayer's hematoxylin (37° C.; 4 minutes) and then incubated with Bluing Reagent (37° C.; 4 minutes). The slides were rinsed with a detergent water mixture, air dried and manually cover-slipped.

This example demonstrates than once a reporter (in this case the NP hapten) is deposited by QMP methodology then an alternate detection system to DAB can also be used. In this case an anti-NP AP conjugate is used to visualize the target with AP Fast Red chemistry. FIG. 14(B) shows a significant amplification in signal over the control slide (FIG. 14(A)). FIGS. 14(C) and 14(D) show strong intensity staining for normally weakly visualized biomarkers Bcl2 and Her3.

Example 8

Monofluoro-QMP-Fluorophore and Quantum Dot Amplified by Monofluoro-QMP-NP (FIGS. 15(A)-(D)

Figure 15B:
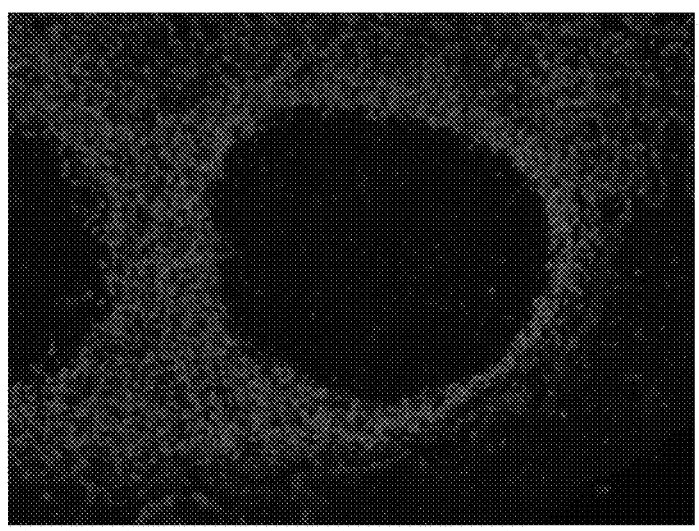
FIG. 15(B) is a microphotograph illustrating functional staining amplification of an AF700 detectable moiety.
Figure 15C:
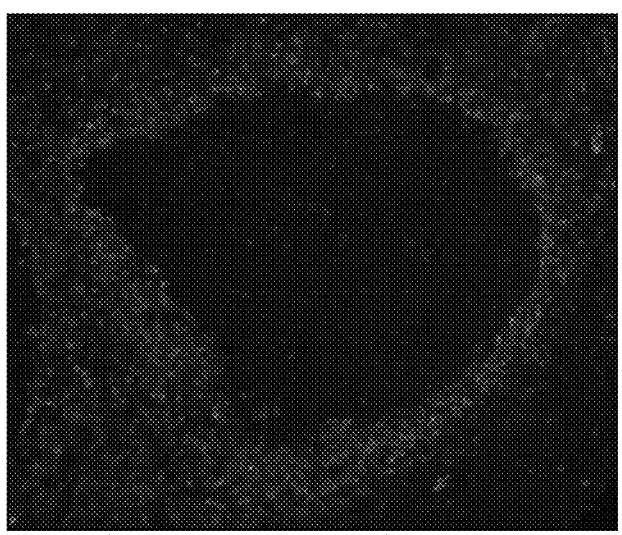
FIG. 15(C) is a microphotograph illustrating functional staining amplification of nitropyrazole detectable followed by a quantum dot (QD525)-labeled, anti-nitropyrazole antibody.

(a) QMP fluorophore (FIGS. 15(A), 15(B)). The tissue was deparaffinized and retrieved as described in the general procedures. Mouse-anti-Bcl-2 antibody incubation (37° C., 16 minutes) and washing were followed by secondary antibody incubation with a goat polyclonal anti-mouse antibody, hapten labeled with nitropyrazole (NP) (37° C.; 8 minutes). After washing AP-conjugated mouse anti-NP monoclonal antibody was added (37° C.; 12 minutes). After incubating with the AP conjugate the slides were washed with Special Stains wash. Monofluoro QMP-TAMRA (FIG. 15(A)) or monofluoro QMP-Alexa Fluor® 700 (FIG. 15(B)) was dissolved in 100 mM CHES, pH 10.0, 0.05% Brij-35. QMP turnover was achieved by adding 100 µL of AP Enhancer followed by 100 µL of fluorophore labeled QMP and incubating at 37° C. for 16 minutes. The slides were washed with Reaction Buffer, dehydrated through a graded ethanol series, cleared with xylene, and manually cover-slipped. The slides were viewed by fluorescence microscopy using the appropriate filter sets.

(b) QMP amplified Quantum Dot (FIG. 15(C)). The tissue was deparaffinized and retrieved as described in the general procedures. Mouse-anti-Bcl-2 antibody incubation (37° C., 16 minutes) and washing were followed by secondary antibody incubation with a goat polyclonal anti-mouse antibody, hapten labeled with nitropyrazole (NP) (37° C.; 8 minutes). After washing AP-conjugated mouse anti-NP monoclonal antibody was added (37° C.; 12 minutes). After incubating with the AP conjugate the slides were washed with Special Stains wash. Monofluoro QMP-NP was dissolved in 100 mM CHES, pH 10.0, 0.05% Brij-35. QMP turnover was achieved by adding 100 µL of AP Enhancer followed by 100 µL of NP labeled QMP and incubating at 37° C. for 16 minutes. The deposited hapten was subsequently visualized by incubation with a mouse-anti-NP Quantum Dot 525 conjugate (37° C.; 32 minutes). The slides were washed with Reaction Buffer, dehydrated through a graded ethanol series, cleared with xylene, and manually cover-slipped. The slides were viewed by fluorescence microscopy using the appropriate filter sets.

When fluorophores are used as the reporter in a QMP molecule (FIGS. 15(A) and 15(B)) then the results can be visualized with any further detection chemistries generating an amplified fluorescent signal. QMP-NP can be detected fluorescently using a streptavidin-quantum conjugate. This offers an alternative way of detecting the deposited hapten compared to the HRP/DAB method outlined in Examples 3-6. This illustrates that the QMP methodology can be used to generate both brightfield and darkfield (fluorescent) amplified signals and is easily adapted to work with existing detection chemistries.

Example 9

Figure 13B:
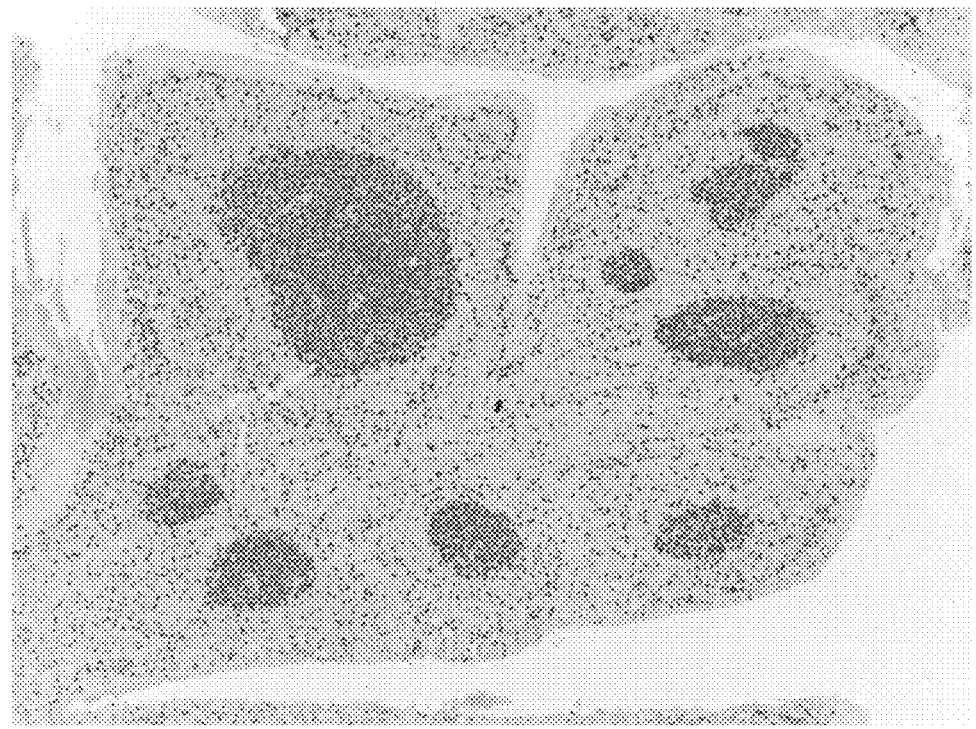
FIG. 13(B) is a microphotograph illustrating a VENTANA ultraView DAB control of the assay illustrated in FIG. 13(A).

HRP DAB Amplified by QMP-NP (FIGS. 13(A)-(B). 24(A)-(B). 25(A)-(B)

Figure 24A:
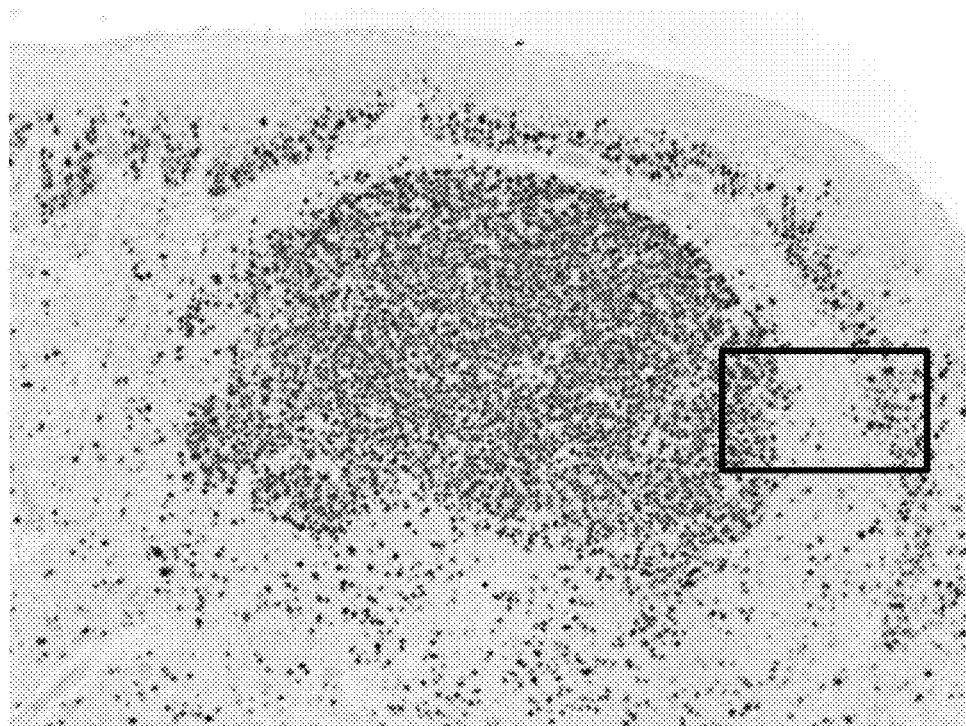
FIG. 24(A) is a further magnification of the microphotographs in FIG. 17(B).
Figure 24B:
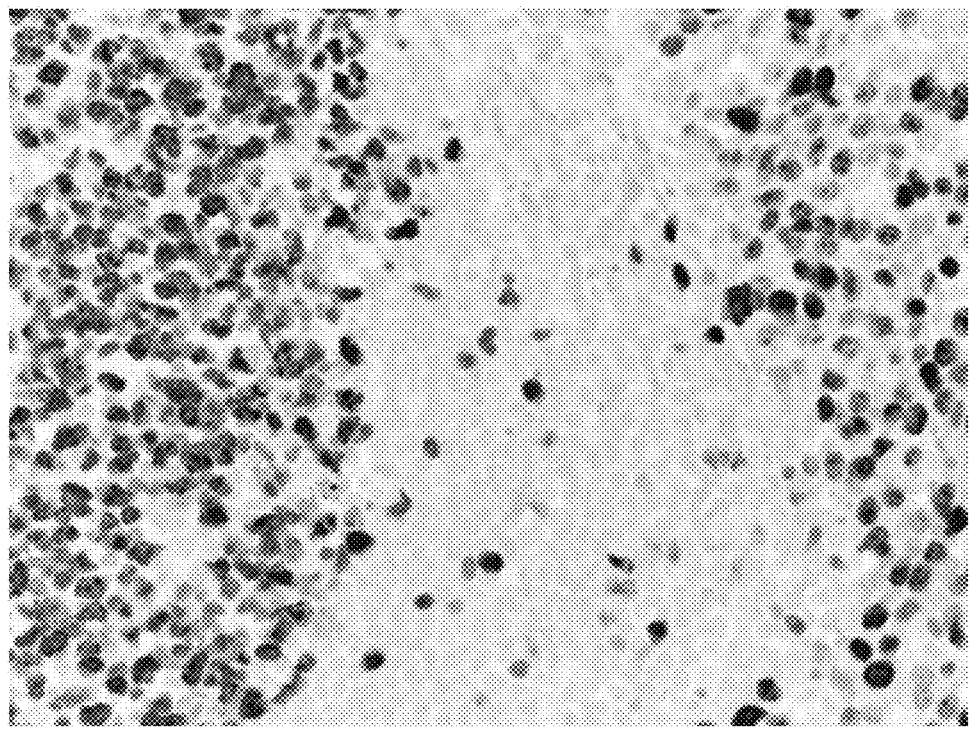
FIG. 24(B) is a further magnification of the microphotographs in FIG. 17(B).

(a) ultraView Control (FIG. 13(B), FIGS. 24(A)-24(B); 24(B) shows the region of 24(A) demarcated by a black box at higher magnification). See Example 4(a).

Figure 25A:
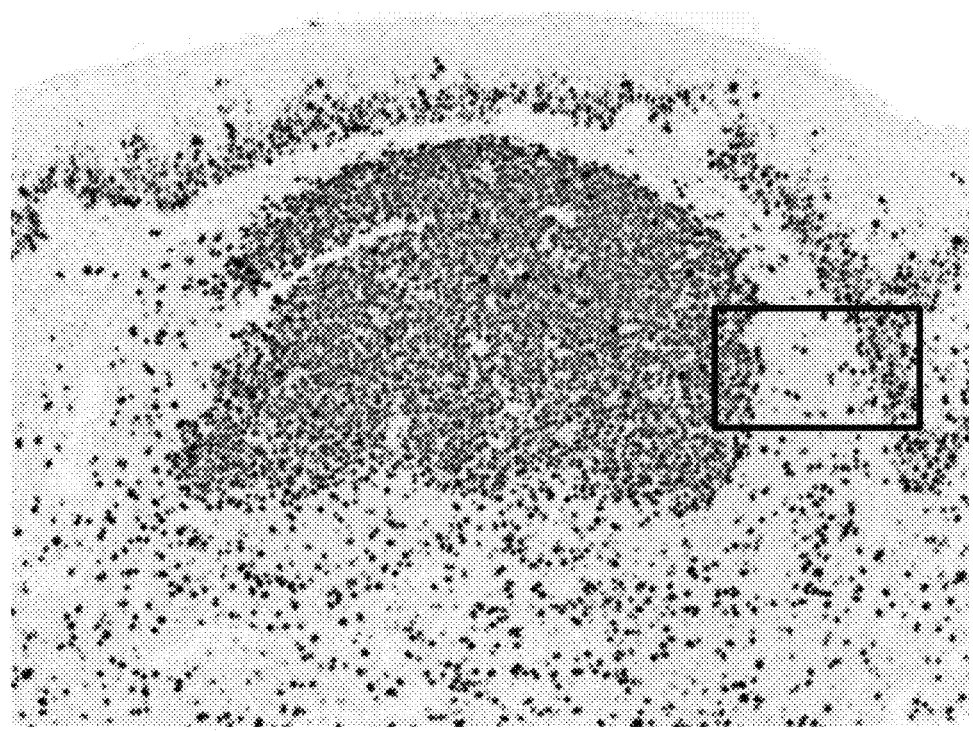
FIG. 25(A) is a further magnification of the microphotographs in FIG. 17(A).
Figure 25B:
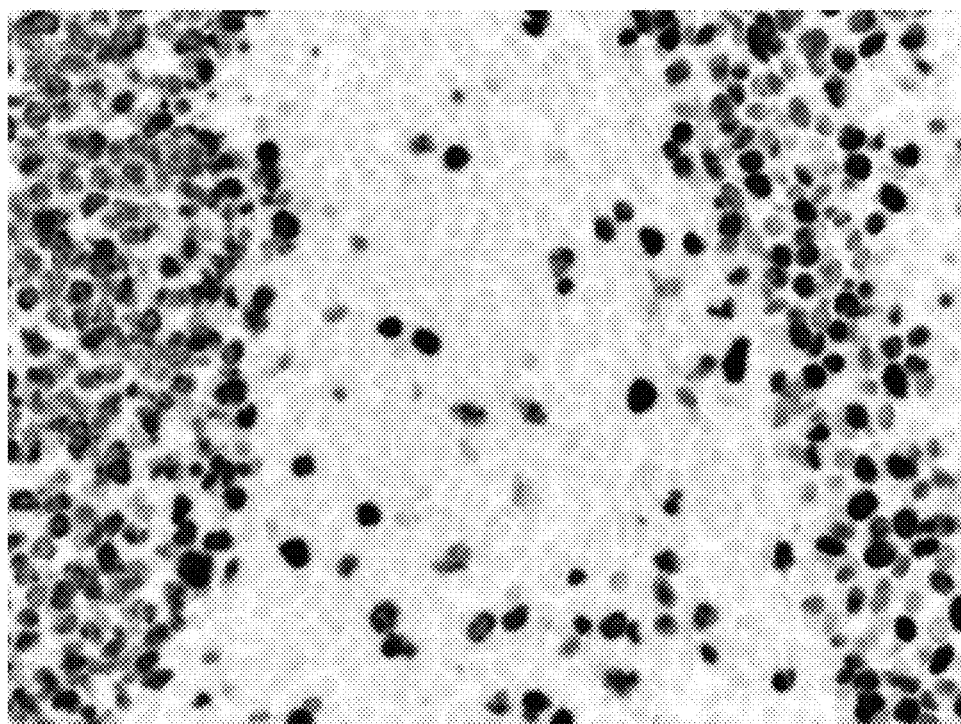
FIG. 25(B) is a further magnification of the microphotographs in FIG. 17(A).

QMP amplified DAB (FIG. 13(A), FIGS. 25(A)-25(B); 25(B) shows the region of 25(A) demarcated by a black box at higher magnification). The tissue was deparaffinized and retrieved as described in the general procedures. Rabbit-anti-Ki-67 antibody incubation (37° C., 16 minutes) and washing were followed by secondary antibody incubation with a goat polyclonal anti-rabbit antibody conjugated to AP (37° C.; 12 minutes). After incubating with the AP conjugate the slides were washed with Special Stains wash. Monofluoro QMP-NP (100 nM) was dissolved in 100 mM CHES, pH 10.0, 0.05% Brij-35 to a final concentration of 100 nM. QMP turnover was achieved by adding 100 µL of AP Enhancer followed by 100 µL of NP labeled QMP and incubating at 37° C. for 16 minutes. The deposited hapten was subsequently bound by a mouse-anti-NP HRP conjugate (37° C.; 8 minutes), and visualized via a brown precipitate produced by HRP upon the addition of hydrogen peroxide and DAB (37° C.; 8 minutes). The DAB was toned by the addition of copper sulfate (37° C.; 4 minutes). The stained tissue sections were counterstained with modified Mayer's hematoxylin (37° C.; 4 minutes) and then incubated with Bluing Reagent (37° C.; 4 minutes). They were then dehydrated through a graded ethanol series, cleared with xylene, and manually cover-slipped.

This example demonstrates the amplification of signal using QMP-NP followed by HRP/DAB detection. While the signal intensity is greater, no additional background is generated and the signal localization is equivalent to the control slide.

Example 10

QMP with Chromophore Detectable Label Moieties (FIGS. 16(A)-(D)

QMP with chromophore detectable label moieties (FIGS. 16(A)-16(D)). The tissue was deparaffinized and retrieved as described in the general procedures. Rabbit-anti-Ki-67 antibody incubation (37° C., 16 minutes) and washing were followed by secondary incubation with a goat polyclonal anti-rabbit, hapten labeled with nitropyrazole (NP) (37° C.; 8 minutes). After washing AP-conjugated mouse anti-NP monoclonal antibody was added (37° C.; 12 minutes). After incubating with the AP conjugate the slides were washed with SSC. Monofluoro QMP-PEG8-Dabsyl (250 µM) (FIG. 16(A)) or monofluoro QMP-TAMRA (250 µM) (FIG. 16(B)) or monofluoro QMP-Cy5 (250 µM) (FIG. 16(C)) or monofluoro QMP-Rhodamine 110 (250 µM) (FIG. 16(D)) were dissolved in 250 mM Tris, pH 10.0, 0.05% Brij-35. QMP turnover was achieved by adding 100 µL of AP Enhancer followed by 100 µL the appropriate QMP and incubating at 37° C. for 32 minutes. The stained tissue sections were counterstained with modified Mayer's hematoxylin (37° C.; 4 minutes) and then incubated with Bluing Reagent (37° C.; 4 minutes). The slides were then dehydrated through a graded ethanol series, cleared with xylene, and manually cover-slipped.

Examples 2-9 have demonstrated that QMP-reporters can be visualized by existing detection chemistries (HRP/DAB & AP/Fast Red) and directly by fluorescence. This example demonstrates that if a chromophore with a large extinction coefficient is the reporter molecule then the amplified QMP signal can be seen directly by brightfield microscopy. By selecting chromophores with different absorption wavelengths then a large range of discrete colors can be created (FIGS. 16(A)-(D)). The ability to use a single core molecule (QMP) with different reporters to generate multiple chromogenic detection systems is of fundamental importance for multiplex applications. Previously to generate new chromogenic detection systems, new chemistries needed to be invented and each enzyme needed a different approach. The ability to use a single QMP core molecule with different reporter molecules and/or different enzymatic recognition groups provides new tools for multiplex brightfield (and fluorescent) assays.

Example 11

Trapping Experiments

Figure 26:
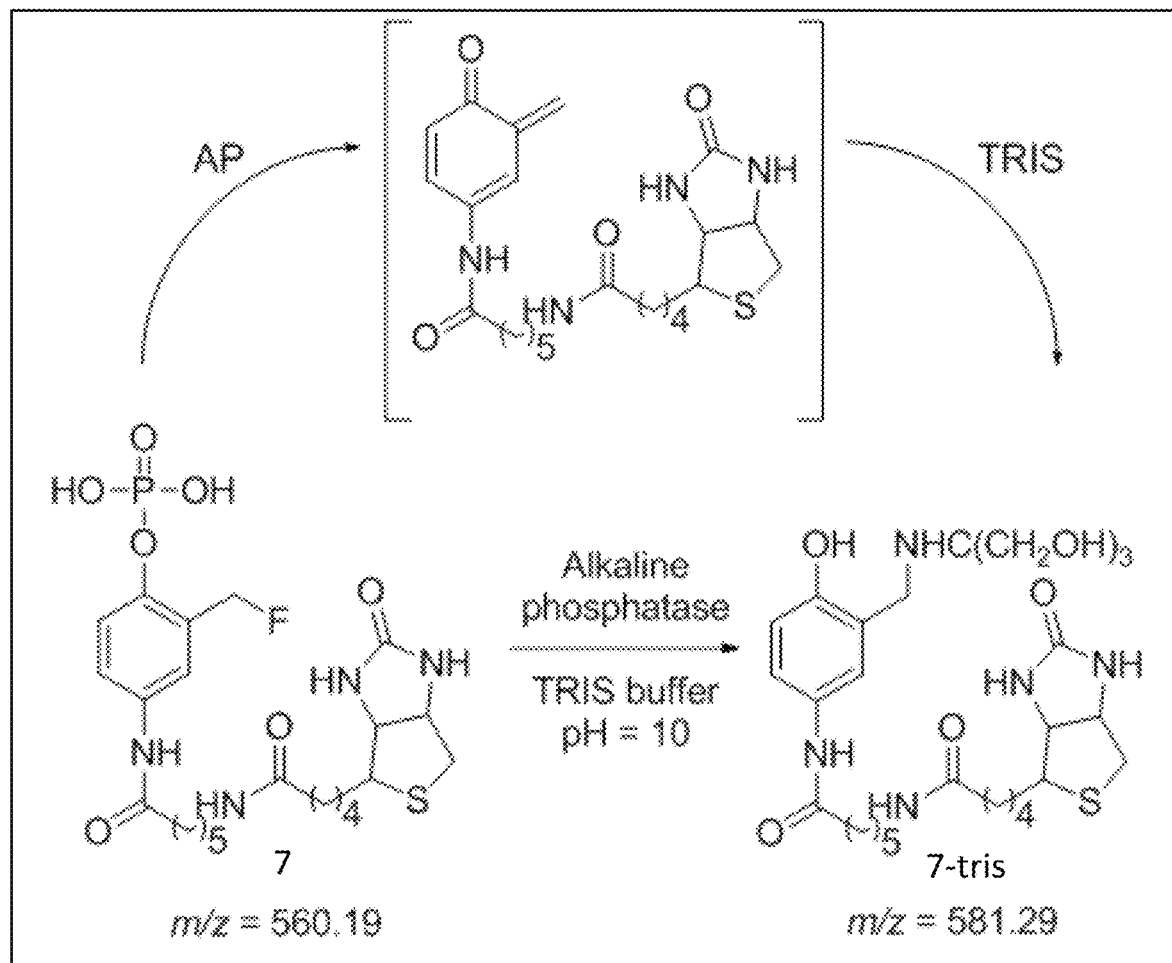
FIG. 26 illustrates the trapping the QM intermediate from a monofluroinated QM precursor with Tris.
Figure 27:
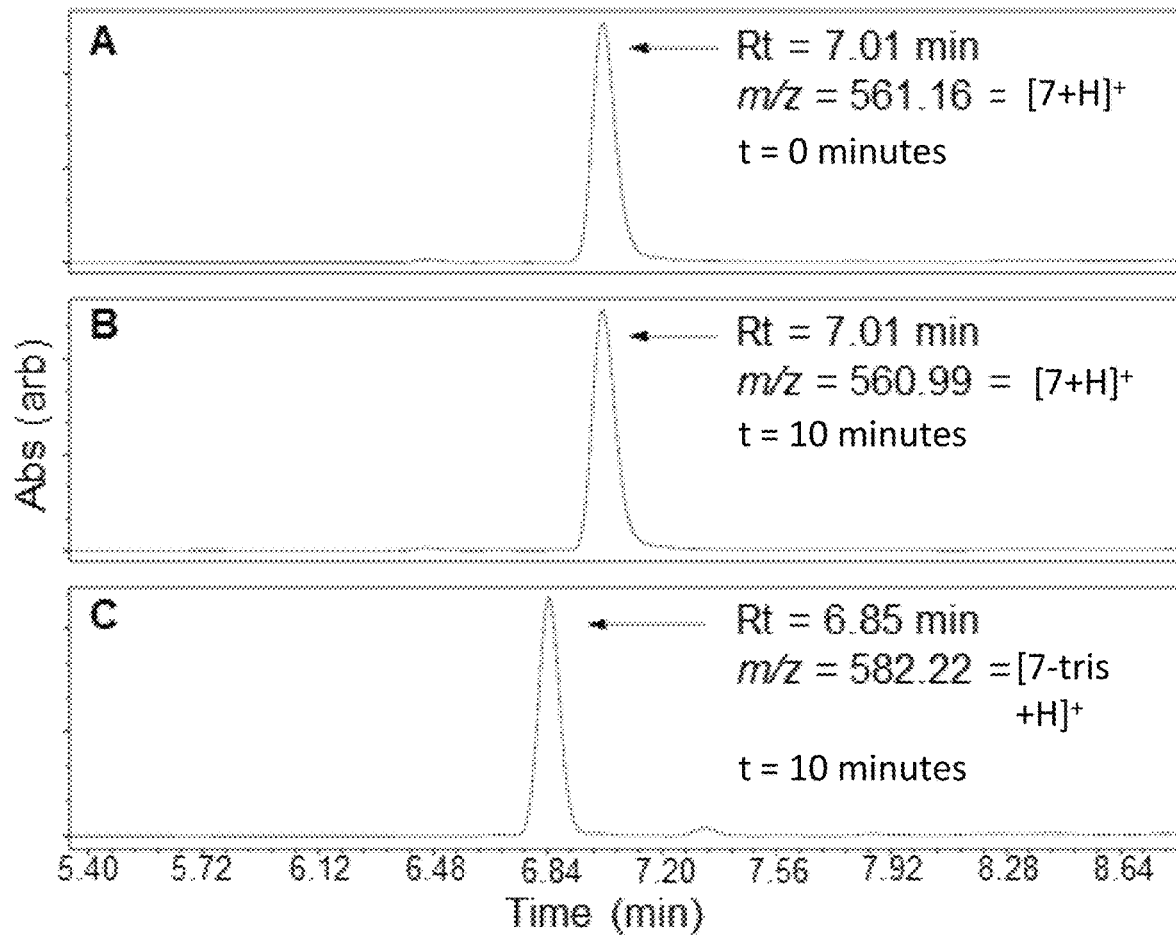
FIG. 27 is a HPLC chromatograms of the compounds from the reaction illustrated in FIGS. 24(A)-(B), where panel A t=0 min., panel B t=10 min., panel C t=10 min.

To probe the mechanism of staining and quenching, an attempt was made to trap the QM intermediate formed by monofluoro QM precursor 7 in solution-phase under similar conditions to those utilized in the staining experiments (FIG. 26). QM precursor 7 was dissolved in pH 10 Tris buffer followed by addition of a catalytic amount of AP. The reaction progress was monitored by HPLC-MS (FIG. 27, panels A-C). Within 10 minutes, complete conversion to the Tris adduct 7-tris was observed (panel C). In the absence of AP, no reaction took place, suggesting a high level of stability under the desired reaction conditions (panel B). These results strongly support the proposed mechanism of QM-mediated staining and elucidates Tris base as the primary source of quenchers under the IHC staining conditions.

Additional trapping experiments were performed to demonstrate the ability to generate and trap quinone methides in solution from QM precursors comprising a phosphate, a galactoside and an acetate as the enzyme recognition group. Each QM precursor was treated in solution with the corresponding enzyme, and the reaction progress was monitored by HPLC-MS (data not shown). Each substrate was diluted to 1 mM in a 250 mM Tris solution at suitable pH for the cognate enzyme (10 for alkaline phosphatase, 8.0 for β-galactosidase, and 8.0 for lipase), followed by addition of the cognate enzyme such that the final concentration of enzyme in solution was 1 mM. The reactions were incubated at room temperature for 30 minutes, at which point the HPLC-MS was performed. In each case, the Tris-adduct was detected, demonstrating that the QM was being successfully formed.

Example 12

Stability

One aspect of the present disclosure is that compounds with sufficient instability are preferred in that the reaction should proceed quickly upon interacting with the activating enzyme; however, this instability must be balanced against the goal of making these compositions useful within the scope of their intended use, as described herein. In particular, the use of these reagents as detection reagents for automated IHC and ISH requires that the reagents be sufficiently stable in a container so that can be shipped to clinicians who can then store and use the reagents over a significant period of time. Relevant shelf-lives for compositions of this type would be 12-month, 18-month, 24-month, or greater stability. While storage conditions can be specified, the use of the reagents on a clinical instrument often requires that the reagent have significant room temperature stability. According to one embodiment, compositions of the present disclosure have suitable stability for automated IHC and ISH. It should be noted that suitability for automated ISH and IHC does not require absolute stability; rather, that a substantial amount of the compound remains after an established amount of time so that the use of the reagent is not adversely affected by the decomposition of the reagent.

Figure 28:
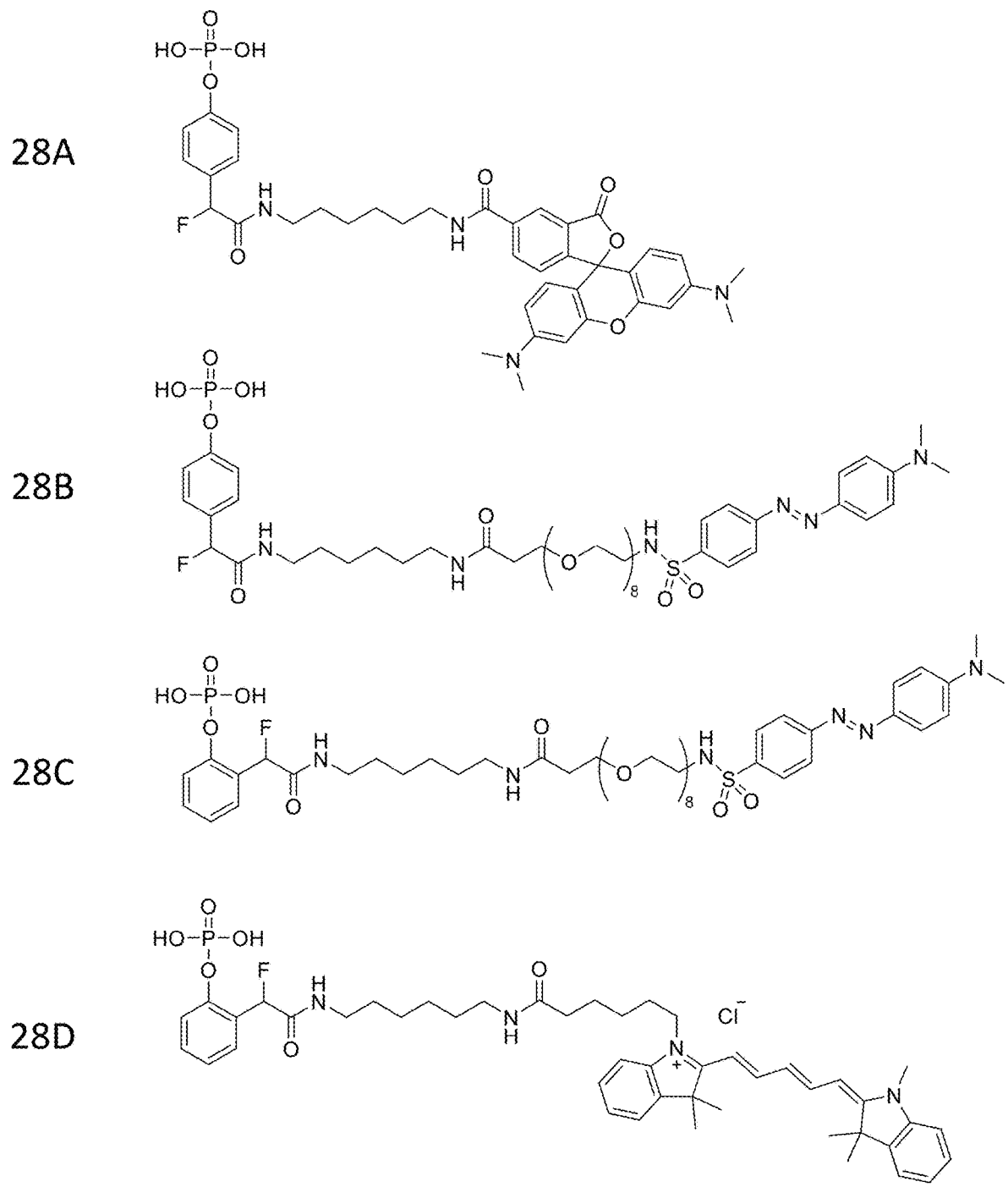
FIG. 28 provides exemplary structures of QMPs disclosed herein where panel A is a para-di-substituted QMP conjugated to a TAMRA, panel B is a para-di-substituted QMP conjugated to a Dabsyl, panel C is an ortho-di-substituted QMP conjugated to a Dabsyl, and panel D is an ortho-di-substituted QMP conjugated to a Cy5.

Referring now to FIG. 28, shown are four structures for compounds tested for suitable stability. Panel A is a para-di-substituted QMP conjugated to a TAMRA, panel B is a para-di-substituted QMP conjugated to a Dabsyl, panel C is an ortho-di-substituted QMP conjugated to a Dabsyl, and panel D is an ortho-di-substituted QMP conjugated to a Cy5. Referring now to Table 1, shown is the stability of compounds shown in FIG. 28 panels A and B in water at ambient temperature (20-25° C.). The degradation of the QMP dye conjugate appears to be independent of the identity of the dye. While not limited to a particular theory or mechanism, it was understood that the main mode of degradation was the displacement of the fluoride by water to generate a compound that does not have the ability to stain tissue. Scheme 14 shows the hydrolytic degradation of a representative QMP A to the non-staining compound B.

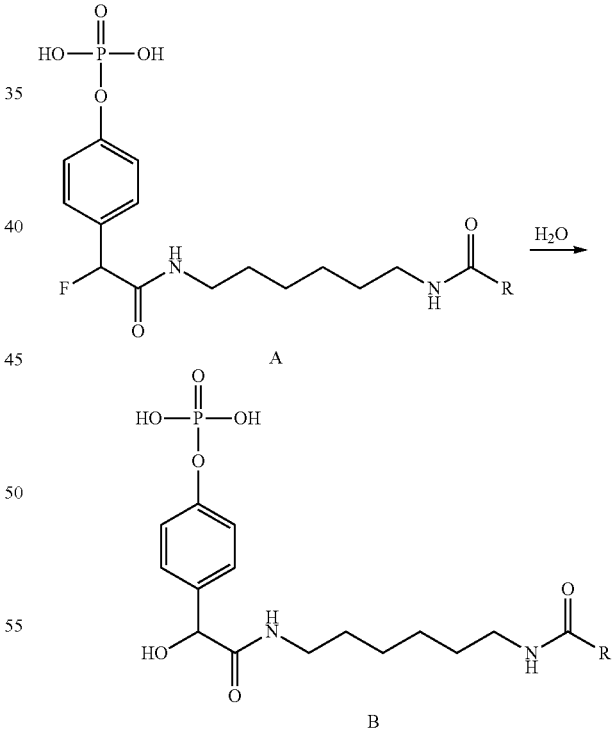

Scheme 14

It was discovered that the compounds degrade too quickly to be stored in an un-buffered aqueous solution. In particular, it was observed that only about 42% of the QMP of FIG. 28 panel A and about 44% of the QMP of FIG. 28 panel B remained after 12 days. The reagents were used on an autostainer and it was confirmed that the signal was diminished in comparison to a freshly synthesized reagent.

TABLE 1

| | | Compound from FIG. 28 | | | | | | |
|---|---|---|---|---|---|---|---|---|
| | | 28(A) | 28(B) | 28(A) | 28(A) | 28(A) | 28(B) | 28(B) | 28(B) |
| | | | | | Solvent | | | | |
| | | H₂O | H₂O | DMSO | DMSO | DMSO | DMSO | DMSO | DMSO |
| | | | | | Temperature (° C.) | | | | |
| | | 20-25 | 20-25 | 30 | 45 | 60 | 30 | 45 | 60 |
| Time (Days) | 0.0 | 100.0 | 100.0 | 96.7 | 96.6 | 94.3 | 93.9 | 94.0 | 94.3 |
| | 0.2 | 88.5 | 90.6 | — | — | — | — | — | — |
| | 2.0 | 76.1 | 81.3 | 96.8 | 96.4 | 94.7 | 94.0 | 93.6 | 92.6 |
| | 4.0 | — | — | 96.4 | 96.2 | 93.4 | 94.2 | 93.8 | 91.6 |
| | 5.0 | 68.8 | 73.8 | — | — | — | — | — | — |
| | 7.0 | 61.1 | 64.1 | 96.4 | 96.0 | 91.4 | 97.9 | 97.6 | 94.2 |
| | 9.0 | — | — | 96.3 | 95.9 | 89.5 | 98.0 | 97.3 | 92.4 |
| | 11.0 | — | — | 96.2 | 95.4 | 87.5 | 97.7 | 97.0 | 91.0 |
| | 12.0 | 41.9 | 44.1 | — | — | — | — | — | — |
| | 14.0 | — | — | 96.4 | 95.6 | 84.4 | 97.7 | 97.0 | 89.4 |
| | 16.0 | — | — | 96.5 | 95.0 | 83.5 | 97.8 | 97.0 | 87.8 |
| | 18.0 | — | — | 96.0 | 95.3 | 83.3 | 97.2 | 96.6 | 83.0 |
| | 21.0 | — | — | 95.7 | 94.5 | 77.9 | 93.6 | 92.8 | 80.4 |
| | 23.0 | — | — | 95.8 | 94.8 | 77.2 | 93.4 | 92.3 | 77.0 |
| | 25.0 | — | — | 95.6 | 94.5 | 76.5 | 93.3 | 91.6 | 75.9 |
| | 28.0 | — | — | 95.8 | 94.0 | 74.0 | 93.1 | 91.7 | 75.2 |

To avoid the hydrolysis issue, one solution was to store the compounds in an anhydrous, non-nucleophilic organic solvent (e.g. DMSO or propylene carbonate). Table 1 shows data for an accelerated stability study where compounds of FIG. 28 panels A and B were stored at three elevated temperatures (30, 45 and 60° C.). Again the behavior of different dye conjugates, when the QMP portion of the compound is kept the same, is very similar. At elevated temperature a different degradation pathway was observed (Scheme 15). In particular, the degradation of QMP in DMSO with trace water at elevated temperatures was found to hydrolyze at both the fluoro-group and the phosphate. When stored in DMSO, the QMP materials were diluted with a staining buffer close to the time of use. It is understood that some autostainers are capable of a pre-dilution step for preparing reagents; thus, this approach is provides the needed long term stability in a format which could operate within an intended use for the compounds.

Scheme 15

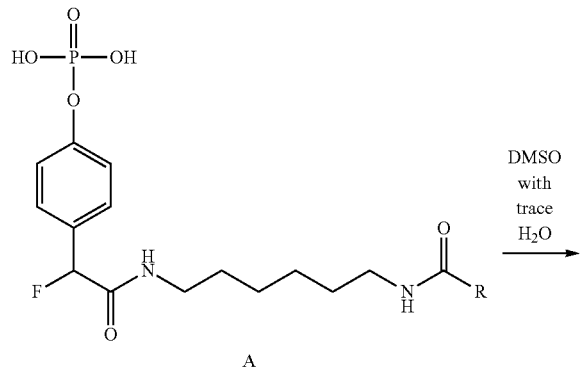

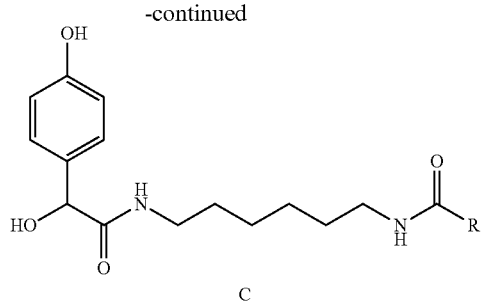

To further investigate the aqueous stability of these compounds compound from FIG. 28(A) was stored in three different buffers at various pH (see Table 2). It was observed that lower pH's of the buffer solution extend the shelf-life of the active staining compound.

TABLE 2

| Compound from FIG. 28 | | 28(B) | 28(B) | 28(B) |
|---|---|---|---|---|
| Solvent | | Tris | Acetate | Glycine |
| | | pH 10 | pH 4 | pH 2 |
| Temperature (° C.) | | 20-25 | 20-25 | 20-25 |
| Time (Days) | 0.0 | 100.0 | 100.0 | 100.0 |
| | 0.1 | 69.8 | 97.2 | — |
| | 0.2 | 55.1 | 95.0 | 99.6 |
| | 1.0 | 11.1 | 89.9 | 93.7 |
| | 1.2 | 7.6 | 88.5 | 94.4 |
| | 1.9 | 2.5 | 86.3 | 93.0 |
| | 2.0 | — | — | — |
| | 2.1 | 1.9 | 85.6 | 91.3 |
| | 4.0 | — | — | — |
| | 5.0 | 1.3 | 73.4 | 87.2 |
| | 7.0 | — | — | — |
| | 8.0 | 1.3 | 64.8 | 82.6 |
| | 9.0 | 1.3 | 62.5 | 82.2 |

With an understanding of the degradation pathways and characteristics, a solvent system was designed for the purpose of extending shelf-life of QMP compounds. It was discovered that a solvent system comprising a 50/50 mixture of DMSO and 10 mM glycine buffer (pH 2.0), referred to as Buffer A herein, exhibits suitable stability. Table 3 shows data for an accelerated stability study where compounds were stored at different temperatures (2, 25, 37 and 45° C.) in a 50/50 mixture of DMSO and 10 mM glycine buffer (pH 2.0). At elevated temperature the degradation pathway described in FIG. 3C was still observed. However, at normal storage conditions (2-25° C.) the rate of decomposition of the QMP is reduced compared to 100% aqueous systems.

TABLE 3

| | | Compound from FIG. 28 | | | | |
|---|---|---|---|---|---|---|
| | 28(A) | 28(A) | 28(A) | 28(A) | 28(C) | 28(D) |
| | | | Solvent | | | |
| | Buffer A | Buffer A | Buffer A | Buffer A | Buffer A | Buffer A |
| | | | Temperature (° C.) | | | |
| | 2 | 25 | 37 | 45 | 20-25 | 20-25 |
| Time (Days) 0.0 | 96.3 | 96.3 | 94.3 | 94.2 | 100.0 | 99.9 |
| 1.0 | — | — | — | — | 100.0 | 99.8 |
| 4.0 | — | — | — | — | 100.0 | 95.4 |
| 8.0 | 96.2 | 94.1 | 76.9 | 80.1 | 100.0 | 95.6 |
| 10.0 | — | — | — | — | 100.0 | 95.7 |
| 14.0 | — | — | — | — | 100.0 | 95.1 |
| 15.0 | 96.2 | 93.3 | 64.9 | 68.4 | — | — |
| 17.0 | — | — | — | — | 100.0 | 95.8 |
| 22.0 | 96.7 | 92.4 | 55.2 | 59.1 | — | — |
| 25.0 | — | — | — | — | 97.8 | 95.5 |
| 30.0 | 96.7 | 91.2 | 46.4 | 49.9 | — | — |
| 36.0 | — | — | — | — | 96.7 | 94.0 |
| 60.0 | 97.1 | 86.1 | 19.0 | 25.5 | — | — |

Table 3 also shows data for the stability of alternative QMP compounds (shown as FIG. 28 panels C and D in the same 50/50 mixture of DMSO and 10 mM glycine buffer (pH 2.0). The initial data indicates that the ortho-QMPs have an improved stability over the para-QMPs under these storage conditions.

Example 13—Salt and Cofactors

Figure 29A:
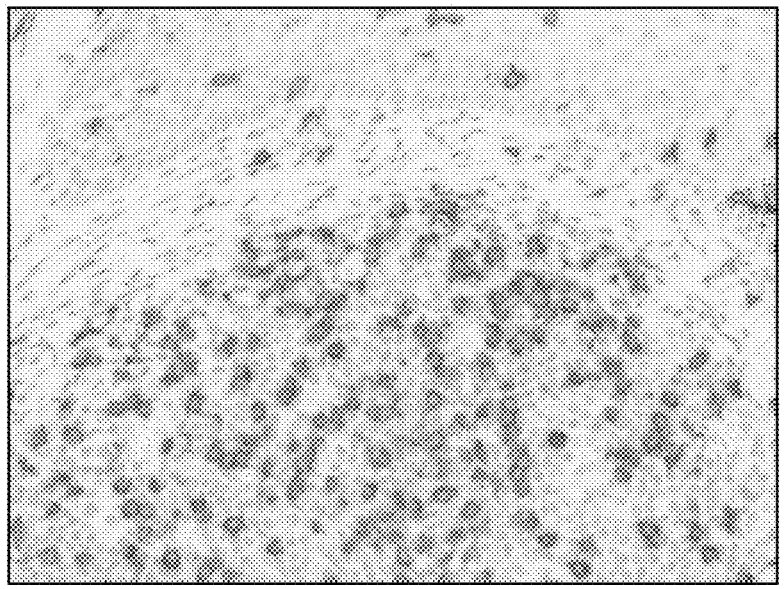
FIG. 29(A) is a microphotograph illustrating the improvement in staining quality of CD8 on tonsil tissue using 0.125 M magnesium chloride.
Figure 29B:
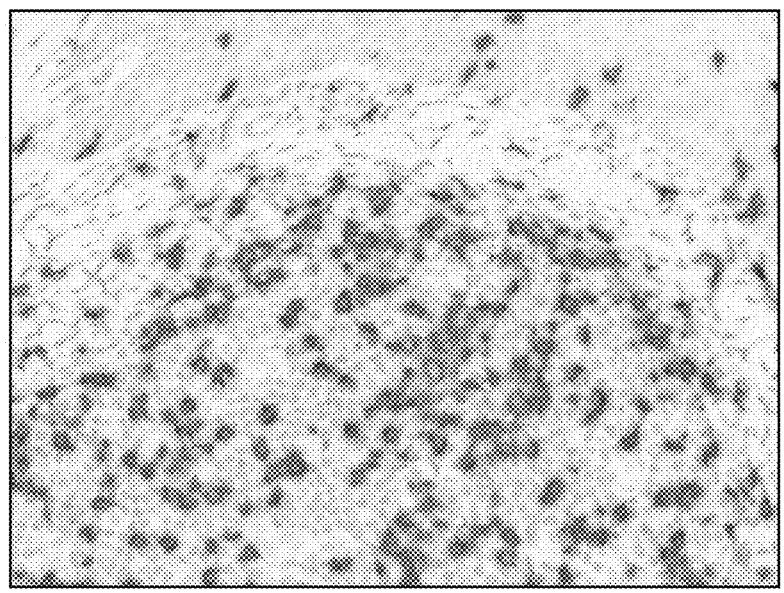
FIG. 29(B) is a microphotograph illustrating the improvement in staining quality of CD8 on tonsil tissue using 1.05 M magnesium chloride.

Magnesium is a required cofactor for alkaline phosphatase (AP) and thus it is expected the turnover rate of a QMP by AP would be dependent on the concentration of magnesium. However, a surprising effect of the concentration of magnesium salts on the staining quality was discovered. Again, it was understood that signal intensity would improve with increasing concentration of magnesium because of its role as a cofactor. However, it was not expected that the quality of signal would improve. In particular, the qualities improved were signal localization, discreteness, and reduced diffusion. In fact, it was expected that these qualities could actually be diminished by increasing magnesium as the greater signal intensity could either bleed away or enhance the ability to see bleeding away from the target location. Referring now to FIGS. 29(A)-29(B), shown are photomicrographs of tonsil tissue stained for the presence of CD8 with a QMP-TAMRA, with the singular variable of 0.125 M magnesium chloride (FIG. 29(B)) and 1.05 M magnesium chloride (FIG. 29(A)). While photomicrographs and reproductions thereof do not show the significance of the difference as dramatically as one would wish, the 1.05 M magnesium chloride sample exhibited much better stain quality compared to the 0.125 M magnesium sample. In illustrative embodiments, methods and compositions according to the present disclosure include greater than about 0.1 M, 0.25 M, 0.5 M, 1.0 M or 1.25 M salt, such as magnesium chloride. In other embodiments, the methods and compositions according to the present disclosure include between about 0.1 M and about 2 M, between about 0.25 M and 1.5 M, about 0.5 M to about 1.25 M or about 1.0 M magnesium chloride. A similar effect was also observed for NaCl concentration, but the effect was not as great.

This combined data, combined with the magnesium chloride concentration study, led to the current kit configuration where there can be at least two components; the first is a pH adjust (0.5 M Tris, pH 10.0) and the second is the QMP formulated in combination of organic solvent (e.g. DMSO) and 10 mM glycine (pH 2.0) with up to 1.0 M magnesium chloride.

Example 14

Figure 30A:
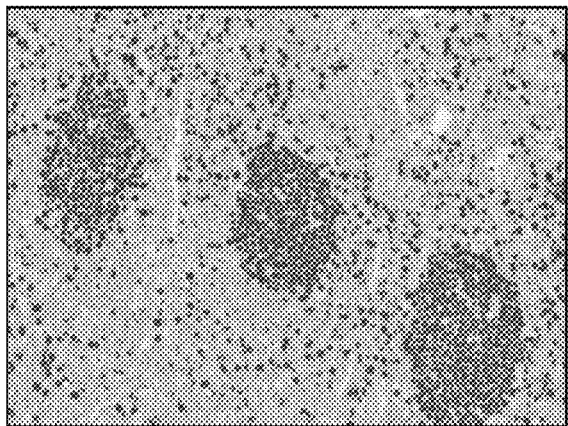
FIG. 30(A) is a microphotograph illustrating functional staining of Ki-67 on tonsil tissue at 20× magnification with β-galactosidase enzyme and with β-galactoside-QMP-Cy5 (125 uM) and Nuclear Fast Red CS.
Figure 30B:
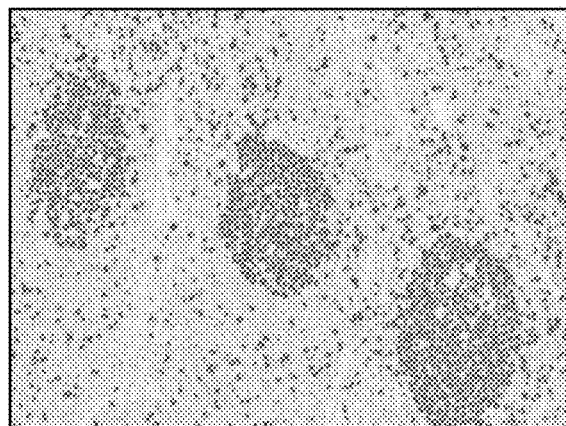
FIG. 30(B) is a microphotograph illustrating functional staining of Ki-67 on tonsil tissue at 20× magnification with β-galactosidase enzyme and with β-galactoside-QMP-Cy5 (125 uM) and Hematoxylin CS.
Figure 30C:
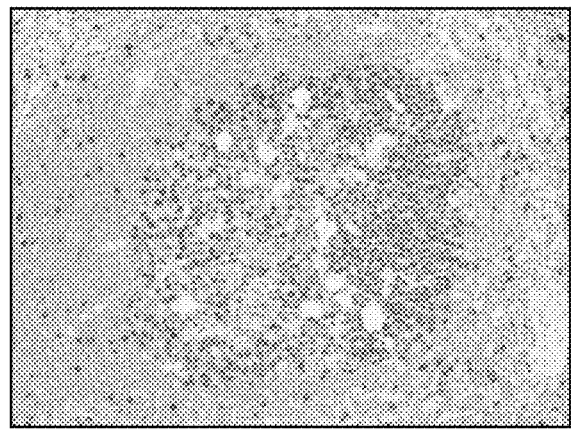
FIG. 30(C) is a microphotograph illustrating functional staining of Ki-67 on tonsil tissue at 20× magnification with β-galactosidase enzyme and with β-galactoside-QMP-Cy3 (100 uM) and Hematoxylin CS.

QMP with β-Galactosidase Trigger and Chromophore Reporter Moieties (FIGS. 30(A)-(C)

The tissue was deparaffinized and retrieved as described in the general procedures. Rabbit-anti-Ki-67 antibody incubation (37° C., 16 minutes) and washing were followed by secondary incubation with a goat polyclonal anti-rabbit, hapten labeled with biotin (37° C.; 8 minutes). After washing, β-galactosidase (β-Gal) conjugated streptavidin (Life Technologies #S-931) was added (37° C.; 32 minutes). After incubating with the β-Gal conjugate the slides were washed with SSC. Monofluoro β-Gal-QMP-Cy5 (125 μM) (FIGS. 30(A)-30(B)) or β-Gal-QMP-Cy3 (100 μM) (FIG. 30(C)) were dissolved in 250 mM Tris, pH 8.0, 0.05% Brij-35. QMP turnover was achieved by adding 100 μL of AP Enhancer followed by 100 μL the appropriate β-Gal-QMP and incubating at 37° C. for 32 minutes. The stained tissue sections were counterstained with modified Mayer's hematoxylin (37° C.; 4 minutes) and then incubated with Bluing Reagent (37° C.; 4 minutes) (FIGS. 30(B)-30(C)) or Red Counterstain II (VMSI #780-2218) (37° C.; 4 minutes) (FIG. 30(A)). The slides were then rinsed with a detergent water mixture, dehydrated through a graded ethanol series, cleared with xylene, and manually cover-slipped.

β-Galactosidase has been as an enzyme for IHC detection previously with 5-bromo-4-chloro-3-indolyl-β-D-galactopyranoside (BCIG) as the detection reagent. However, it is the only color available, it is inconsistent, has poor sensitivity, and prone to fading (or washing out) during post processing of the slides. The examples in FIGS. 30(A)-30(C) show a β-galactosidase based chromogenic IHC detection system that is not susceptible to alcohol dehydration, has good sensitivity and can be easily modified to generate a wide range of colors.

Example 15

Figure 31:
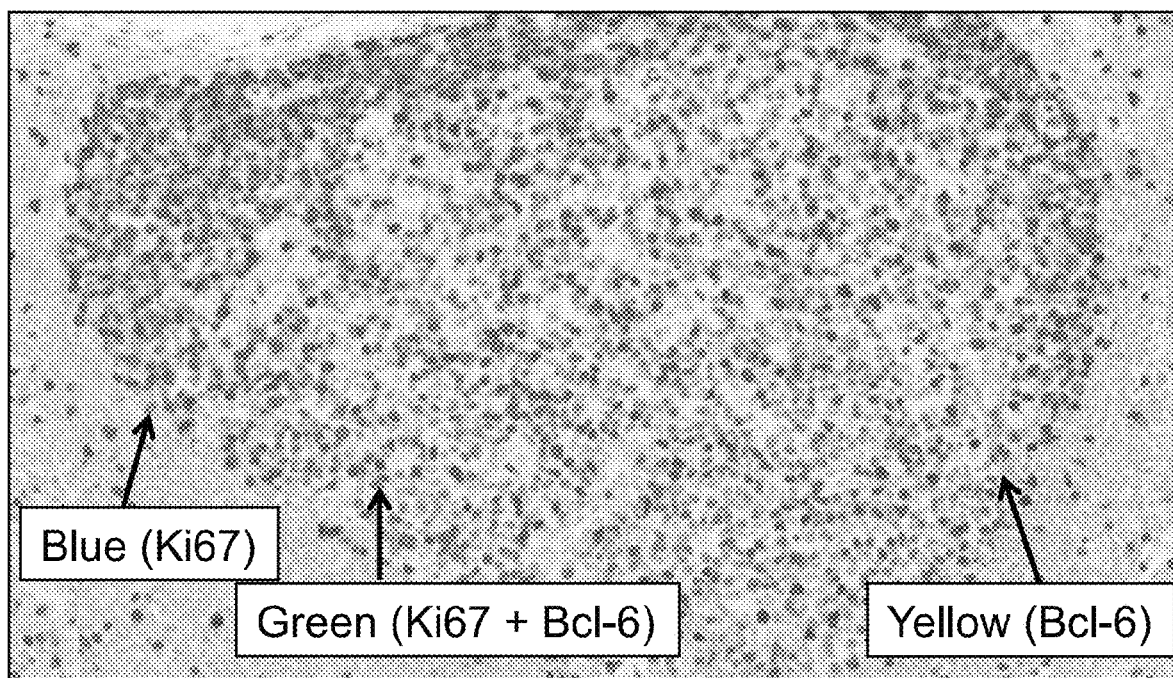
FIG. 31 is a microphotograph from a duplex brightfield IHC assay, illustrating simultaneous detection of Bcl-6 (Phospho-QM-PEG8-Dabsyl, yellow) and Ki67 (β-Gal-QM-Cy5, blue) on tonsil tissue with a hematoxylin counterstain, using simultaneous antibody incubation and simultaneous chromogenic detection.

Duplex Stain with Simultaneous Detection of AP and β-Gal Triggered QMP (FIG. 31

The tissue was deparaffinized and retrieved as described in the general procedures. Incubation with rabbit-anti-Ki-67 antibody and mouse-anti-Bcl-6 antibody (37° C., 16 minutes) and washing were followed by secondary antibody incubation with a goat polyclonal anti-rabbit antibody conjugated to biotin and a goat polyclonal anti-mouse antibody conjugated to AP (37° C.; 12 minutes). The slides were subsequently incubated with β-Gal conjugated streptavidin (37° C.; 32 minutes) followed by washing with SSC. Phospho-QMP-Cy5 and β-Gal-QMP-Peg8-Dabsyl were dissolved in 250 mM Tris, pH 8.0, 0.05% Brij-35 to a final concentration of 250 µM each. QMP turnover was achieved by adding 100 µL of AP Enhancer followed by 100 µL of QMP mixture and incubating at 37° C. for 60 minutes. The stained tissue sections were counterstained with modified Mayer's hematoxylin (37° C.; 4 minutes) and then incubated with Bluing Reagent (37° C.; 4 minutes). They were then rinsed with a detergent water mixture, dehydrated through a graded ethanol series, cleared with xylene, and manually cover-slipped.

Some of the advantages of using multiple enzymes for multiplex assays are the overall reduction in assay time and reduction of enzyme inactivation/elution steps. This example shows a dual chromogenic IHC detection system where both enzymatic detections are carried out at the same time. This result demonstrates the specificity of each QMP to its cognate enzyme and also the availability of sufficient binding sites for both detections to occur unimpeded.

Example 16

Triplex Stain with Simultaneous Detection of HRP. AP and β-Gal Substrates (FIGS. 32(A)-(B)

Figure 32A:
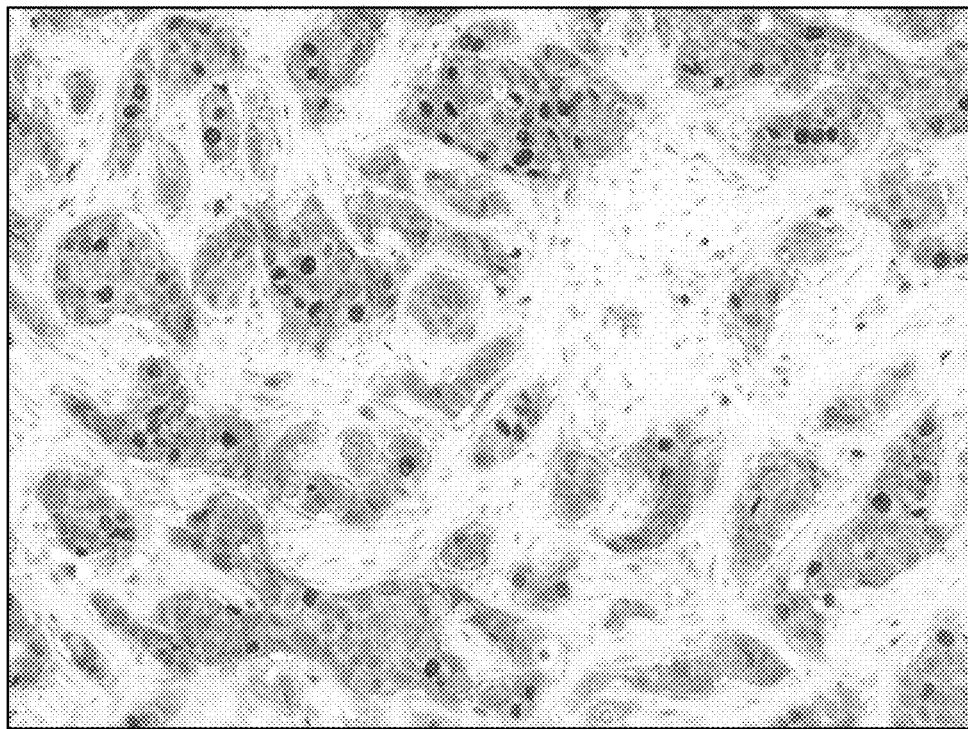
FIG. 32(A) is a microphotograph from a triplex brightfield IHC assay, illustrating simultaneous detection of Her2, ER, PR on breast tissue with Phospho-QM-PEG8-Dabsyl, β-Gal-QM-Cy5, Tyr-Tamra, with a hematoxylin counterstain, using simultaneous antibody incubation and simultaneous chromogenic detection.
Figure 32B:
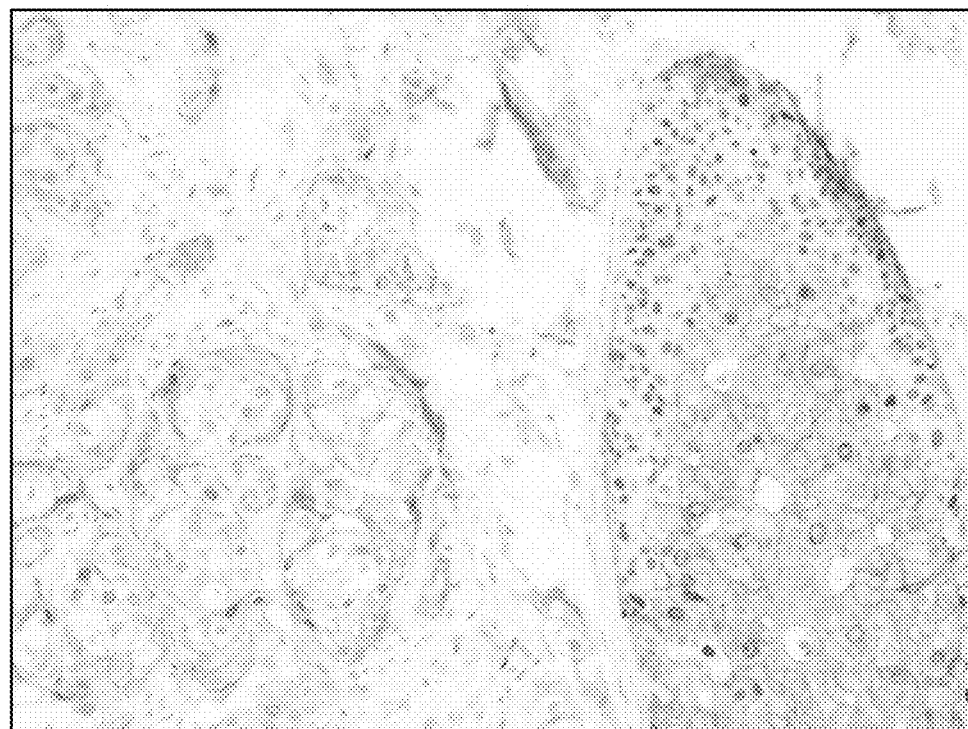
FIG. 32(B) is a microphotograph from a triplex brightfield IHC assay, illustrating simultaneous detection of Her2, ER, PR on breast tissue with Phospho-QM-PEG8-Dabsyl, β-Gal-QM-Cy5, Tyr-Tamra, with a hematoxylin counterstain, using simultaneous antibody incubation and simultaneous chromogenic detection.

The tissue was deparaffinized and retrieved as described in the general procedures (FIGS. 32(A)-(B)). Rabbit-anti-PR (37° C., 16 minutes) incubation and washing were followed by secondary antibody incubation with a goat polyclonal anti-rabbit antibody conjugated to biotin (37° C.; 8 minutes) and subsequently rabbit serum (37° C.; 8 minutes). After washing, benzofuran (BF) labeled rabbit-anti-ER and dinitrophenol (DNP) labeled rabbit-anti-HER2 were simultaneously incubated (37° C.; 16 minutes). The three enzyme conjugates: β-Gal conjugated streptavidin, HRP conjugated to mouse-anti-BF and AP conjugated to mouse-anti-NP; were then applied (37° C.; 32 minutes) followed by washing with SSC. β-Gal-QMP-Cy5 and Phospho-QMP-PEG8-Dabsyl were dissolved in 250 mM Tris, pH 8.0, 0.05% Brij-35 to a final concentration of 300 µM each. Chromogen turnover was achieved by adding 100 µL of AP Enhancer followed by 100 µL of QMP mixture, 100 µL of DISCOVERY Purple (VMSI #760-229) and 100 µL of $H_2O_2$ (0.01%) and incubating at 37° C. for 32 minutes. The stained tissue sections were counterstained with Hematoxylin II (37° C.; 4 minutes) and then incubated with Bluing Reagent (37° C.; 4 minutes). They were then rinsed with a detergent water mixture, dehydrated through a graded ethanol series, cleared with xylene, and manually cover-slipped.

This example shows a triple chromogenic IHC detection system where all enzymatic detections are carried out at the same time. This result reinforces the specificity of each QMP to its cognate enzyme. It shows the availability of sufficient binding sites for not only the QMP detections to occur unimpeded, but also the fact that the HRP/tyramide detection can still proceed.

Example 17

Figure 33:
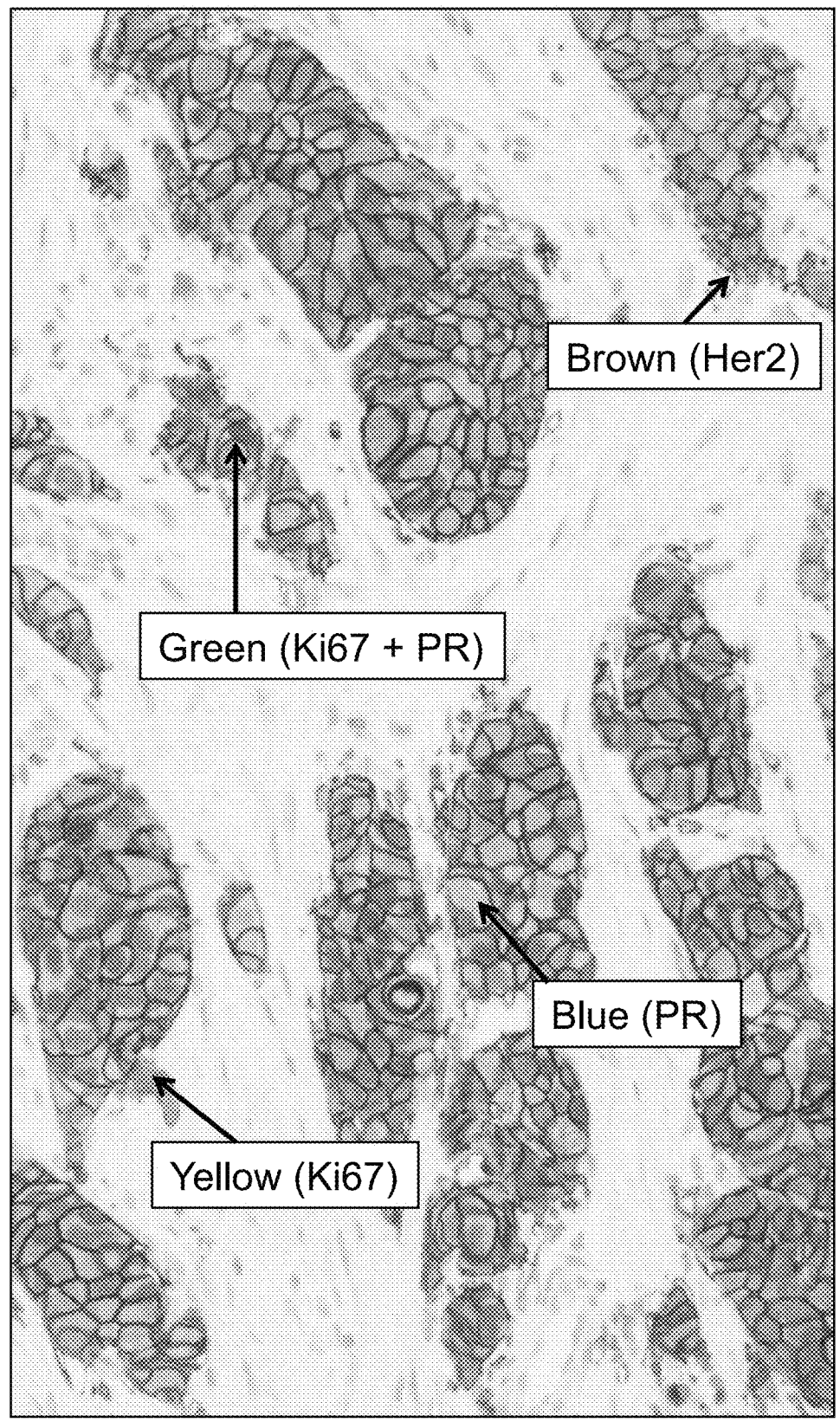
FIG. 33 is a microphotograph from a quadruplex brightfield IHC assay, illustrating sequential detection of Her2 (HRP DAB, brown), PR (β-Gal-QM-Cy5, blue), ER (Tyr-Tamra, purple) and Ki67 (Phospho-QM-PEG8-Dabsyl, yellow) on breast tissue.
Figure 34:
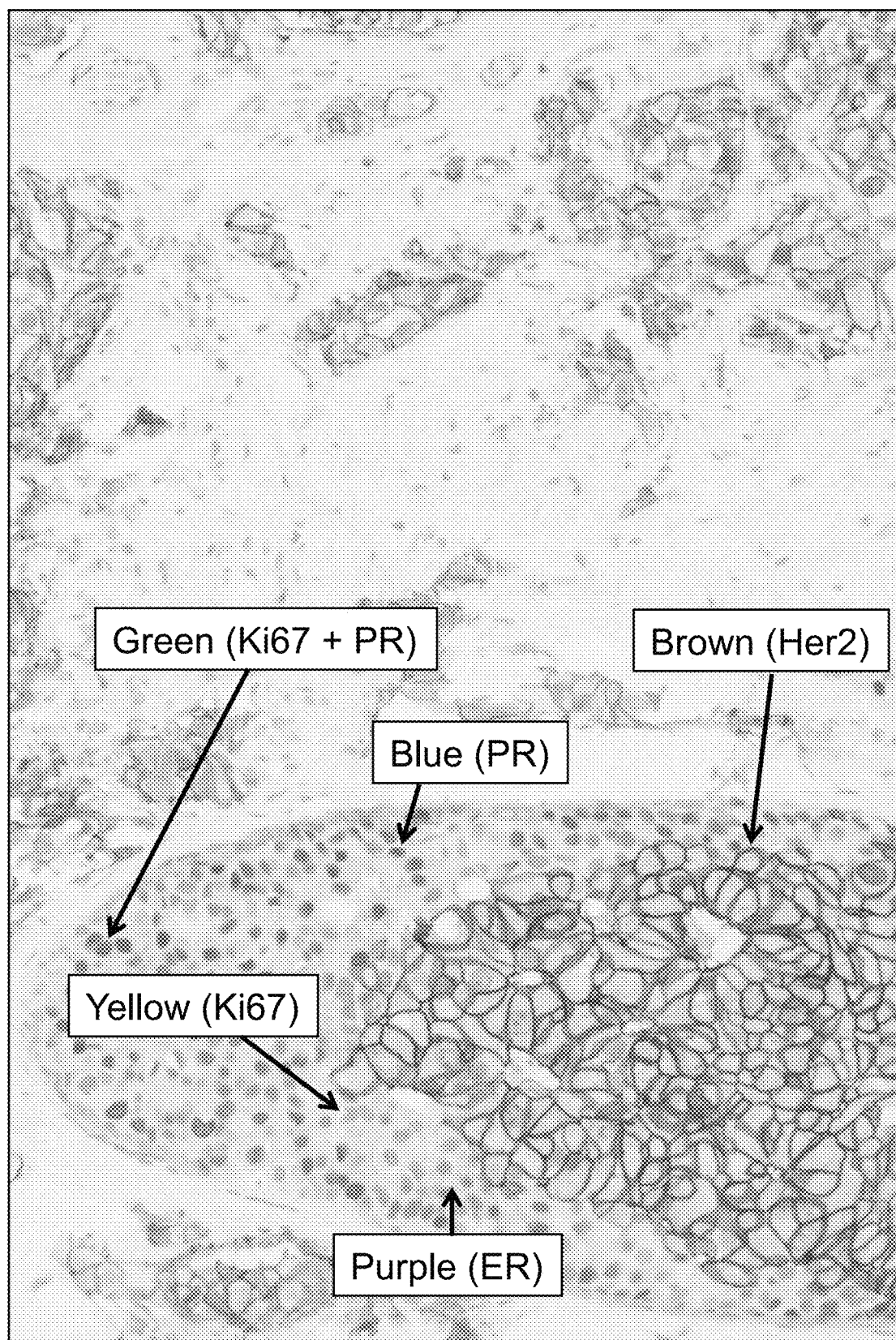
FIG. 34 is a second microphotograph from a quadruplex brightfield IHC assay, illustrating sequential detection of Her2 (HRP DAB, brown), PR (β-Gal-QM-Cy5, blue), ER (Tyr-Tamra, purple) and Ki67 (Phospho-QM-PEG8-Dabsyl, yellow) on breast tissue.

Quadruplex Stain with Sequential Detection of HRP (Twice), AP and β-Gal Substrates (FIGS. 33-34

The tissue was deparaffinized and retrieved as described in the general procedures. Rabbit-anti-PR (37° C., 16 minutes) incubation and washing were followed by secondary antibody incubation with a goat polyclonal anti-rabbit antibody conjugated to biotin (37° C.; 8 minutes) and subsequently rabbit serum (37° C.; 8 minutes). After washing, benzofurazan (BF) labeled rabbit-anti-ER, NP labeled rabbit anti-Ki67 and dinitrophenol (DNP) labeled rabbit-anti-HER2 were simultaneously incubated (37° C.; 16 minutes). HRP conjugated to mouse-anti-DNP was added (37° C.; 8 minutes), and visualized via a brown precipitate produced by HRP upon the addition of hydrogen peroxide and DAB (37° C.; 8 minutes) which was further toned with copper sulfate. 0-Gal conjugated to streptavidin, HRP conjugated to mouse-anti-BF and AP conjugated to mouse-anti-NP were then applied (37° C.; 32 minutes). The HRP was detected with 100 µL of DISCOVERY Purple (VMSI #760-229) and 100 µL of $H_2O_2$ (0.01%) (37° C.; 32 minutes) followed by washing with SSC. β-Gal-QMP-Cy5 and Phospho-QMP-$PEG_8$-Dabsyl were dissolved in 250 mM Tris, pH 8.0, 0.05% Brij-35 to a final concentration of 300 µM each. Chromogen turnover was achieved by adding 100 µL of AP Enhancer followed by 100 µL of QMP mixture, and incubating at 37° C. for 32 minutes. The stained tissue sections were counterstained with Hematoxylin II (37° C.; 4 minutes) and then incubated with Bluing Reagent (37° C.; 4 minutes). They were then rinsed with a detergent water mixture, dehydrated through a graded ethanol series, cleared with xylene, and manually cover-slipped.

Example 18

Figure 35A:
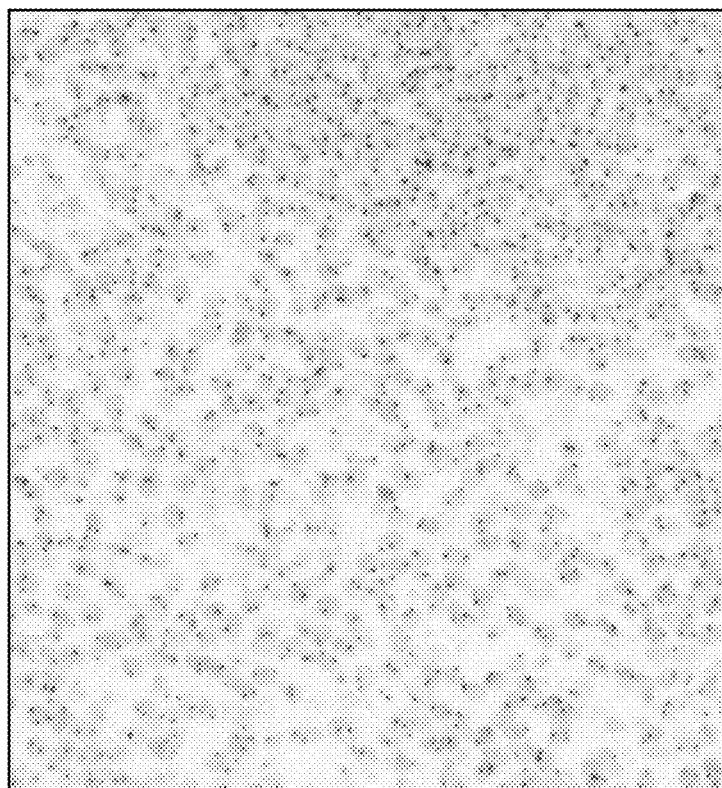
FIG. 35(A) is a microphotograph of chromosome 17 centromere ISH on tonsil tissue with QM-green (PEG8-Dabsyl and Cy5).
Figure 35B:
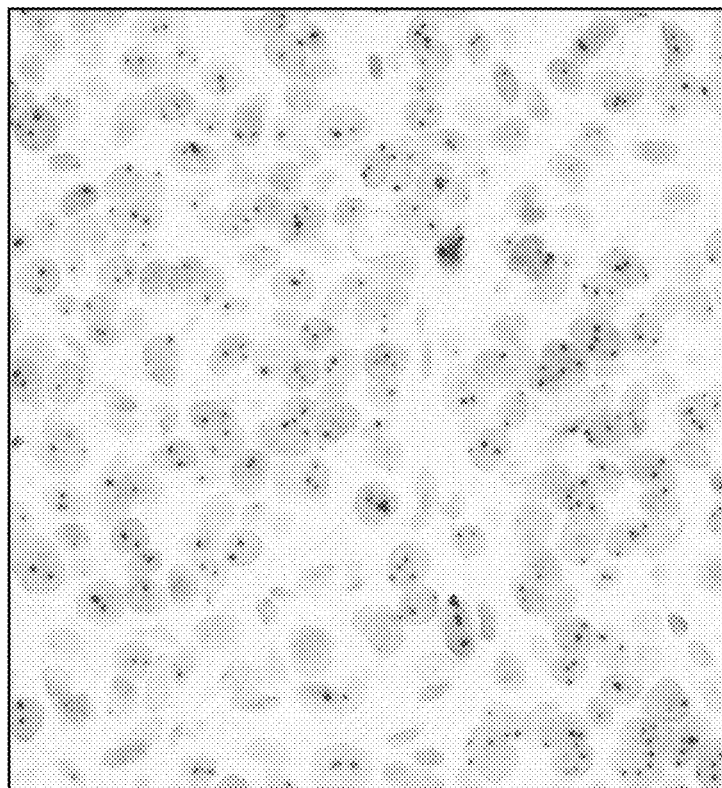
FIG. 35(B) MCF-7 is a microphotograph of chromosome 17 centromere ISH on xenografts with QM-green (PEG8-Dabsyl and Cy5).

Chromogenic ISH (FIGS. 35(A)-35(B

The tissue was deparaffinized as described in the general procedures followed by pretreatment with Cell Conditioning 2 (VMSI #950-123) (90° C.; 28 minutes) and treatment with Protease 3 (VMSI #780-4149) (37° C.; 20 minutes). Chromosome 17 probe, DIG labeled (VMSI #760-1224) was applied to the tissue, denatured (80° C.; 20 minutes) and hybridized at 44° C. for 6 hours. After three stringency washes at 76° C. with SSC, the sample was incubated with mouse-anti-DIG antibody (37° C.; 20 minutes), followed by AP conjugated goat-anti-mouse antibody (37° C.; 24 minutes). Phospho-QMP-$PEG_8$-Dabsyl and phospho-QMP-Cy5 were dissolved in 1:1 DMSO: 10 mM glycine buffer (pH 2.0) to a final concentration of 120 µM QMP-Dabsyl and 30 µM QMP-Cy5 with 1 mM magnesium chloride. After washing with SSC then 200 µL of pH adjust solution (500 mM Tris, pH 10.0) and 100 uL of the QMP mixture were added (37° C.; 32 minutes). The stained tissue sections were counterstained with Hematoxylin II (37° C.; 4 minutes) and then incubated with Bluing Reagent (37° C.; 4 minutes). They were then rinsed with a detergent water mixture, dehydrated through a graded ethanol series, cleared with xylene, and manually cover-slipped.

For ISH applications the ortho-QMP compounds showed better performance than the para-QMP compounds. While the para-QMP compounds did generate ISH signals, the intensity was low, the number of cells stained (cell coverage) was inconsistent and the signal quality was not optimal. The ortho-QMP compounds generated stronger intensity signals, with increased cell coverage and much better signal resolution with reduced diffusion.

Example 19

Figure 36:
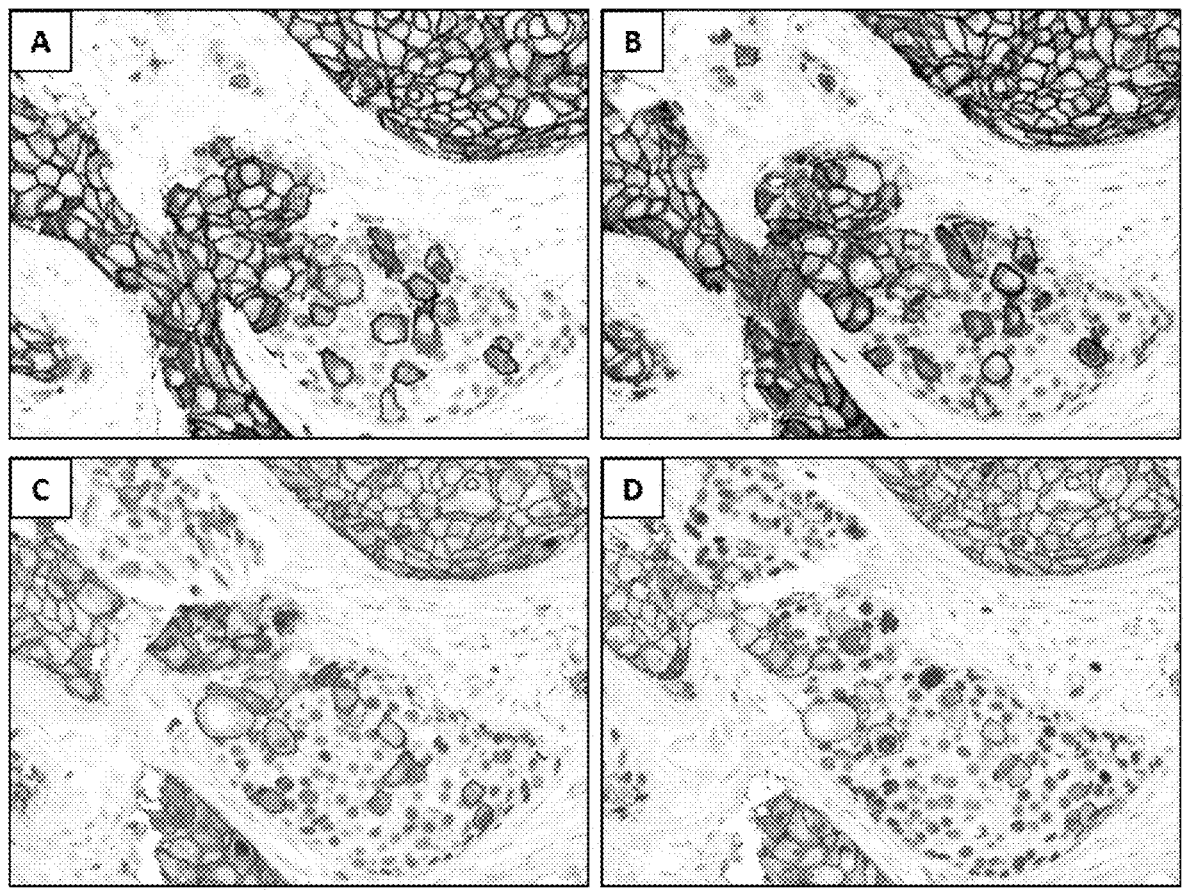
FIG. 36) is a microphotograph of four different staining protocols showing the same biomarkers (panel A—Her2, panel B— Ki-67, panel C— ER and panel C— PR) on FFPE breast tissue at 40× magnification, stained by sequential detection using two HRP based detections and two AP QMP based detection systems.

Quadruplex Stain with Sequential Detection of HRP (Twice) and AP (Twice) (FIG. 36

FIG. 36 provides examples of four different staining protocols (A-D) showing the same biomarkers (panel A—Her2 (membrane), panel B— Ki-67 (nuclear), panel C— ER (nuclear) and panel D—PR (nuclear)) on FFPE breast tissue with interchanged and/or different color combinations (40× magnification). As there were three nuclear markers and one membrane marker, it was possible to use DAB for the Her2 membrane stain in some protocols, avoiding the overlap of DAB with other colors. Mixes of the nuclear detections (yellow, blue & purple) generated different color combinations depending on intensity.

The assay included sequential detection of the biomarkers using two HRP based detections and two AP QMP based detections. This demonstrated the flexibility and interchangeability of the disclosed detection systems.

Example 20

Figure 37:
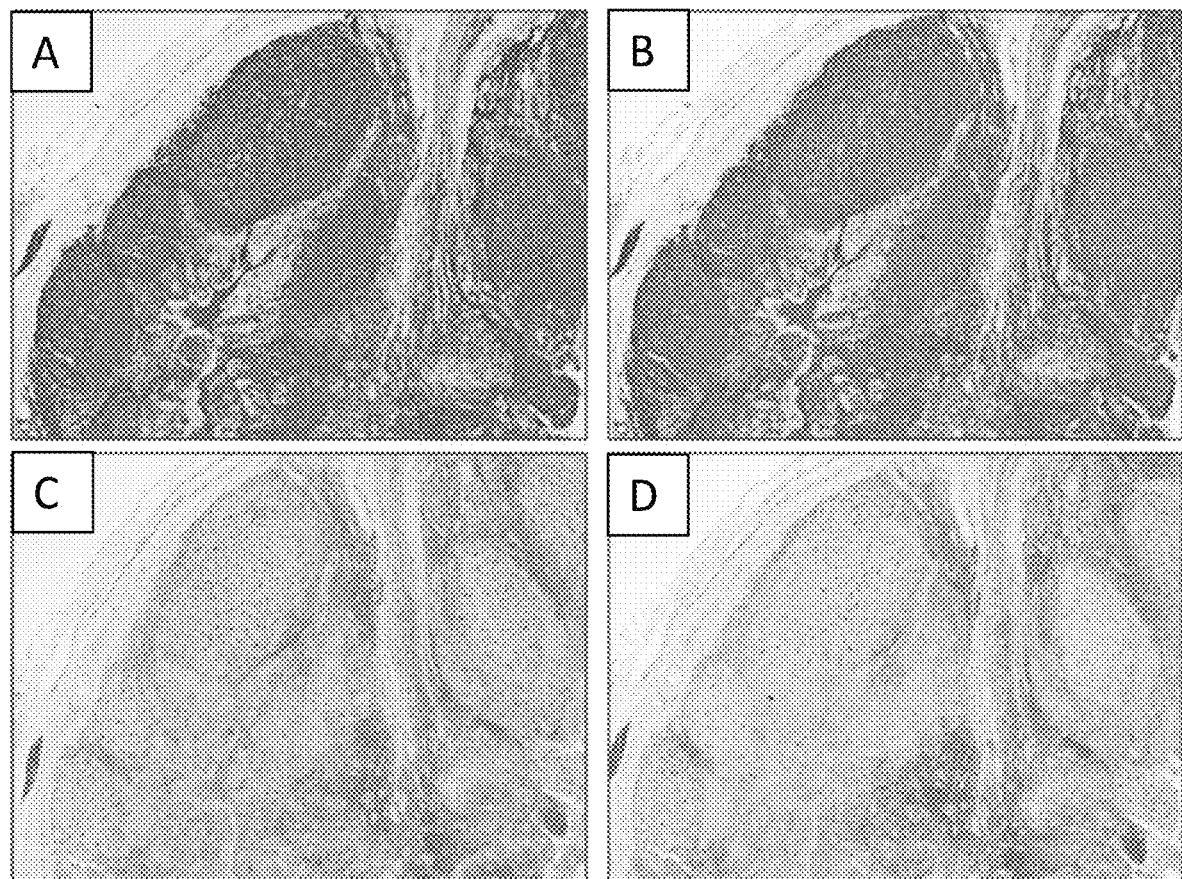
FIG. 37 is a microphotograph of different staining protocols (panels A-B or panels C-D) of panel A—CD3, panel B— CD8, panel C— CD20 (or CD68) and panel D-FoxP3 at 5× magnification on FFPE tonsil tissue, stained by sequential detection using two HRP based detections and two AP QMP based detection systems.

Quadruplex Stain with Sequential Detection of HRP (Twice) and AP (Twice) (FIG. 37

FIG. 37 provides examples of different staining protocols (panels A-B or panels C-D) showing the same biomarkers (panel A—CD3 (membrane), panel B— CD8 (membrane), panel C— CD20 (membrane) (or CD68 (membrane)) and panel D—FoxP3 (nuclear) on FFPE tonsil tissue) with interchanged and/or different color combinations (5× magnification). Sequential detection was utilized, using two HRP based detections and two AP QMP based detections, further demonstrating the flexibility and interchangeability of the disclosed detection systems.

Example 21

Figure 38A:
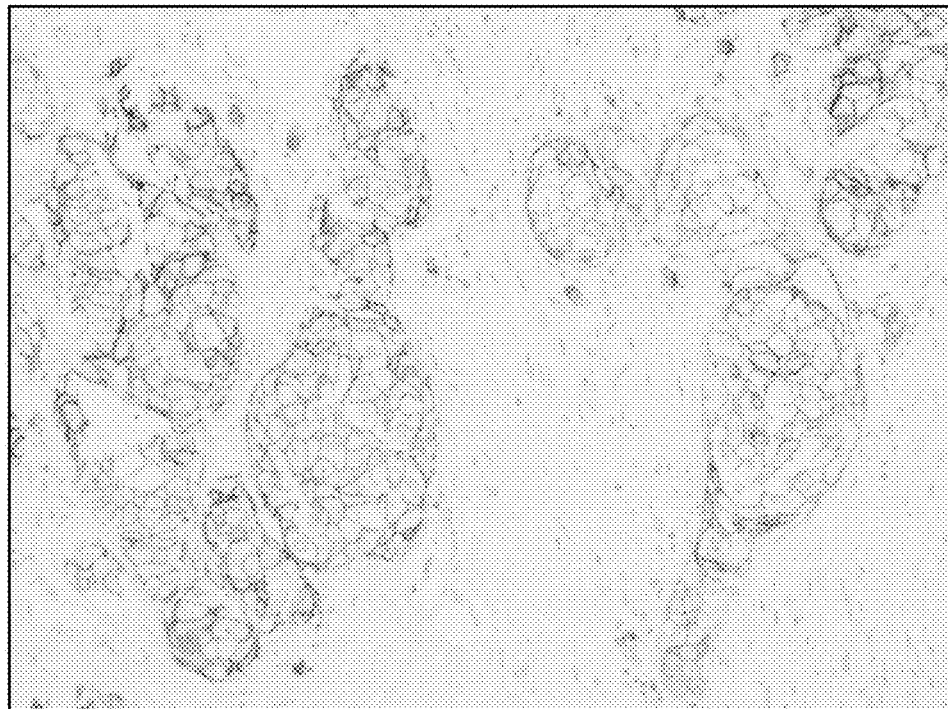
FIG. 38(A) is a microphotograph illustrating functional staining amplification of E-cadherin on FFPE breast tissue by an ortho- and para-QMP-Tamra at 10× magnification using compound 36.
Figure 38B:
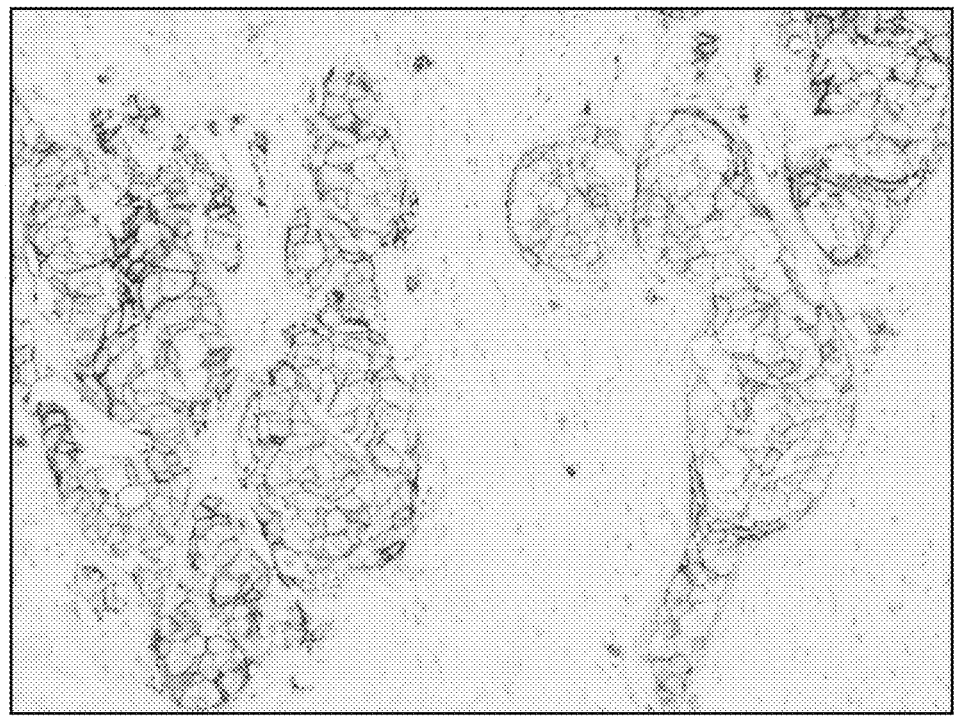
FIG. 38(B) is a microphotograph illustrating functional staining amplification of E-cadherin on FFPE breast tissue by an ortho- and para-QMP-Tamra at 10× magnification using compound 28.

Following the protocol outlined in Example 10, breast tissue was stained with a mouse-anti-E-cadherin monoclonal primary antibody (Ventana #790-4497) using either compound 36 at a concentration of 500 μM (FIG. 38(A)) or compound 28 at a concentration of 400 μM (FIG. 38(B)). It was expected that both would give equivalent results, but surprisingly compound 28 (the ortho-QMP) showed better performance than compound 36 (the para-QMP). The staining quality (signal localization and discreteness) was the same for both compounds, but the staining intensity was higher for compound 28, even using 20% lower concentration than compound 36.

The ortho-QMP compounds offer significant improvement to IHC staining performance, ISH staining performance and improved aqueous stability compared to any of the compounds described previously.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

ADDITIONAL EXEMPLARY EMBODIMENTS

The following additional embodiments are also specifically disclosed. This is not an exhaustive list.

1. A compound, having a formula

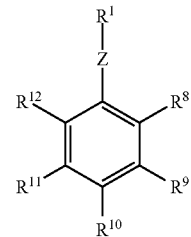

or a salt or solvate thereof, wherein:
  Z is O, S or $NR^a$ and $R^1$ is an enzyme recognition group, or $ZR^1$ is an enzyme recognition group;
  $R^8$ is —C(LG)($R^5$)($R^3R^4$), —$R^3R^4$ or —C(LG)($R^5$)($R^6$);
  $R^9$, $R^{11}$ and $R^{12}$ are each independently hydrogen, halo, cyano, aliphatic, alkoxy, $NO_2$, $N(R^c)_2$, aryl, haloalkyl, —C(O)alkyl, —C(S)alkyl, —C(O)OH, —C(O)Oalkyl, —C(O)$NHR^c$, —C(O)$N(R^c)_2$, —$R^3R^4$ or two adjacent groups together form an aliphatic ring or aryl ring;
  $R^{10}$ is hydrogen, halo, cyano, aliphatic, alkoxy, $NO_2$, $N(R^c)_2$, aryl, haloalkyl, —C(O)alkyl, —C(S)alkyl, —C(O)OH, —C(O)Oalkyl, —C(O)$NHR^c$, —C(O)$N(R^c)_2$, —$R^3R^4$, —C(LG)($R^5$)($R^6$) or with one of $R^9$ or $R^{11}$ form an aliphatic ring or aryl ring;
  LG is a leaving group, or $ZR^1$ and LG together form a phosphodiester;
  $R^3$ is a linker or a bond;
  $R^4$ is a detectable label;
  each $R^5$ is independently hydrogen, halo, cyano, lower alkyl, lower haloalkyl, —C(O)alkyl, —C(S)alkyl, —C(O)OH, —C(O)Oalkyl, —C(O)$NHR^c$ or —C(O)$N(R^c)_2$;
  each $R^6$ is independently hydrogen, halo, cyano, lower alkyl, lower haloalkyl, —C(O)alkyl, —C(S)alkyl, —C(O)OH, —C(O)Oalkyl, —C(O)$NHR^c$ or —C(O)$N(R^c)_2$;
  $R^a$ is hydrogen or aliphatic;
  each $R^c$ independently is hydrogen, aryl, aliphatic or heteroaliphatic, or two $R^c$ moieties together form a heteroaliphatic ring; and
  at least one of $R^8$ and $R^{10}$ comprises LG, and at least one of $R^8$ and $R^{10}$ comprises $R^3R^4$; and
  if LG is halo, then $R^5$ and $R^6$ are not halo.

2. The compound of embodiment 1, wherein the compound has a formula

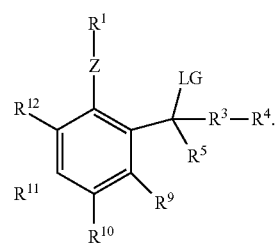

3. The compound of embodiment 1, wherein the compound has a formula selected from

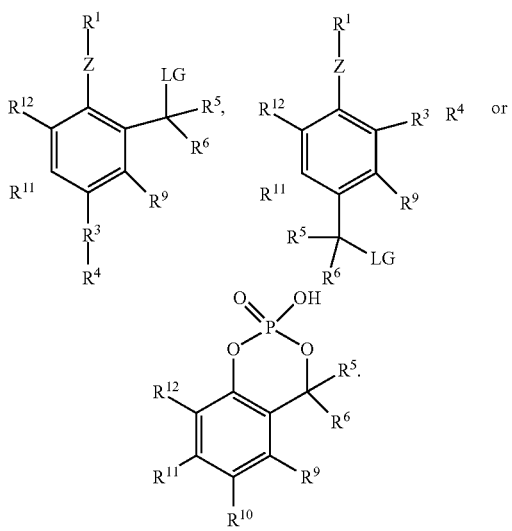

4. The compound of embodiment 1, wherein $R^1$ or $ZR^1$ is a phosphate, amide, nitro, urea, sulfate, methyl, ester, beta-lactam, sugar, or LG and $ZR^1$ together form a phosphodiester.

5. The compound of embodiment 4, wherein Z is O.

6. The compound of embodiment 4, wherein $ZR^1$ is —OP(O)(OH)$_2$, NO$_2$, —NHC(O)R, —OC(O)CH$_3$, —OC(O)CH$_2$CH$_3$, —NHC(O)NH$_2$, —OS(O)$_2$OH, OCH$_3$, or a salt thereof.

7. The compound of embodiment 4, wherein the sugar is α-glucose, β-glucose, α-galactoside, β-galactoside, α-glucuronose or β-glucuronose. 8. The compound of embodiment 4, wherein the beta-lactam is

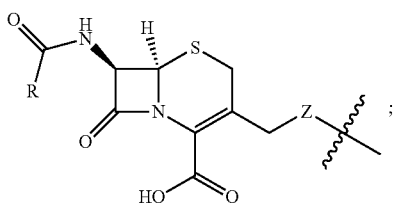

R is alkyl; and
Z is O or S.

9. The compound of embodiment 1, wherein LG is halide, sulfate ester, carboxylate, inorganic ester, thiolate, amine, aryloxy, alkoxy, or heteroaryl.

10. The compound of embodiment 1, wherein:
LG is fluoride, chloride, azide, acetate, methoxy, ethoxy, isopropoxy, phenoxide, —OS(O)$_2$CH$_3$, —OS(O)$_2$C$_6$H$_4$CH$_3$, —OS(O)$_2$C$_6$H$_5$, —OS(O)$_2$C$_6$H$_4$CX$_3$, —OC$_6$H$_5$, —N$_2$$^+$, —NH$_3$$^+$, —NC$_6$H$_5$$^+$, —O-alkyl, —OC(O)alkyl, —OC(O)H, —N(R$^b$)$_3$$^+$ or 1,4-diazabicyclo[2.2.2]octane;
each X independently is fluoro, chloro, bromo or iodo; and
each R$^b$ independently is hydrogen or lower alkyl, or two R$^b$ moieties together form a heteroaliphatic ring.

11. The compound of embodiment 10, wherein LG is F.

12. The compound of embodiment 1, wherein $R^3$ is —(CH$_2$)$_n$NH—, —O(CH$_2$)$_n$NH—, —N(H)C(O)(CH$_2$)$_n$NH—, —C(O)N(H)(CH$_2$)$_n$NH—, —(CH$_2$)$_n$O—, —O(CH$_2$)$_n$O—, —O(CH$_2$CH$_2$O)$_n$—, —N(H)C(O)(CH$_2$)$_n$O—, —C(O)N(H)(CH$_2$)$_n$O—, —C(O)N(H)(CH$_2$CH$_2$O)$_n$—, —(CH$_2$)$_n$S—, —O(CH$_2$)$_n$S—, —N(H)C(O)(CH$_2$)$_n$S—, —C(O)N(H)(CH$_2$)$_n$S—, —(CH$_2$)$_n$NH—, —C(O)N(H)(CH$_2$CH$_2$O)$_n$CH$_2$CH$_2$NH, —C(O)(CH$_2$CH$_2$O)$_n$CH$_2$CH$_2$NH—, —C(O)N(H)(CH$_2$)$_n$NHC(O)CH(CH$_3$)(CH$_2$)$_n$NH— or —N(H)(CH$_2$)$_n$NH—, where each n independently is 1, 2, 3, 4, 5, 6, 7, 8, 9, 10, 11 or 12.

13. The compound of embodiment 1, wherein $R^3$ is —CH$_2$CH$_2$NH—, —OCH$_2$CH$_2$NH—, —NHCO(CH$_2$)$_5$NH—, —CONH(CH$_2$)$_5$NH—, —NHCO(CH$_2$)$_6$NH—, —CONH(CH$_2$)$_6$NH—, —CONH(CH$_2$)$_2$NH—, —(CH$_2$CH$_2$O)$_4$—, —(CH$_2$CH$_2$O)$_8$—, —C(O)N(H)(CH$_2$CH$_2$O)$_2$CH$_2$CH$_2$NH—, —CO(CH$_2$CH$_2$O)$_4$CH$_2$CH$_2$NH—, —CO(CH$_2$CH$_2$O)$_8$CH$_2$CH$_2$NH—, —C(O)N(H)(CH$_2$)$_6$NHC(O)CH(CH$_3$)(CH$_2$)$_4$NH—,

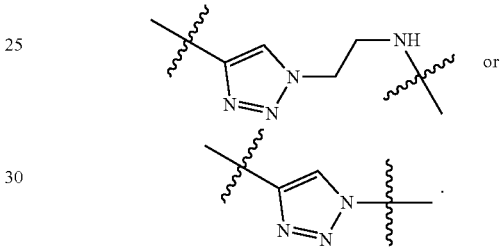

14. The compound of embodiment 1, wherein $R^4$ is a chromogen, a fluorophore, a luminophore, a hapten or a combination thereof.

15. The compound of embodiment 14, wherein $R^4$ is

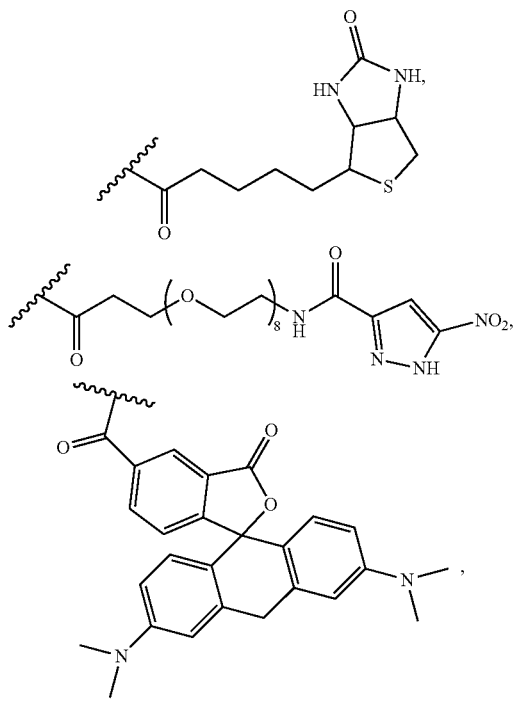

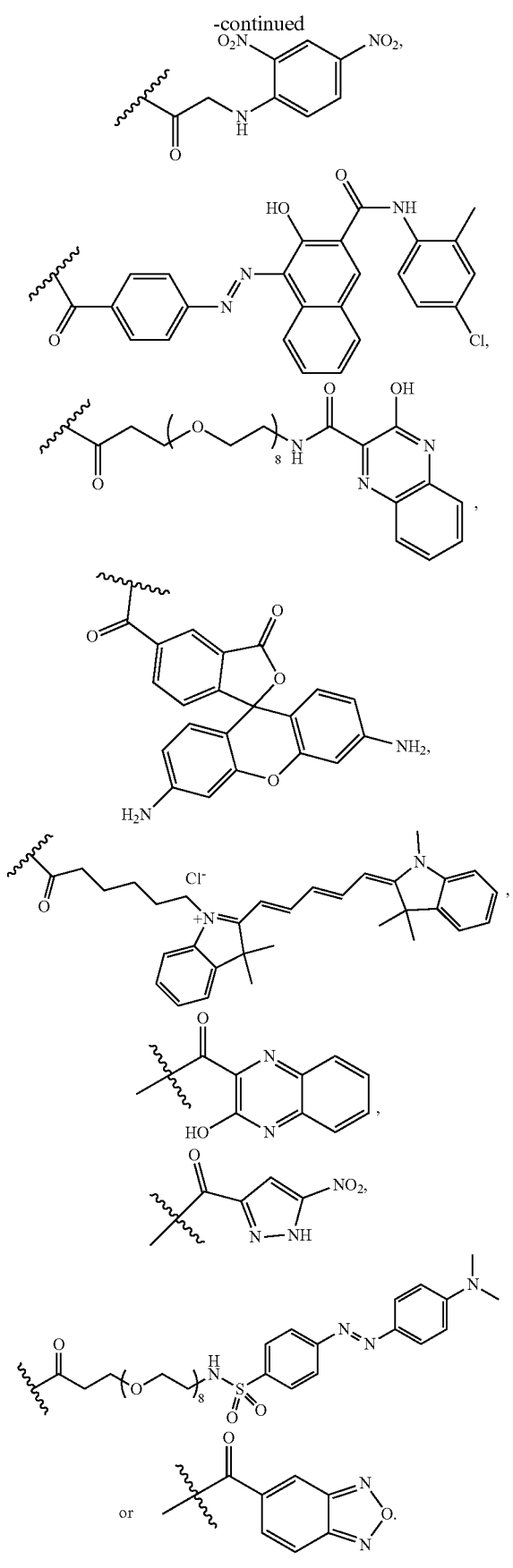
16. The compound of embodiment 1, wherein the compound is
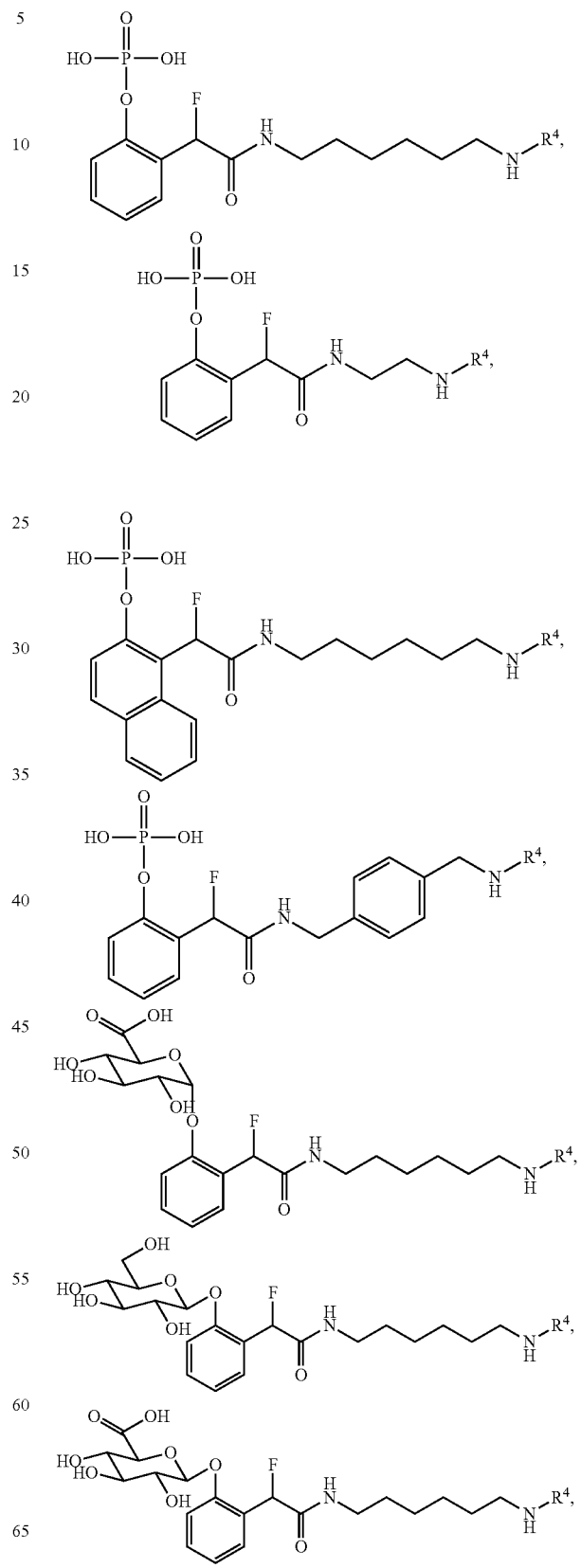

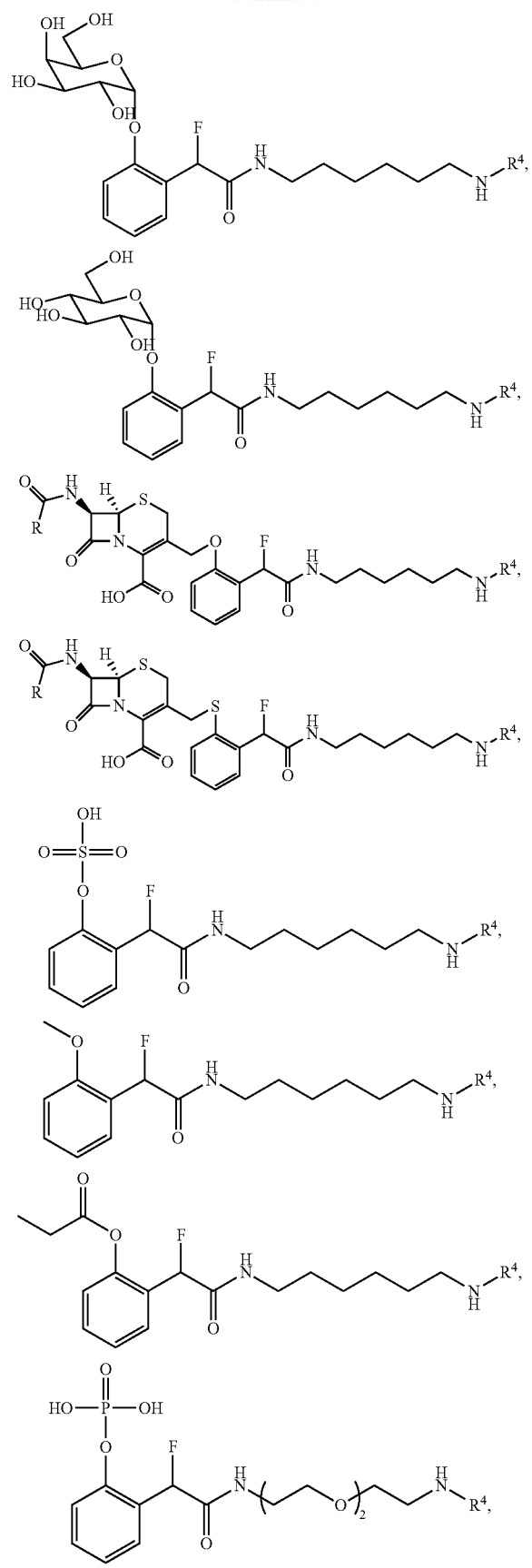
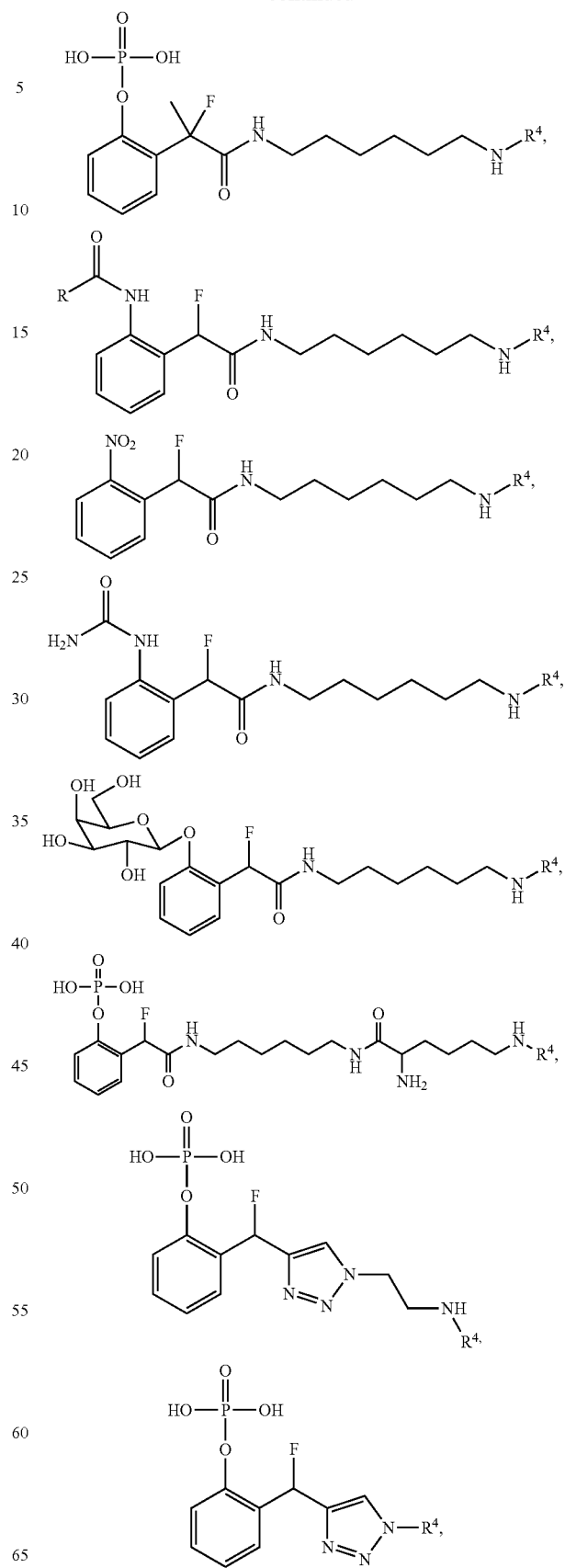

119
-continued
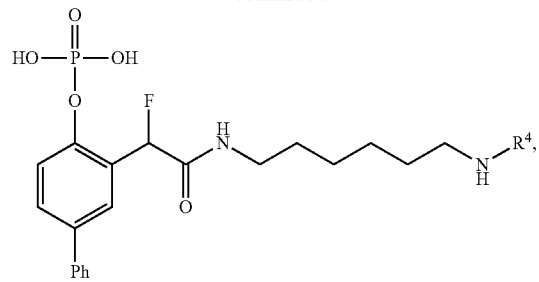
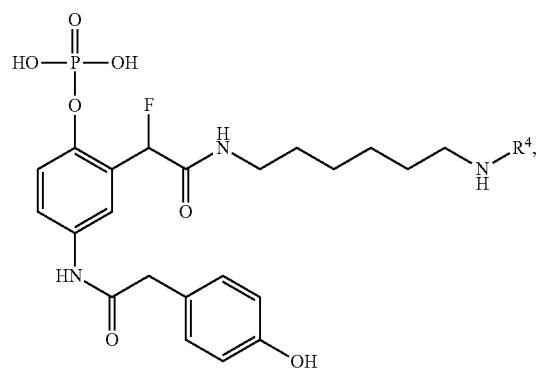
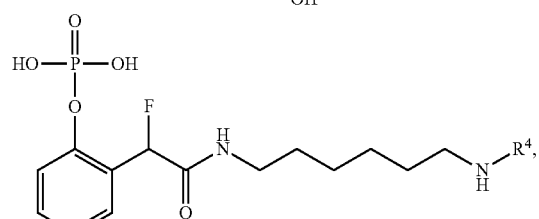
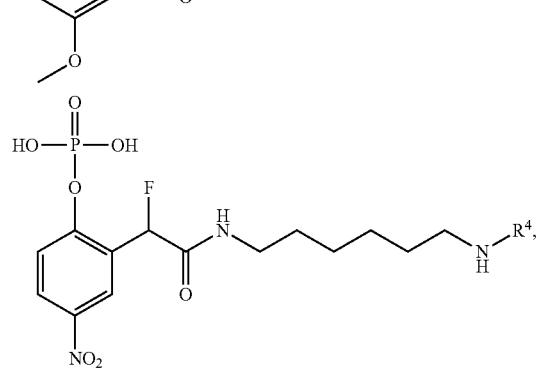
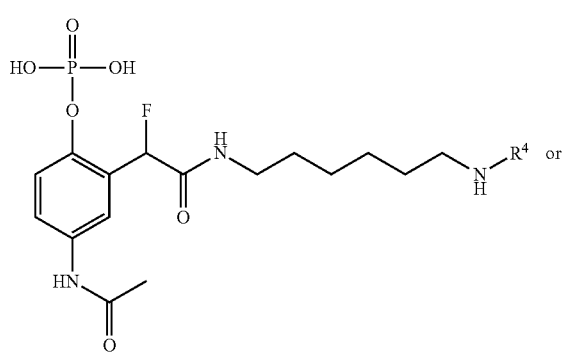
120
-continued
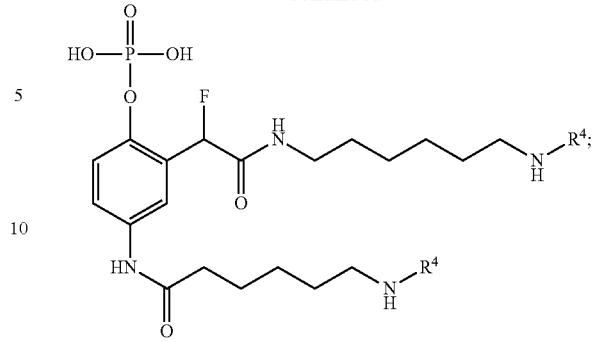
and
R[4] is a chromogen, a fluorophore, a luminophore, or a hapten.
17. The compound of embodiment U wherein the compound is
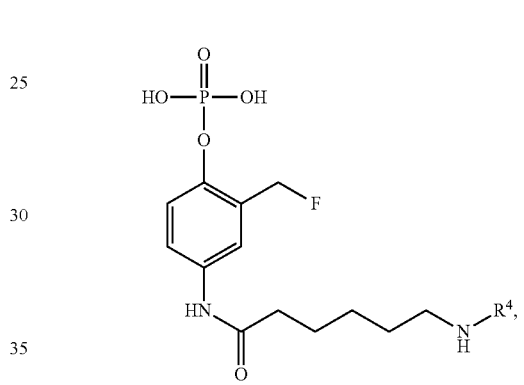
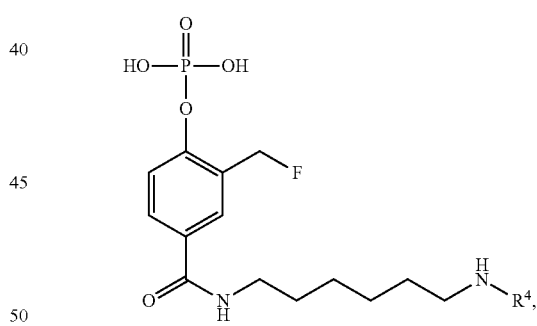
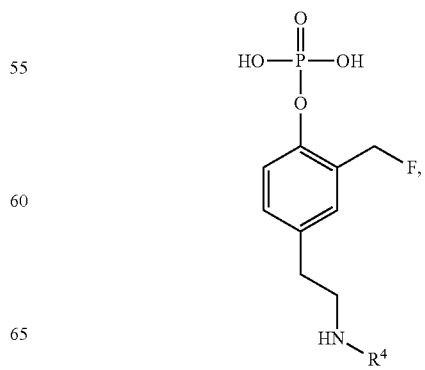

121
-continued
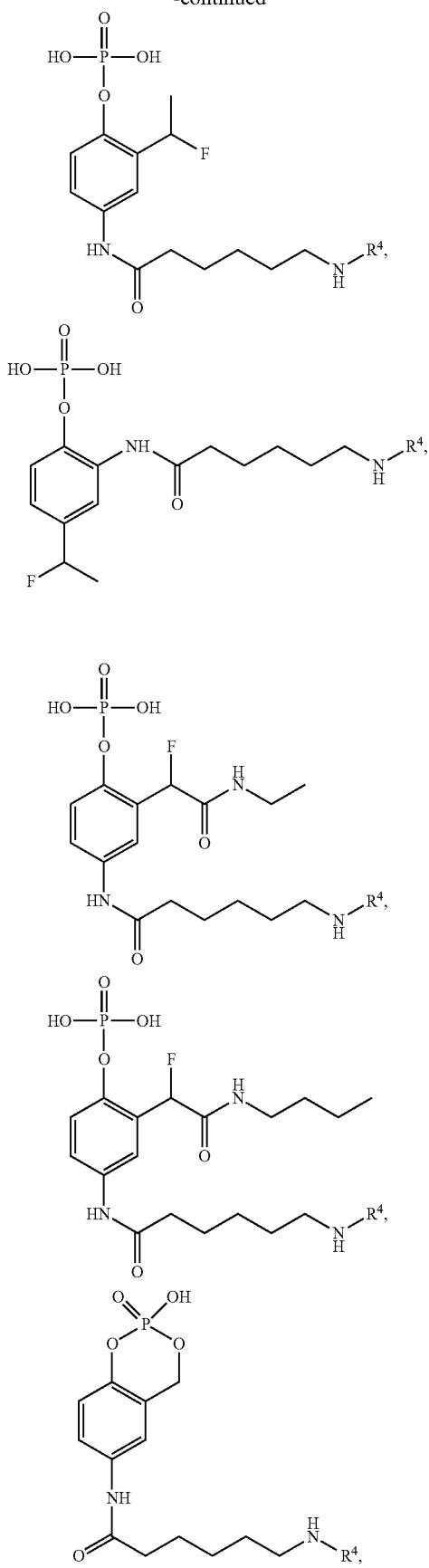
122
-continued
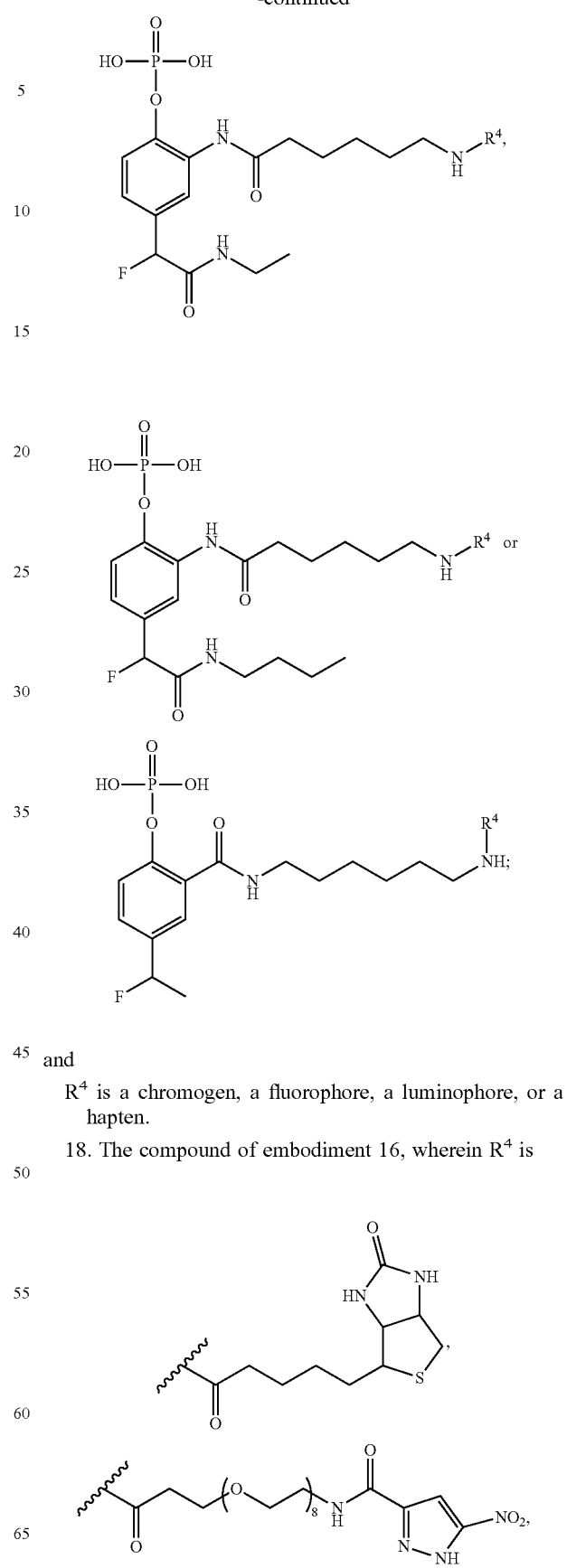
and
$R^4$ is a chromogen, a fluorophore, a luminophore, or a hapten.
18. The compound of embodiment 16, wherein $R^4$ is 123
-continued

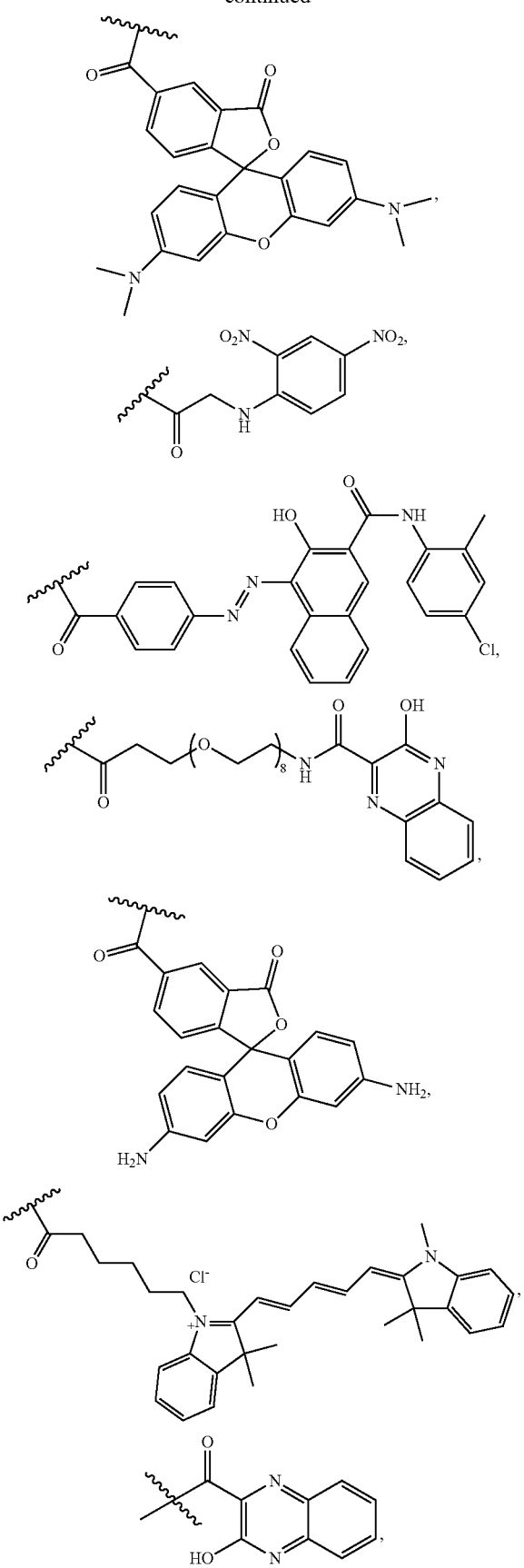

124
-continued

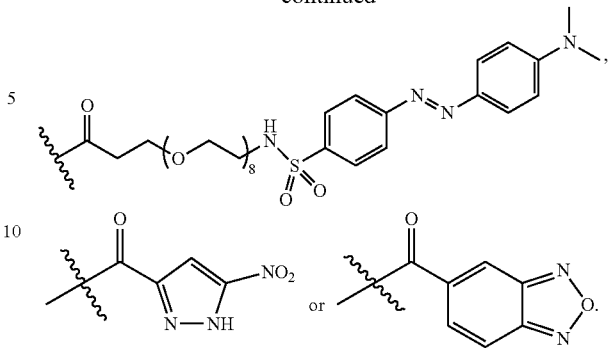

19. A method of detecting a first target in a biological sample, comprising:
contacting the biological sample with a first detection probe specific to the first target;
contacting the biological sample with a first labeling conjugate, comprising a first enzyme;
contacting the biological sample with a first quinone methide analog precursor comprising a first enzyme recognition group and a first detectable label, wherein the first enzyme cleaves the first enzyme recognition group, thereby converting the first quinone methide analog precursor into a first reactive quinone methide analog which covalently binds to the biological sample proximally to or directly on the first target, contacting the biological sample comprising
(i) contacting the biological sample with the first quinone methide analog precursor at a precursor concentration effective to give a desired level of amplification;
(ii) contacting the biological sample with the first quinone methide analog precursor at a pH effective to reduce diffusion and/or off-target staining to a desired amount;
(iii) contacting the biological sample with the first quinone methide analog precursor in the presence of a salt at a salt concentration effective to reduce diffusion and/or off-target staining to a desired amount;
(iv) contacting the biological sample with a compound according to claim 1; or
(v) any combination thereof; and
detecting the first target by detecting the first detectable label.

20. The method of embodiment 19, wherein contacting the biological sample comprises contacting the biological sample with a compound according to claim 1.

21. The method of embodiment 19, wherein the salt concentration is from 0.1 M to 2 M.

22. The method of embodiment 21, wherein the salt concentration is from 0.5 M to 1.25 M.

23. The method of embodiment 19, wherein the salt is magnesium chloride.

24. The method of embodiment 19, comprising contacting the biological sample with a first quinone methide analog precursor at a pH effective to reduce diffusion and/or off-target staining to a desired amount.

25. The method of embodiment 24, wherein the pH is from greater than 7 to 14.

26. The method of embodiment 25, wherein the pH is from 8 to 12.

27. The method of embodiment 19, comprising contacting the biological sample with a first quinone methide analog precursor at a precursor concentration effective to give a desired level of amplification.

28. The method of embodiment 27, wherein the precursor concentration is from greater than zero to 1 mM.

29. The method of embodiment 28, wherein the precursor concentration is from 50 nM to 100 μM 30. The method of embodiment 29, wherein the precursor concentration is from 100 nM to 1 μM.

31. The method of embodiment 19, wherein the biological sample comprises formalin-fixed, paraffin-embedded tissue.

32. The method of embodiment 19, wherein the method is an automated process.

33. The method of embodiment 19 wherein the first detection probe comprises an oligonucleotide, an antibody, or an antibody fragment.

34. The method of embodiment 33, wherein the first detection probe comprises a hapten-labeled oligonucleotide.

35. The method of embodiment 19, wherein the first detection probe comprises an oxazole hapten, pyrazole hapten, thiazole hapten, nitroaryl hapten, benzofuran hapten, triterpene hapten, urea hapten, thiourea hapten, rotenoid hapten, coumarin hapten, cyclolignan hapten, di-nitrophenyl hapten, biotin hapten, digoxigenin hapten, fluorescein hapten, or rhodamine hapten.

36. The method of embodiment 19, wherein the first labeling conjugate comprises an antibody coupled to the first enzyme.

37. The method of embodiment 36, wherein the antibody is an anti-species or an anti-hapten antibody.

38. The method of embodiment 19, wherein the first labeling conjugate is associated with the first detection probe.

39. The method of embodiment 38, wherein the first labeling conjugate is directly associated with the first detection probe.

40. The method of embodiment 38, wherein the first labeling conjugate is indirectly associated with the first detection probe.

41. The method of embodiment 36, wherein the first detection probe comprises a first anti-species antibody and the first labeling probe comprises a second anti-species antibody.

42. The method of embodiment 36, wherein the first detection probe comprises a hapten and the first labeling probe comprises an anti-hapten antibody.

43. The method of embodiment 19, wherein the first enzyme is a phosphatase, phosphodiesterase, esterase, lipase, amidase, protease, nitroreductase, urease, sulfatase, cytochrome P450, alpha-glucosidase, beta-glucosidase, beta-lactamase, alpha-glucoronidase, beta-glucoronidase, alpha-galactosidase, beta-galactosidase, alpha-lactase or beta-lactase.

44. The method of embodiment 19, wherein the first enzyme recognition group is a phosphate, phosphodiester, amide, nitro, urea, sulfate, methyl, ester, alpha-glucose, beta-glucose, beta-lactam, alpha-galactoside, beta-galactoside, alpha-lactose, beta-lactose, alpha-glucuronoside or beta-glucuronoside.

45. The method of embodiment 19, wherein the first reactive quinone methide analog reacts with a nucleophilic site within the biological sample, the first labeling conjugate, the first detection probe, or combinations thereof.

46. The method of embodiment 45, wherein the nucleophilic site comprises an amino, sulfhydryl, or hydroxyl group on an amino acid or nucleic acid residue.

47. The method of embodiment 19, wherein the first quinone methide analog precursor has a formula

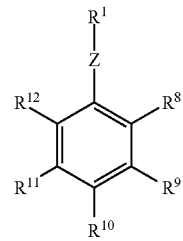

or a salt or solvate thereof;

Z is O, S or $NR^a$ and $R^1$ is an enzyme recognition group, or $ZR^1$ is an enzyme recognition group;

$R^8$ is $—C(LG)(R^5)(R^3R^4)$, $—R^3R^4$ or $—C(LG)(R^5)(R^6)$;

$R^9$, $R^{11}$ and $R^{12}$ are each independently hydrogen, halo, cyano, aliphatic, alkoxy, $NO_2$, $N(R^c)_2$, aryl, haloalkyl, $—C(O)alkyl$, $—C(S)alkyl$, $—C(O)OH$, $—C(O)Oalkyl$, $—C(O)NHR^c$, $—C(O)N(R^c)_2$, $—R^3R^4$ or two adjacent groups together form an aliphatic ring or aryl ring;

$R^{10}$ is hydrogen, halo, cyano, aliphatic, alkoxy, $NO_2$, $N(R^c)_2$, aryl, haloalkyl, $—C(O)alkyl$, $—C(S)alkyl$, $—C(O)OH$, $—C(O)Oalkyl$, $—C(O)NHR^c$, $—C(O)N(R^c)_2$, $—R^3R^4$, $—C(LG)(R^5)(R^6)$ or with one of $R^9$ or $R^{11}$ form an aliphatic ring or aryl ring;

LG is a leaving group, or $ZR^1$ and LG together form a phosphodiester;

$R^3$ is a bond or a linker;

$R^4$ is a detectable label;

each $R^a$ independently is hydrogen or aliphatic;

each $R^c$ independently is hydrogen, aryl, aliphatic or heteroaliphatic, or two $R^c$ moieties together form a heteroaliphatic ring;

each $R^5$ is independently hydrogen, halo, cyano, lower alkyl, lower haloalkyl, $—C(O)alkyl$, $—C(S)alkyl$, $—C(O)OH$, $—C(O)Oalkyl$, $—C(O)NHR^c$ or $—C(O)N(R^c)_2$;

each $R^6$ is independently hydrogen, halo, cyano, lower alkyl, lower haloalkyl, $—C(O)alkyl$, $—C(S)alkyl$, $—C(O)OH$, $—C(O)Oalkyl$, $—C(O)NHR^c$ or $—C(O)N(R^c)_2$;

at least one of $R^8$ and $R^{10}$ comprises LG;

at least one of $R^8$-$R^{12}$ comprises $R^3R^4$; and if LG is halo, then $R^5$ and $R^6$ are not halo.

48. The method of embodiment 47, wherein the first quinone methide precursor has a formula

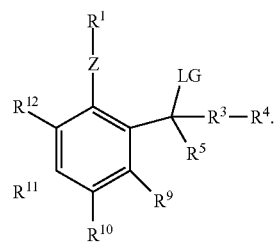

49. The method of embodiment 48, wherein the first quinone methide analog precursor has a structure selected from 127
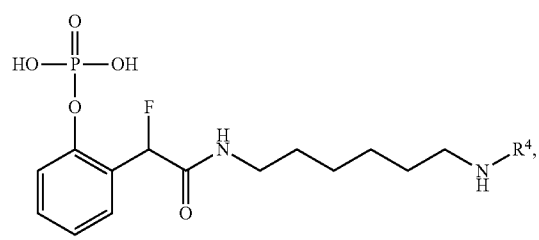
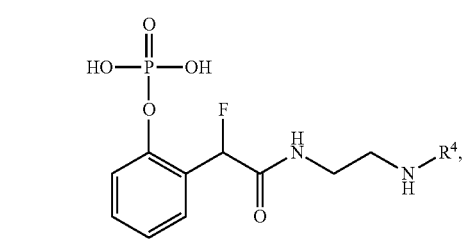
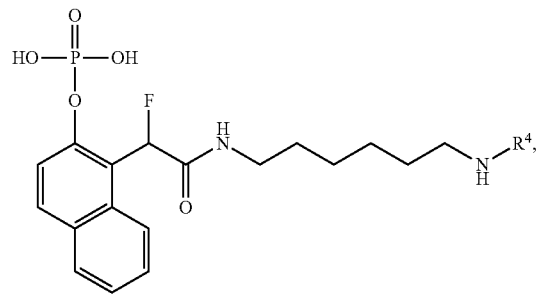
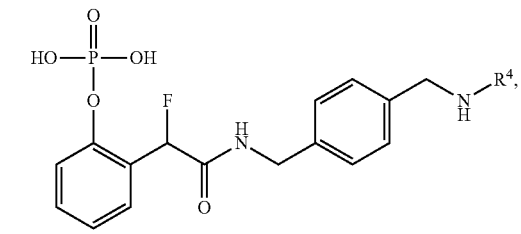
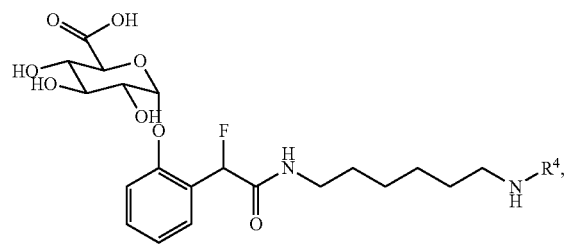
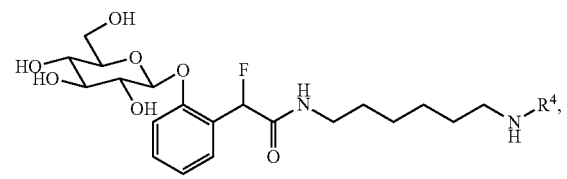
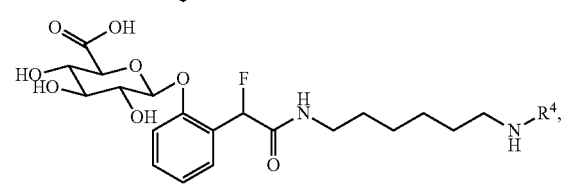
128
-continued
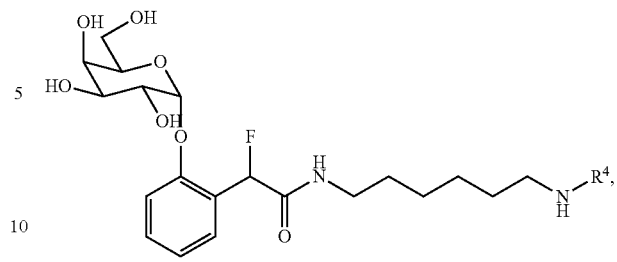
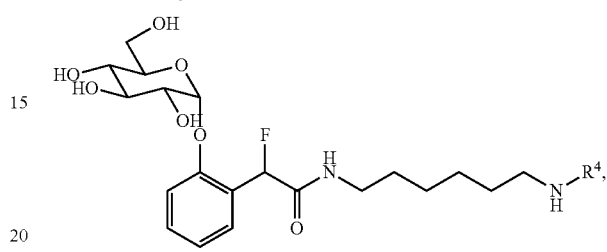
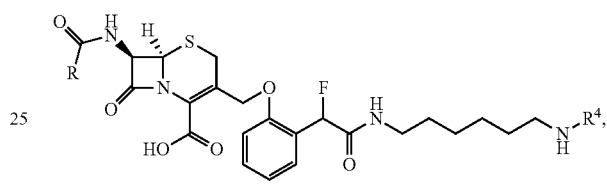
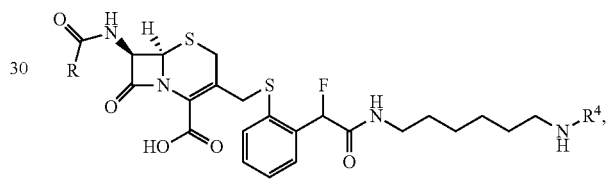
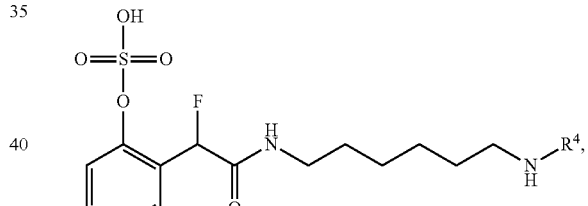
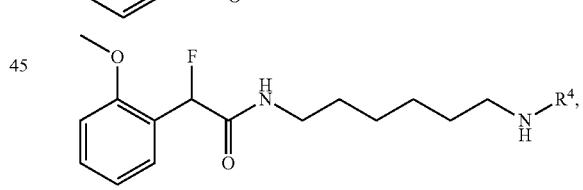
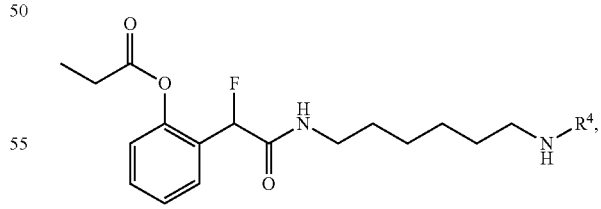
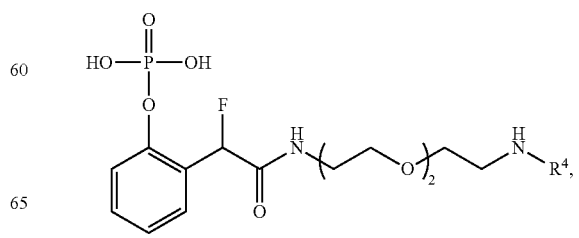

129
-continued
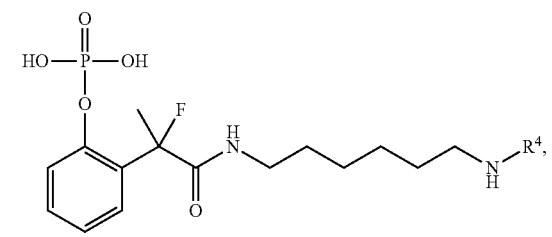
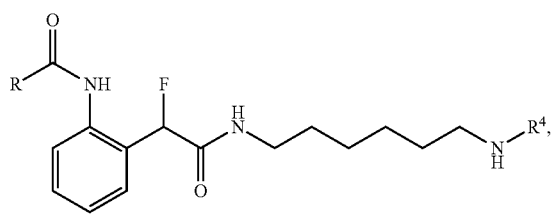
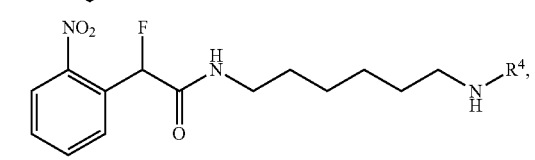
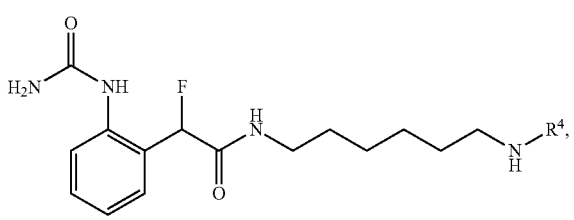
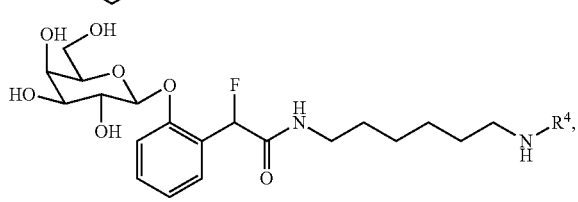
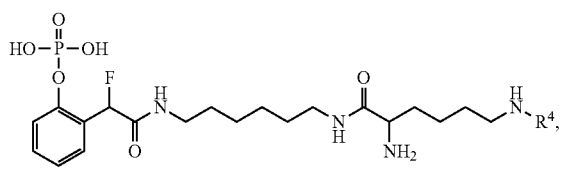
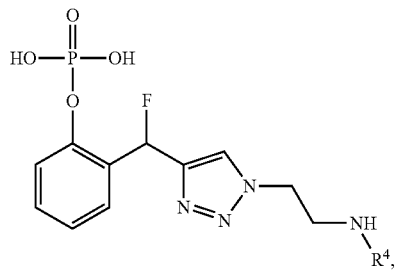
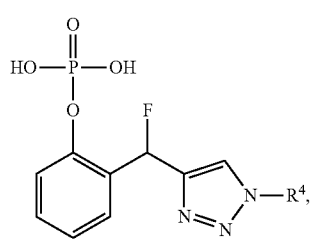
130
-continued
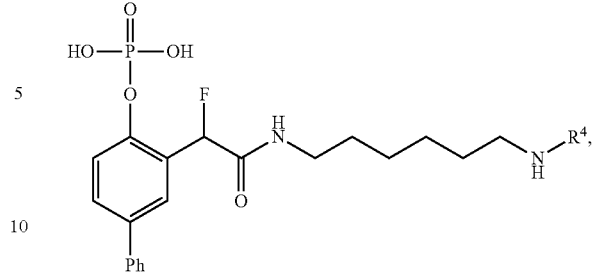
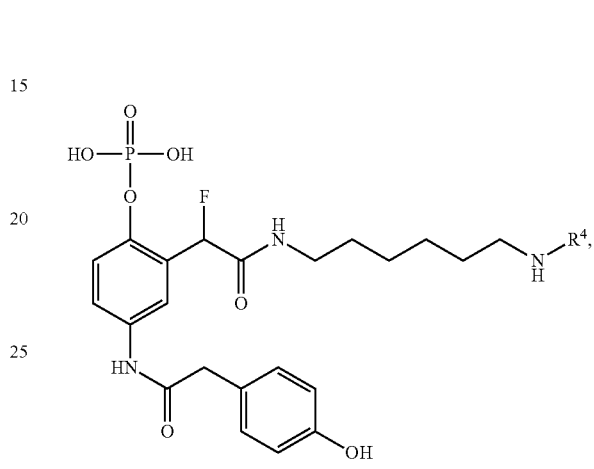
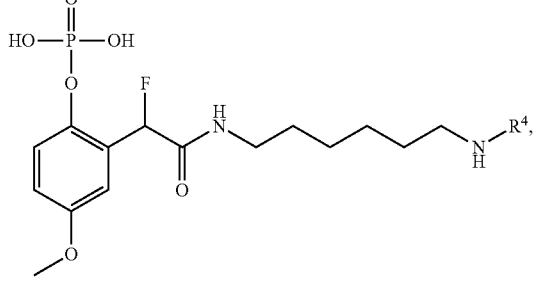
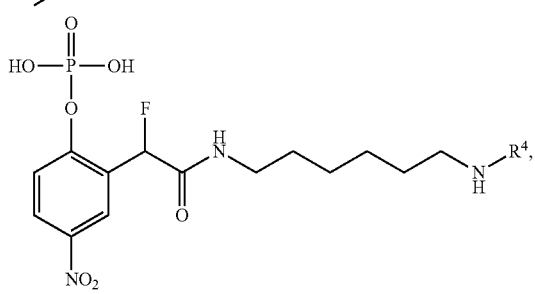
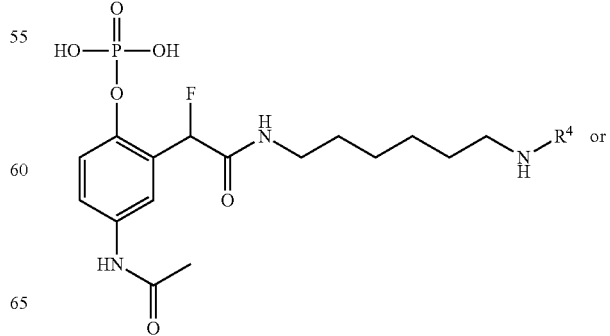

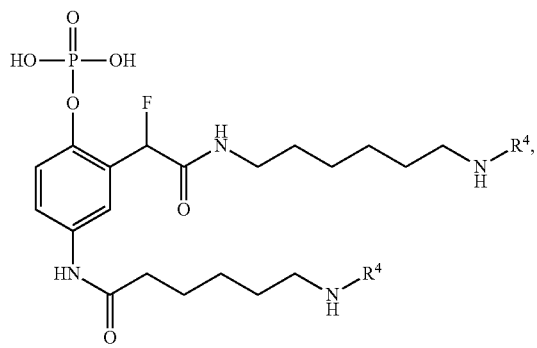
wherein $R^4$ is a chromogen, a fluorophore, a luminophore, or a hapten.
50. The method of embodiment 47, wherein the first quinone methide analog precursor has a formula selected from
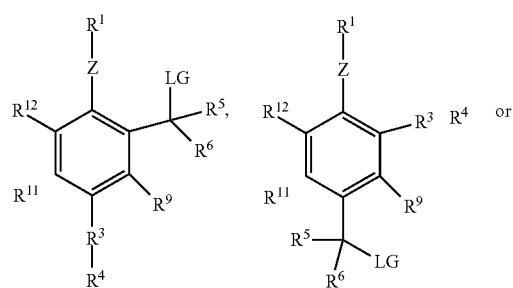
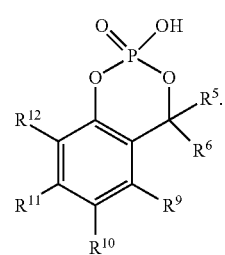
51. The method of embodiment 50, wherein the first quinone methide analog precursor has a structure selected from
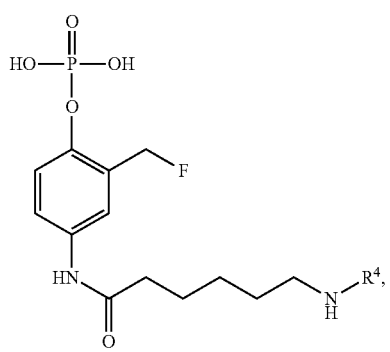
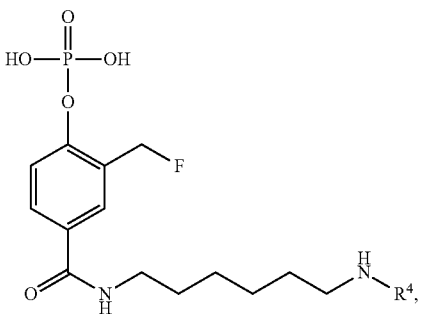
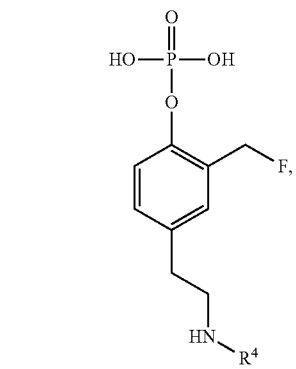
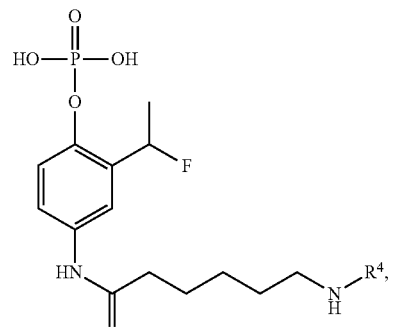
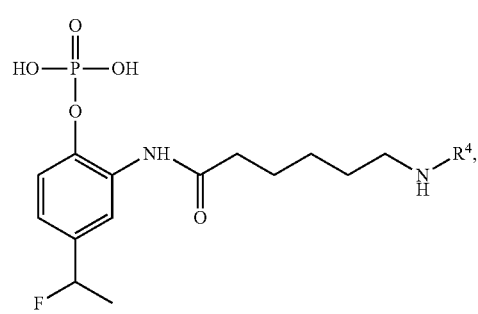
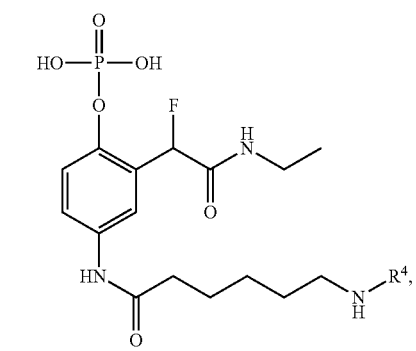

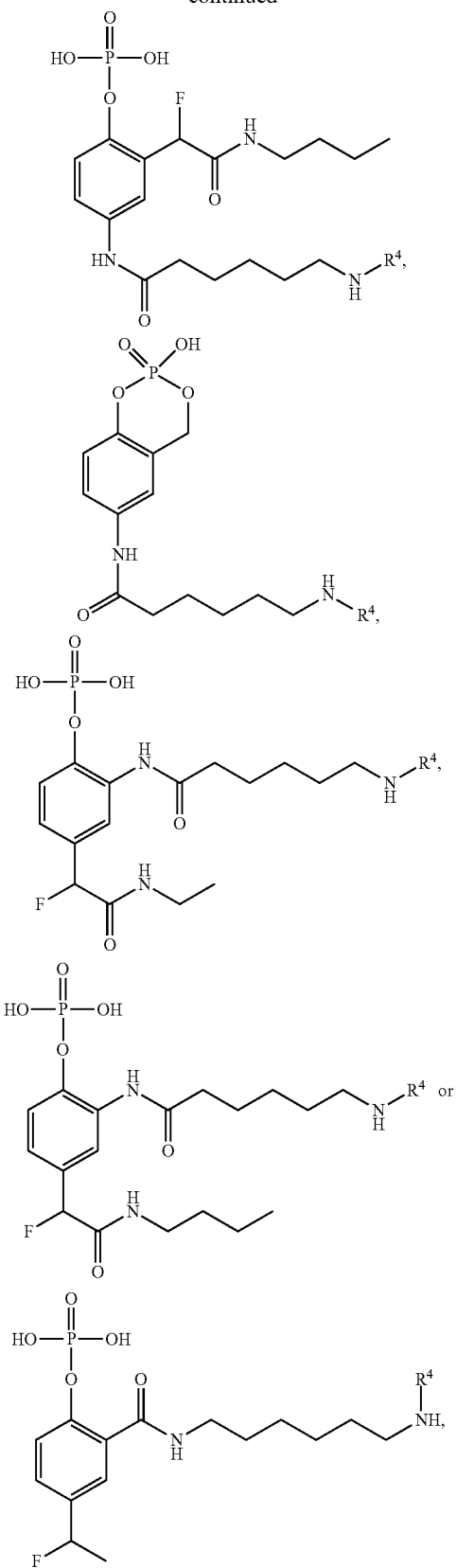

wherein R⁴ is a chromogen, a fluorophore, a luminophore, or a hapten.

52. The method of embodiment 19, wherein the first quinone methide analog precursor has a structure selected from

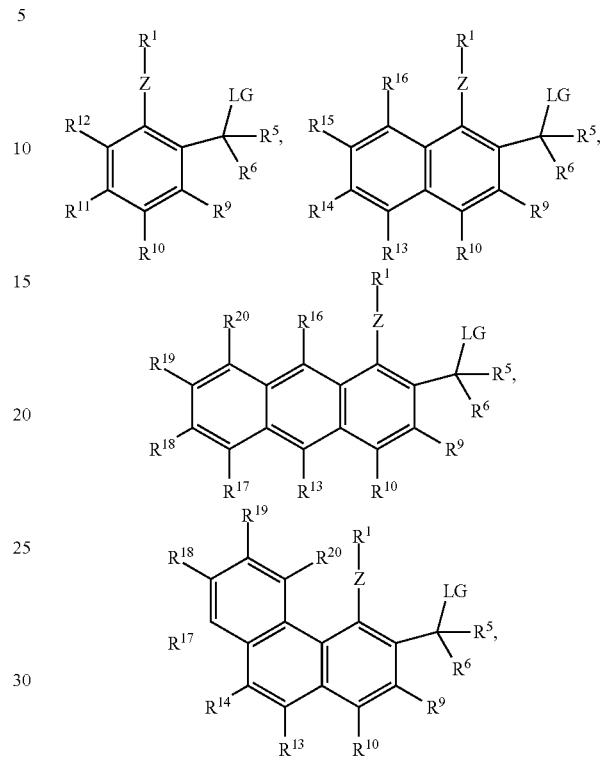

or a salt or solvate thereof;
Z is O, S or NR$^a$ and R$^1$ is an enzyme recognition group, or ZR$^1$ is an enzyme recognition group;
R$^9$ and R$^{11}$-R$^{20}$ are each independently hydrogen, halo, cyano, aliphatic, alkoxy, NO$_2$, N(R$^c$)$_2$, aryl, haloalkyl, —C(O)alkyl, —C(S)alkyl, —C(O)OH, —C(O)Oalkyl, —C(O)NHR$^c$, —C(O)N(R$^c$)$_2$, —R$^3$R$^4$ or two adjacent groups together form an aliphatic ring or aryl ring;
R$^{10}$ is hydrogen, halo, cyano, aliphatic, alkoxy, NO$_2$, N(R$^c$)$_2$, aryl, haloalkyl, —C(O)alkyl, —C(S)alkyl, —C(O)OH, —C(O)Oalkyl, —C(O)NHR$^c$, —C(O)N (R$^c$)$_2$, —R$^3$R$^4$, —C(LG)(R$^5$)(R$^6$) or with one of R$^9$ or R$^{11}$ form an aliphatic ring or aryl ring;
LG is a leaving group, or ZR$^1$ and LG together form a phosphodiester;
R$^3$ is a bond or a linker;
R$^4$ is a detectable label;
each R$^a$ independently is hydrogen or aliphatic;
each R$^c$ independently is hydrogen, aryl, aliphatic or heteroaliphatic, or two R$^c$ moieties together form a heteroaliphatic ring;
each R$^5$ is independently hydrogen, halo, cyano, lower alkyl, lower haloalkyl, —C(O)alkyl, —C(S)alkyl, —C(O)OH, —C(O)Oalkyl, —C(O)NHR$^c$ or —C(O)N (R$^c$)$_2$;
each R$^6$ is independently hydrogen, halo, cyano, lower alkyl, lower haloalkyl, —C(O)alkyl, —C(S)alkyl, —C(O)OH, —C(O)Oalkyl, —C(O)NHR$^c$ or —C(O)N (R$^c$)$_2$;
at least one of R$^8$ and R$^{10}$ comprises LG;
at least one of R$^9$-R$^{20}$ comprises R$^3$R$^4$; and
if LG is halo, then R$^5$ and R$^6$ are not halo.

53. The method of embodiment 19, wherein the first quinone methide analog precursor has a formula selected from

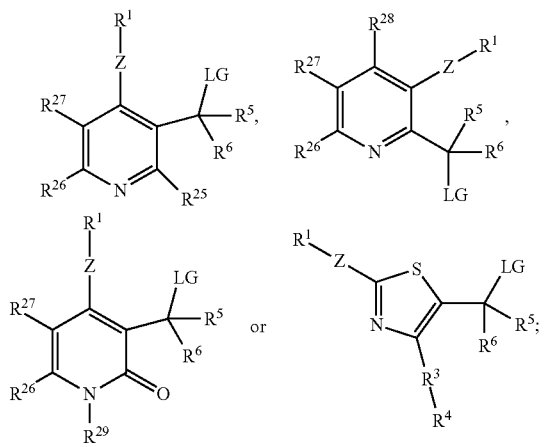

Z is O, S or NR$^a$ and R$^1$ is an enzyme recognition group, or ZR$^1$ is an enzyme recognition group;

R$^5$ and R$^6$ are each independently hydrogen, halo, cyano, lower alkyl, lower haloalkyl, —C(O)alkyl, —C(S)alkyl, —C(O)OH, —C(O)Oalkyl, —C(O)NHR$^c$ or —C(O)N(R$^c$)$_2$;

R$^{25}$-R$^{29}$ are each independently hydrogen, halo, cyano, aliphatic, alkoxy, NO$_2$, N(R$^c$)$_2$, aryl, haloalkyl, —C(O)alkyl, —C(S)alkyl, —C(O)OH, —C(O)Oalkyl, —C(O)NHR$^c$, —C(O)N(R$^c$)$_2$, —R$^3$R$^4$, or two adjacent groups together form an aliphatic ring or aryl ring; each R$^c$ independently is hydrogen, aryl, aliphatic or heteroaliphatic, or two R$^c$ moieties together form a heteroaliphatic ring;

LG is a leaving group, or ZR$^1$ and LG together form a phosphodiester;

R$^3$ is a bond or a linker;

R$^4$ is a detectable label;

each R$^a$ independently is hydrogen or aliphatic;

each R$^c$ independently is hydrogen, aryl, aliphatic or heteroaliphatic, or two R$^c$ moieties together form a heteroaliphatic ring;

at least one of R$^5$, R$^6$ and R$^{25}$-R$^{29}$ comprises R$^3$R$^4$; and when LG is halo, R$^5$ and R$^6$ are not halo.

54. The method of embodiment 19, wherein the first quinone methide analog precursor has a formula

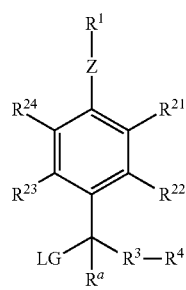

or a salt or solvate thereof;

Z is O, S or NR$^a$ and R$^1$ is an enzyme recognition group, or ZR$^1$ is an enzyme recognition group;

LG is a leaving group;

R$^3$ is a bond or a linker;

R$^4$ is a detectable label;

R$^{21}$, R$^{22}$, R$^{23}$ and R$^{24}$ are each independently hydrogen, halo, cyano, aliphatic, alkoxy, NO$_2$, N(R$^c$)$_2$, aryl, haloalkyl, —C(O)alkyl, —C(S)alkyl, —C(O)OH, —C(O)Oalkyl, —C(O)NHR$^c$, —C(O)N(R$^c$)$_2$, —R$^3$R$^4$, or two adjacent groups together form an aliphatic ring or aryl ring;

each R$^a$ independently is hydrogen or aliphatic; and each R$^c$ independently is hydrogen, aryl, aliphatic or heteroaliphatic, or two R$^c$ moieties together form a heteroaliphatic ring.

55. The method of embodiment 54, wherein the first quinone methide analog precursor is selected from

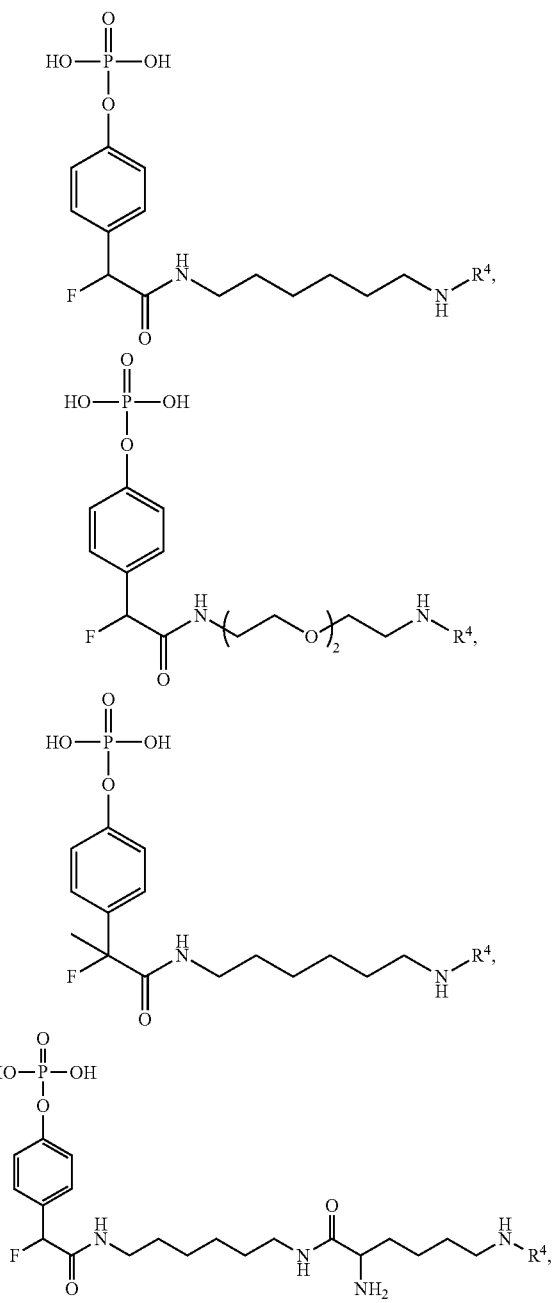

137
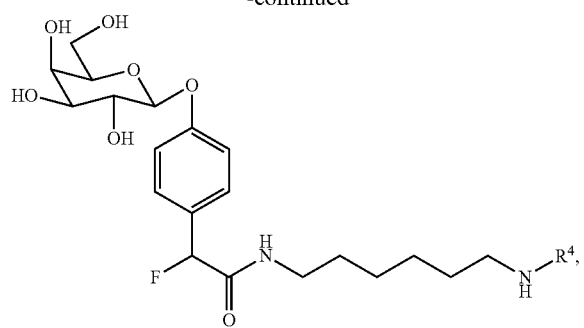
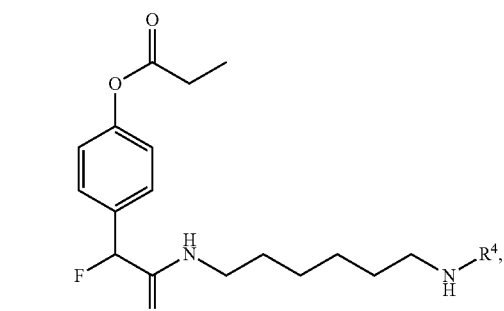
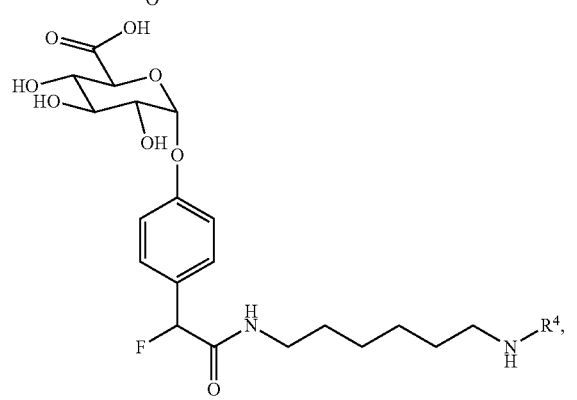
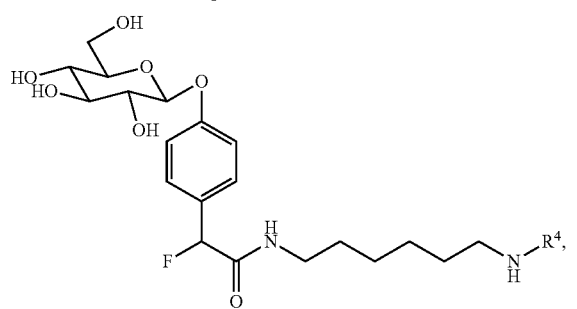
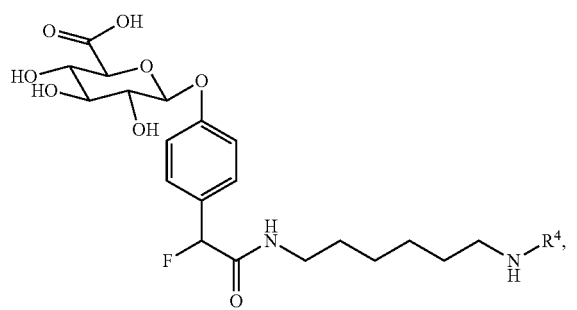
138
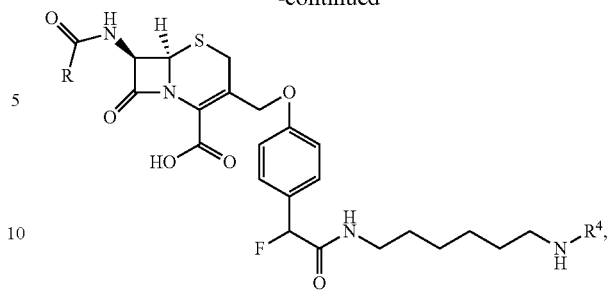
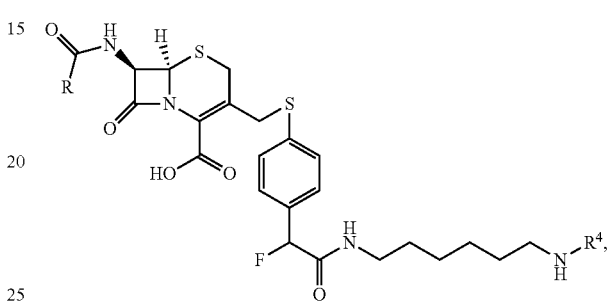
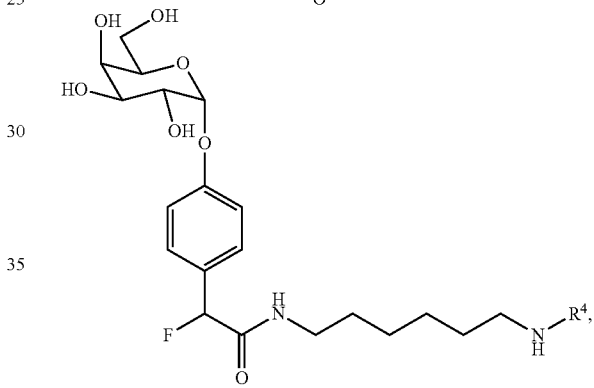
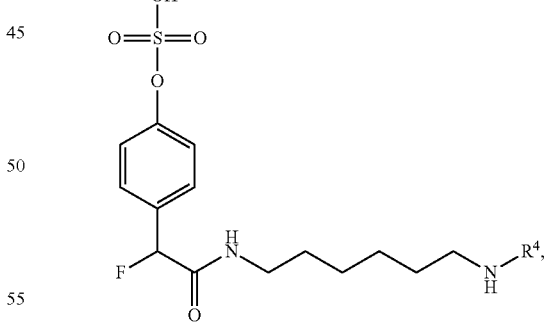
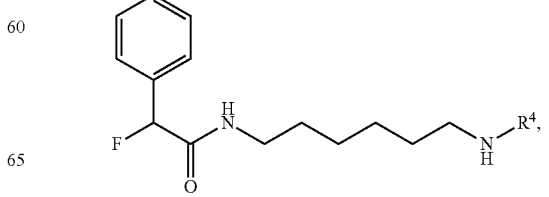

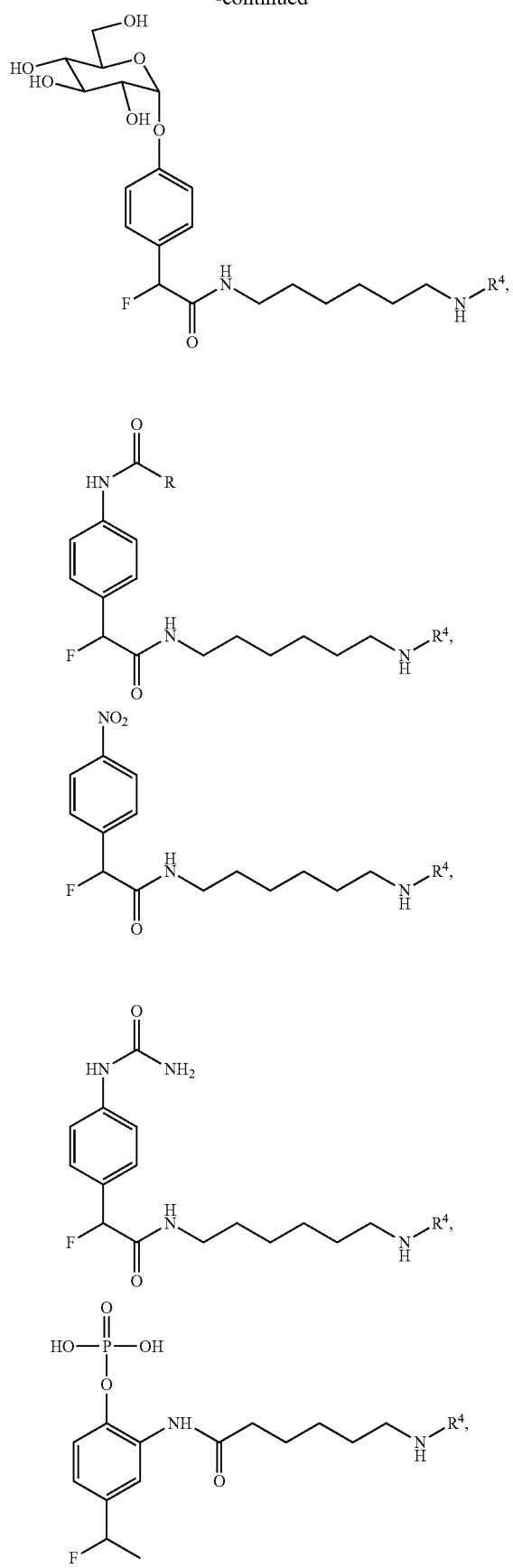
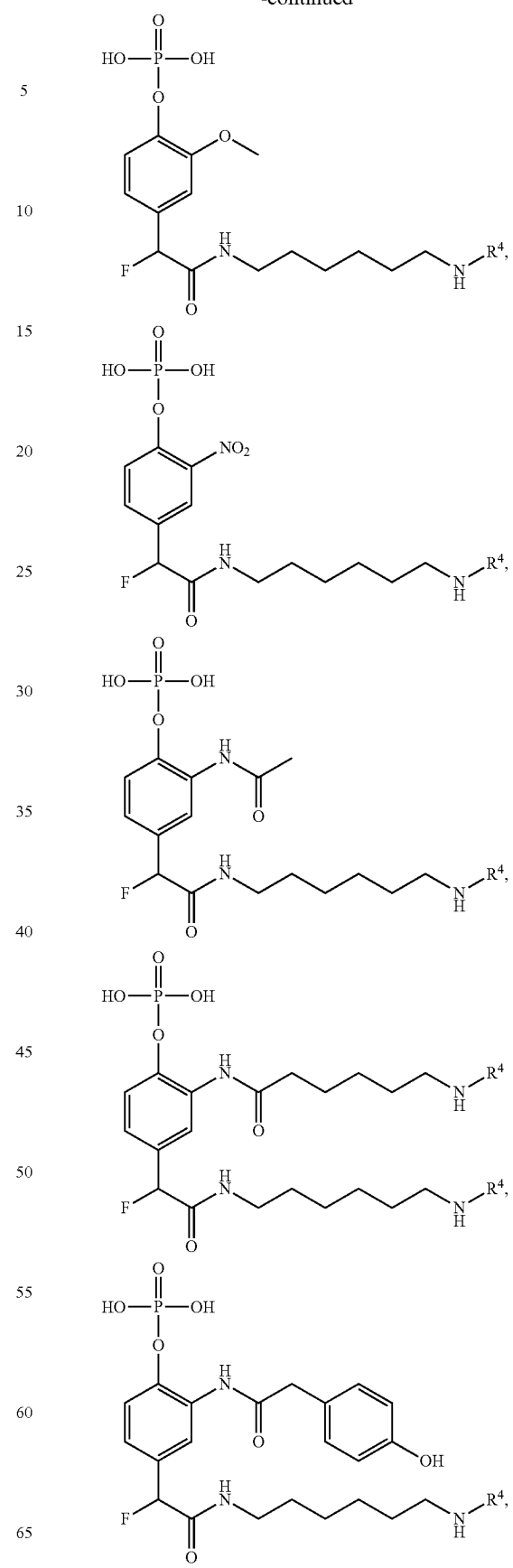

-continued

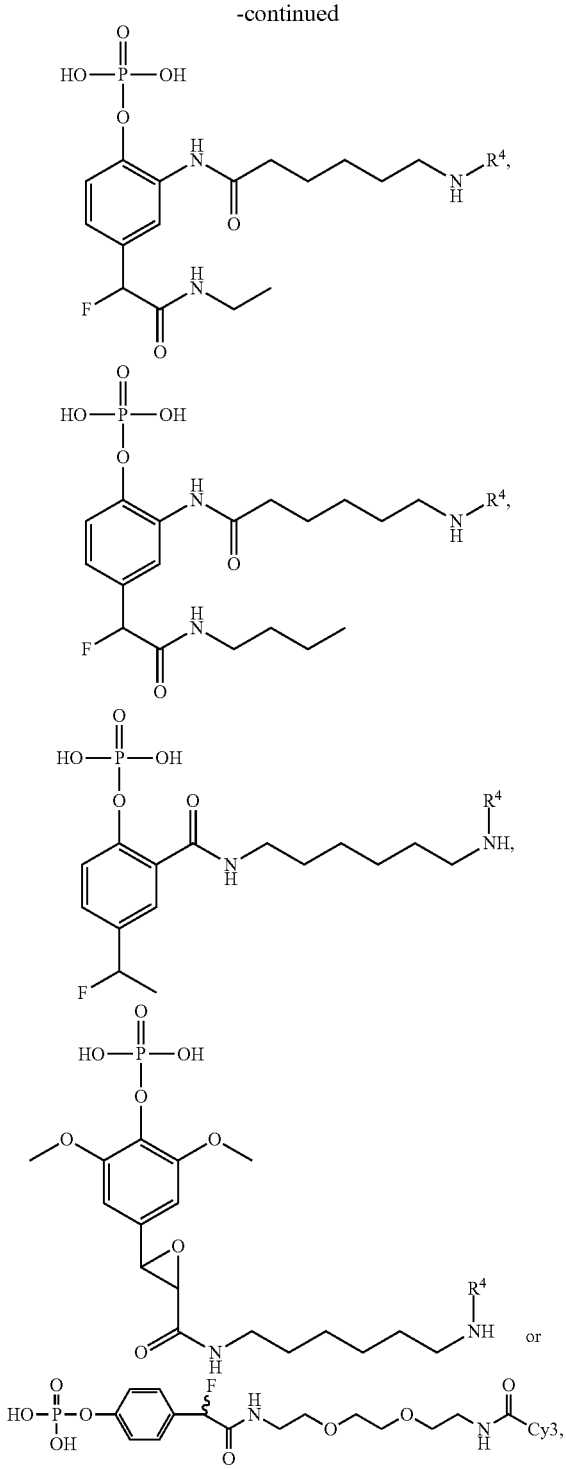

where R⁴ is selected from a hapten, fluorophore, luminophore, or chromogen.

56. The method of embodiment 19, wherein the target is a peptide, polypeptide, protein or nucleic acid sequence.

57. The method of embodiment 19, wherein the method is a multiplexed method.

58. The method of embodiment 57, further comprising:
contacting the biological sample with a second binding moiety specific to a second target;
labeling the second target with a second enzyme through the second binding moiety;
contacting the biological sample with a second detection precursor compound, the second detection precursor compound interacting with the second enzyme to deposit a second detection compound directly on or proximally to the second target; and detecting the second detection compound.

59. The method of embodiment 58, wherein the first enzyme and second enzyme are different enzymes.

60. The method of embodiment 58, wherein the first enzyme reacts selectively with the first quinone methide analog precursor, and the second enzyme reacts selectively with the second detection precursor compound.

61. The method of embodiment 58, where the method does not comprise an enzyme deactivation step.

62. The method of embodiment 58, wherein the first enzyme is a phosphatase, phosphodiesterase, esterase, lipase, amidase, protease, nitroreductase, urease, sulfatase, cytochrome P450, alpha-glucosidase, beta-glucosidase, beta-lactamase, alpha-glucoronidase, beta-glucoronidase, alpha-galactosidase, beta-galactosidase, alpha-lactase or beta-lactase.

63. The method of embodiment 58, wherein the first enzyme is an alkaline phosphatase and the first enzyme recognition group is a phosphate.

64. The method of embodiment 58, wherein the second enzyme is a peroxidase.

65. The method of embodiment 58 wherein the second detection precursor compound is a second quinone methide analog precursor comprising a second enzyme recognition group and a second detectable label, the second quinone methide analog precursor interacting with the second enzyme to form a second quinone methide analog which covalently binds to the biological sample proximally to or directly on the second target, and wherein detecting the second detection compound comprises detecting the second detectable label.

66. The method of embodiment 58, wherein the second enzyme is a β-galactosidase and the second enzyme recognition group is a β-galactoside.

67. The method of embodiment 58, wherein contacting the tissue with the first binding moiety specific to the first target and contacting the tissue with the second binding moiety specific to the second target occur substantially contemporaneously.

68. The method of embodiment 58, wherein labeling the first target with the first enzyme through the first binding moiety and labeling the second target with the second enzyme through the second binding moiety occur substantially contemporaneously.

69. The method of embodiment 58, wherein contacting the tissue with the first binding moiety specific to the first target and contacting the tissue with the second binding moiety specific to the second target occur sequentially.

70. The method of embodiment 58, wherein labeling the first target with the first enzyme through the first binding moiety and labeling the second target with the second enzyme through the second binding moiety occur sequentially.

71. The method of embodiment 58, further comprising:
contacting the biological sample with a third binding moiety specific to a third distinct target;
labeling the third target with a third enzyme through the third binding moiety; contacting the biological sample with a third detection precursor compound, the third detection precursor compound interacting with the third enzyme to deposit a third detection compound directly on or proximally to the third target; and
detecting the third detection compound.

72. The method of embodiment 71, wherein the first enzyme is an alkaline phosphatase and the first enzyme recognition group is a phosphate, the second enzyme is a β-galactosidase and second detection precursor compound is a second quinone methide analog precursor comprising a β-galactoside, and the third enzyme is a peroxidase.

73. A kit, comprising:
an enzyme-antibody conjugate;
a quinone methide analog precursor;
a solvent mixture; and
a pH adjust solution.

74. The kit of embodiment 73, wherein the solvent mixture comprises an organic solvent and an aqueous buffer.

75. The kit of embodiment 74, wherein the organic solvent is DMSO.

76. The kit of embodiment 74, wherein the aqueous buffer has a pH range of from pH 0 to pH 5.

77. The kit of embodiment 76, wherein the pH range is from pH 1 to pH 3.

78. The kit of embodiment 73, wherein the pH adjust solution has a pH range of from pH 8 to pH 12.

79. The kit of embodiment 73, further comprising magnesium chloride at a concentration of from 0.25M to 1.5M.

80. The kit of embodiment 73, wherein the quinone methide analog precursor is a compound according to embodiment 1.

81. The kit of embodiment 73, wherein:
the quinone methide analog precursor is a compound according to claim 1;
the solvent mixture comprises DMSO and a glycine buffer at pH 2;
the pH adjust solution is a Tris buffer with a pH range of from pH 8 to pH 10; and
further comprising magnesium chloride at a concentration of from 0.5M to 1.25M.

The invention claimed is:

1. A method of detecting a first target in a biological sample, comprising:
contacting the biological sample with a first detection probe specific to the first target;
labeling the first target with a first enzyme through the first detection probe;
contacting the biological sample with a first quinone methide analog precursor comprising a first enzyme recognition group and a first detectable label, and
detecting the first target by detecting the first detectable label,
wherein the first quinone methide analog precursor has a formula

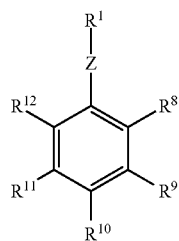

or a salt or solvate thereof;
Z is O, S or $NR^a$ and $R^1$ is an enzyme recognition group, or $ZR^1$ is an enzyme recognition group;
$R^8$ is —C(LG)($R^5$)($R^3R^4$);
$R^9$, $R^{11}$ and $R^{12}$ are each independently hydrogen, halo, cyano, aliphatic, alkoxy, $NO_2$, $N(R^c)_2$, aryl, —C(O)alkyl, —C(S)alkyl, —C(O)OH, —C(O)Oalkyl, —C(O)NHR$^c$, —C(O)N($R^c$)$_2$, —$R^3R^4$ or two adjacent groups together form an aliphatic ring or aryl ring;
$R^{10}$ is hydrogen, halo, cyano, aliphatic, alkoxy, $NO_2$, $N(R^c)_2$, aryl, haloalkyl, —C(O)alkyl, —C(S)alkyl, —C(O)OH, —C(O)Oalkyl, —C(O)NHR$^c$, —C(O)N($R^c$)$_2$, or with one of $R^9$ or $R^{11}$ form an aliphatic ring or aryl ring;
LG is a leaving group, or $ZR^1$ and LG together form a phosphodiester;
$R^3$ is —N(H)C(O)(CH$_2$)$_n$NH—, —C(O)N(H)(CH$_2$)$_n$NH—, —C(O)N(H)(CH$_2$)$_n$O—, —N(H)C(O)(CH$_2$)$_n$S—, —C(O)N(H)(CH$_2$)$_n$S—, —C(O)N(H)(CH$_2$)$_n$NHC(O)CH(CH$_3$)(CH$_2$)$_n$NH—, or —N(H)(CH$_2$)$_n$NH—, where each n is independently an integer ranging from 1 to 12;
$R^4$ is a chromogen, a fluorophore, a luminophore, or a hapten, wherein the hapten is selected from the group consisting of a pyrazole, a nitrophenyl compound, a benzofuran, a urea, a thiourea, a phenyl urea, a phenyl thiourea, a rotenone, a rotenone derivative, an oxazole, a thiazole, a coumarin, a coumarin derivative, or a cyclolignan;
each $R^a$ independently is hydrogen or aliphatic;
each $R^c$ independently is hydrogen, aryl, aliphatic or heteroaliphatic, or two $R^c$ moieties together form a heteroaliphatic ring;
each $R^5$ is independently hydrogen, halo, cyano, lower alkyl, lower haloalkyl, —C(O)alkyl, —C(S)alkyl, —C(O)OH, —C(O)Oalkyl, —C(O)NHR$^c$ or —C(O)N($R^c$)$_2$;
and
if LG is halo, then $R^5$ is not halo.

2. The method of claim 1, wherein the first enzyme cleaves the first enzyme recognition group, thereby converting the first quinone methide analog precursor into a first reactive quinone methide analog which covalently binds to the biological sample proximally to or directly on the first target.

3. The method of claim 1, wherein the first enzyme is a phosphatase, phosphodiesterase, esterase, lipase, amidase, protease, nitroreductase, urease, sulfatase, cytochrome P450, alpha-glucosidase, beta-glucosidase, beta-lactamase, alpha-glucoronidase, beta-glucoronidase, alpha-galactosidase, beta-galactosidase, alpha-lactase or beta-lactase.

4. The method of claim 1, wherein Z is O; $R^1$ is a sugar recognized by an enzyme; $R^3$ is —C(O)N(H)(CH$_2$)$_n$NH—; and LG is a halide.

5. The method of claim 1, further comprising: contacting the biological sample with a second detection probe specific to a second target; labeling the second target with a second enzyme through the second detection probe; contacting the biological sample with a second detection precursor compound, the second detection precursor compound interacting with the second enzyme to deposit a second detection compound directly on or proximally to the second target; and detecting the second detection compound.

6. The method of claim 5, wherein the first enzyme and second enzyme are different enzymes.

7. The method of claim 6, wherein the first enzyme reacts selectively with the first quinone methide analog precursor, and the second enzyme reacts selectively with the second detection precursor compound.

8. The method of claim 6, wherein the first enzyme is an alkaline phosphatase and the first enzyme recognition group is a phosphate, the second enzyme is a glycosidase.

9. The method of claim 6, wherein the first enzyme is an alkaline phosphatase and the first enzyme recognition group is a phosphate, the second enzyme is a horseradish peroxidase.

10. The method of claim 5, wherein the second detection precursor compound comprises a tyramide group.

11. The method of claim 5, wherein the second detection precursor compound is a second quinone methide analog.

12. The method of claim 11, wherein the second detection precursor compound has a formula

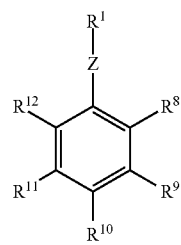

or a salt or solvate thereof;
- Z is O, S or $NR^a$ and $R^1$ is an enzyme recognition group, or $ZR^1$ is an enzyme recognition group;
- $R^8$ is —C(LG)($R^5$)($R^3R^4$), —$R^3R^4$ or —C(LG)($R^5$)($R^6$);
- $R^9$, $R^{11}$ and $R^{12}$ are each independently hydrogen, halo, cyano, aliphatic, alkoxy, $NO_2$, $N(R^c)_2$, aryl, haloalkyl, —C(O)alkyl, —C(S)alkyl, —C(O)OH, —C(O)Oalkyl, —C(O)$NHR^c$, —C(O)N($R^c$)$_2$, —$R^3R^4$ or two adjacent groups together form an aliphatic ring or aryl ring;
- $R^{10}$ is hydrogen, halo, cyano, aliphatic, alkoxy, $NO_2$, $N(R^c)_2$, aryl, haloalkyl, —C(O)alkyl, —C(S)alkyl, —C(O)OH, —C(O)Oalkyl, —C(O)$NHR^c$, —C(O)N($R^c$)$_2$, —$R^3R^4$, —C(LG)($R^5$)($R^6$) or with one of $R^9$ or $R^{11}$ form an aliphatic ring or aryl ring;
- LG is a leaving group, or $ZR^1$ and LG together form a phosphodiester;
- $R^3$ is a bond or a linker;
- $R^4$ is a detectable label;
- each $R^a$ independently is hydrogen or aliphatic;
- each $R^c$ independently is hydrogen, aryl, aliphatic or heteroaliphatic, or two $R^c$ moieties together form a heteroaliphatic ring;
- each $R^5$ is independently hydrogen, halo, cyano, lower alkyl, lower haloalkyl, —C(O)alkyl, —C(S)alkyl, —C(O)OH, —C(O)Oalkyl, —C(O)$NHR^c$ or —C(O)N($R^c$)$_2$;
- each $R^6$ is independently hydrogen, halo, cyano, lower alkyl, lower haloalkyl, —C(O)alkyl, —C(S)alkyl, —C(O)OH, —C(O)Oalkyl, —C(O)$NHR^c$ or —C(O)N($R^c$)$_2$;
- at least one of $R^8$ and $R^{10}$ comprises LG;
- at least one of R8-R12 comprises $R^3R^4$; and
- if LG is halo, then $R^5$ and $R^6$ are not halo.

13. The method of claim 1, wherein Z is O, S or $NR^a$, and $R^1$ is selected from the group consisting of phosphate, phosphodiester, amide, nitro, urea, sulfate, methyl, ester, and an enzyme-recognizable sugar.

14. The method of claim 13, wherein the first enzyme a glycosidsase.

15. The method of claim 13, wherein the sugar includes an O-glycosidic bond or an S-glycosidic bond.

16. The method of claim 1, wherein the first quinone methide analog precursor is selected from the group consisting of:

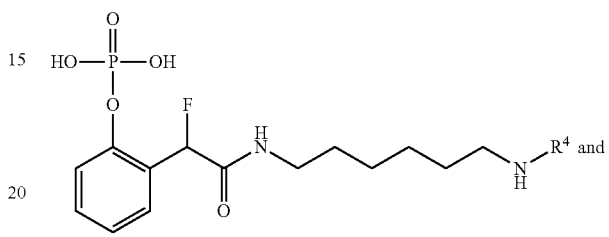

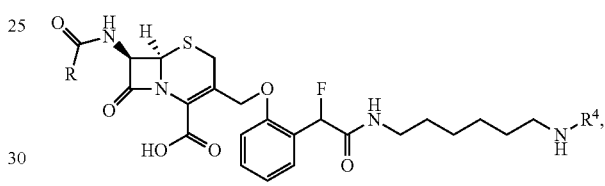

where $R^4$ is a detectable label.

17. The method of claim 1, wherein the first quinone methide analog precursor is selected from the group consisting of:

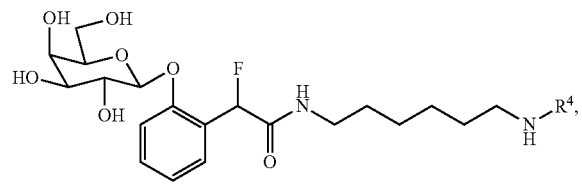

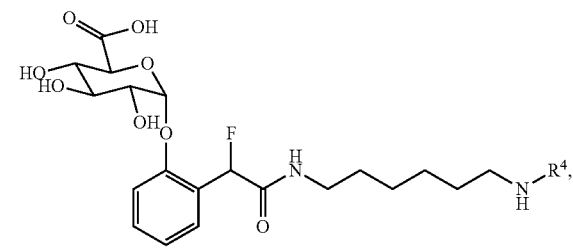

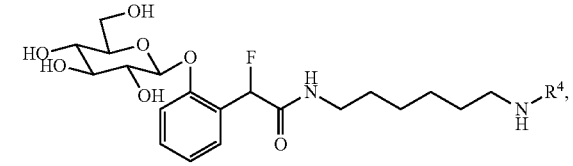

-continued
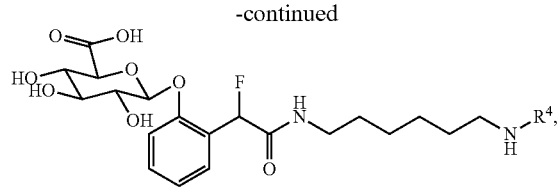
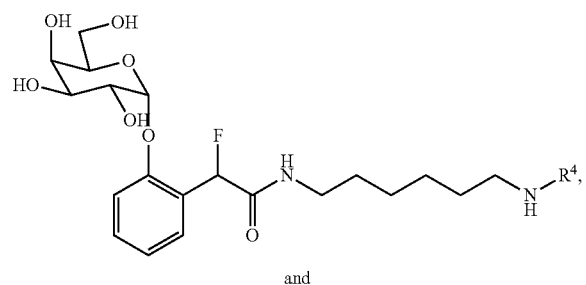
and
-continued
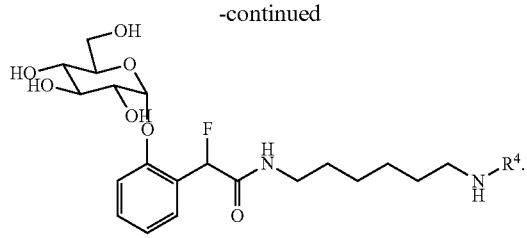
18. The method of claim 1, wherein the first quinone methide analog precursor is
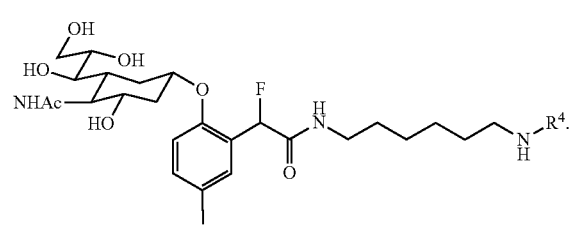
* * * * *